(12) United States Patent
Abeliovich et al.

(10) Patent No.: US 10,837,028 B2
(45) Date of Patent: Nov. 17, 2020

(54) GENE THERAPIES FOR LYSOSOMAL DISORDERS

(71) Applicant: Prevail Therapeutics, Inc., New York, NY (US)

(72) Inventors: Asa Abeliovich, New York, NY (US); Laura Heckman, New York, NY (US); Herve Rhinn, New York, NY (US)

(73) Assignee: Prevail Therapeutics, Inc., New York, NY (US)

( * ) Notice: Subject to any disclaimer, the term of this patent is extended or adjusted under 35 U.S.C. 154(b) by 0 days.

(21) Appl. No.: 16/689,865

(22) Filed: Nov. 20, 2019

(65) Prior Publication Data

US 2020/0071726 A1 Mar. 5, 2020

Related U.S. Application Data

(63) Continuation of application No. PCT/US2018/054225, filed on Oct. 3, 2018.

(60) Provisional application No. 62/567,296, filed on Oct. 3, 2017.

(51) Int. Cl.

| *C12N 15/86* | (2006.01) |
|---|---|
| *C12N 15/864* | (2006.01) |
| *A61K 48/00* | (2006.01) |
| *C12N 15/113* | (2010.01) |
| *C12N 15/52* | (2006.01) |
| *C12N 15/861* | (2006.01) |
| *C07K 14/435* | (2006.01) |
| *C07K 14/705* | (2006.01) |
| *C12N 7/00* | (2006.01) |
| *C12N 9/24* | (2006.01) |
| *A61K 9/00* | (2006.01) |

(52) U.S. Cl.
CPC ........ *C12N 15/861* (2013.01); *A61K 48/0058* (2013.01); *C07K 14/435* (2013.01); *C07K 14/70596* (2013.01); *C12N 7/00* (2013.01); *C12N 9/2402* (2013.01); *C12N 15/113* (2013.01); *C12N 15/86* (2013.01); *C12Y 302/01045* (2013.01); *A61K 9/0019* (2013.01); *A61K 48/00* (2013.01); *C12N 2310/14* (2013.01); *C12N 2310/141* (2013.01); *C12N 2710/14043* (2013.01); *C12N 2750/14143* (2013.01)

(58) Field of Classification Search
None
See application file for complete search history.

(56) References Cited

U.S. PATENT DOCUMENTS

| 5,879,680 | A | 3/1999 | Ginns et al. |
|---|---|---|---|
| 6,696,272 | B1 | 2/2004 | Mahuran et al. |
| 7,172,893 | B2 | 2/2007 | Rabinowitz |
| 7,452,716 | B2 | 11/2008 | Yew |
| 8,454,954 | B2 | 6/2013 | Schlossmacher et al. |
| 8,962,273 | B2 | 2/2015 | Reczek |
| 9,347,107 | B2 | 5/2016 | Lai et al. |
| 10,213,494 | B2 | 2/2019 | Schlossmacher et al. |
| 2003/0133924 | A1 | 7/2003 | Canfield |
| 2006/0292117 | A1* | 12/2006 | Loiler ............... C07K 14/005 424/93.2 |
| 2008/0003204 | A1* | 1/2008 | Flotte ............... A61K 48/005 424/93.2 |
| 2015/0284472 | A1* | 10/2015 | Sardi ............... C07K 16/18 424/158.1 |
| 2017/0035860 | A1 | 2/2017 | Flynn |
| 2018/0071373 | A1 | 3/2018 | Melvor et al. |
| 2018/0147300 | A1* | 5/2018 | Park ............... A61K 38/47 |
| 2019/0038773 | A1 | 2/2019 | Esteves et al. |
| 2019/0055578 | A1 | 2/2019 | Sah et al. |

FOREIGN PATENT DOCUMENTS

| WO | WO 2004/098648 A1 | 11/2004 |
|---|---|---|
| WO | WO 2014/186579 A1 | 11/2014 |
| WO | WO 2016/081927 A2 | 3/2016 |
| WO | WO 2017/136202 A1 | 8/2017 |
| WO | WO 2019/070894 A1 | 4/2019 |

OTHER PUBLICATIONS

*Homo sapiens* glucosidase, beta, GenBank AAP36904, p. 1, Jul. 25, 2016.*
Synthetic construct *Homo sapiens* glucosidase, beta; acid, Genbank BT008212.1, p. 1-2, Jul. 25, 2016.*
GenBank Accession No. NP_000148.2 "lysosomal acid glucosylceramidase isoform 1 precursor [*Homo sapiens*]" Jan. 8, 2020 [online].
GenBank Accession No. NP_005497.1 "lysosome membrane protein 2 isoform 1 precursor [*Homo sapiens*]" Jan. 1, 2020 [online].
GenBank Accession No. NP_002769.1 "prosaposin isoform a preproprotein [*Homo sapiens*]" Sep. 27, 2019 [online].
GenBank Accession No. NP_001191184.1 "lysosome membrane protein 2 isoform 2 precursor [*Homo sapiens*]" Jan. 4, 2020 [online].
GenBank Accession No. AAH01503.1 "Prosaposin [*Homo sapiens*]" Aug. 4, 2008 [online].
GenBank Accession No. AAH07612.1 "Prosaposin [*Homo sapiens*]" Aug. 4, 2008 [online].
GenBank Accession No. AAH04275.1 "Prosaposin [*Homo sapiens*]" Aug. 4, 2008 [online].

(Continued)

*Primary Examiner* — Maria Marvich
(74) *Attorney, Agent, or Firm* — Cooley LLP; Ivory R. Elrifi

(57) ABSTRACT

The disclosure relates, in some aspects, to compositions and methods for treatment of diseases associated with aberrant lysosomal function, for example Parkinson's disease and Gaucher disease. In some embodiments, the disclosure provides expression constructs comprising a transgene encoding beta-Glucocerebrosidase (GBA) or a portion thereof, Lysosomal Membrane Protein 2 (LIMP2), Prosaposin, or any combination of the foregoing. In some embodiments, the disclosure provides methods of Parkinson's disease by administering such expression constructs to a subject in need thereof.

17 Claims, 26 Drawing Sheets

Specification includes a Sequence Listing.

(56) References Cited

OTHER PUBLICATIONS

GenBank Accession No. AAA60303.1 "Prosaposin [*Homo sapiens*]" Jan. 9, 1995 [online].
GenBank Accession No. NP_001005742.1 "lysosomal acid glucosylceramidase isoform 1 precursor [*Homo sapiens*]" Nov. 11, 2019 [online].
GenBank Accession No. NP_001165282.1 "lysosomal acid glucosylceramidase isoform 2 [*Homo sapiens*]" Nov. 11, 2019 [online].
GenBank Accession No. NP_001165283.1 "lysosomal acid glucosylceramidase isoform 3 [*Homo sapiens*]" Nov. 11, 2019 [online].
GenBank Accession No. NP_065995.1 "non-lysosomal glucosylceramidase isoform 1 [*Homo sapiens*]" Aug. 22, 2019 [online].
GenBank Accession No. NP_000144.2 "galactocerebrosidase isoform a precursor [*Homo sapiens*]" Sep. 26, 2019 [online].
GenBank Accession No. NP_001899.1 "cathepsin B isoform 1 preproprotein [*Homo sapiens*]" Jan. 27, 2020 [online].
GenBank Accession No. NP_000534.3 "sphingomyelin phosphodiesterase isoform 1 precursor [*Homo sapiens*]" Jan. 13, 2020 [online].
GenBank Accession No. NP_003920.1 "ras-related protein Rab-7L1 isoform 1 [*Homo sapiens*]" Dec. 31, 2019 [online].
GenBank Accession No. NP_060676.2 "vacuolar protein sorting-associated protein 35 [*Homo sapiens*]" Oct. 11, 2019 [online].
GenBank Accession No. NP_689669.2 "interleukin-34 isoform 1 precursor [*Homo sapiens*]" Dec. 25, 2019 [online].
GenBank Accession No. NP_061838.1 "triggering receptor expressed on myeloid cells 2 precursor isoform 1 precursor [*Homo sapiens*]" Feb. 2, 2020 [online].
GenBank Accession No. NP_060844.2 "transmembrane protein 106B [*Homo sapiens*]" Jul. 28, 2019 [online].
GenBank Accession No. NP_002078.1 "progranulin precursor [*Homo sapiens*]" Jan. 21, 2020 [online].
GenBank Accession No. NP_001317589.1 "non-lysosomal glucosylceramidase isoform 2 [*Homo sapiens*]" Aug. 7, 2019 [online].
GenBank Accession No. EAW81359.1 "galactosylceramidase, isoform CRA_a [*Homo sapiens*]" Mar. 23, 2015 [online].
GenBank Accession No. EAW81360.1 "galactosylceramidase, isoform CRA_b [*Homo sapiens*]" Mar. 23, 2015 [online].
GenBank Accession No. EAW81362.1 "galactosylceramidase, isoform CRA_c [*Homo sapiens*]" Mar. 23, 2015 [online].
GenBank Accession No. EAW68726.1 "sphingomyelin phosphodiesterase 1, acid lysosomal (acid sphingomyelinase), isoform CRA_a [*Homo sapiens*]" Mar. 23, 2015 [online].
GenBank Accession No. EAW68727.1 "sphingomyelin phosphodiesterase 1, acid lysosomal (acid sphingomyelinase), isoform CRA_b [*Homo sapiens*]" Mar. 23, 2015 [online].
GenBank Accession No. EAW68728.1 "sphingomyelin phosphodiesterase 1, acid lysosomal (acid sphingomyelinase), isoform CRA_c [*Homo sapiens*]" Mar. 23, 2015 [online].
GenBank Accession No. EAW68729.1 "sphingomyelin phosphodiesterase 1, acid lysosomal (acid sphingomyelinase), isoform CRA_d [*Homo sapiens*]" Mar. 23, 2015 [online].
GenBank Accession No. AAC37547.1 "cathepsin B [*Homo sapiens*]" Apr. 7, 1994 [online].
GenBank Accession No. AAH95408.1 "Cathepsin B [*Homo sapiens*]" Jul. 17, 2006 [online].
GenBank Accession No. AAH10240.1 "Cathepsin B [*Homo sapiens*]" Jul. 15, 2006 [online].
GenBank Accession No. AAH02585.1 "RAB7, member RAS oncogene family-like 1 [*Homo sapiens*]" Jul. 15, 2006 [online].
GenBank Accession No. AAH25415.1 "GTP cyclohydrolase 1 [*Homo sapiens*]" Aug. 7, 2008 [online].
GenBank Accession No. AAH29804.1 "Interleukin 34 [*Homo sapiens*]" Jun. 9, 2008 [online].
GenBank Accession No. AAF69824.1 "triggering receptor expressed on myeloid cells 2 [*Homo sapiens*]" May 23, 2000 [online].
GenBank Accession No. NP_002087.1 "general transcription factor IIF, polypeptide 1, 74kDa [*Homo sapiens*]" Jun. 3, 2007 [online].
GenBank Accession No. NP_000152.1 "GTP cyclohydrolase 1 isoform 1 [*Homo sapiens*]" Dec. 30, 2019 [online].

\* cited by examiner

```
                              SEQUENCE LISTING

<160> NUMBER OF SEQ ID NOS: 31

<210> SEQ ID NO 1
<211> LENGTH: 10697
<212> TYPE: DNA
<213> ORGANISM: Artificial Sequence
<220> FEATURE:
<223> OTHER INFORMATION: Synthetic polynucleotide

<400> SEQUENCE: 1
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
cctagttatt aatagtaatc aattacgggg tcattagttc atagcccata tatggagttc     360
cgcgttacat aacttacggt aaatggcccg cctggctgac cgcccaacga ccccgccca     420 ttgacgtcaa taatgacgta tgttcccata gtaacgccaa tagggacttt ccattgacgt     480
caatgggtgg actatttacg gtaaactgcc cacttggcag tacatcaagt gtatcatatg     540
ccaagtacgc cccctattga cgtcaatgac ggtaaatggc ccgcctggca ttatgcccag     600
tacatgacct tatgggactt tcctacttgg cagtacatct acgtattagt catcgctatt     660
accatggtcg aggtgagccc cacgttctgc ttcactctcc ccatctcccc ccctcccca     720 cccccaattt tgtatttatt tattttttaa ttattttgtg cagcgatggg ggcggggggg     780
gggggggggc gcgcgccagg cggggcgggg cggggcgagg ggcggggcgg ggcgaggcgg     840
agaggtgcgg cggcagccaa tcagagcggc gcgctccgaa agtttccttt tatggcgagg     900
cggcggcggc ggcggcccta taaaaagcga agcgcgcggc gggcgggagt cgctgcgacg     960
ctgccttcgc cccgtgcccc gctccgccgc cgcctcgcgc cgcccgcccc ggctctgact    1020
gaccgcgtta ctcccacagg tgagcgggcg ggacggccct tctcctccgg gctgtaatta    1080
gcgcttggtt taatgacggc ttgttttctg tggctgcgtg aaagccttga ggggctccgg    1140
gagctagagc ctctgctaac catgttcatg ccttcttctt tttcctacag ctcctgggca    1200
```

```
acgtgctggt tattgtgctg tctcatcatt ttggcaaaga attcctcgaa gatccgaagg    1260
gaaagtcttc cacgactgtg ggatccgttc gaagatatca ccggttgagc caccatggaa    1320
ttcagcagcc ccagcagaga ggaatgcccc aagcctctga gccgggtgtc aatcatggcc    1380
ggatctctga caggactgct gctgcttcag gccgtgtctt gggcttctgg cgctagacct    1440
tgcatcccca agagcttcgg ctacagcagc gtcgtgtgcg tgtgcaatgc cacctactgc    1500
gacagcttcg accctcctac ctttcctgct ctgggcacct tcagcagata cgagagcacc    1560
agatccggca gacggatgga actgagcatg ggacccatcc aggccaatca cacaggcact    1620
ggcctgctgc tgacactgca gcctgagcag aaattccaga agtgaaaggc ttcggcgga    1680
gccatgacag atgccgccgc tctgaatatc ctggctctgt ctccaccagc tcagaacctg    1740
ctgctcaaga gctacttcag cgaggaaggc atcggctaca acatcatcag agtgcccatg    1800
gccagctgcg acttcagcat caggacctac acctacgccg acacacccga cgatttccag    1860
ctgcacaact tcagcctgcc tgaagaggac accaagctga agatccctct gatccacaga    1920
gccctgcagc tggcacaaag acccgtgtca ctgctggcct ctccatggac atctcccacc    1980
tggctgaaaa caaatggcgc cgtgaatggc aagggcagcc tgaaaggcca acctggcgac    2040
atctaccacc agacctgggc cagatacttc gtgaagttcc tggacgccta tgccgagcac    2100
aagctgcagt tttgggccgt gacagccgag aacgaaacctt ctgctggact gctgagcggc    2160
taccccttc agtgcctggg ctttacaccc gagcaccagc gggactttat cgcccgtgat    2220
ctgggaccca cactggccaa tagcacccac cataatgtgc ggctgctgat gctggacgac    2280
cagagactgc ttctgcccca ctgggctaaa gtggtgctga cagatcctga ggccgccaaa    2340
tacgtgcacg gaatcgccgt gcactggtat ctggactttc tggcccctgc caaggccaca    2400
ctgggagaga cacacagact gttccccaac accatgctgt cgccagcga agcctgtgtg    2460
ggcagcaagt tttgggaaca gagcgtgcgg ctcggcagct gggatagagg catgcagtac    2520
agccacagca tcatcaccaa cctgctgtac cacgtcgtcg gctggaccga ctggaatctg    2580
gccctgaatc ctgaaggcgg ccctaactgg gtccgaaact cgtggacag ccccatcatc    2640
gtggacatca ccaaggacac cttctacaag cagcccatgt tctaccacct gggacacttc    2700
agcaagttca tccccgaggg ctctcagcgc gttggactgg tggcttccca aagaacgat    2760
ctggacgccg tggctctgat gcaccctgat ggatctgctg tggtggtggt cctgaaccgc    2820
agcagcaaag atgtgcccct gaccatcaag gatcccgccg tgggattcct ggaaacaatc    2880
agccctggct actccatcca cacctacctg tggcgtagac agtgacaatt gttaattaag    2940
tttaacccct cgaggccgca agcttatcga taatcaacct ctggattaca aaatttgtga    3000
aagattgact ggtattctta actatgttgc tccttttacg ctatgtggat acgctgcttt    3060
aatgcctttg tatcatgcta ttgcttcccg tatggctttc atttctcct ccttgtataa    3120
atcctggttg ctgtctcttt atgaggagtt gtggcccgtt gtcaggcaac gtggcgtggt    3180
gtgcactgtg tttgctgacg caaccccac tggttgggc attgccacca cctgtcagct    3240
cctttccggg actttcgctt tccccctccc tattgccacg gcggaactca tcgccgcctg    3300
ccttgcccgc tgctgacag gggctcggct gttgggcact gacaattccg tggtgttgtc    3360
ggggaaatca tcgtcctttc cttggctgct cgcctgtgtt gccacctgga ttctgcgcgg    3420
gacgtccttc tgctacgtcc cttcggccct caatccagcg gaccttcctt cccgcggcct    3480
gctgccggct ctgcggcctc ttccgcgtct tcgccttcgc cctcagacga gtcggatctc    3540
cctttgggcc gcctccccgc atcgataccg tcgactagag ctcgctgatc agcctcgact    3600
```

```
gtgccttcta gttgccagcc atctgttgtt tgcccctccc ccgtgccttc cttgaccctg    3660
gaaggtgcca ctcccactgt cctttcctaa taaaatgagg aaattgcatc gcattgtctg    3720
agtaggtgtc attctattct ggggggtggg gtggggcagg acagcaaggg ggaggattgg    3780
gaagacaata gcaggcatgc tggggagaga tccacgataa caaacagctt ttttggggtg    3840
aacatattga ctgaattccc tgcaggttgg ccactccctc tctgcgcgct cgctcgctca    3900
ctgaggccgc ccgggcaaag cccgggcgtc gggcgacctt tggtcgcccg gcctcagtga    3960
gcgagcgagc gcgcagagag ggagtggcca actccatcac taggggttcc tgcggccgct    4020
cgtacggtct cgaggaattc tgcaggata  acttgccaac ctcattctaa aatgtatata    4080
gaagcccaaa agacaataac aaaaatattc ttgtagaaca aatgggaaa  gaatgttcca    4140 ctaaatatca agatttagag caaagcatga gatgtgtggg gatagacagt gaggctgata    4200
aaatagagta gagctcagaa acagacccat tgatatatgt aagtgaccta tgaaaaaaat    4260
atggcatttt acaatgggaa aatgatggtc tttttctttt ttagaaaaac agggaaatat    4320
atttatatgt aaaaaataaa agggaaccca tatgtcatac catacacaca aaaaaattcc    4380
agtgaattat aagtctaaat ggagaaggca aaacttttaa  tcttttagaa aataatatag   4440
aagcatgcag accagcctgg ccaacatgat gaaaccctct ctactaataa taaaatcagt    4500
agaactactc aggactactt tgagtgggaa gtccttttct atgaagactt ctttggccaa    4560
aattaggctc taaatgcaag gagatagtgc atcatgcctg gctgcactta ctgataaatg    4620
atgttatcac catctttaac caatgcaca  ggaacaagtt atggtactga tgtgctggat    4680
tgagaaggag ctctacttcc ttgacaggac acatttgtat caacttaaaa aagcagattt    4740
ttgccagcag aactattcat tcagaggtag gaaacttaga atagatgatg tcactgatta    4800
gcatggcttc cccatctcca cagctgcttc ccacccaggt tgcccacagt tgagtttgtc    4860
cagtgctcag ggctgcccac tctcagtaag aagccccaca ccagcccctc tccaaatatg    4920
ttggctgttc cttccattaa agtgaccca  ctttagagca gcaagtggat ttctgtttct    4980
tacagttcag gaaggaggag tcagctgtga gaacctggag cctgagatgc ttctaagtcc    5040
cactgctact ggggtcaggg aagccagact ccagcatcag cagtcaggag cactaagccc    5100
ttgccaacat cctgtttctc agagaaactg cttccattat aatggttgtc ctttttttaag   5160 ctatcaagcc aaacaaccag tgtctaccat tattctcatc acctgaagcc aagggttcta    5220
gcaaaagtca agctgtcttg taatggttga tgtgcctcca gcttctgtct tcagtcactc    5280
cactcttagc ctgctctgaa tcaactctga ccacagttcc ctggagcccc tgccacctgc    5340
tgcccctgcc accttctcca tctgcagtgc tgtgcagcct tctgcactct tgcagagcta    5400
ataggtggag acttgaagga agaggaggaa agtttctcat aatagccttg ctgcaagctc    5460
aaatgggagg tgggcactgt gcccaggagc cttggagcaa aggctgtgcc caacctctga    5520
ctgcatccag gttggtcttt gacagagata agaagccctg cttttggag  ccaaaatcta    5580 ggtcagactt aggcaggatt ctcaaagttt atcagcagaa catgaggcag aagacccttt    5640
ctgctccagc ttcttcaggc tcaaccttca tcagaataga tagaaagaga ggctgtgagg    5700
gttcttaaaa cagaagcaaa tctgactcag agaataaaca acctcctagt aaactacagc    5760
ttagacagag catctggtgg tgagtgtgct cagtgtccta ctcaactgtc tggtatcagc    5820
cctcatgagg acttctcttc tttccctcat agacctccat ctctgttttc cttagcctgc    5880
agaaatctgg atggctattc acagaatgcc tgtgctttca gagttgcatt ttttctctgg    5940
```

-continued

| | |
|---|---|
| tattctggtt caagcatttg aaggtaggaa aggttctcca agtgcaagaa agccagccct | 6000 |
| gagcctcaac tgcctggcta gtgtggtcag taggatgcaa aggctgttga atgccacaag | 6060 |
| gccaaactTt aacctgtgta ccacaagcct agcagcagag gcagctctgc tcactggaac | 6120 |
| tctctgtctt ctttctcctg agccttttct tttcctgagt tttctagctc tcctcaacct | 6180 |
| tacctctgcc ctacccagga caaacccaag agccactgtt tctgtgatgt cctctccagc | 6240 |
| cctaattagg catcatgact tcagcctgac cttccatgct cagaagcagt gctaatccac | 6300 |
| ttcagatgag ctgctctatg caacacaggc agagcctaca aacctttgca ccagagccct | 6360 |
| ccacatatca gtgtttgttc atactcactt caacagcaaa tgtgactgct gagattaaga | 6420 |
| ttttacacaa gatggtctgt aatttcacag ttagttttat cccattaggt atgaaagaat | 6480 |
| tagcataatt ccccttaaac atgaatgaat cttagatttt ttaataaata gttttggaag | 6540 |
| taaagacaga gacatcagga gcacaaggaa tagcctgaga ggacaaacag aacaagaaag | 6600 |
| agtctggaaa tacacaggat gttcttggcc tcctcaaagc aagtgcaagc agatagtacc | 6660 |
| agcagcccca ggctatcaga gcccagtgaa gagaagtacc atgaaagcca cagctctaac | 6720 |
| caccctgttc cagagtgaca gacagtcccc aagacaagcc agcctgagcc agagagagaa | 6780 |
| ctgcaagaga agtttctaa tttaggttct gttagattca gacaagtgca ggtcatcctc | 6840 |
| tctccacagc tactcacctc tccagcctaa caaagcctgc agtccacact ccaaccctgg | 6900 |
| tgtctcacct cctagcctct cccaacatcc tgctctctga ccatcttctg catctctcat | 6960 |
| ctcaccatct cccactgtct acagcctact cttgcaacta ccatctcatt ttctgacatc | 7020 |
| ctgtctacat cttctgccat actctgccat ctaccatacc acctcttacc atctaccaca | 7080 |
| ccatctttta tctccatccc tctcagaagc ctccaagctg aatcctgctt tatgtgttca | 7140 |
| tctcagcccc tgcatggaaa gctgacccca gaggcagaac tattcccaga gagcttggcc | 7200 |
| aagaaaaaca aaactaccag cctggccagg ctcaggagta gtaagctgca gtgtctgttg | 7260 |
| tgttctagct tcaacagctg caggagttcc actctcaaat gctccacatt tctcacatcc | 7320 |
| tcctgattct ggtcactacc catcttcaaa gaacagaata tctcacatca gcatactgtg | 7380 |
| aaggactagt catgggtgca gctgctcaga gctgcaaagt cattctggat ggtgggagagc | 7440 |
| ttacaaacat tcatgatgc tcccccccgct ctgatggctg gagcccaatc cctacacaga | 7500 |
| ctcctgctgt atgtgttttc ctttcactct gagccacagc cagagggcag gcattcagtc | 7560 |
| tcctcttcag gctggggctg gggcactgag aactcaccca acaccttgct ctcactcctt | 7620 |
| ctgcaaaaca agaagagct ttgtgctgca gtagccatga agaatgaaag gaaggcttta | 7680 |
| actaaaaaat gtcagagatt attttcaacc ccttactgtg gatcaccagc aaggaggaaa | 7740 |
| cacaacacag agacattttt tcccctcaaa ttatcaaaag aatcactgca tttgttaaag | 7800 |
| agagcaactg aatcaggaag cagagttttg aacatatcag aagttaggaa tctgcatcag | 7860 |
| agacaaatgc agtcatggtt gtttgctgca taccagccct aatcattaga agcctcatgg | 7920 |
| acttcaaaca tcattccctc tgacaagatg ctctagccta actccatgag ataaaataaa | 7980 |
| tctgcctttc agagccaaag aagagtccac cagcttcttc tcagtgtgaa caagagctcc | 8040 |
| agtcaggtta gtcagtccag tgcagtagag gagaccagtc tgcatcctct aattttcaaa | 8100 |
| ggcaagaaga tttgtttacc ctggacacca ggcacaagtg aggtcacaga gctcttagat | 8160 |
| atgcagtcct catgagtgag gagactaaag cgcatgccat caagacttca gtgtagagaa | 8220 |
| aacctccaaa aaagcctcct cactacttct ggaatagctc agaggccgag gcggcctcgg | 8280 |
| cctctgcata aataaaaaaa attagtcagc catggggcgg agaatgggcg gaactgggcg | 8340 |

```
gagttagggg cgggatgggc ggagttaggg gcgggactat ggttgctgac taattgagat    8400
gcatgctttg catacttctg cctgctgggg agcctgggga cttttccacac ctggttgctg    8460 actaattgag atgcatgctt tgcatacttc tgcctgctgg ggagcctggg gactttccac    8520
accctaactg acacacattc cacagctgca ttaatgaatc ggccaacgcg cggggagagg    8580
cggtttgcgt attgggcgct cttccgcttc ctcgctcact gactcgctgc gctcggtcgt    8640
tcggctgcgg cgagcggtat cagctcactc aaaggcggta atacggttat ccacagaatc    8700
aggggataac gcaggaaaga acatgtgagc aaaaggccag caaaaggcca ggaaccgtaa    8760
aaaggccgcg ttgctggcgt ttttccatag gctccgcccc cctgacgagc atcacaaaaa    8820
tcgacgctca agtcagaggt ggcgaaaccc gacaggacta taaagatacc aggcgtttcc    8880
ccctggaagc tccctcgtgc gctctcctgt tccgaccctg ccgcttaccg gatacctgtc    8940
cgcctttctc ccttcgggaa gcgtggcgct ttctcatagc tcacgctgta ggtatctcag    9000
ttcggtgtag gtcgttcgct ccaagctggg ctgtgtgcac gaaccccccg ttcagcccga    9060
ccgctgcgcc ttatccggta actatcgtct tgagtccaac ccggtaagac acgacttatc    9120
gccactggca gcagccactg gtaacaggat tagcagagcg aggtatgtag gcggtgctac    9180
agagttcttg aagtggtggc ctaactacgg ctacactaga agaacagtat ttggtatctg    9240
cgctctgctg aagccagtta ccttcggaaa aagagttggt agctcttgat ccggcaaaca    9300
aaccaccgct ggtagcggtg gtttttttgt ttgcaagcag cagattacgc gcagaaaaaa    9360
aggatctcaa gaagatcctt tgatcttttc tacgggtctg acgctcagtg gaacgaaaa    9420 ctcacgttaa gggattttgg tcatgagatt atcaaaaagg atcttcacct agatcctttt    9480
aaattaaaaa tgaagtttta atcaatcta agtatatat gagtaaactt ggtctgacag    9540
ttaccaatgc ttaatcagtg aggcacctat ctcagcgatc tgtctatttc gttcatccat    9600
agttgcctga ctcctgcaaa ccacgttgtg tctcaaaatc tctgatgtta cattgcacaa    9660
gataaaaata tcatcatg aacaataaaa ctgtctgctt acataaacag taatacaagg    9720
ggtgttatga ccatattca acgggaaacg tcttgctcga ggccgcgatt aaattccaac    9780
atggatgctg atttatatgg gtataaatgg gctcgcgata atgtcgggca atcaggtgcg    9840
acaatctatc gattgtatgg gaagcccgat gcgccagagt tgtttctgaa acatggcaaa    9900
ggtagcgttg ccaatgatgt tacagatgag atggtcagac taaactggct gacgaatttt    9960
atgcctcttc cgaccatcaa gcattttatc cgtactcctg atgatgcatg gttactcacc   10020
actgcgatcc ccgggaaaac agcattccag gtattagaag aatatcctga ttcaggtgaa   10080
aatattgttg atgcgctggc agtgttcctg cgccggttgc attcgattcc tgtttgtaat   10140 tgtccttta acagcgatcg cgtatttcgt ctcgctcagg cgcaatcacg aatgaataac   10200
ggtttggttg atgcgagtga ttttgatgac gagcgtaatg gctggcctgt gaacaagtc   10260 tggaaagaaa tgcataagct tttgccattc tcaccggatt cagtcgtcac tcatggtgat   10320
ttctcacttg ataaccttat ttttgacgag gggaaattaa taggttgtat tgatgttgga   10380
cgagtcggaa tcgcagaccg ataccaggat cttgccatcc tatggaactg cctcggtgag   10440
ttttctcctt cattacagaa acggcttttt caaaatatg gtattgataa tcctgatatg   10500
aataaattgc agtttcattt gatgctcgat gagtttttct aagggcggcc tgccaccata   10560
cccacgccga aacaagcgct catgagcccg aagtggcgag cccgatcttc ccatccggtg   10620
atgtcggcga tataggcgcc agcaaccgca cctgtggcgc cggtgatgag ggcgcgccaa   10680
```

| | |
|---|---|
| gtcgacgtcc ggcagtc | 10697 |

<210> SEQ ID NO 2
<211> LENGTH: 11355
<212> TYPE: DNA
<213> ORGANISM: Artificial Sequence
<220> FEATURE:
<223> OTHER INFORMATION: Synthetic polynucleotide

<400> SEQUENCE: 2

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg agggcggagt | 300 |
| tagggcggag ccaatcagcg tgcgccgttc cgaaagttgc ctttatggc tgggcggaga | 360 |
| atgggcggtg aacgccgatg attatataag gacgcgccgg gtgtggcaca gctagttccg | 420 |
| tcgcagccgg gatttgggtc gcggttcttg tttgtggatc cctgtgatcg tcacttggta | 480 |
| agtcactgac tgtctatgcc tgggaaaggg tgggcaggag atgggcagt gcaggaaaag | 540 |
| tggcactatg aaccctgcag ccctaggaat gcatctagac aattgtacta accttcttct | 600 |
| ctttcctctc ctgacagtcc ggaaagccac catgggccgc tgctgcttct acaccgccgg | 660 |
| caccctgagc ctgctgctgc tggtgaccag cgtgaccctg ctggtggccc gcgtgttcca | 720 |
| gaaggccgtg gaccagagca tcgagaagaa gatcgtgctg cgcaacggca ccgaggcctt | 780 |
| cgacagctgg gagaagcccc ccctgcccgt gtacacccag ttctacttct tcaacgtgac | 840 |
| caaccccgag gagatcctgc gcggcgagac ccccgcgtg gaggaggtgg ccccctacac | 900 |
| ctaccgcgag ctgcgcaaca aggccaacat ccagttcggc gacaacggca ccaccatcag | 960 |
| cgccgtgagc aacaaggcct acgtgttcga gcgcgaccag agcgtgggcg accccaagat | 1020 |
| cgacctgatc cgcaccctga acatccccgt gctgaccgtg atcgagtgga ccaggtgca | 1080 |
| cttcctgcgc gagatcatcg aggccatgct gaaggcctac cagcagaagc tgttcgtgac | 1140 |
| ccacaccgtg gacgagctgc tgtggggcta caaggacgag atcctgagcc tgatccacgt | 1200 |
| gttccgcccc gacatcagcc cctacttcgg cctgttctac gagaagaacg caccaacga | 1260 |
| cggcgactac gtgttcctga ccggcgagga cagctacctg aacttcacca gatcgtgga | 1320 |
| gtggaacggc aagaccagcc tggactggtg gatcaccgac aagtgcaaca tgatcaacgg | 1380 |
| caccgacggc gacagcttcc accccctgat caccaaggac gaggtgctgt acgtgttccc | 1440 |
| cagcgacttc tgccgcagcg tgtacatcac cttcagcgac tacgagagcg tgcagggcct | 1500 |
| gccgccttc cgctacaagg tgcccgccga gatcctggcc aacaccagcg acaacgccgg | 1560 |
| cttctgcatc cccagggca actgcctggg cagcggcgtg ctgaacgtga gcatctgcaa | 1620 |
| gaacggcgcc cccatcatca tgagcttccc ccacttctac caggccgacg agcgcttcgt | 1680 |
| gagcgccatc gagggcatgc accccaacca ggaggaccac gagaccttcg tggacatcaa | 1740 |
| cccccctgacc ggcatcatcc tgaaggccgc caagcgcttc cagatcaaca tctacgtgaa | 1800 |
| gaagctggac gacttcgtgg agaccggcga catccgcacc atggtgttcc ccgtgatgta | 1860 |
| cctgaacgag agcgtgcaca tcgacaagga gaccgccagc cgcctgaaga gcatgatcaa | 1920 |
| caccaccctg atcatcacca acatccccta tcatcatg ccctgggcg tgttcttcgg | 1980 |
| cctggtgttc acctggctgg cctgcaaggg ccagggcagc atggacgagg gcaccgccga | 2040 |

```
cgagcgcgcc cccctgatcc gcacctgatt gtggccgaac cgccgaactc agaggccggc    2100
cccagaaaac ccgagcgagt aggggggcggc gcgcaggagg gaggagaact gggggcgcgg    2160
gaggctggtg ggtgtggggg gtggagatgt agaagatgtg acgccgcggc ccggcgggtg    2220
ccagattagc ggacgcggtg cccgcggttg caacgggatc ccgggcgctg cagcttggga    2280
ggcggctctc cccaggcggc gtccgcggag acacccatcc gtgaaccccca ggtcccgggc    2340 cgccggctcg ccgcgcacca ggggccggcg gacagaagag cggccgagcg gctcgaggct    2400
gggggaccgc gggcgcggcc gcgcgctgcc gggcgggagg ctgggggggcc ggggccgggg    2460 ccgtgccccg gagcgggtcg gaggccgggg ccggggccgg gggacggcgg ctccccgcgc    2520
ggctccagcg gctcggggat cccggccggg ccccgcaggg accatgatgg aattcagcag    2580
ccccagcaga gaggaatgcc ccaagcctct gagccgggtg tcaatcatgg ccggatctct    2640
gacaggactg ctgctgcttc aggccgtgtc ttgggcttct ggcgctagac cttgcatccc    2700
caagagcttc ggctacagca gcgtcgtgtg cgtgtgcaat gccacctact gcgacagctt    2760
cgaccctcct acctttcctg ctctgggcac cttcagcaga tacgagagca ccagatccgg    2820
cagacggatg gaactgagca tgggacccat ccaggccaat cacacaggca ctggcctgct    2880
gctgacactg cagcctgagc agaaattcca gaaagtgaaa ggcttcggcg agccatgac    2940 agatgccgcc gctctgaata tcctggctct gtctccacca gctcagaacc tgctgctcaa    3000
gagctacttc agcgaggaag gcatcggcta caacatcatc agagtgccca tggccagctg    3060
cgacttcagc atcaggacct acacctacgc cgacacaccc gacgatttcc agctgcacaa    3120
cttcagcctg cctgaagagg acaccaagct gaagatccct ctgatccaca gagccctgca    3180
gctggcacaa agaccgtgt cactgctggc ctctccatgg acatctccca cctggctgaa    3240
aacaaatggc gccgtgaatg caagggcag cctgaaaggc caacctggcg acatctacca    3300
ccagacctgg gccagatact tcgtgaagtt cctggacgcc tatgccgagc acaagctgca    3360
gttttgggcc gtgacagccg agaacgaacc ttctgctgga ctgctgagcg gctacccctt    3420
tcagtgcctg ggctttacac ccgagcacca gcgggacttt atcgcccgtg atctgggacc    3480
cacactggcc aatagcaccc accataatgt gcggctgctg atgctggacg accagagact    3540
gcttctgccc cactgggcta aagtggtgct gacagatcct gaggccgcca atacgtgca    3600 cggaatcgcc gtgcactggt atctggactt tctggcccct gccaaggcca cactgggaga    3660
gacacacaga ctgttcccca caccatgct gttcgccagc gaagcctgtg tgggcagcaa    3720
gttttgggaa cagagcgtgc ggctcggcag ctgggtataga ggcatgcagt acagccacag    3780
catcatcacc aacctgctgt accacgtcgt cggctggacc gactggaatc tggccctgaa    3840
tcctgaaggc ggccctaact gggtccgaaa cttcgtggac agccccatca tcgtggacat    3900
caccaaggac accttctaca agcagcccat gttctaccac ctgggacact tcagcaagtt    3960
catccccgag ggctctcagc gcgttggact ggtggcttcc cagaagaacg atctggacgc    4020
cgtggctctg atgcaccctg atggatctgc tgtggtggtg gtcctgaacc gcagcagcaa    4080
agatgtgccc ctgaccatca aggatcccgc cgtgggattc ctggaaacaa tcagccctgg    4140
ctactccatc cacacctacc tgtggcgtag acagtgacaa ttgttaatta agtttaaacc    4200
ctcgaggccg caagccgcat cgataccgtc gactagagct cgctgatcag cctcgactgt    4260
gccttctagt tgccagccat ctgttgtttg ccctcccccc gtgccttcct tgaccctgga    4320
aggtgccact cccactgtcc tttcctaata aaatgaggaa attgcatcgc attgtctgag    4380
```

```
taggtgtcat tctattctgg ggggtggggt ggggcaggac agcaagggag aggattggga    4440
agacaatagc aggcatgctg gggagagatc cacgataaca aacagctttt ttggggtgaa    4500
catattgact gaattccctg caggttggcc actccctctc tgcgcgctcg ctcgctcact    4560
gaggccgccc gggcaaagcc cgggcgtcgg gcgacctttg gtcgcccggc ctcagtgagc    4620
gagcgagcgc gcagagaggg agtggccaac tccatcacta ggggttcctg cggccgctcg    4680
tacggtctcg aggaattcct gcaggataac ttgccaacct cattctaaaa tgtatataga    4740
agcccaaaag acaataacaa aaatattctt gtagaacaaa atgggaaaga atgttccact    4800
aaatatcaag atttagagca aagcatgaga tgtgtgggga tagacagtga ggctgataaa    4860
atagagtaga gctcagaaac agacccattg atatatgtaa gtgacctatg aaaaaaatat    4920
ggcattttac aatgggaaaa tgatggtctt tttcttttt agaaaaacag ggaaatatat    4980
ttatatgtaa aaaataaaag ggaacccata tgtcatacca tacacacaaa aaaattccag    5040
tgaattataa gtctaaatgg agaaggcaaa actttaaatc ttttagaaaa taatatagaa    5100
gcatgcagac cagcctggcc aacatgatga accctctct actaataata aaatcagtag    5160
aactactcag gactactttg agtgggaagt ccttttctat gaagacttct ttggccaaaa    5220
ttaggctcta aatgcaagga gatagtgcat catgcctggc tgcacttact gataaatgat    5280
gttatcacca tctttaacca aatgcacagg aacaagttat ggtactgatg tgctggattg    5340
agaaggagct ctacttcctt gacaggacac atttgtatca acttaaaaaa gcagattttt    5400
gccagcagaa ctattcattc agaggtagga aacttagaat agatgatgtc actgattagc    5460
atggcttccc catctccaca gctgcttccc acccaggttg cccacagttg agtttgtcca    5520
gtgctcaggg ctgcccactc tcagtaagaa gccccacacc agcccctctc caaatatgtt    5580
ggctgttcct tccattaaag tgaccccact ttagagcagc aagtggattt ctgtttctta    5640
cagttcagga aggaggagtc agctgtgaga acctggagcc tgagatgctt ctaagtccca    5700
ctgctactgg ggtcagggaa gccagactcc agcatcagca gtcaggagca ctaagccctt    5760
gccaacatcc tgtttctcag agaaactgct tccattataa tggttgtcct ttttaagct    5820
atcaagccaa acaaccagtg tctaccatta ttctcatcac ctgaagccaa gggttctagc    5880
aaaagtcaag ctgtcttgta atggttgatg tgcctccagc ttctgtcttc agtcactcca    5940
ctcttagcct gctctgaatc aactctgacc acagttccct ggagcccctg ccacctgctg    6000
cccctgccac cttctccatc tgcagtgctg tgcagccttc tgcactcttg cagagctaat    6060
aggtggagac ttgaaggaag aggaggaaag tttctcataa tagccttgct gcaagctcaa    6120
atgggaggtg ggcactgtgc ccaggagcct tggagcaaag gctgtgccca acctctgact    6180
gcatccaggt ttggtcttga cagagataag aagccctggc ttttggagcc aaaatctagg    6240
tcagacttag gcaggattct caaagtttat cagcagaaca tgaggcagaa gacccttct    6300
gctccagctt cttcaggctc aaccttcatc agaatagata gaaagagagg ctgtgagggt    6360
tcttaaaaca gaagcaaatc tgactcagag aataaacaac ctcctagtaa actacagctt    6420
agacagagca tctggtggtg agtgtgctca gtgtcctact caactgtctg gtatcagccc    6480
tcatgaggac ttctcttctt tccctcatag acctccatct ctgttttcct tagcctgcag    6540
aaatctggat ggctattcac agaatgcctg tgctttcaga gttgcatttt ttctctggta    6600
ttctggttca agcatttgaa ggtaggaaag gttctccaag tgcaagaaag ccagccctga    6660
gcctcaactg cctggctagt gtggtcagta ggatgcaaag gctgttgaat gccacaaggc    6720
caaacttaa cctgtgtacc acaagcctag cagcagaggc agctctgctc actggaactc    6780
```

-continued

```
tctgtcttct ttctcctgag ccttttcttt tcctgagttt tctagctctc ctcaacctta   6840
cctctgccct acccaggaca aacccaagag ccactgtttc tgtgatgtcc tctccagccc   6900
taattaggca tcatgacttc agcctgacct tccatgctca gaagcagtgc taatccactt   6960
cagatgagct gctctatgca acacaggcag agcctacaaa cctttgcacc agagccctcc   7020
acatatcagt gtttgttcat actcacttca acagcaaatg tgactgctga gattaagatt   7080
ttacacaaga tggtctgtaa tttcacagtt agttttatcc cattaggtat gaaagaatta   7140
gcataattcc ccttaaacat gaatgaatct tagatttttt aataaatagt tttggaagta   7200
aagacagaga catcaggagc acaaggaata gcctgagagg acaaacagaa caagaaagag   7260
tctggaaata cacaggatgt tcttggcctc tcaaagcaa gtgcaagcag atagtaccag    7320
cagccccagg ctatcagagc ccagtgaaga gaagtaccat gaaagccaca gctctaacca   7380
ccctgttcca gagtgacaga cagtccccaa gacaagccag cctgagccag agagagaact   7440
gcaagagaaa gtttctaatt taggttctgt tagattcaga caagtgcagg tcatcctctc   7500
tccacagcta ctcacctctc cagcctaaca aagcctgcag tccacactcc aaccctggtg   7560
tctcacctcc tagcctctcc caacatcctg ctctctgacc atcttctgca tctctcatct   7620
caccatctcc cactgtctac agcctactct tgcaactacc atctcatttt ctgacatcct   7680
gtctacatct tctgccatac tctgccatct accataccac ctcttaccat ctaccacacc   7740 atctttatc tccatccctc tcagaagcct ccaagctgaa tcctgcttta tgtgttcatc    7800
tcagcccctg catggaaagc tgaccccaga ggcagaacta ttcccagaga gcttggccaa   7860
gaaaaacaaa actaccagcc tggccaggct caggagtagt aagctgcagt gtctgttgtg   7920
ttctagcttc aacagctgca ggagttccac tctcaaatgc tccacatttc tcacatcctc   7980
ctgattctgg tcactaccca tcttcaaaga acagaatatc tcacatcagc atactgtgaa   8040
ggactagtca tgggtgcagc tgctcagagc tgcaaagtca ttctggatgg tggagagctt   8100
acaaacattt catgatgctc cccccgctct gatggctgga gcccaatccc tacacagact   8160
cctgctgtat gtgttttcct ttcactctga gccacagcca gagggcaggc attcagtctc   8220
ctcttcaggc tggggctggg gcactgagaa ctcacccaac accttgctct cactccttct   8280
gcaaaacaag aaagagcttt gtgctgcagt agccatgaag aatgaaagga aggctttaac   8340
taaaaaatgt cagagattat tttcaacccc ttactgtgga tcaccagcaa ggaggaaaca   8400
caacacagag acatttttc ccctcaaatt atcaaaagaa tcactgcatt tgttaaagag    8460
agcaactgaa tcaggaagca gagttttgaa catatcagaa gttaggaatc tgcatcagag   8520
acaaatgcag tcatggttgt ttgctgcata ccagccctaa tcattagaag cctcatggac   8580
ttcaaacatc attccctctg acaagatgct ctagcctaac tccatgagat aaaataaatc   8640
tgcctttcag agccaaagaa gagtccacca gcttcttctc agtgtgaaca agagctccag   8700
tcaggttagt cagtccagtg cagtagagga gaccagtctg catcctctaa ttttcaaagg   8760
caagaagatt tgtttaccct ggacaccagg cacaagtgag gtcacagagc tcttagatat   8820
gcagtcctca tgagtgagga gactaaagcg catgccatca agacttcagt gtagagaaaa   8880
cctccaaaaa agcctcctca ctacttctgg aatagctcag aggccgaggc ggcctcggcc   8940
tctgcataaa taaaaaaaat tagtcagcca tggggcggag aatgggcgga actgggcgga   9000
gttaggggcg ggatgggcgg agttaggggc gggactatgg ttgctgacta attgagatgc   9060
atgctttgca tacttctgcc tgctggggag cctggggact ttccacacct ggttgctgac   9120
```

```
taattgagat gcatgctttg catacttctg cctgctgggg agcctgggga ctttccacac    9180
cctaactgac acacattcca cagctgcatt aatgaatcgg ccaacgcgcg gggagaggcg    9240
gtttgcgtat tgggcgctct tccgcttcct cgctcactga ctcgctgcgc tcggtcgttc    9300
ggctgcggcg agcggtatca gctcactcaa aggcggtaat acggttatcc acagaatcag    9360
gggataacgc aggaaagaac atgtgagcaa aaggccagca aaaggccagg aaccgtaaaa    9420
aggccgcgtt gctggcgttt ttccataggc tccgcccccc tgacgagcat cacaaaaatc    9480
gacgctcaag tcagaggtgg cgaaacccga caggactata aagataccag gcgtttcccc    9540
ctggaagctc cctcgtgcgc tctcctgttc cgaccctgcc gcttaccgga tacctgtccg    9600
cctttctccc ttcgggaagc gtggcgcttt ctcatagctc acgctgtagg tatctcagtt    9660
cggtgtaggt cgttcgctcc aagctgggct gtgtgcacga accccccgtt cagcccgacc    9720
gctgcgcctt atccggtaac tatcgtcttg agtccaaccc ggtaagacac gacttatcgc    9780
cactggcagc agccactggt aacaggatta gcagagcgag gtatgtaggc ggtgctacag    9840
agttcttgaa gtggtggcct aactacggct acactagaag aacagtattt ggtatctgcg    9900
ctctgctgaa gccagttacc ttcggaaaaa gagttggtag ctcttgatcc ggcaaacaaa    9960
ccaccgctgg tagcggtggt ttttttgttt gcaagcagca gattacgcgc agaaaaaaag   10020
gatctcaaga agatcctttg atcttttcta cggggtctga cgctcagtgg aacgaaaact   10080
cacgttaagg gattttggtc atgagattat caaaaaggat cttcacctag atccttttaa   10140
attaaaaatg aagttttaaa tcaatctaaa gtatatatga gtaaacttgg tctgacagtt   10200
accaatgctt aatcagtgag gcacctatct cagcgatctg tctatttcgt tcatccatag   10260
ttgcctgact ccctgcaaac acgttgtgtc tcaaaatctc tgatgttaca ttgcacaaga   10320
taaaaatata tcatcatgaa caataaaact gtctgcttac ataaacagta atacaagggg   10380
tgttatgagc catattcaac gggaaacgtc ttgctcgagg ccgcgattaa attccaacat   10440
ggatgctgat ttatatgggt ataaatgggc tcgcgataat gtcgggcaat caggtgcgac   10500
aatctatcga ttgtatggga agcccgatgc gccagagttg tttctgaaac atggcaaagg   10560
tagcgttgcc aatgatgtta cagatgagat ggtcagacta aactggctga cggaatttat   10620
gcctcttccg accatcaagc attttatccg tactcctgat gatgcatggt tactcaccac   10680
tgcgatcccc gggaaaacag cattccaggt attagaagaa tatcctgatt caggtgaaaa   10740
tattgttgat gcgctggcag tgttcctgcg ccggttgcat tcgattcctg tttgtaattg   10800
tccttttaac agcgatcgcg tatttcgtct cgctcaggcg caatcacgaa tgaataacgg   10860
tttggttgat gcgagtgatt ttgatgacga gcgtaatggc tggcctgttg aacaagtctg   10920
gaaagaaatg cataagcttt tgccattctc accggattca gtcgtcactc atggtgattt   10980
ctcacttgat aaccttattt ttgacgaggg gaaattaata ggttgtattg atgttggacg   11040
agtcggaatc gcagaccgat accaggatct tgccatccta tggaactgcc tcggtgagtt   11100
ttctccttca ttacagaaac ggctttttca aaaatatggt attgataatc ctgatatgaa   11160
taaattgcag tttcatttga tgctcgatga gttttctaa gggcggcctg ccaccatacc   11220
cacgccgaaa caagcgctca tgagcccgaa gtggcgagcc cgatcttccc catcggtgat   11280
gtcggcgata taggcgccag caaccgcacc tgtggcgccg gtgatgaggg cgcgccaagt   11340
cgacgtccgg cagtc                                                    11355

<210> SEQ ID NO 3
<211> LENGTH: 11420
```

<212> TYPE: DNA
<213> ORGANISM: Artificial Sequence
<220> FEATURE:
<223> OTHER INFORMATION: Synthetic polynucleotide

<400> SEQUENCE: 3

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctgctag | ctctgggtat | ttaagcccga | gtgagcacgc | 180 |
| agggtctcca | ttttgaagcg | ggaggttacg | cgttcgtcga | ctactagtgg | gtaccagagc | 240 |
| tccctaggtt | ctagaaccgg | tgacgtctcc | catggtgaag | cttggatctg | agggcggagt | 300 |
| tagggcggag | ccaatcagcg | tgcgccgttc | cgaaagttgc | cttttatggc | tgggcggaga | 360 |
| atgggcggtg | aacgccgatg | attatataag | gacgcgccgg | gtgtggcaca | gctagttccg | 420 |
| tcgcagccgg | gatttgggtc | gcggttcttg | tttgtggatc | cctgtgatcg | tcacttggta | 480 |
| agtcactgac | tgtctatgcc | tgggaaaggg | tgggcaggag | atggggcagt | gcaggaaaag | 540 |
| tggcactatg | aaccctgcag | ccctaggaat | gcatctagac | aattgtacta | accttcttct | 600 |
| ctttcctctc | ctgacagtcc | ggaaagccac | catggaattc | agcagcccca | gcagagagga | 660 |
| atgccccaag | cctctgagcc | gggtgtcaat | catggccgga | tctctgacag | gactgctgct | 720 |
| gcttcaggcc | gtgtcttggg | cttctggcgc | tagaccttgc | atccccaaga | gcttcggcta | 780 |
| cagcagcgtc | gtgtgcgtgt | gcaatgccac | ctactgcgac | agcttcgacc | tcctaccttt | 840 |
| tcctgctctg | gcaccttca | gcagatacga | gagcaccaga | tccggcagac | ggatggaact | 900 |
| gagcatggga | cccatccagg | ccaatcacac | aggcactggc | ctgctgctga | cactgcagcc | 960 |
| tgagcagaaa | ttccagaaag | tgaaaggctt | cggcggagcc | atgacagatg | ccgccgctct | 1020 |
| gaatatcctg | gctctgtctc | caccagctca | gaacctgctg | ctcaagagct | acttcagcga | 1080 |
| ggaaggcatc | ggctacaaca | tcatcagagt | gcccatggcc | agctgcgact | tcagcatcag | 1140 |
| gacctacacc | tacgccgaca | caccgacga | tttccagctg | cacaacttca | gcctgcctga | 1200 |
| agaggacacc | aagctgaaga | tccctctgat | ccacagagcc | ctgcagctgg | cacaaagacc | 1260 |
| cgtgtcactg | ctggcctctc | catggacatc | tcccacctgg | ctgaaaacaa | atggcgccgt | 1320 |
| gaatggcaag | ggcagcctga | aaggccaacc | tggcgacatc | taccaccaga | cctgggccag | 1380 |
| atacttcgtg | aagttcctgg | acgcctatgc | cgagcacaag | ctgcagtttt | gggccgtgac | 1440 |
| agccgagaac | gaaccttctg | ctggactgct | gagcggctac | ccctttcagt | gcctgggctt | 1500 |
| tacacccgag | caccagcggg | actttatcgc | ccgtgatctg | ggaccacac | tggccaatag | 1560 |
| cacccaccat | aatgtgcggc | tgctgatgct | ggacgaccag | agactgcttc | tgcccactg | 1620 |
| ggctaaagtg | gtgctgacag | atcctgaggc | cgccaaatac | gtgcacggaa | tcgccgtgca | 1680 |
| ctggtatctg | gactttctgg | cccctgccaa | ggccacactg | ggagagacac | acagactgtt | 1740 |
| ccccaacacc | atgctgttcg | ccagcgaagc | ctgtgtgggc | agcaagtttt | gggaacagag | 1800 |
| cgtgcggctc | ggcagctggg | atagaggcat | gcagtacagc | cacagcatca | tcaccaacct | 1860 |
| gctgtaccac | gtcgtcggct | ggaccgactg | gaatctggcc | ctgaatcctg | aaggcggccc | 1920 |
| taactgggtc | cgaaacttcg | tggacagccc | catcatcgtg | gacatcacca | aggacaccctt | 1980 |
| ctacaagcag | cccatgttct | accacctggg | acacttcagc | aagttcatcc | ccgagggctc | 2040 |
| tcagcgcgtt | ggactggtgg | cttcccagaa | gaacgatctg | gacgccgtgg | ctctgatgca | 2100 |
| ccctgatgga | tctgctgtgg | tggtggtcct | gaaccgcagc | agcaaagatg | tgcccctgac | 2160 |

```
catcaaggat cccgccgtgg gattcctgga aacaatcagc cctggctact ccatccacac    2220
ctacctgtgg cgtagacagt gacaattgtt aattaagttt catcgatacc gtcgactaga    2280
gctcgctgat cagcctcgac tgtgccttct agttgccagc catctgttgt tgcccctcc     2340
cccgtgcctt ccttgaccct ggaaggtgcc actcccactg tcctttccta ataaaatgag    2400
gaaattgcat cgcattgtct gagtaggtgt cattctattc tggggggtgg ggtggggcag    2460
gacagcaagg gggaggattg ggaagacaat agcaggcatg ctggggagag atccacgata    2520
acaaacagct ttttggggg gcggagtta gggcggagcc aatcagcgtg cgccgttccg       2580
aaagttgcct tttatggctg gcggagaat gggcggtgaa cgccgatgat tatataagga      2640
cgcgccgggt gtggcacagc tagttccgtc gcagccggga tttgggtcgc ggttcttgtt    2700
tgtggatccc tgtgatcgtc acttggtaag tcactgactg tctatgcctg ggaaagggtg    2760
ggcaggagat ggggcagtgc aggaaaagtg gcactatgaa ccctgcagcc ctaggaatgc    2820
atctagacaa ttgtactaac cttcttctct ttcctctcct gacagtccgg aaagccacca    2880
tgggccgctg ctgcttctac accgccggca ccctgagcct gctgctgctg gtgaccagcg    2940
tgaccctgct ggtggcccgc gtgttccaga aggccgtgga ccagagcatc gagaagaaga    3000
tcgtgctgcg caacggcacc gaggccttcg acagctggga aagcccccc ctgcccgtgt      3060
acaccccagtt ctacttcttc aacgtgacca ccccgagga gatcctgcgc ggcgagaccc    3120
cccgcgtgga ggaggtgggc ccctacacct accgcgagct gcgcaacaag gccaacatcc    3180
agttcggcga aacggcacc accatcagcg ccgtgagcaa caaggcctac gtgttcgagc     3240
gcgaccagag cgtgggcgac cccaagatcg acctgatccg caccctgaac atccccgtgc    3300
tgaccgtgat cgagtggagc caggtgcact cctgcgcga gatcatcgag gccatgctga     3360
aggcctacca gcagaagctg ttcgtgaccc acaccgtgga cgagctgctg tggggctaca    3420
aggacgagat cctgagcctg atccacgtgt tccgccccga catcagcccc tacttcggcc    3480
tgttctacga gaagaacggc accaacgacg gcgactacgt gttcctgacc ggcgaggaca    3540
gctacctgaa cttcaccaag atcgtggagt ggaacggcaa gaccagcctg actggtgga    3600
tcaccgacaa gtgcaacatg atcaacggca ccgacgcga cagcttccac ccctgatca      3660
ccaaggacga ggtgctgtac gtgttcccca gcgacttctg ccgcagcgtg tacatcacct    3720
tcagcgacta cgagagcgtg cagggcctgc ccgccttccg ctacaaggtg cccgccgaga    3780
tcctggccaa caccagcgac aacgccggct ctgcatccc cgagggcaac tgcctgggca    3840
gcggcgtgct gaacgtgagc atctgcaaga acggcgcccc catcatcatg agcttccccc    3900
acttctacca ggccgacgag cgcttcgtga gcgccatcga gggcatgcac cccaaccagg    3960
aggaccacga gaccttcgtg gacatcaacc ccctgaccgg catcatcctg aaggccgcca    4020
agcgcttcca gatcaacatc tacgtgaaga agctggacga cttcgtggag accggcgaca    4080
tccgcaccat ggtgttcccc gtgatgtacc tgaacgagag cgtgcacatc gacaaggaga    4140
ccgccagccg cctgaagagc atgatcaaca ccaccctgat catcaccaac atcccctaca    4200
tcatcatggc cctgggcgtg ttcttcggcc tggtgttcac ctggctggcc tgcaagggcc    4260
agggcagcat ggacgagggc accgccgacg agcgcgcccc cctgatccgc acctgaccca    4320
ggggactcaa tcagcctcga agacatgata agatacattg atgagtttgg acaaaccaca    4380
acaagaatgc agtgaaaaaa atgctttatt tgtgaaattt gtgatgctat tgctttattt    4440
gtaaccatta taagctgcaa taaacaagtt aacaacaaca attgcattca ttttatgttt    4500
caggttcagg gggagatgtg ggaggttttt taaagcaagt aaaacctcta caaatgtggt    4560
```

```
atgaacatat tgactgaatt ccctgcaggt tggccactcc ctctctgcgc gctcgctcgc      4620
tcactgaggc cgcccgggca aagcccgggc gtcgggcgac ctttggtcgc ccggcctcag      4680
tgagcgagcg agcgcgcaga gagggagtgg ccaactccat cactaggggt tcctgcggcc      4740
gctcgtacgg tctcgaggaa ttcctgcagg ataacttgcc aacctcattc taaaatgtat      4800
atagaagccc aaaagacaat aacaaaaata ttcttgtaga acaaatggga aagaatgtt       4860 ccactaaata tcaagattta gagcaaagca tgagatgtgt ggggatagac agtgaggctg      4920
ataaaataga gtagagctca gaaacagacc cattgatata tgtaagtgac ctatgaaaaa     4980
aatatggcat tttacaatgg gaaaatgatg gtcttttct tttttagaaa aacagggaaa      5040
tatatttata tgtaaaaaat aaagggaac ccatatgtca taccatacac acaaaaaaat      5100
tccagtgaat tataagtcta aatggagaag gcaaaacttt aaatctttta gaaataata      5160 tagaagcatg cagaccagcc tggccaacat gatgaaaccc tctctactaa taataaaatc     5220
agtagaacta ctcaggacta ctttgagtgg gaagtccttt tctatgaaga cttctttggc     5280
caaaattagg ctctaaatgc aaggagatag tgcatcatgc ctggctgcac ttactgataa     5340
atgatgttat caccatctttt aaccaaatgc acaggaacaa gttatggtac tgatgtgctg    5400
gattgagaag gagctctact tccttgacag gacacatttg tatcaactta aaaaagcaga    5460 ttttttgccag cagaactatt cattcagagg taggaaactt agaatagatg atgtcactga    5520
ttagcatggc ttccccatct ccacagctgc ttcccaccca ggttgcccac agttgagttt     5580
gtccagtgct cagggctgcc cactctcagt aagaagcccc acaccagccc ctctccaaat    5640
atgttggctg ttccttccat taaagtgacc ccactttaga gcagcaagtg gatttctgtt    5700
tcttacagtt caggaaggag gagtcagctg tgagaacctg gagcctgaga tgcttctaag     5760
tcccactgct actggggtca gggaagccag actccagcat cagcagtcag gagcactaag    5820
cccttgccaa catcctgttt ctcagagaaa ctgcttccat tataatggtt gtccttttt     5880 aagctatcaa gccaaacaac cagtgtctac cattattctc atcacctgaa gccaagggtt     5940
ctagcaaaag tcaagctgtc ttgtaatggt tgatgtgcct ccagcttctg tcttcagtca     6000
ctccactctt agcctgctct gaatcaactc tgaccacagt tccctggagc ccctgccacc     6060
tgctgcccct gccaccttct ccatctgcag tgctgtgcag ccttctgcac tcttgcagag     6120
ctaataggtg gagacttgaa ggaagaggag gaaagtttct cataatagcc ttgctgcaag     6180
ctcaaatggg aggtgggcac tgtgcccagg agccttggag caaaggctgt gcccaacctc     6240
tgactgcatc caggtttggt cttgacagag ataagaagcc ctggcttttg gagccaaaat     6300
ctaggtcaga cttaggcagg attctcaaag tttatcagca gaacatgagg cagaagaccc     6360
tttctgctcc agcttcttca ggctcaacct tcatcagaat agatagaaag agaggctgtg     6420
agggttctta aaacagaagc aaatctgact cagagaataa caacctcct agtaaactac      6480 agcttagaca gagcatctgg tggtgagtgt gctcagtgtc ctactcaact gtctggtatc     6540
agccctcatg aggacttctc ttctttccct catagacctc catctctgtt ttccttagcc    6600
tgcagaaatc tggatggcta ttcacagaat gcctgtgctt tcagagttgc atttttctc     6660 tggtattctg gttcaagcat ttgaaggtag gaaaggttct ccaagtgcaa gaaagccagc     6720
cctgagcctc aactgcctgg ctagtgtggt cagtaggatg caaaggctgt tgaatgccac     6780
aaggccaaac tttaacctgt gtaccacaag cctagcagca gaggcagctc tgctcactgg     6840
aactctctgt cttctttctc ctgagccttt tcttttcctg agttttctag ctctcctcaa     6900
```

```
ccttacctct gccctaccca ggacaaaccc aagagccact gtttctgtga tgtcctctcc    6960
agccctaatt aggcatcatg acttcagcct gaccttccat gctcagaagc agtgctaatc    7020
cacttcagat gagctgctct atgcaacaca ggcagagcct acaaaccttt gcaccagagc    7080
cctccacata tcagtgtttg ttcatactca cttcaacagc aaatgtgact gctgagatta    7140
agattttaca caagatggtc tgtaatttca cagttagttt tatcccatta ggtatgaaag    7200
aattagcata attcccctta aacatgaatg aatcttagat tttttaataa atagttttgg    7260
aagtaaagac agagacatca ggagcacaag gaatagcctg agaggacaaa cagaacaaga    7320
aagagtctgg aaatacacag gatgttcttg gcctcctcaa agcaagtgca agcagatagt    7380
accagcagcc ccaggctatc agagcccagt gaagagaagt accatgaaag ccacagctct    7440
aaccaccctg ttccagagtg acagacagtc cccaagacaa gccagcctga gccagagaga    7500
gaactgcaag agaaagtttc taatttaggt tctgttagat tcagacaagt gcaggtcatc    7560
ctctctccac agctactcac ctctccagcc taacaaagcc tgcagtccac actccaaccc    7620
tggtgtctca cctcctagcc tctcccaaca tcctgctctc tgaccatctt ctgcatctct    7680
catctcacca tctcccactg tctacagcct actcttgcaa ctaccatctc attttctgac    7740
atcctgtcta tcttctgc catactctgc catctaccat accacctctt accatctacc    7800
acaccatctt ttatctccat ccctctcaga agcctccaag ctgaatcctg ctttatgtgt    7860
tcatctcagc ccctgcatgg aaagctgacc ccagaggcag aactattccc agagagcttg    7920
gccaagaaaa acaaaactac cagcctggcc aggctcagga gtagtaagct gcagtgtctg    7980
ttgtgttcta gcttcaacag ctgcaggagt tccactctca aatgctccac atttctcaca    8040
tcctcctgat tctggtcact acccatcttc aaagaacaga atatctcaca tcagcatact    8100
gtgaaggact agtcatgggt gcagctgctc agagctgcaa agtcattctg gatggtggag    8160
agcttacaaa catttcatga tgctccccc gctctgatgg ctggagccca atccctacac    8220
agactcctgc tgtatgtgtt ttcctttcac tctgagccac agccagaggg caggcattca    8280
gtctcctctt caggctgggg ctggggcact gagaactcac ccaacacctt gctctcactc    8340
cttctgcaaa acaagaaaga gctttgtgct gcagtagcca tgaagaatga aaggaaggct    8400
ttaactaaaa aatgtcagag attattttca accccttact gtggatcacc agcaaggagg    8460
aaacacaaca cagagacatt ttttcccctc aaattatcaa aagaatcact gcatttgtta    8520
aagagagcaa ctgaatcagg aagcagagtt ttgaacatat cagaagttag gaatctgcat    8580
cagagacaaa tgcagtcatg gttgtttgct gcataccagc cctaatcatt agaagcctca    8640
tggacttcaa acatcattcc ctctgacaag atgctctagc ctaactccat gagataaaat    8700
aaatctgcct ttcagagcca aagaagagtc caccagcttc ttctcagtgt gaacaagagc    8760
tccagtcagg ttagtcagtc cagtgcagta gaggagacca gtctgcatcc tctaattttc    8820
aaaggcaaga agatttgttt accctggaca ccaggcacaa gtgaggtcac agagctctta    8880
gatatgcagt cctcatgagt gaggagacta aagcgcatgc catcaagact tcagtgtaga    8940
gaaaacctcc aaaaaagcct cctcactact tctggaatag ctcagaggcc gaggcggcct    9000
cggcctctgc ataaataaaa aaaattagtc agccatgggg cggagaatgg gcggaactgg    9060
gcggagttag gggcgggatg ggcggagtta ggggcgggac tatggttgct gactaattga    9120
gatgcatgct ttgcatactt ctgcctgctg gggagcctgg ggactttcca cacctggttg    9180
ctgactaatt gagatgcatg ctttgcatac ttctgcctgc tggggagcct ggggactttc    9240
cacaccctaa ctgacacaca ttccacagct gcattaatga atcggccaac gcgcggggag    9300
```

```
aggcggtttg cgtattgggc gctcttccgc ttcctcgctc actgactcgc tgcgctcggt   9360
cgttcggctg cggcgagcgg tatcagctca ctcaaaggcg gtaatacggt tatccacaga   9420
atcaggggat aacgcaggaa agaacatgtg agcaaaaggc cagcaaaagg ccaggaaccg   9480
taaaaaggcc gcgttgctgg cgttttccca taggctccgc cccctgacg agcatcacaa    9540
aaatcgacgc tcaagtcaga ggtggcgaaa cccgacagga ctataaagat accaggcgtt   9600
tccccctgga agctccctcg tgcgctctcc tgttccgacc ctgccgctta ccggatacct   9660
gtccgccttt ctcccttcgg gaagcgtggc gctttctcat agctcacgct gtaggtatct   9720
cagttcggtg taggtcgttc gctccaagct gggctgtgtg cacgaacccc ccgttcagcc   9780
cgaccgctgc gccttatccg gtaactatcg tcttgagtcc aacccggtaa gacacgactt   9840
atcgccactg gcagcagcca ctggtaacag gattagcaga gcgaggtatg taggcggtgc   9900
tacagagttc ttgaagtggt ggcctaacta cggctacact agaagaacag tatttggtat   9960
ctgcgctctg ctgaagccag ttaccttcgg aaaaagagtt ggtagctctt gatccggcaa  10020
acaaaccacc gctggtagcg gtggtttttt tgtttgcaag cagcagatta cgcgcagaaa  10080
aaaaggatct caagaagatc ctttgatctt ttctacgggg tctgacgctc agtggaacga  10140
aaactcacgt taagggattt tggtcatgag attatcaaaa aggatcttca cctagatcct  10200
tttaaattaa aaatgaagtt ttaaatcaat ctaaagtata tatgagtaaa cttggtctga  10260
cagttaccaa tgcttaatca gtgaggcacc tatctcagcg atctgtctat ttcgttcatc  10320
catagttgcc tgactcctgc aaaccacgtt gtgtctcaaa atctctgatg ttacattgca  10380
caagataaaa atatatcatc atgaacaata aaactgtctg cttacataaa cagtaataca  10440
aggggtgtta tgagccatat tcaacgggaa acgtcttgct cgaggccgcg attaaattcc  10500
aacatggatg ctgatttata tgggtataaa tgggctcgcg ataatgtcgg gcaatcaggt  10560
gcgacaatct atcgattgta tgggaagccc gatgcgccag agttgtttct gaaacatggc  10620
aaaggtagcg ttgccaatga tgttacagat gagatggtca gactaaactg gctgacggaa  10680
tttatgcctc ttccgaccat caagcatttt atccgtactc ctgatgatgc atggttactc  10740
accactgcga tccccgggaa aacagcattc aggtattag aagaatatcc tgattcaggt   10800
gaaaatattg ttgatgcgct ggcagtgttc ctgcgccggt tgcattcgat tcctgtttgt  10860
aattgtcctt ttaacagcga tcgcgtattt cgtctcgctc aggcgcaatc acgaatgaat  10920
aacggtttgg ttgatgcgag tgattttgat gacgagcgta atggctggcc tgttgaacaa  10980
gtctggaaag aaatgcataa gcttttgcca ttctcaccgg attcagtcgt cactcatggt  11040
gatttctcac ttgataaccct tatttttgac gaggggaaat taataggttg tattgatgtt  11100
ggacgagtcg gaatcgcaga ccgataccag gatcttgcca tcctatggaa ctgcctcggt  11160
gagtttctc cttcattaca gaaacggctt tttcaaaaat atggtattga taatcctgat   11220
atgaataaat tgcagtttca tttgatgctc gatgagtttt tctaagggcg gcctgccacc  11280
atacccacgc cgaaacaagc gctcatgagc ccgaagtggc gagcccgatc ttccccatcg  11340
gtgatgtcgg cgatataggc gccagcaacc gcacctgtgg cgccggtgat gagggcgcgc  11400
caagtcgacg tccggcagtc                                              11420
```

<210> SEQ ID NO 4
<211> LENGTH: 11171
<212> TYPE: DNA
<213> ORGANISM: Artificial Sequence
<220> FEATURE:

<223> OTHER INFORMATION: Synthetic polynucleotide

<400> SEQUENCE: 4

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctgctag | ctctgggtat | ttaagcccga | gtgagcacgc | 180 |
| agggtctcca | ttttgaagcg | ggaggttacg | cgttcgtcga | ctactagtgg | gtaccagagc | 240 |
| tccctaggtt | ctagaaccgg | tgacgtctcc | catggtgaag | cttggatctg | agggcggagt | 300 |
| tagggcggag | ccaatcagcg | tgcgccgttc | cgaaagttgc | cttttatggc | tgggcggaga | 360 |
| atgggcggtg | aacgccgatg | attatataag | gacgcgccgg | gtgtggcaca | gctagttccg | 420 |
| tcgcagccgg | gatttgggtc | gcggttcttg | tttgtggatc | cctgtgatcg | tcacttggta | 480 |
| agtcactgac | tgtctatgcc | tgggaaaggg | tgggcaggag | atgggcagt | gcaggaaaag | 540 |
| tggcactatg | aaccctcctg | gtggcgaggg | gaggggggtg | gtcctcgaac | gccttgcaga | 600 |
| actggcctgg | atacagagtg | gaccggctgg | ccccatctgg | aagacttcga | gatacactgt | 660 |
| tgtcttactg | cgctcaacag | tgtatctcga | agtcttccaa | atggtgccag | ccatcgcagc | 720 |
| ggggtgcagg | aaatggggc | agccccctt | tttggctatc | cttccacgtg | ttctttttg | 780 |
| tatcttttgt | gtttcctaga | aaacatctca | gtcaccaccg | cagccctagg | aatgcatcta | 840 |
| gacaattgta | ctaaccttct | tctctttcct | ctcctgacag | tccggaaagc | caccatgggc | 900 |
| cgctgctgct | tctacaccgc | cggcaccctg | agcctgctgc | tgctggtgac | cagcgtgacc | 960 |
| ctgctggtgg | cccgcgtgtt | ccagaaggcc | gtggaccaga | gcatcgagaa | gaagatcgtg | 1020 |
| ctgcgcaacg | gcaccgaggc | cttcgacagc | tgggagaagc | ccccctgcc | cgtgtacacc | 1080 |
| cagttctact | tcttcaacgt | gaccaacccc | gaggagatcc | tgcgcggcga | ccccccgc | 1140 |
| gtggaggagg | tgggccccta | cacctaccgc | gagctgcgca | caaggccaa | catccagttc | 1200 |
| ggcgacaacg | gcaccaccat | cagcgccgtg | agcaacaagg | cctacgtgtt | cgagcgcgac | 1260 |
| cagagcgtgg | gcgaccccaa | gatcgacctg | atccgcaccc | tgaacatccc | cgtgctgacc | 1320 |
| gtgatcgagt | ggagccaggt | gcacttcctg | cgcgagatca | tcgaggccat | gctgaaggcc | 1380 |
| taccagcaga | agctgttcgt | gacccacacc | gtggacgagc | tgctgtgggg | ctacaaggac | 1440 |
| gagatcctga | gcctgatcca | cgtgttccgc | cccgacatca | gccctactt | cggcctgttc | 1500 |
| tacgagaaga | acggcaccaa | cgacggcgac | tacgtgttcc | tgaccggcga | ggacagctac | 1560 |
| ctgaacttca | ccaagatcgt | ggagtggaac | ggcaagacca | gcctggactg | gtggatcacc | 1620 |
| gacaagtgca | acatgatcaa | cggcaccgac | ggcgacagct | ccaccccct | gatcaccaag | 1680 |
| gacgaggtgc | tgtacgtgtt | ccccagcgac | ttctgccgca | gcgtgtacat | caccttcagc | 1740 |
| gactacgaga | gcgtgcaggg | cctgcccgcc | ttccgctaca | aggtgcccgc | cgagatcctg | 1800 |
| gccaacacca | gcgacaacgc | cggcttctgc | atccccgagg | gcaactgcct | gggcagcggc | 1860 |
| gtgctgaacg | tgagcatctg | caagaacggc | gccccccatca | tcatgagctt | ccccccacttc | 1920 |
| taccaggccg | acgagcgctt | cgtgagcgcc | atcgagggca | tgcaccccaa | ccaggaggac | 1980 |
| cacgagacct | tcgtggacat | caaccccctg | accggcatca | tcctgaaggc | cgccaagcgc | 2040 |
| ttccagatca | acatctacgt | gaagaagctg | gacgacttcg | tggagaccgg | cgacatccgc | 2100 |
| accatggtgt | tccccgtgat | gtacctgaac | gagagcgtgc | acatcgacaa | ggagaccgcc | 2160 |
| agccgcctga | agagcatgat | caacaccacc | ctgatcatca | ccaacatccc | ctacatcatc | 2220 |
| atggcctgg | gcgtgttctt | cggcctggtg | ttcacctggc | tggcctgcaa | gggccagggc | 2280 |

```
agcatggacg agggcaccgc cgacgagcgc gcccccctga tccgcaccga gggcagagga    2340
agtcttctga catgcggaga cgtggaagag aatcccggcc ctatggaatt cagcagcccc    2400
agcagagagg aatgccccaa gcctctgagc cgggtgtcaa tcatggccgg atctctgaca    2460
ggactgctgc tgcttcaggc cgtgtcttgg gcttctggcg ctagaccttg catccccaag    2520
agcttcggct acagcagcgt cgtgtgcgtg tgcaatgcca cctactgcga cagcttcgac    2580
cctcctacct ttcctgctct gggcaccttc agcagatacg agagcaccag atccggcaga    2640
cggatggaac tgagcatggg acccatccag gccaatcaca caggcactgg cctgctgctg    2700
acactgcagc ctgagcagaa attccagaaa gtgaaggct cggcggagc catgacagat    2760
gccgccgctc tgaatatcct ggctctgtct ccaccagctc agaacctgct gctcaagagc    2820
tacttcagcg aggaaggcat cggctacaac atcatcagag tgcccatggc cagctgcgac    2880
ttcagcatca ggacctacac ctacgccgac acacccgacg atttccagct gcacaacttc    2940
agcctgcctg aagaggacac caagctgaag atccctctga tccacagagc cctgcagctg    3000
gcacaaagac ccgtgtcact gctggcctct ccatggacat ctcccacctg ctgaaaaca    3060
aatggcgccg tgaatggcaa gggcagcctg aaaggccaac ctggcgacat ctaccaccag    3120
acctgggcca gatacttcgt gaagttcctg gacgcctatg ccgagcacaa gctgcagttt    3180
tgggccgtga cagccgagaa cgaaccttct gctggactgc tgagcggcta ccccttcag    3240
tgcctgggct ttacacccga gcaccagcgg gactttatcg cccgtgatct gggacccaca    3300
ctggccaata gcacccacca taatgtgcgg ctgctgatgc tggacgacca gagactgctt    3360
ctgccccact gggctaaagt ggtgctgaca gatcctgagg ccgccaaata cgtgcacgga    3420
atcgccgtgc actggtatct ggactttctg gcccctgcca aggccacact gggagagaca    3480
cacagactgt tccccaacac catgctgttc gccagcgaag cctgtgtggg cagcaagttt    3540
tgggaacaga gcgtgcggct cggcagctgg gatagaggca tgcagtacag ccacagcatc    3600
atcaccaacc tgctgtacca cgtcgtcggc tggaccgact ggaatctggc cctgaatcct    3660
gaaggcggcc ctaactgggt ccgaaacttc gtggacagcc ccatcatcgt ggacatcacc    3720
aaggacacct tctacaagca gcccatgttc taccacctgg gacacttcag caagttcatc    3780
cccgagggct ctcagcgcgt tggactggtg gcttcccaga gaacgatct ggacgccgtg    3840
gctctgatgc accctgatgg atctgctgtg gtggtggtcc tgaaccgcag cagcaaagat    3900
gtgcccctga ccatcaagga tcccgccgtg ggattcctgg aaacaatcag ccctggctac    3960
tccatccaca cctacctgtg gcgtagacag tgacaattgt taattaagtt taaaccctcg    4020
aggccgcaag ccgcatcgat accgtcgact agagctcgct gatcagcctc gactgtgcct    4080
tctagttgcc agccatctgt tgtttgcccc tcccccgtgc cttccttgac cctggaaggt    4140
gccactccca ctgtcctttc ctaataaaat gaggaaattg catcgcattg tctgagtagg    4200
tgtcattcta ttctgggggg tggggtgggg caggacagca aggggagga ttgggaagac    4260
aatagcaggc atgctgggga gagatccacg ataacaaaca gcttttttgg ggtgaacata    4320
ttgactgaat tccctgcagg ttggccactc cctctctgcg cgctcgctcg ctcactgagg    4380
ccgcccgggc aaagcccggg cgtcgggcga ccttggtcg cccggcctca gtgagcgagc    4440
gagcgcgcag agagggagtg gccaactcca tcactagggg ttcctgcggc cgctcgtacg    4500
gtctcgagga attcctgcag gataacttgc aacctcatt ctaaaatgta tatagaagcc    4560
caaaagacaa taacaaaaat attcttgtag aacaaaatgg gaagaatgt tccactaaat    4620
```

```
atcaagattt agagcaaagc atgagatgtg tggggataga cagtgaggct gataaaatag    4680
agtagagctc agaaacagac ccattgatat atgtaagtga cctatgaaaa aaatatggca    4740
ttttacaatg ggaaaatgat ggtcttttc tttttagaa aaacagggaa atatatttat    4800
atgtaaaaaa taaagggaa cccatatgtc ataccataca cacaaaaaaa ttccagtgaa    4860
ttataagtct aaatggagaa ggcaaaactt taaatctttt agaaaataat atagaagcat    4920
gcagaccagc ctggccaaca tgatgaaacc ctctctacta ataataaaat cagtagaact    4980
actcaggact actttgagtg ggaagtcctt ttctatgaag acttctttgg ccaaaattag    5040
gctctaaatg caaggagata gtgcatcatg cctggctgca cttactgata aatgatgtta    5100
tcaccatctt taaccaaatg cacaggaaca agttatggta ctgatgtgct ggattgagaa    5160
ggagctctac ttccttgaca ggacacattt gtatcaactt aaaaaagcag attttttgcca   5220 gcagaactat tcattcagag gtaggaaact tagaatagat gatgtcactg attagcatgg    5280
cttccccatc tccacagctg cttcccaccc aggttgccca cagttgagtt tgtccagtgc    5340
tcagggctgc ccactctcag taagaagccc cacaccagcc cctctccaaa tatgttggct    5400
gttccttcca ttaaagtgac cccacttag agcagcaagt ggatttctgt ttcttacagt    5460
tcaggaagga ggagtcagct gtgagaacct ggagcctgag atgcttctaa gtcccactgc    5520
tactggggtc agggaagcca gactccagca tcagcagtca ggagcactaa gcccttgcca    5580
acatcctgtt tctcagagaa actgcttcca ttataatggt tgtccttttt taagctatca    5640
agccaaacaa ccagtgtcta ccattattct catcacctga agccaagggt tctagcaaaa    5700
gtcaagctgt cttgtaatgg ttgatgtgcc tccagcttct gtcttcagtc actccactct    5760
tagcctgctc tgaatcaact ctgaccacag ttccctggag cccctgccac ctgctgcccc    5820
tgccaccttc tccatctgca gtgctgtgca gccttctgca ctcttgcaga gctaataggt    5880
ggagacttga aggaagagga ggaaagtttc tcataatagc cttgctgcaa gctcaaatgg    5940
gaggtgggca ctgtgcccag gagccttgga gcaaaggctg tgcccaacct ctgactgcat    6000
ccaggtttgg tcttgacaga gataagaagc cctggctttt ggagccaaaa tctaggtcag    6060
acttaggcag gattctcaaa gtttatcagc agaacatgag gcagaagacc ctttctgctc    6120
cagcttcttc aggctcaacc ttcatcagaa tagatagaaa gagaggctgt gagggttctt    6180
aaaacagaag caaatctgac tcagagaata aacaacctcc tagtaaacta cagcttagac    6240
agagcatctg gtggtgagtg tgctcagtgt cctactcaac tgtctggtat cagccctcat    6300 gaggacttc cttctttccc tcatagacct ccatctctgt tttccttagc ctgcagaaat    6360
ctggatggct attcacagaa tgcctgtgct ttcagagttg cattttttct ctggtattct    6420
ggttcaagca tttgaaggta ggaaaggttc tccaagtgca agaaagccag ccctgagcct    6480
caactgcctg gctagtgtgg tcagtaggat gcaaaggctg ttgaatgcca caaggccaaa    6540
ctttaacctg tgtaccacaa gcctagcagc agaggcagct ctgctcactg gaactctctg    6600
tcttcttcct cctgagcctt ttcttttcct gagttttcta gctctcctca accttacctc    6660
tgccctaccc aggacaaacc caagagccac tgtttctgtg atgtcctctc cagccctaat    6720
taggcatcat gacttcagcc tgaccttcca tgctcagaag cagtgctaat ccacttcaga    6780
tgagctgctc tatgcaacac aggcagagcc tacaaacctt tgcaccagag ccctccacat    6840
atcagtgttt gttcatactc acttcaacag caaatgtgac tgctgagatt aagattttac    6900
acaagatggt ctgtaatttc acagttagtt ttatcccatt aggtatgaaa gaattagcat    6960 aattccccctt aaacatgaat gaatcttaga ttttttaata aatagttttg gaagtaaaga    7020
```

```
cagagacatc aggagcacaa ggaatagcct gagaggacaa acagaacaag aaagagtctg    7080
gaaatacaca ggatgttctt ggcctcctca aagcaagtgc aagcagatag taccagcagc    7140
cccaggctat cagagcccag tgaagagaag taccatgaaa gccacagctc taaccaccct    7200
gttccagagt gacagacagt ccccaagaca agccagcctg agccagagag agaactgcaa    7260
gagaaagttt ctaatttagg ttctgttaga ttcagacaag tgcaggtcat cctctctcca    7320
cagctactca cctctccagc ctaacaaagc ctgcagtcca cactccaacc ctggtgtctc    7380
acctcctagc ctctcccaac atcctgctct ctgaccatct tctgcatctc tcatctcacc    7440
atctcccact gtctacagcc tactcttgca actaccatct cattttctga catcctgtct    7500
acatcttctg ccatactctg ccatctacca taccacctct taccatctac cacaccatct    7560
tttatctcca tccctctcag aagcctccaa gctgaatcct gctttatgtg ttcatctcag    7620
cccctgcatg gaaagctgac cccagaggca gaactattcc agagagcttg gccaagaaa    7680 aacaaaacta ccagcctggc caggctcagg agtagtaagc tgcagtgtct gttgtgttct    7740
agcttcaaca gctgcaggag ttccactctc aaatgctcca catttctcac atcctcctga    7800
ttctggtcac tacccatctt caaagaacag aatatctcac atcagcatac tgtgaaggac    7860
tagtcatggg tgcagctgct cagagctgca aagtcattct ggatggtgga gagcttacaa    7920
acatttcatg atgctccccc cgctctgatg gctggagccc aatccctaca cagactcctg    7980
ctgtatgtgt tttcctttca ctctgagcca cagccagagg gcaggcattc agtctcctct    8040
tcaggctggg gctggggcac tgagaactca cccaacacct tgctctcact ccttctgcaa    8100
aacaagaaag agctttgtgc tgcagtagcc atgaagaatg aaaggaaggc tttaactaaa    8160
aaatgtcaga gattattttc aaccccttac tgtggatcac cagcaaggag gaaacacaac    8220
acagagacat tttttcccct caaattatca aaagaatcac tgcatttgtt aaagagagca    8280
actgaatcag gaagcagagt tttgaacata tcagaagtta ggaatctgca tcagagacaa    8340
atgcagtcat ggttgtttgc tgcataccag ccctaatcat tagaagcctc atggacttca    8400
aacatcattc cctctgacaa gatgctctag cctaactcca tgagataaaa taaatctgcc    8460
tttcagagcc aaagaagagt ccaccagctt cttctcagtg tgaacaagag ctccagtcag    8520
gttagtcagt ccagtgcagt agaggagacc agtctgcatc ctctaatttt caaaggcaag    8580
aagatttgtt taccctggac accaggcaca agtgaggtca cagagctctt agatatgcag    8640
tcctcatgag tgaggagact aaagcgcatg ccatcaagac ttcagtgtag agaaaacctc    8700 caaaaagcc tcctcactac ttctggaata gctcagaggc cgaggcggcc tcggcctctg    8760
cataaataaa aaaaattagt cagccatggg gcggagaatg ggcggaactg ggcggagtta    8820
ggggcgggat gggcggagtt aggggcggga ctatggttgc tgactaattg agatgcatgc    8880
tttgcatact tctgcctgct ggggagcctg gggactttcc acacctggtt gctgactaat    8940
tgagatgcat gctttgcata cttctgcctg ctggggagcc tggggacttt ccacacccta    9000
actgacacac attccacagc tgcattaatg aatcggccaa cgcgcgggga gaggcggttt    9060
gcgtattggg cgctcttccg cttcctcgct cactgactcg ctgcgctcgg tcgttcggct    9120
gcggcgagcg gtatcagctc actcaaaggc ggtaatacgg ttatccacag aatcagggga    9180
taacgcagga agaacatgt gagcaaaagg ccagcaaaag gccaggaacc gtaaaaaggc    9240
cgcgttgctg gcgttttcc ataggctccg ccccctgac gagcatcaca aaaatcgacg    9300
ctcaagtcag aggtggcgaa acccgacagg actataaaga taccaggcgt ttcccctgg    9360
```

```
aagctccctc gtgcgctctc ctgttccgac cctgccgctt accggatacc tgtccgcctt    9420
tctcccttcg ggaagcgtgg cgctttctca tagctcacgc tgtaggtatc tcagttcggt    9480
gtaggtcgtt cgctccaagc tgggctgtgt gcacgaaccc cccgttcagc ccgaccgctg    9540
cgccttatcc ggtaactatc gtcttgagtc caacccggta agacacgact tatcgccact    9600
ggcagcagcc actggtaaca ggattagcag agcgaggtat gtaggcggtg ctacagagtt    9660
cttgaagtgg tggcctaact acggctacac tagaagaaca gtatttggta tctgcgctct    9720
gctgaagcca gttaccttcg gaaaagagt tggtagctct tgatccggca acaaaccac    9780 cgctggtagc ggtggttttt ttgtttgcaa gcagcagatt acgcgcagaa aaaaggatc    9840 tcaagaagat cctttgatct tttctacggg gtctgacgct cagtggaacg aaaactcacg    9900
ttaagggatt ttggtcatga gattatcaaa aaggatcttc acctagatcc ttttaaatta    9960
aaaatgaagt tttaaatcaa tctaaagtat atatgagtaa acttggtctg acagttacca    10020
atgcttaatc agtgaggcac ctatctcagc gatctgtcta tttcgttcat ccatagttgc    10080
ctgactcctg caaaccacgt tgtgtctcaa aatctctgat gttacattgc acaagataaa    10140
aatatatcat catgaacaat aaaactgtct gcttacataa acagtaatac aaggggtgtt    10200
atgagccata ttcaacggga aacgtcttgc tcgaggccgc gattaaattc caacatggat    10260
gctgatttat atgggtataa atgggctcgc gataatgtcg ggcaatcagg tgcgacaatc    10320
tatcgattgt atgggaagcc cgatgcgcca gagttgtttc tgaaacatgg caaaggtagc    10380
gttgccaatg atgttacaga tgagatggtc agactaaact ggctgacgga atttatgcct    10440
cttccgacca tcaagcattt tatccgtact cctgatgatg catggttact caccactgcg    10500
atccccggga aaacagcatt ccaggtatta gaagaatatc ctgattcagg tgaaaatatt    10560
gttgatgcgc tggcagtgtt cctgcgccgg ttgcattcga ttcctgtttg taattgtcct    10620
tttaacagcg atcgcgtatt tcgtctcgct caggcgcaat cacgaatgaa taacggtttg    10680
gttgatgcga gtgattttga tgacgagcgt aatggctggc ctgttgaaca agtctggaaa    10740
gaaatgcata agcttttgcc attctcaccg gattcagtcg tcactcatgg tgatttctca    10800
cttgataacc ttatttttga cgaggggaaa ttaataggtt gtattgatgt tggacgagtc    10860
ggaatcgcag accgatacca ggatcttgcc atcctatgga actgcctcgg tgagttttct    10920
ccttcattac agaaacggct ttttcaaaaa tatggtattg ataatcctga tatgaataaa    10980
ttgcagtttc atttgatgct cgatgagttt ttctaagggc ggcctgccac catacccacg    11040
ccgaaacaag cgctcatgag cccgaagtgg cgagcccgat cttccccatc ggtgatgtcg    11100
gcgatatagg cgccagcaac cgcacctgtg gcgccggtga tgagggcgcg ccaagtcgac    11160
gtccggcagt c                                                         11171
```

<210> SEQ ID NO 5  
<211> LENGTH: 11309  
<212> TYPE: DNA  
<213> ORGANISM: Artificial Sequence  
<220> FEATURE:  
<223> OTHER INFORMATION: Synthetic polynucleotide

<400> SEQUENCE: 5

```
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg    120
gccaactcca tcactagggg ttcctgctag ctctgggtat ttaagcccga gtgagcacgc    180
agggtctcca ttttgaagcg ggaggttacg cgttcgtcga ctactagtgg gtaccagagc    240
```

-continued

```
tccctaggtt ctagaaccgg tgacgtctcc catggtgaag cttggatctg agggcggagt      300
tagggcggag ccaatcagcg tgcgccgttc cgaaagttgc cttttatggc tgggcggaga      360
atgggcggtg aacgccgatg attatataag gacgcgccgg gtgtggcaca gctagttccg      420
tcgcagccgg gatttgggtc gcggttcttg tttgtggatc cctgtgatcg tcacttggta      480
agtcactgac tgtctatgcc tgggaaaggg tgggcaggag atggggcagt gcaggaaaag      540
tggcactatg aaccctcctg gtggcgaggg gaggggggtg gtcctcgaac gccttgcaga      600
actggcctgg atacagagtg gaccggctgg ccccatctgg aagacttcga gatacactgt      660
tgtcttactg cgctcaacag tgtatctcga agtcttccaa atggtgccag ccatcgcagc      720
ggggtgcagg aaatgggggc agccccccctt tttggctatc cttccacgtg ttcttttttg      780
tatcttttgt gtttcctaga aaacatctca gtcaccaccg cagccctagg aatgcatcta      840
gacaattgta ctaaccttct tctctttcct ctcctgacag tccggaaagc caccatgtac      900
gccctgttcc tgctgccag cctgctgggc gccgcctgg ccggcccgt gctgggcctg      960 aaggagtgca cccgcggcag cgccgtgtgg tgccagaacg tgaagaccgc cagcgactgc      1020
ggcgccgtga agcactgcct gcagaccgtg tggaacaagc ccaccgtgaa gagcctgccc      1080
tgcgacatct gcaaggacgt ggtgaccgcc gccggcgaca tgctgaagga caacgccacc      1140
gaggaggaga tcctggtgta cctggagaag acctgcgact ggctgcccaa gcccaacatg      1200
agcgccagct gcaaggagat cgtggacagc tacctgcccg tgatcctgga catcatcaag      1260
ggcgagatga gccgccccgg cgaggtgtgc agcgccctga acctgtgcga gagcctgcag      1320
aagcacctgg ccgagctgaa ccaccagaag cagctggaga gcaacaagat ccccgagctg      1380
gacatgaccg aggtggtggc ccccttcatg gccaacatcc ccctgctgct gtaccccag      1440 gacggccccc gcagcaagcc ccagcccaag gacaacggcc acgtgtgcca ggactgcatc      1500
cagatggtga ccgacatcca gaccgccgtg cgcaccaaca gcaccttcgt gcaggccctg      1560
gtggagcacg tgaaggagga gtgcgaccgc ctgggccccg gcatggccga catctgcaag      1620
aactacatca gccagtacag cgagatcgcc atccagatga tgatgcacat gcagcccaag      1680
gagatctgcg ccctggtggg cttctgcgac gaggtgaagg agatgccat gcagaccctg      1740 gtgcccgcca aggtggccag caagaacgtg atccccgccc tggagctggt ggagcccatc      1800
aagaagcacg aggtgcccgc caagagcgac gtgtactgcg aggtgtgcga gttcctggtg      1860
aaggaggtga ccaagctgat cgacaacaac aagaccgaga aggagatcct ggacgccttc      1920
gacaagatgt gcagcaagct gcccaagagc ctgagcgagg agtgccagga ggtggtggac      1980
acctacggca gcagcatcct gagcatcctg ctggaggagg tgagccccga gctggtgtgc      2040
agcatgctgc acctgtgcag cggcacccgc ctgcccgccc tgaccgtgca cgtgacccag      2100
cccaaggacg gcggcttctg cgaggtgtgc aagaagctgg tgggctacct ggaccgcaac      2160
ctggagaaga cagcaccaa gcaggagatc ctggccgccc tggagaaggg ctgcagcttc      2220
ctgcccgacc cctaccagaa gcagtgcgac cagttcgtgg ccgagtacga gcccgtgctg      2280
atcgagatcc tggtggaggt gatggacccc agcttcgtgt gcctgaagat cggcgcctgc      2340
cccagcgccc acaagcccct gctgggcacc gagaagtgca tctggggccc cagctactgg      2400
tgccagaaca ccgagaccgc cgcccagtgc aacgccgtgg agcactgcaa cgccacgtg      2460 tggaacgagg gcagaggaag tcttctgaca tgccggacgc tggaagagaa tcccggccct      2520
atggaattca gcagccccag cagagaggaa tgccccaagc ctctgagccg ggtgtcaatc      2580
```

```
atggccggat ctctgacagg actgctgctg cttcaggccg tgtcttgggc ttctggcgct    2640
agaccttgca tccccaagag cttcggctac agcagcgtcg tgtgcgtgtg caatgccacc    2700
tactgcgaca gcttcgaccc tcctacctt cctgctctgg gcaccttcag cagatacgag    2760
agcaccagat ccggcagacg gatggaactg agcatgggac ccatccaggc caatcacaca    2820
ggcactggcc tgctgctgac actgcagcct gagcagaaat ccagaaagt gaaaggcttc     2880 ggcggagcca tgacagatgc cgccgctctg aatatcctgg ctctgtctcc accagctcag    2940
aacctgctgc tcaagagcta cttcagcgag gaaggcatcg gctacaacat catcagagtg    3000
cccatggcca gctgcgactt cagcatcagg acctacacct acgccgacac acccgacgat    3060
ttccagctgc acaacttcag cctgcctgaa gaggacacca agctgaagat ccctctgatc    3120
cacagagccc tgcagctggc acaaagaccc gtgtcactgc tggcctctcc atggacatct    3180
cccacctggc tgaaaacaaa tggcgccgtg aatggcaagg gcagcctgaa aggccaacct    3240
ggcgacatct accaccagac ctgggccaga tacttcgtga gttcctgga cgcctatgcc     3300 gagcacaagc tgcagttttg ggccgtgaca gccgagaacaa accttctgc tggactgctg     3360 agcggctacc cctttcagtg cctgggcttt acacccgagc accagcggga ctttatcgcc    3420
cgtgatctgg gacccacact ggccaatagc acccaccata tgtgcggct gctgatgctg     3480 gacgaccaga gactgcttct gccccactgg gctaaagtgg tgctgacaga tcctgaggcc    3540
gccaaatacg tgcacggaat cgccgtgcac tggtatctgg actttctggc ccctgccaag    3600
gccacactgg gagagacaca cagactgttc cccaacacca tgctgttcgc cagcgaagcc    3660
tgtgtgggca gcaagttttg ggaacagagc gtgcggctcg gcagctggga tagaggcatg    3720
cagtacagcc acagcatcat caccaacctg ctgtaccacg tcgtcggctg gaccgactgg    3780
aatctggccc tgaatcctga aggcggccct aactgggtcc gaaacttcgt ggacagcccc    3840
atcatcgtgg acatcaccaa ggacaccttc tacaagcagc ccatgttcta ccacctggga    3900
cacttcagca agttcatccc cgagggctct cagcgcgttg gactggtggc ttcccagaag    3960
aacgatctgg acgccgtggc tctgatgcac cctgatggat ctgctgtggt ggtggtcctg    4020
aaccgcagca gcaaagatgt gccccctgacc atcaaggatc ccgccgtggg attcctggaa    4080
acaatcagcc ctggctactc catccacacc tacctgtggc gtagacagtg acaattgtta    4140
attaagttta aaccctcgag gccgcaagcc gcatcgatac cgtcgactag agctcgctga    4200
tcagcctcga ctgtgccttc tagttgccag ccatctgttg tttgcccctc ccccgtgcct    4260
tccttgaccc tggaaggtgc cactcccact gtcctttcct aataaaatga ggaaattgca    4320
tcgcattgtc tgagtaggtg tcattctatt ctggggggtg gggtggggca ggacagcaag    4380
ggggaggatt gggaagacaa tagcaggcat gctggggaga gatccacgat aacaaacagc    4440
ttttttgggg tgaacatatt gactgaattc cctgcaggtt ggccactccc tctctgcgcg    4500
ctcgctcgct cactgaggcc gcccgggcaa agcccgggcg tcgggcgacc tttggtcgcc    4560
cggcctcagt gagcgagcga gcgcgcagag agggagtggc caactccatc actaggggtt    4620
cctgcggccg ctcgtacggt ctcgaggaat tcctgcagga taacttgcca acctcattct    4680
aaaatgtata tagaagccca aaagacaata acaaaaatat tcttgtagaa caaaatggga    4740
aagaatgttc cactaaatat caagatttag agcaaagcat gagatgtgtg gggatagaca    4800
gtgaggctga taaatagag tagagctcag aaacagaccc attgatatat gtaagtgacc    4860
tatgaaaaaa atatggcatt ttacaatggg aaaatgatga tcttttttctt tttagaaaa    4920 acagggaaat atatttatat gtaaaaaata aaagggaacc catatgtcat accatacaca    4980
```

```
caaaaaaatt ccagtgaatt ataagtctaa atggagaagg caaaacttta aatcttttag    5040
aaaataatat agaagcatgc agaccagcct ggccaacatg atgaaaccct ctctactaat    5100
aataaaatca gtagaactac tcaggactac tttgagtggg aagtccttt ctatgaagac    5160 ttctttggcc aaaattaggc tctaaatgca aggagatagt gcatcatgcc tggctgcact    5220
tactgataaa tgatgttatc accatcttta accaaatgca caggaacaag ttatggtact    5280
gatgtgctgg attgagaagg agctctactt ccttgacagg acacatttgt atcaacttaa    5340
aaaagcagat ttttgccagc agaactattc attcagaggt aggaaactta gaatagatga    5400
tgtcactgat tagcatggct tccccatctc cacagctgct tcccacccag gttgcccaca    5460
gttgagtttg tccagtgctc agggctgccc actctcagta agaagcccca caccagcccc    5520
tctccaaata tgttggctgt tccttccatt aaagtgaccc cactttagag cagcaagtgg    5580
atttctgttt cttacagttc aggaaggagg agtcagctgt gagaacctgg agcctgagat    5640
gcttctaagt cccactgcta ctggggtcag ggaagccaga ctccagcatc agcagtcagg    5700
agcactaagc ccttgccaac atcctgtttc tcagagaaac tgcttccatt ataatggttg    5760
tcctttttta agctatcaag ccaaacaacc agtgtctacc attattctca tcacctgaag    5820
ccaagggttc tagcaaaagt caagctgtct tgtaatggtt gatgtgcctc cagcttctgt    5880
cttcagtcac tccactctta gcctgctctg aatcaactct gaccacagtt ccctggagcc    5940
cctgccacct gctgcccctg ccaccttctc catctgcagt gctgtgcagc cttctgcact    6000
cttgcagagc taataggtgg agacttgaag gaagaggagg aaagtttctc ataatagcct    6060
tgctgcaagc tcaaatggga ggtgggcact gtgcccagga gccttggagc aaaggctgtg    6120
cccaacctct gactgcatcc aggtttggtc ttgacagaga taagaagccc tggcttttgg    6180
agccaaaatc taggtcagac ttaggcagga ttctcaaagt ttatcagcag aacatgaggc    6240
agaagaccct ttctgctcca gcttcttcag gctcaacctt catcagaata gatagaaaga    6300
gaggctgtga gggttcttaa aacagaagca aatctgactc agagaataaa caacctccta    6360
gtaaactaca gcttagacag agcatctggt ggtgagtgtg ctcagtgtcc tactcaactg    6420
tctggtatca gccctcatga ggacttctct tctttccctc atagacctcc atctctgttt    6480
tccttagcct gcagaaatct ggatggctat tcacagaatg cctgtgcttt cagagttgca    6540
ttttttctct ggtattctgg ttcaagcatt tgaaggtagg aaaggttctc caagtgcaag    6600
aaagccagcc ctgagcctca actgcctggc tagtgtggtc agtaggatgc aaaggctgtt    6660
gaatgccaca aggccaaact ttaacctgtg taccacaagc ctagcagcag aggcagctct    6720
gctcactgga actctctgtc ttctttctcc tgagcctttt cttttcctga gttttctagc    6780
tctcctcaac cttacctctg ccctacccag gacaaaccca agagccactg tttctgtgat    6840
gtcctctcca gccctaatta ggcatcatga cttcagcctg accttccatg ctcagaagca    6900
gtgctaatcc acttcagatg agctgctcta tgcaacacag gcagagccta caaacctttg    6960
caccagagcc ctccacatat cagtgtttgt tcatactcac ttcaacagca aatgtgactg    7020
ctgagattaa gatttacac aagatggtct gtaatttcac agttagtttt atcccattag    7080
gtatgaaaga attagcataa ttcccctaa acatgaatga atcttagatt ttttaataaa    7140
tagttttgga agtaaagaca gagacatcag gagcacaagg aatagcctga gaggacaaac    7200
agaacaagaa agagtctgga aatacacagg atgttcttgg cctcctcaaa gcaagtgcaa    7260
gcagatagta ccagcagccc caggctatca gagcccagtg aagagaagta ccatgaaagc    7320
```

| | |
|---|---|
| cacagctcta accaccctgt tccagagtga cagacagtcc caagacaag ccagcctgag | 7380 |
| ccagagagag aactgcaaga gaaagtttct aatttaggtt ctgttagatt cagacaagtg | 7440 |
| caggtcatcc tctctccaca gctactcacc tctccagcct aacaaagcct gcagtccaca | 7500 |
| ctccaaccct ggtgtctcac ctcctagcct ctcccaacat cctgctctct gaccatcttc | 7560 |
| tgcatctctc atctcaccat ctcccactgt ctacagccta ctcttgcaac taccatctca | 7620 |
| ttttctgaca tcctgtctac atcttctgcc atactctgcc atctaccata ccacctctta | 7680 |
| ccatctacca caccatcttt tatctccatc cctctcagaa gcctccaagc tgaatcctgc | 7740 |
| tttatgtgtt catctcagcc cctgcatgga aagctgaccc cagaggcaga actattccca | 7800 |
| gagagcttgg ccaagaaaaa caaaactacc agcctggcca ggctcaggag tagtaagctg | 7860 |
| cagtgtctgt tgtgttctag cttcaacagc tgcaggagtt ccactctcaa atgctccaca | 7920 |
| tttctcacat cctcctgatt ctggtcacta cccatcttca aagaacagaa tatctcacat | 7980 |
| cagcatactg tgaaggacta gtcatgggtg cagctgctca gagctgcaaa gtcattctgg | 8040 |
| atggtggaga gcttacaaac atttcatgat gctcccccg ctctgatggc tggagcccaa | 8100 |
| tccctacaca gactcctgct gtatgtgttt cctttcact ctgagccaca gccagagggc | 8160 |
| aggcattcag tctcctcttc aggctggggc tggggcactg agaactcacc caacaccttg | 8220 |
| ctctcactcc ttctgcaaaa caagaaagag ctttgtgctg cagtagccat gaagaatgaa | 8280 |
| aggaaggctt taactaaaaa atgtcagaga ttattttcaa cccccttactg tggatcacca | 8340 |
| gcaaggagga aacacaacac agagacattt tttcccctca aattatcaaa gaatcactg | 8400 |
| catttgttaa agagagcaac tgaatcagga agcagagttt tgaacatatc agaagttagg | 8460 |
| aatctgcatc agagacaaat gcagtcatgg ttgtttgctg cataccagcc ctaatcatta | 8520 |
| gaagcctcat ggacttcaaa catcattccc tctgacaaga tgctctagcc taactccatg | 8580 |
| agataaaata atctgccctt tcagagccaa agaagagtcc accagcttct tctcagtgtg | 8640 |
| aacaagagct ccagtcaggt tagtcagtcc agtgcagtag aggagaccag tctgcatcct | 8700 |
| ctaattttca aaggcaagaa gatttgttta ccctggacac caggcacaag tgaggtcaca | 8760 |
| gagctcttag atatgcagtc ctcatgagtg aggagactaa agcgcatgcc atcaagactt | 8820 |
| cagtgtagag aaaacctcca aaaaagcctc ctcactactt ctggaatagc tcagaggccg | 8880 |
| aggcggcctc ggcctctgca taaataaaaa aaattagtca gccatggggc ggagaatggg | 8940 |
| cggaactggg cggagttagg ggcgggatgg gcggagttag gggcgggact atggttgctg | 9000 |
| actaattgag atgcatgctt tgcatacttc tgcctgctgg ggagcctggg gactttccac | 9060 |
| acctggttgc tgactaattg agatgcatgc tttgcatact tctgcctgct ggggagcctg | 9120 |
| gggactttcc acaccctaac tgacacacat tccacagctg cattaatgaa tcggccaacg | 9180 |
| cgcggggaga ggcggtttgc gtattgggcg ctcttccgct tcctcgctca ctgactcgct | 9240 |
| gcgctcggtc gttcggctgc ggcgagcggt atcagctcac tcaaaggcgg taatacggtt | 9300 |
| atccacagaa tcagggata acgcaggaaa gaacatgtga gcaaaaggcc agcaaaaggc | 9360 |
| caggaaccgt aaaaaggccg cgttgctggc gtttttccat aggctccgcc cccctgacga | 9420 |
| gcatcacaaa aatcgacgct caagtcagag gtggcgaaac ccgacaggac tataaagata | 9480 |
| ccaggcgttt ccccctggaa gctccctcgt gcgctctcct gttccgaccc tgccgcttac | 9540 |
| cggatacctg tccgcctttc tcccttcggg aagcgtggcg ctttctcata gctcacgctg | 9600 |
| taggtatctc agttcggtgt aggtcgttcg ctccaagctg ggctgtgtgc acgaaccccc | 9660 |
| cgttcagccc gaccgctgcg ccttatccgg taactatcgt cttgagtcca acccggtaag | 9720 |

| | | | | |
|---|---|---|---|---|
| acacgactta | tcgccactgg | cagcagccac | tggtaacagg | attagcagag cgaggtatgt | 9780 |
| aggcggtgct | acagagttct | tgaagtggtg | gcctaactac | ggctacacta gaagaacagt | 9840 |
| atttggtatc | tgcgctctgc | tgaagccagt | taccttcgga | aaaagagttg gtagctcttg | 9900 |
| atccggcaaa | caaccaccg | ctggtagcgg | tggttttttt | gtttgcaagc agcagattac | 9960 |
| gcgcagaaaa | aaaggatctc | aagaagatcc | tttgatcttt | tctacggggt ctgacgctca | 10020 |
| gtggaacgaa | aactcacgtt | aagggatttt | ggtcatgaga | ttatcaaaaa ggatcttcac | 10080 |
| ctagatcctt | ttaaattaaa | aatgaagttt | taaatcaatc | taaagtatat atgagtaaac | 10140 |
| ttggtctgac | agttaccaat | gcttaatcag | tgaggcacct | atctcagcga tctgtctatt | 10200 |
| tcgttcatcc | atagttgcct | gactcctgca | aaccacgttg | tgtctcaaaa tctctgatgt | 10260 |
| tacattgcac | aagataaaaa | tatatcatca | tgaacaataa | aactgtctgc ttacataaac | 10320 |
| agtaatacaa | ggggtgttat | gagccatatt | caacgggaaa | cgtcttgctc gaggccgcga | 10380 |
| ttaaattcca | acatggatgc | tgatttatat | gggtataaat | gggctcgcga taatgtcggg | 10440 |
| caatcaggtg | cgacaatcta | tcgattgtat | gggaagcccg | atgcgccaga gttgtttctg | 10500 |
| aaacatggca | aaggtagcgt | tgccaatgat | gttacagatg | agatggtcag actaaactgg | 10560 |
| ctgacggaat | ttatgcctct | tccgaccatc | aagcatttta | tccgtactcc tgatgatgca | 10620 |
| tggttactca | ccactgcgat | ccccgggaaa | acagcattcc | aggtattaga agaatatcct | 10680 |
| gattcaggtg | aaaatattgt | tgatgcgctg | gcagtgttcc | tgcgccggtt gcattcgatt | 10740 |
| cctgtttgta | attgtccttt | taacagcgat | cgcgtatttc | gtctcgctca ggcgcaatca | 10800 |
| cgaatgaata | acggtttggt | tgatgcgagt | gattttgatg | acgagcgtaa tggctggcct | 10860 |
| gttgaacaag | tctggaaaga | aatgcataag | cttttgccat | tctcaccgga ttcagtcgtc | 10920 |
| actcatggtg | atttctcact | tgataacctt | attttttgacg | aggggaaatt aataggttgt | 10980 |
| attgatgttg | gacgagtcgg | aatcgcagac | cgataccagg | atcttgccat cctatggaac | 11040 |
| tgcctcggtg | agttttctcc | ttcattacag | aaacggcttt | ttcaaaaata tggtattgat | 11100 |
| aatcctgata | tgaataaatt | gcagtttcat | ttgatgctcg | atgagttttt ctaagggcgg | 11160 |
| cctgccacca | tacccacgcc | gaaacaagcg | ctcatgagcc | cgaagtggcg agcccgatct | 11220 |
| tccccatcgg | tgatgtcggc | gatataggcg | ccagcaaccg | cacctgtggc gccggtgatg | 11280 |
| agggcgcgcc | aagtcgacgt | ccggcagtc | | | 11309 |

<210> SEQ ID NO 6
<211> LENGTH: 11293
<212> TYPE: DNA
<213> ORGANISM: Artificial Sequence
<220> FEATURE:
<223> OTHER INFORMATION: Synthetic polynucleotide

<400> SEQUENCE: 6

| | | | | |
|---|---|---|---|---|
| ttggccactc | cctctctgcg | cgctcgctcg | ctcactgagg | ccgggcgacc aaaggtcgcc | 60 |
| cgacgcccgg | gctttgcccg | gcggcctca | gtgagcgagc | gagcgcgcag agagggagtg | 120 |
| gccaactcca | tcactagggg | ttcctgctag | ctctgggtat | ttaagcccga gtgagcacgc | 180 |
| agggtctcca | ttttgaagcg | ggaggttacg | cgttcgtcga | ctactagtgg gtaccagagc | 240 |
| tccctaggtt | ctagaaccgg | tgacgtctcc | catggtgaag | cttggatctg agggcggagt | 300 |
| tagggcggag | ccaatcagcg | tgcgccgttc | cgaaagttgc | cttttatggc tgggcggaga | 360 |
| atgggcggtg | aacgccgatg | attatataag | gacgcgccgg | gtgtggcaca gctagttccg | 420 |

-continued

```
tcgcagccgg gatttgggtc gcggttcttg tttgtggatc cctgtgatcg tcacttggta    480
agtcactgac tgtctatgcc tgggaaaggg tgggcaggag atggggcagt gcaggaaaag    540
tggcactatg aaccctgcag ccctaggaat gcatctagac aattgtacta accttcttct    600
ctttcctctc ctgacagtcc ggaaagccac catgtacgcc ctgttcctgc tggccagcct    660
gctgggcgcc gccctggccg gccccgtgct gggcctgaag gagtgcaccc gcggcagcgc    720
cgtgtggtgc cagaacgtga agaccgccag cgactgcggc gccgtgaagc actgcctgca    780
gaccgtgtgg aacaagccca ccgtgaagag cctgccctgc gacatctgca aggacgtggt    840
gaccgccgcc ggcgacatgc tgaaggacaa cgccaccgag gaggagatcc tggtgtacct    900
ggagaagacc tgcgactggc tgcccaagcc caacatgagc gccagctgca aggagatcgt    960
ggacagctac ctgcccgtga tcctggacat catcaagggc gagatgagcc gccccggcga   1020
ggtgtgcagc gccctgaacc tgtgcgagag cctgcagaag cacctggccg agctgaacca   1080
ccagaagcag ctggagagca caagatccc cgagctggac atgaccgagg tggtggcccc   1140
cttcatggcc aacatccccc tgctgctgta ccccccaggac ggccccgca gcaagcccca   1200 gcccaaggac aacggcgacg tgtgccagga ctgcatccag atggtgaccg acatccagac   1260
cgccgtgcgc accaacagca ccttcgtgca ggccctggtg gagcacgtga aggaggagtg   1320
cgaccgcctg ggccccggca tggccgacat ctgcaagaac tacatcagcc agtacagcga   1380
gatcgccatc cagatgatga tgcacatgca gcccaaggga atctgcgccc tggtgggctt   1440
ctgcgacgag gtgaaggaga tgcccatgca gaccctggtg cccgccaagg tggccagcaa   1500
gaacgtgatc cccgccctgg agctggtgga gcccatcaag aagcacgagg tgcccgccaa   1560
gagcgacgtg tactgcgagg tgtgcgagtt cctggtgaag gaggtgacca agctgatcga   1620
caacaacaag accgagaagg agatcctgga cgccttcgac aagatgtgca gcaagctgcc   1680
caagagcctg agcgaggagt gccaggaggt ggtggacacc tacggcagca gcatcctgag   1740
catcctgctg gaggaggtga gcccgagct ggtgtgcagc atgctgcacc tgtgcagcgg   1800 caccccgcctg cccgccctga ccgtgcacgt gacccagccc aaggacggcg cttctgcga   1860 ggtgtgcaag aagctggtgg gctacctgga ccgcaacctg gagaagaaca gcaccaagca   1920
ggagatcctg gccgccctgg agaagggctg cagcttcctg cccgacccct accagaagca   1980
gtgcgaccag ttcgtggccg agtacgagcc cgtgctgatc gagatcctgg tggaggtgat   2040
ggaccccagc ttcgtgtgcc tgaagatcgg cgcctgcccc agcgcccaca gcccctgct   2100 gggcaccgag aagtgcatct ggggcccag ctactggtgc cagaacaccg agaccgccgc   2160
ccagtgcaac gccgtggagc actgcaagcg ccacgtgtgg aactgattgt ggccgaaccg   2220
ccgaactcag aggccggccc cagaaaaccc gagcgagtag ggggcggcgc gcaggaggga   2280
ggagaactgg gggcgcggga ggctggtggg tgtgggggt ggagatgtag aagatgtgac   2340
gccgcggccc ggcgggtgcc agattagcgg acgcggtgcc cgcggttgca acgggatccc   2400
gggcgctgca gcttgggagg cggctctccc caggcggcgt ccgcggagac acccatccgt   2460
gaaccccagg tcccgggccg ccggctcgcc gcgcaccagg ggccggcgga cagaagagcg   2520
gccgagcggc tcgaggctgg gggaccgcg gcgcggccgc gcgctgccgg gcgggaggct   2580 gggggggccgg ggcgggggcc gtgccccgga gcgggtcgga ggccggggcc ggggccgggg   2640
gacggcggct ccccgcgcgg ctccagcggc tcggggatcc cggccgggcc ccgcagggac   2700
catgatggaa ttcagcagcc ccagcagaga ggaatgcccc aagcctctga gccgggtgtc   2760
aatcatggcc ggatctctga caggactgct gctgcttcag gccgtgtctt gggcttctgg   2820
```

```
cgctagacct tgcatcccca agagcttcgg ctacagcagc gtcgtgtgcg tgtgcaatgc    2880
cacctactgc gacagcttcg accctcctac ctttcctgct ctgggcacct tcagcagata    2940
cgagagcacc agatccggca gacggatgga actgagcatg ggacccatcc aggccaatca    3000
cacaggcact ggcctgctgc tgacactgca gcctgagcag aaattccaga agtgaaagg     3060 cttcggcgga gccatgacag atgccgccgc tctgaatatc ctggctctgt ctccaccagc    3120
tcagaacctg ctgctcaaga gctacttcag cgaggaaggc atcggctaca acatcatcag    3180
agtgcccatg gccagctgcg acttcagcat caggacctac acctacgccg acacacccga    3240
cgatttccag ctgcacaact tcagcctgcc tgaagaggac accaagctga agatccctct    3300
gatccacaga gccctgcagc tggcacaaag accgtgtca ctgctggcct ctccatggac     3360
atctcccacc tggctgaaaa caaatggcgc cgtgaatggc aagggcagcc tgaaaggcca    3420
acctggcgac atctaccacc agacctgggc cagatacttc gtgaagttcc tggacgccta    3480
tgccgagcac aagctgcagt tttgggccgt gacagccgag aacgaacctt ctgctggact    3540
gctgagcggc tacccctttc agtgcctggg ctttacaccc gagcaccagc gggactttat    3600
cgcccgtgat ctgggaccca cactggccaa tagcacccac cataatgtgc ggctgctgat    3660
gctggacgac cagagactgc ttctgccccca ctgggctaaa gtggtgctga cagatcctga    3720
ggccgccaaa tacgtgcacg gaatcgccgt gcactggtat ctggactttc tggcccctgc    3780
caaggccaca ctgggagaga cacacagact gttccccaac accatgctgt cgccagcga    3840 agcctgtgtg ggcagcaagt tttgggaaca gagcgtgcgg ctcggcagct gggatagagg    3900
catgcagtac agccacagca tcatcaccaa cctgctgtac cacgtcgtcg gctggaccga    3960
ctggaatctg gccctgaatc ctgaaggcgg ccctaactgg gtccgaaact tcgtggacag    4020
ccccatcatc gtggacatca ccaaggacac cttctacaag cagcccatgt ctaccacct     4080 gggacacttc agcaagttca tccccgaggg ctctcagcgc gttggactgg tggcttccca    4140
gaagaacgat ctggacgccg tggctctgat gcaccctgat ggatctgctg tggtggtggt    4200
cctgaaccgc agcagcaaag atgtgccccct gaccatcaag gatcccgccg tgggattcct    4260
ggaaacaatc agccctggct actccatcca cacctacctg tggcgtagac agtgacaatt    4320
gttaattaag tttaaaccct cgaggccgca agcaataaaa tatctttatt ttcattacat    4380
ctgtgtgttg gttttttgtg tggagatcca cgataacaaa cagctttttt ggggtgaaca    4440
tattgactga attccctgca ggttggccac tccctctctg cgcgctcgct cgctcactga    4500
ggccgcccgg gcaaagcccg ggcgtcgggc gacctttggt cgcccggcct cagtgagcga    4560
gcgagcgcgc agagagggag tggccaactc catcactagg ggttcctgcg gccgctcgta    4620
cggtctcgag gaattcctgc aggataactt gccaacctca ttctaaaatg tatatagaag    4680
cccaaaagac aataacaaaa atattcttgt agaacaaaat gggaaagaat gttccactaa    4740
atatcaagat ttagagcaaa gcatgagatg tgtggggata gacagtgagg ctgataaaat    4800
agagtagagc tcagaaacag acccattgat atatgtaagt gacctatgaa aaaaatatgg    4860
cattttacaa tgggaaaatg atggtctttt tcttttttag aaaacaggg aaatatattt      4920 atatgtaaaa aataaagggg aacccatatg tcataccata cacacaaaaa aattccagtg    4980
aattataagt ctaaatggag aaggcaaaac tttaaatctt ttagaaaata atatagaagc    5040
atgcagacca gcctggccaa catgatgaaa ccctctctac taataataaa atcagtagaa    5100
ctactcagga ctactttgag tgggaagtcc ttttctatga agacttcttt ggccaaaatt    5160
```

| | |
|---|---|
| aggctctaaa tgcaaggaga tagtgcatca tgcctggctg cacttactga taaatgatgt | 5220 |
| tatcaccatc tttaaccaaa tgcacaggaa caagttatgg tactgatgtg ctggattgag | 5280 |
| aaggagctct acttccttga caggacacat ttgtatcaac ttaaaaaagc agatttttgc | 5340 |
| cagcagaact attcattcag aggtaggaaa cttagaatag atgatgtcac tgattagcat | 5400 |
| ggcttcccca tctccacagc tgcttcccac ccaggttgcc cacagttgag tttgtccagt | 5460 |
| gctcagggct gcccactctc agtaagaagc cccacaccag cccctctcca aatatgttgg | 5520 |
| ctgttccttc cattaaagtg accccacttt agagcagcaa gtggatttct gtttcttaca | 5580 |
| gttcaggaag gaggagtcag ctgtgagaac ctggagcctg agatgcttct aagtcccact | 5640 |
| gctactgggg tcagggaagc cagactccag catcagcagt caggagcact aagcccttgc | 5700 |
| caacatcctg tttctcagag aaactgcttc cattataatg gttgtccttt tttaagctat | 5760 |
| caagccaaac aaccagtgtc taccattatt ctcatcacct gaagccaagg gttctagcaa | 5820 |
| aagtcaagct gtcttgtaat ggttgatgtg cctccagctt ctgtcttcag tcactccact | 5880 |
| cttagcctgc tctgaatcaa ctctgaccac agttccctgg agccctgcc acctgctgcc | 5940 |
| cctgccacct tctccatctg cagtgctgtg cagccttctg cactcttgca gagctaatag | 6000 |
| gtggagactt gaaggaagag gaggaaagtt tctcataata gccttgctgc aagctcaaat | 6060 |
| gggaggtggg cactgtgccc aggagccttg agcaaaggc tgtgcccaac ctctgactgc | 6120 |
| atccaggttt ggtcttgaca gagataagaa gccctggctt ttggagccaa aatctaggtc | 6180 |
| agacttaggc aggattctca aagtttatca gcagaacatg aggcagaaga ccctttctgc | 6240 |
| tccagcttct tcaggctcaa ccttcatcag aatagataga aagagaggct gtgagggttc | 6300 |
| ttaaaacaga agcaaatctg actcagagaa taaacaacct cctagtaaac tacagcttag | 6360 |
| acagagcatc tggtggtgag tgtgctcagt gtcctactca actgtctggt atcagccctc | 6420 |
| atgaggactt ctcttctttc cctcatagac ctccatctct gttttcctta gcctgcagaa | 6480 |
| atctggatgg ctattcacag aatgcctgtg ctttcagagt tgcatttttt tctctggtatt | 6540 |
| ctggttcaag catttgaagg taggaaaggt tctccaagtg caagaaagcc agccctgagc | 6600 |
| ctcaactgcc tggctagtgt ggtcagtagg atgcaaaggc tgttgaatgc cacaaggcca | 6660 |
| aactttaacc tgtgtaccac aagcctagca gcagaggcag ctctgctcac tggaactctc | 6720 |
| tgtcttcttt ctcctgagcc tttttctttc ctgagttttc tagctctcct caaccttacc | 6780 |
| tctgccctac ccaggacaaa cccaagagcc actgtttctg tgatgtcctc tccagcccta | 6840 |
| attaggcatc atgacttcag cctgaccttc catgctcaga agcagtgcta atccacttca | 6900 |
| gatgagctgc tctatgcaac acaggcagag cctacaaacc tttgcaccag agccctccac | 6960 |
| atatcagtgt ttgttcatac tcacttcaac agcaaatgtg actgctgaga ttaagatttt | 7020 |
| acacaagatg gtctgtaatt tcacagttag ttttatccca ttaggtatga aagaattagc | 7080 |
| ataattcccc ttaaacatga atgaatctta gattttttaa taaatagttt tggaagtaaa | 7140 |
| gacagagaca tcaggagcac aaggaatagc ctgagaggac aaacagaaca agaaagagtc | 7200 |
| tggaaataca caggatgttc ttggcctcct caaagcaagt gcaagcagat agtaccagca | 7260 |
| gccccaggct atcagagccc agtgaagaga agtaccatga aagccacagc tctaaccacc | 7320 |
| ctgttccaga gtgacagaca gtccccaaga caagccagcc tgagccagag agagaactgc | 7380 |
| aagagaaagt ttctaattta ggttctgtta gattcagaca agtgcaggtc atcctctctc | 7440 |
| cacagctact cacctctcca gcctaacaaa gcctgcagtc cacactccaa ccctggtgtc | 7500 |
| tcacctccta gcctctccca acatcctgct ctctgaccat cttctgcatc tctcatctca | 7560 |

```
ccatctccca ctgtctacag cctactcttg caactaccat ctcattttct gacatcctgt    7620
ctacatcttc tgccatactc tgccatctac cataccacct cttaccatct accacaccat    7680
cttttatctc catccctctc agaagcctcc aagctgaatc ctgctttatg tgttcatctc    7740
agcccctgca tggaaagctg accccagagg cagaactatt cccagagagc ttggccaaga    7800
aaaacaaaac taccagcctg gccaggctca ggagtagtaa gctgcagtgt ctgttgtgtt    7860
ctagcttcaa cagctgcagg agttccactc tcaaatgctc cacatttctc acatcctcct    7920
gattctggtc actacccatc ttcaaagaac agaatatctc acatcagcat actgtgaagg    7980
actagtcatg ggtgcagctg ctcagagctg caaagtcatt ctggatggtg gagagcttac    8040
aaacatttca tgatgctccc cccgctctga tggctggagc ccaatcccta cacagactcc    8100
tgctgtatgt gttttccttt cactctgagc cacagccaga gggcaggcat tcagtctcct    8160
cttcaggctg ggctggggc actgagaact cacccaacac cttgctctca ctccttctgc     8220
aaaacaagaa agagctttgt gctgcagtag ccatgaagaa tgaaaggaag ctttaacta    8280 aaaaatgtca gagattattt tcaaccccct actgtggatc accagcaagg aggaaacaca    8340
acacagagac atttttttccc ctcaaattat caaaagaatc actgcatttg ttaaagagag    8400
caactgaatc aggaagcaga gttttgaaca tatcagaagt taggaatctg catcagagac    8460
aaatgcagtc atggttgttt gctgcatacc agccctaatc attagaagcc tcatggactt    8520
caaacatcat tccctctgac aagatgctct agcctaactc catgagataa aataaatctg    8580
cctttcagag ccaaagaaga gtccaccagc ttcttctcag tgtgaacaag agctccagtc    8640
aggttagtca gtccagtgca gtagaggaga ccagtctgca tcctctaatt ttcaaaggca    8700
agaagatttg tttaccctgg acaccaggca caagtgaggt cacagagctc ttagatatgc    8760
agtcctcatg agtgaggaga ctaaagcgca tgccatcaag acttcagtgt agagaaaacc    8820
tccaaaaaag cctcctcact acttctggaa tagctcagag gccgaggcgg cctcggcctc    8880
tgcataaata aaaaaaatta gtcagccatg gggcggagaa tgggcggaac tgggcggagt    8940
tagggcgggg atgggcggag ttaggggcgg gactatggtt gctgactaat tgagatgcat    9000
gctttgcata cttctgcctg ctggggagcc tggggacttt ccacacctgg ttgctgacta    9060
attgagatgc atgctttgca tacttctgcc tgctggggag cctggggact ttccacaccc    9120
taactgacac acattccaca gctgcattaa tgaatcggcc aacgcgcggg gagaggcggt    9180
ttgcgtattg ggcgctcttc cgcttcctcg ctcactgact cgctgcgctc ggtcgttcgg    9240
ctgcggcgag cggtatcagc tcactcaaag gcggtaatac ggttatccac agaatcaggg    9300
gataacgcag gaaagaacat gtgagcaaaa ggccagcaaa aggccaggaa ccgtaaaaag    9360
gccgcgttgc tggcgttttt ccataggctc cgcccccctg acgagcatca caaaaatcga    9420
cgctcaagtc agaggtggcg aaacccgaca ggactataaa gataccaggc gtttccccct    9480
ggaagctccc tcgtgcgctc tcctgttccg accctgccgc ttaccggata cctgtccgcc    9540
tttctccctt cgggaagcgt ggcgctttct catagctcac gctgtaggta tctcagttcg    9600
gtgtaggtcg ttcgctccaa gctgggctgt gtgcacgaac cccccgttca gcccgaccgc    9660
tgcgccttat ccggtaacta tcgtcttgag tccaacccgg taagacacga cttatcgcca    9720
ctggcagcag ccactggtaa caggattagc agagcgaggt atgtaggcgg tgctacagag    9780
ttcttgaagt ggtggcctaa ctacggctac actagaagaa cagtatttgg tatctgcgct    9840
ctgctgaagc cagttacctt cggaaaaaga gttggtagct cttgatccgg caaacaaacc    9900
```

| | |
|---|---|
| accgctggta gcggtggttt ttttgtttgc aagcagcaga ttacgcgcag aaaaaaagga | 9960 |
| tctcaagaag atcctttgat cttttctacg gggtctgacg ctcagtggaa cgaaaactca | 10020 |
| cgttaaggga ttttggtcat gagattatca aaaggatct tcacctagat ccttttaaat | 10080 |
| taaaaatgaa gttttaaatc aatctaaagt atatatgagt aaacttggtc tgacagttac | 10140 |
| caatgcttaa tcagtgaggc acctatctca gcgatctgtc tatttcgttc atccatagtt | 10200 |
| gcctgactcc tgcaaaccac gttgtgtctc aaaatctctg atgttacatt gcacaagata | 10260 |
| aaaatatatc atcatgaaca ataaaactgt ctgcttacat aaacagtaat acaaggggtg | 10320 |
| ttatgagcca tattcaacgg gaaacgtctt gctcgaggcc gcgattaaat tccaacatgg | 10380 |
| atgctgattt atatgggtat aaatgggctc gcgataatgt cgggcaatca ggtgcgacaa | 10440 |
| tctatcgatt gtatgggaag cccgatgcgc cagagttgtt tctgaaacat ggcaaaggta | 10500 |
| gcgttgccaa tgatgttaca gatgagatgg tcagactaaa ctggctgacg aatttatgc | 10560 |
| ctcttccgac catcaagcat tttatccgta ctcctgatga tgcatggtta ctcaccactg | 10620 |
| cgatccccgg gaaaacagca ttccaggtat tagaagaata tcctgattca ggtgaaaata | 10680 |
| ttgttgatgc gctggcagtg ttcctgcgcc ggttgcattc gattcctgtt tgtaattgtc | 10740 |
| cttttaacag cgatcgcgta tttcgtctcg ctcaggcgca atcacgaatg aataacggtt | 10800 |
| tggttgatgc gagtgatttt gatgacgagc gtaatggctg gcctgttgaa caagtctgga | 10860 |
| aagaaatgca taagcttttg ccattctcac cggattcagt cgtcactcat ggtgatttct | 10920 |
| cacttgataa ccttattttt gacgagggga aattaatagg ttgtattgat gttggacgag | 10980 |
| tcggaatcgc agaccgatac caggatcttg ccatcctatg gaactgcctc ggtgagtttt | 11040 |
| ctccttcatt acagaaacgg ctttttcaaa aatatggtat tgataatcct gatatgaata | 11100 |
| aattgcagtt tcatttgatg ctcgatgagt ttttctaagg cggcctgcc accatacccca | 11160 |
| cgccgaaaca gcgctcatg agcccgaagt ggcgagcccg atcttcccca tcggtgatgt | 11220 |
| cggcgatata ggcgccagca accgcacctg tggcgccggt gatgagggcg cgccaagtcg | 11280 |
| acgtccggca gtc | 11293 |

```
<210> SEQ ID NO 7
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 7
```

| | |
|---|---|
| ttggccactc cctctctgcg cgctcgctcg ctcactgagg ccgcccgggc aaagcccggg | 60 |
| cgtcgggcga cctttggtcg cccggcctca gtgagcgagc gagcgcgcag agagggagtg | 120 |
| gccaactcca tcactagggg ttcctgctag ctctgggtat ttaagcccga gtgagcacgc | 180 |
| agggtctcca ttttgaagcg ggaggttacg cgttcgtcga ctactagtgg gtaccagagc | 240 |
| tccctaggtt ctagaaccgg tgacgtctcc catggtgaag cttggatctg aattcggtac | 300 |
| ctagttatta atagtaatca attacggggt cattagttca tagcccatat atggagttcc | 360 |
| gcgttacata acttacggta aatggcccgc ctggctgacc gcccaacgac ccccgcccat | 420 |
| tgacgtcaat aatgacgtat gttcccatag taacgccaat agggactttc cattgacgtc | 480 |
| aatgggtgga gtatttacgg taaactgccc acttggcagt acatcaagtg tatcatatgc | 540 |
| caagtacgcc ccctattgac gtcaatgacg gtaaatggcc cgcctggcat tatgcccagt | 600 |
| acatgacctt atgggacttt cctacttggc agtacatcta cgtattagtc atcgctatta | 660 |

```
ccatggtcga ggtgagcccc acgttctgct tcactctccc catctccccc cctccccac     720
ccccaatttt gtatttattt attttttaat tattttgtgc agcgatgggg gcggggggg     780
ggggggggcg cgcgccaggc ggggcgggc ggggcgaggg gcgggcgggg gcgaggcgga     840
gaggtgcggc ggcagccaat cagagcgcg cgctccgaaa gtttccttt atggcgaggc     900
ggcggcggcg gcggccctat aaaaagcgaa gcgcgcggcg ggcgggagtc gctgcgacgc    960
tgccttcgcc ccgtgccccg ctccgccgcc gcctcgcgcc gcccgccccg gctctgactg   1020
accgcgttac tcccacaggt gagcgggcgg gacggccctt ctcctccggg ctgtaattag   1080
cgcttggttt aatgacggct tgtttctttt ctgtggctgc gtgaaagcct tgagggctc    1140
cgggagctag agcctctgct aaccatgttc atgccttctt ctttttccta cagctcctgg   1200
gcaacgtgct ggtattgtg ctgtctcatc attttggcaa agaattcctc gaagatccga   1260
agggaaagtc ttccacgact gtgggatccg ttcgaagata tcaccggttg agccaccatg   1320
gaattcagca gccccagcag agaggaatgc cccaagcctc tgagccgggt gtcaatcatg   1380
gccggatctc tgacaggact gctgctgctt caggccgtgt cttggcttc tggcgctaga   1440
ccttgcatcc ccaagagctt cggctacagc agcgtcgtgt gcgtgtgcaa tgccacctac   1500
tgcgacagct tcgaccctcc tacctttcct gctctgggca ccttcagcag atacgagagc   1560
accagatccg gcagacggat ggaactgagc atgggaccca tccaggccaa tcacacaggc   1620
actggcctgc tgctgacact gcagcctgag cagaaattcc agaaagtgaa aggcttcggc   1680
ggagccatga cagatgccgc cgctctgaat atcctggctc tgtctccacc agctcagaac   1740
ctgctgctca agagctactt cagcgaggaa ggcatcggct acaacatcat cagagtgccc   1800
atggccagct gcgacttcag catcaggacc tacacctacg ccgacacacc cgacgatttc   1860
cagctgcaca acttcagcct gcctgaagag gacaccaagc tgaagatccc tctgatccac   1920
agagccctgc agctggcaca agacccgtg tcactgctgg cctctccatg gacatctccc   1980
acctggctga aaacaaatgg cgccgtgaat ggcaagggca gcctgaaagg ccaacctggc   2040
gacatctacc accagacctg gccagatac ttcgtgaagt tcctggacgc ctatgccgag   2100
cacaagctgc agttttgggc cgtgacagcc gagaacgaac cttctgctgg actgctgagc   2160
ggctacccct ttcagtgcct gggctttaca cccgagcacc agcgggactt tatcgcccgt   2220
gatctgggac ccacactggc caatagcacc caccataatg tgcggctgct gatgctggac   2280
gaccagagac tgcttctgcc ccactgggct aaagtggtgc tgacagatcc tgaggccgcc   2340
aaatacgtgc acggaatcgc cgtgcactgg tatctggact tctctggcccc tgccaaggcc   2400
acactgggag agacacacag actgttcccc aacaccatgc tgttcgccag cgaagcctgt   2460
gtgggcagca gtttgggga acagagcgtg cggctcggca gctgggatag aggcatgcag   2520
tacagccaca gcatcatcac caacctgctg taccacgtcg tcggctggac cgactggaat   2580
ctggccctga tcctgaagg cggccctaac tgggtccgaa acttcgtgga cagccccatc   2640
atcgtggaca tcaccaagga caccttctac aagcagccca tgttctacca cctgggacac   2700
ttcagcaagt tcatccccga gggctctcag cgcgttggac tggtggcttc ccagaagaac   2760
gatctggacg ccgtggctct gatgcaccct gatggatctg ctgtggtggt ggtcctgaac   2820
cgcagcagca agatgtgcc cctgaccatc aaggatcccg ccgtgggatt cctggaaaca   2880
atcagccctg gctactccat ccacacctac ctgtggcgta gacagtgaca attgttaatt   2940
aagtttaaac cctcgaggcc gcaagcttat cgataatcaa cctctggatt acaaaatttg   3000
```

```
tgaaagattg actggtattc ttaactatgt tgctccttttt acgctatgtg gatacgctgc      3060
tttaatgcct ttgtatcatg ctattgcttc ccgtatggct ttcattttct cctccttgta      3120
taaatcctgg ttgctgtctc tttatgagga gttgtggccc gttgtcaggc aacgtggcgt      3180
ggtgtgcact gtgtttgctg acgcaacccc cactggttgg ggcattgcca ccacctgtca      3240
gctcctttcc gggactttcg cttcccccct ccctattgcc acggcggaac tcatcgccgc      3300
ctgccttgcc cgctgctgga caggggctcg gctgttgggc actgacaatt ccgtggtgtt      3360
gtcgggaaa tcatcgtcct ttccttggct gctcgcctgt gttgccacct ggattctgcg      3420
cgggacgtcc ttctgctacg tcccttcggc cctcaatcca gcggaccttc cttcccgcgg      3480
cctgctgccg gctctgcggc ctcttccgcg tcttcgcctt cgccctcaga cgagtcggat      3540
ctcccttggg gccgcctccc cgcatcgata ccgtcgacta gagctcgctg atcagcctcg      3600
actgtgcctt ctagttgcca gccatctgtt gtttgcccct ccccgtgcc ttccttgacc      3660
ctggaaggtg ccactcccac tgtcctttcc taataaaatg aggaaattgc atcgcattgt      3720
ctgagtaggt gtcattctat tctgggggt ggggtgggc aggacagcaa ggggaggat       3780
tgggaagaca atagcaggca tgctgggag agatccacga taacaaacag cttttttggg      3840
gtgaacatat tgactgaatt ccctgcaggt tggccactcc ctctctgcgc gctcgctcgc      3900
tcactgaggc cgcccgggca aagcccgggc gtcgggcgac cttggtcgc ccggcctcag      3960
tgagcgagcg agcgcgcaga gagggagtgg ccaactccat cactagggt tcctgcggcc      4020
gctcgtacgg tctcgaggaa ttcctgcagg ataacttgcc aacctcattc taaaatgtat      4080
atagaagccc aaaagacaat aacaaaaata ttcttgtaga acaaatggg aaagaatgtt       4140
ccactaaata tcaagattta gagcaaagca tgagatgtgt ggggatagac agtgaggctg      4200
ataaaataga gtagagctca gaaacagacc cattgatata tgtaagtgac ctatgaaaaa      4260
aatatggcat tttacaatgg gaaaatgatg gtcttttct tttttagaaa acagggaaa       4320
tatatttata tgtaaaaaat aaaagggaac ccatatgtca taccatacac acaaaaaat       4380
tccagtgaat tataagtcta aatggagaag gcaaactttt aaatctttta gaaaataata      4440
tagaagcatg cagaccagcc tggccaacat gatgaaaccc tctctactaa taataaaatc      4500
agtagaacta ctcaggacta ctttgagtgg gaagtccttt tctatgaaga cttctttggc      4560
caaaattagg ctctaaatgc aaggagatag tgcatcatgc ctggctgcac ttactgataa      4620
atgatgttat caccatcttt aaccaaatgc acaggaacaa gttatggtac tgatgtgctg      4680
gattgagaag gagctctact tccttgacag gacacatttg tatcaactta aaaaagcaga      4740
ttttttgccag cagaactatt cattcagagg taggaaactt agaatagatg atgtcactga      4800
ttagcatggc ttccccatct ccacagctgc ttcccaccca ggttgcccac agttgagttt      4860
gtccagtgct cagggctgcc cactctcagt aagaagcccc acaccagccc ctctccaaat      4920
atgttggctg ttccttccat taaagtgacc ccactttaga gcagcaagtg gatttctgtt      4980
tcttacagtt caggaaggag gagtcagctg tgagaacctg gagcctgaga tgcttctaag      5040
tcccactgct actggggtca gggaagccag actccagcat cagcagtcag gagcactaag      5100
cccttgccaa catcctgttt ctcagagaaa ctgcttccat tataatggtt gtcctttttt      5160
aagctatcaa gccaaacaac cagtgtctac cattattctc atcacctgaa gccaagggtt      5220
ctagcaaaag tcaagctgtc ttgtaatggt tgatgtgcct ccagcttctg tcttcagtca      5280
ctccactctt agcctgctct gaatcaactc tgaccacagt tccctggagc ccctgccacc      5340
tgctgcccct gccaccttct ccatctgcag tgctgtgcag ccttctgcac tcttgcagag      5400
```

```
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttcttttccct catagacctc catctctgtt ttccttagcc   5880
tgcagaaatc tggatggcta ttcacagaat gcctgtgctt tcagagttgc atttttcctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attccccttta aacatgaatg aatcttagat ttttaataa atagttttgg   6540 aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gccagagaga   6780
gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
atcctgtcta catcttctgc catactctgc catctaccat accacctctt accatctacc   7080
acaccatctt ttatctccat ccctctcaga agcctccaag ctgaatcctg ctttatgtgt   7140
tcatctcagc ccctgcatgg aaagctgacc ccagaggcag aactattccc agagagcttg   7200
gccaagaaaa acaaaactac cagcctggcc aggctcagga gtagtaagct gcagtgtctg   7260
ttgtgttcta gcttcaacag ctgcaggagt ccactctcca aatgctccac atttctcaca   7320
tcctcctgat tctggtcact acccatcttc aaagaacaga atatctcaca tcagcatact   7380
gtgaaggact agtcatgggt gcagctgctc agagctgcaa agtcattctg gatggtggag   7440
agcttacaaa catttcatga tgctccccc gctctgatgg ctggagccca atccctacac   7500
agactcctgc tgtatgtgtt ttcctttcac tctgagccca agccagaggg caggcattca   7560
gtctcctctt caggctgggg ctggggcact gagaactcac ccaacaccttt gctctcactc   7620 cttctgcaaa acaagaaaga gctttgtgct gcagtagcca tgaagaatga aaggaaggct   7680
ttaactaaaa aatgtcagag attattttca accccttact gtggatcacc agcaaggagg   7740
```

```
aaacacaaca cagagacatt ttttcccctc aaattatcaa aagaatcact gcatttgtta    7800
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700 atcagggga t aacgcaggaa agaacatgtg agcaaaaggc cagcaaaagg ccaggaaccg    8760
taaaaaggcc gcgttgctgg cgttttccca taggctccgc cccctgacg agcatcacaa    8820 aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720 agggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc   10020
accactgcga tccccgggaa aacagcattc caggtattag aagaatatcc tgattcaggt   10080
gaaaatattg ttgatgcgct ggcagtgttc ctgcgccggt tgcattcgat tcctgtttgt   10140
```

```
aattgtcctt taacagcga tcgcgtattt cgtctcgctc aggcgcaatc acgaatgaat    10200
aacggtttgg ttgatgcgag tgattttgat gacgagcgta atggctggcc tgttgaacaa    10260
gtctggaaag aaatgcataa gcttttgcca ttctcaccgg attcagtcgt cactcatggt    10320
gatttctcac ttgataacct tattttgac gaggggaaat taataggttg tattgatgtt    10380
ggacgagtcg gaatcgcaga ccgataccag gatcttgcca tcctatggaa ctgcctcggt    10440
gagttttctc cttcattaca gaaacggctt tttcaaaaat atggtattga taatcctgat    10500
atgaataaat tgcagtttca tttgatgctc gatgagtttt tctaagggcg gcctgccacc    10560 atcccacgc cgaaacaagc gctcatgagc ccgaagtggc gagcccgatc ttccccatcg    10620
gtgatgtcgg cgatataggc gccagcaacc gcacctgtgg cgccggtgat gagggcgcgc    10680
caagtcgacg tccggcagtc                                                10700
```

<210> SEQ ID NO 8
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 8

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactatt agatctgatg gccgcgctag ctctgggtat ttaagcccga gtgagcacgc     180
agggtctcca tttttgaagcg ggaggttacg cgttcgtcga ctactagtgg gtaccagagc     240
tccctaggtt ctagaaccgg tgacgtctcc catggtgaag cttggatctg aattcggtac     300
ctagttatta atagtaatca attacggggt cattagttca tagcccatat atggagttcc     360
gcgttacata acttacggta atggcccgc ctggctgacc gcccaacgac ccccgcccat     420
tgacgtcaat aatgacgtat gttcccatag taacgccaat agggactttc cattgacgtc     480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600 acatgaccctt atgggactttt cctacttggc agtacatcta cgtattagtc atcgctatta     660
ccatggtcga ggtgagcccc acgttctgct tcactctccc catctcccc ccctccccac      720 ccccaattt gtatttattt attttttaat tattttgtgc agcgatgggg gcgggggggg      780
ggggggggcg cgcgccaggc ggggcggggc ggggcgaggg gcgggcggg gcgaggcgga      840 gaggtgcggc ggcagccaat cagagcggcg cgctccgaaa gtttccttt atggcgaggc      900 ggcggcggcg gcggccctat aaaaagcgaa gcgcgcggcg ggcgggagtc gctgcgacgc      960
tgccttcgcc ccgtgccccg ctccgccgcc gcctcgcgcc gcccgccccg gctctgactg     1020
accgcgttac tcccacaggt gagcgggcgg gacggccctt ctcctccggg ctgtaattag     1080
cgcttggttt aatgacggct tgtttctttt ctgtggctgc gtgaaagcct tgaggggctc     1140
cgggagctag agcctctgct aaccatgttc atgccttctt ctttttccta cagctcctgg     1200
gcaacgtgct ggttattgtg ctgtctcatc attttggcaa agaattcctc gaagatccga     1260
agggaaagtc ttccacgact gtgggatccg ttcgaagata tcaccggttg agccaccatg     1320
gaattcagca gccccagcag agaggaatgc ccaagcctc tgagccgggt gtcaatcatg     1380
gccggatctc tgacaggact gctgctgctt caggccgtgt cttgggcttc tggcgctaga     1440
```

-continued

```
ccttgcatcc ccaagagctt cggctacagc agcgtcgtgt gcgtgtgcaa tgccacctac    1500
tgcgacagct tcgaccctcc tacctttcct gctctgggca ccttcagcag atacgagagc    1560
accagatccg gcagacggat ggaactgagc atgggaccca tccaggccaa tcacacaggc    1620
actggcctgc tgctgacact gcagcctgag cagaaattcc agaaagtgaa aggcttcggc    1680
ggagccatga cagatgccgc cgctctgaat atcctggctc tgtctccacc agctcagaac    1740
ctgctgctca agagctactt cagcgaggaa ggcatcggct acaacatcat cagagtgccc    1800
atggccagct gcgacttcag catcaggacc tacacctacg ccgacacacc cgacgatttc    1860
cagctgcaca acttcagcct gcctgaagag gacaccaagc tgaagatccc tctgatccac    1920
agagccctgc agctggcaca agacccgtg tcactgctgg cctctccatg gacatctccc     1980
acctggctga aaacaaatgg cgccgtgaat ggcaagggca gcctgaaagg ccaacctggc    2040
gacatctacc accagacctg ggccagatac ttcgtgaagt tcctggacgc ctatgccgag    2100
cacaagctgc agttttgggc cgtgacagcc gagaacgaac cttctgctgg actgctgagc    2160
ggctacccct ttcagtgcct gggctttaca cccgagcacc agcggacttt atcgcccgt     2220 gatctgggac ccacactggc caatagcacc accataatg tgcggctgct gatgctggac     2280
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400 acactggag agacacacag actgttcccc aacaccatgc tgttcgccag cgaagcctgt     2460
gtgggcagca gttttggga acagagcgtg cggctcggca gctgggatag aggcatgcag     2520
tacagccaca gcatcatcac caacctgctg taccacgtcg tcggctggac cgactggaat    2580
ctggccctga tcctgaagg cggccctaac tgggtccgaa acttcgtgga cagccccatc     2640
atcgtggaca tcaccaagga caccttctac aagcagccca tgttctacca cctgggacac    2700
ttcagcaagt tcatccccga gggctctcag cgcgttggac tggtggcttc ccagaagaac    2760
gatctggacg ccgtggctct gatgcaccct gatggatctg ctgtggtggt ggtcctgaac    2820
cgcagcagca agatgtgcc cctgaccatc aaggatcccg ccgtgggatt cctggaaaca     2880
atcagccctg ctactccat ccacacctac ctgtggcgta cagtgaca attgttaatt        2940 aagtttaaac cctcgaggcc gcaagcttat cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240 gctccttttcc gggactttcg ctttcccct ccctattgcc acggcggaac tcatcgccgc     3300
ctgccttgcc cgctgctgga cagggctcg gctgttgggc actgacaatt ccgtggtgtt     3360
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
actgtgcctt ctagttgcca gccatctgtt gtttgcccct ccccgtgcc ttccttgacc     3660 ctggaaggtg ccactcccac tgtcctttcc taataaaatg aggaaattgc atcgcattgt    3720
ctgagtaggt gtcattctat tctgggggt ggggtgggg aggacagcaa ggggaggat       3780 tgggaagaca atagcaggca tgctggggag agatccacga taacaaacag cttttttggg    3840
```

```
gtgaacatat tgactgaatt ccctgcaggt tggccactcc ctctctgcgc gctcgctcgc    3900
tcactgaggc cgcccgggca aagcccgggc gtcgggcgac ctttggtcgc ccggcctcag    3960
tgagcgagcg agcgcgcaga gagggagtgg ccaactccat cactagggt tcctgcggcc     4020 gctcgtacgg tctcgaggaa ttcctgcagg ataacttgcc aacctcattc taaaatgtat    4080
atagaagccc aaaagacaat aacaaaaata ttcttgtaga acaaatggg aagaatgtt     4140 ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtcttttct tttttagaaa acagggaaa     4320 tatatttata tgtaaaaaat aaagggaac ccatatgtca taccatacac acaaaaaat     4380 tccagtgaat tataagtcta aatggagaag gcaaaacttt aaatctttta gaaataata    4440 tagaagcatg cagaccagcc tggccaacat gatgaaaccc tctctactaa taataaaatc   4500
agtagaacta ctcaggacta ctttgagtgg gaagtccttt tctatgaaga cttctttggc   4560
caaaattagg ctctaaatgc aaggagatag tgcatcatgc ctggctgcac ttactgataa   4620
atgatgttat caccatcttt aaccaaatgc acaggaacaa gttatggtac tgatgtgctg   4680
gattgagaag gagctctact tccttgacag gacacatttg tatcaactta aaaaagcaga   4740
tttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtcctttttt   5160
aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttctttccct catagacctc catctctgtt tccttagcc    5880 tgcagaaatc tggatggcta ttcacagaat gcctgtgctt tcagagttgc atttttctc    5940 tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
```

```
ccttacctct gccctaccca ggacaaaccc aagagccact gtttctgtga tgtcctctcc      6240
agccctaatt aggcatcatg acttcagcct gaccttccat gctcagaagc agtgctaatc      6300
cacttcagat gagctgctct atgcaacaca ggcagagcct acaaaccttt gcaccagagc      6360
cctccacata tcagtgtttg ttcatactca cttcaacagc aaatgtgact gctgagatta      6420
agattttaca caagatggtc tgtaatttca cagttagttt tatcccatta ggtatgaaag      6480
aattagcata attcccctta aacatgaatg aatcttagat tttttaataa atagttttgg      6540
aagtaaagac agagacatca ggagcacaag gaatagcctg agaggacaaa cagaacaaga      6600
aagagtctgg aaatacacag gatgttcttg gcctcctcaa agcaagtgca agcagatagt      6660
accagcagcc ccaggctatc agagcccagt gaagagaagt accatgaaag ccacagctct      6720
aaccaccctg ttccagagtg acagacagtc cccaagacaa gccagcctga gccagagaga      6780
gaactgcaag agaaagtttc taatttaggt tctgttagat tcagacaagt gcaggtcatc      6840
ctctctccac agctactcac ctctccagcc taacaaagcc tgcagtccac actccaaccc      6900
tggtgtctca cctcctagcc tctcccaaca tcctgctctc tgaccatctt ctgcatctct      6960
catctcacca tctcccactg tctacagcct actcttgcaa ctaccatctc attttctgac      7020
atcctgtcta tcttctgc catactctgc catctaccat accacctctt accatctacc      7080
acaccatctt ttatctccat ccctctcaga agcctccaag ctgaatcctg ctttatgtgt      7140
tcatctcagc ccctgcatgg aaagctgacc ccagaggcag aactattccc agagagcttg      7200
gccaagaaaa acaaaactac cagcctggcc aggctcagga gtagtaagct gcagtgtctg      7260
ttgtgttcta gcttcaacag ctgcaggagt tccactctca aatgctccac atttctcaca      7320
tcctcctgat tctggtcact acccatcttc aaagaacaga atatctcaca tcagcatact      7380
gtgaaggact agtcatgggt gcagctgctc agagctgcaa agtcattctg gatggtggag      7440
agcttacaaa catttcatga tgctcccccc gctctgatgg ctggagccca atccctacac      7500
agactcctgc tgtatgtgtt tcctttcac tctgagccac agccagaggg caggcattca      7560
gtctcctctt caggctgggg ctggggcact gagaactcac ccaacaccctt gctctcactc      7620 cttctgcaaa acaagaaaga gctttgtgct gcagtagcca tgaagaatga aaggaaggct      7680
ttaactaaaa aatgtcagag attattttca acccccttact gtggatcacc agcaaggagg      7740
aaacacaaca cagagacatt ttttcccctc aaattatcaa aagaatcact gcatttgtta      7800
aagagagcaa ctgaatcagg aagcagagtt ttgaacatat cagaagttag gaatctgcat      7860
cagagacaaa tgcagtcatg gttgtttgct gcataccagc cctaatcatt agaagcctca      7920
tggacttcaa acatcattcc ctctgacaag atgctctagc ctaactccat gagataaaat      7980
aaatctgcct ttcagagcca agaagagtc caccagcttc ttctcagtgt gaacaagagc      8040
tccagtcagg ttagtcagtc cagtgcagta gaggagacca gtctgcatcc tctaattttc      8100
aaaggcaaga agatttgttt accctggaca ccaggcacaa gtgaggtcac agagctctta      8160
gatatgcagt cctcatgagt gaggagacta aagcgcatgc catcaagact tcagtgtaga      8220
gaaaacctcc aaaaaagcct cctcactact tctggaatag ctcagaggcc gaggcggcct      8280
cggcctctgc ataaataaaa aaaattagtc agccatgggg cggagaatgg gcggaactgg      8340
gcggagttag gggcgggatg ggcggagtta ggggcgggac tatggttgct gactaattga      8400
gatgcatgct ttgcatactt ctgcctgctg gggagcctgg ggactttcca cacctggttg      8460
ctgactaatt gagatgcatg ctttgcatac ttctgcctgc tggggagcct ggggactttc      8520 cacacccta ctgacacaca ttccacagct gcattaatga atcggccaac gcgcggggag      8580
```

```
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttttcca taggctccgc ccccctgacg agcatcacaa    8820
aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720
aggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc    10020
accactgcga tccccgggaa aacagcattc caggtattag aagaatatcc tgattcaggt    10080
gaaaatattg ttgatgcgct ggcagtgttc ctgcgccggt tgcattcgat tcctgtttgt    10140
aattgtcctt ttaacagcga tcgcgtattt cgtctcgctc aggcgcaatc acgaatgaat    10200
aacggtttgg ttgatgcgag tgattttgat gacgagcgta atggctggcc tgttgaacaa    10260
gtctggaaag aaatgcataa gcttttgcca ttctcaccgg attcagtcgt cactcatggt    10320
gatttctcac ttgataacct tattttgac gagggggaaat taataggttg tattgatgtt    10380
ggacgagtcg gaatcgcaga ccgataccag gatcttgcca tcctatggaa ctgcctcggt    10440
gagttttctc cttcattaca gaaacggctt tttcaaaaat atggtattga taatcctgat    10500
atgaataaat tgcagtttca tttgatgctc gatgagtttt tctaagggcg gcctgccacc    10560
atacccacgc cgaaacaagc gctcatgagc ccgaagtggc gagcccgatc ttccccatcg    10620
gtgatgtcgg cgatataggc gccagcaacc gcacctgtgg cgccggtgat gagggcgcgc    10680
caagtcgacg tccggcagtc                                                10700
```

<210> SEQ ID NO 9
<211> LENGTH: 10700
<212> TYPE: DNA
<213> ORGANISM: Artificial Sequence
<220> FEATURE:

<223> OTHER INFORMATION: Synthetic polynucleotide

<400> SEQUENCE: 9

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
ctagttatta atagtaatca attacggggt cattagttca tagcccatat atggagttcc     360
gcgttacata acttacggta aatggcccgc ctggctgacc gcccaacgac ccccgcccat     420
tgacgtcaat aatgacgtat gttcccatag taacgccaat agggactttc cattgacgtc     480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600
acatgacctt atgggacttt cctacttggc agtacatcta cgtattagtc atcgctatta     660
ccatggtcga ggtgagcccc acgttctgct tcactctccc catctccccc cctccccac     720
ccccaattt tgtatttattt attttttaat tattttgtgc agcgatgggg gcggggggggg     780
ggggggggcg cgcgccaggc ggggcgggc ggggcgaggg gcgggggggg gcgaggcgga     840
gaggtgcggc ggcagccaat cagagcggcg cgctccgaaa gtttccttt atggcgaggc     900
ggcggcggcg gcggccctat aaaaagcgaa gcgcgcggcg ggcgggagtc gctgcgacgc     960
tgccttcgcc ccgtgccccg ctccgccgcc gcctcgcgcc gcccgccccg gctctgactg    1020
accgcgttac tcccacaggt gagcgggcgg gacggccctt ctcctccggg ctgtaattag    1080
cgcttggttt aatgacggct tgtttctttt ctgtggctgc gtgaaagcct tgaggggctc    1140
cgggagctag agcctctgct aaccatgttc atgccttctt cttttttccta cagctcctgg    1200
gcaacgtgct ggttattgtg ctgtctcatc attttggcaa agaattcctc gaagatccga    1260
agggaaagtc ttccacgact gtgggatccg ttcgaagata tcaccggttg agccaccatg    1320
gaattcagca gccccagcag agaggaatgc cccaagcctc tgagccgggt gtcaatcatg    1380
gccggatctc tgacaggact gctgctgctt caggccgtgt cttgggcttc tggcgctaga    1440
ccttgcatcc ccaagagctt cggctacagc agcgtcgtgt gcgtgtgcaa tgccacctac    1500
tgcgacagct cgacccctcc tacctttcct gctctgggca ccttcagcag atacgagagc    1560
accagatccg gcagacggat ggaactgagc atgggaccca tccaggccaa tcacacaggc    1620
actggcctgc tgctgacact gcagcctgag cagaaattcc agaaagtgaa aggcttcggc    1680
ggagccatga cagatgccgc cgctctgaat atcctggctc tgtctccacc agctcagaac    1740
ctgctgctca agagctactt cagcgaggaa ggcatcggct acaacatcat cagagtgccc    1800
atggccagct gcgacttcag catcaggacc tacacctacg ccgacacacc cgacgatttc    1860
cagctgcaca acttcagcct gcctgaagag gacaccaagc tgaagatccc tctgatccac    1920
agagccctgc agctggcaca aagacccgtg tcactgctgg cctctccatg gacatctccc    1980
acctggctga aaacaaatgg cgccgtgaat ggcaagggca gcctgaaagg ccaacctggc    2040
gacatctacc accagacctg ggccagatac ttcgtgaagt tcctggacgc ctatgccgag    2100
cacaagctgc agttttggggc cgtgacagcc gagaacgaac cttctgctgg actgctgagc    2160
ggctaccccc ttcagtgcct gggctttaca cccgagcacc agcgggactt tatcgcccgt    2220
gatctgggac ccacactggc caatagcacc caccataatg tgcggctgct gatgctggac    2280
```

```
gaccagagac tgcttctgcc ccactgggct aaagtggtgc tgacagatcc tgaggccgcc    2340
aaatacgtgc acggaatcgc cgtgcactgg tatctggact ttctggcccc tgccaaggcc    2400
acactgggag agacacacag actgttcccc aacaccatgc tgttcgccag cgaagcctgt    2460
gtgggcagca agttttggga acagagcgtg cggctcggca gctgggatag aggcatgcag    2520
tacagccaca gcatcatcac caacctgctg taccacgtcg tcggctggac cgactggaat    2580
ctggccctga atcctgaagg cggccctaac tgggtccgaa acttcgtgga cagccccatc    2640
atcgtggaca tcaccaagga caccttctac aagcagccca tgttctacca cctgggacac    2700
ttcagcaagt tcatcccga gggctctcag cgcgttggac tggtggcttc ccagaagaac    2760
gatctggacg ccgtggctct gatgcaccct gatggatctg ctgtggtggt ggtcctgaac    2820
cgcagcagca aagatgtgcc cctgaccatc aaggatcccg ccgtgggatt cctggaaaca    2880
atcagccctg gctactccat ccacacctac ctgtggcgta acagtgacaa attgttaatt    2940
aagtttaaac cctcgaggcc gcaagcttat cgataatcaa cctctggatt acaaaatttg    3000
tgaaagattg actggtattc ttaactatgt tgctcctttt acgctatgtg gatacgctgc    3060
tttaatgcct ttgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240
gctcctttcc gggactttcg ctttcccct cctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540
ctccctttgg gccgcctccc cgcatcgata ccgtcgacta gagctcgctg atcagcctcg    3600
actgtgcctt ctagttgcca gccatctgtt gtttgcccct ccccgtgcc ttccttgacc    3660 ctggaaggtg ccactcccac tgtcctttcc taataaaatg aggaaattgc atcgcattgt    3720
ctgagtaggt gtcattctat tctggggggt ggggtgggc aggacagcaa gggggaggat    3780
tgggaagaca atagcaggca tgctgggag agatccacga taacaaacag cttttttggg    3840
gtgaacatat tgactgaatt ccctgcaggt tggccactcc ctctctgcgc gctcgctcgc    3900
tcactgaggc cgcccgggca aagcccgggc gtcgggcgac ctttggtcgc ccggcctcag    3960
tgagcgagcg agcgcgcaga gagggagtgg ccaactccat cactaggggt tcctgcggcc    4020
gctcgtacgg tctcgaggaa ttcctgcagg ataacttgcc aacctcattc taaaatgtat    4080
atagaagccc aaaagacaat aacaaaaata ttcttgtaga acaaatggg aaagaatgtt    4140 ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatggcat tttacaatgg gaaaatgatg gtctttttct tttttagaaa aacagggaaa    4320
tatatttata tgtaaaaaat aaagggaac ccatatgtca taccatacac acaaaaaaat    4380
tccagtgaat tataagtcta aatggagaag gcaaactttt aaatctttta gaaataata    4440 tagaagcatg cagaccagcc tggccaacat gatgaaaccc tctctactaa taataaatc    4500 agtagaacta ctcaggacta cttttgagtgg gaagtccttt tctatgaaga cttcttggc    4560 caaaattagg ctctaaatgc aaggagatag tgcatcatgc ctggctgcac ttactgataa    4620
```

```
atgatgttat caccatcttt aaccaaatgc acaggaacaa gttatggtac tgatgtgctg   4680
gattgagaag gagctctact tccttgacag gacacatttg tatcaactta aaaaagcaga   4740 ttttttgccag cagaactatt cattcagagg taggaaactt agaatagatg atgtcactga   4800
ttagcatggc ttccccatct ccacagctgc ttcccaccca ggttgcccac agttgagttt   4860
gtccagtgct cagggctgcc cactctcagt aagaagcccc acaccagccc ctctccaaat   4920
atgttggctg ttccttccat taaagtgacc ccactttaga gcagcaagtg gatttctgtt   4980
tcttacagtt caggaaggag gagtcagctg tgagaacctg gagcctgaga tgcttctaag   5040
tcccactgct actggggtca gggaagccag actccagcat cagcagtcag gagcactaag   5100
cccttgccaa catcctgttt ctcagagaaa ctgcttccat tataatggtt gtccttttt    5160 aagctatcaa gccaaacaac cagtgtctac cattattctc atcacctgaa gccaagggtt   5220
ctagcaaaag tcaagctgtc ttgtaatggt tgatgtgcct ccagcttctg tcttcagtca   5280
ctccactctt agcctgctct gaatcaactc tgaccacagt tccctggagc ccctgccacc   5340
tgctgcccct gccaccttct ccatctgcag tgctgtgcag ccttctgcac tcttgcagag   5400
ctaataggtg gagacttgaa ggaagaggag gaaagtttct cataatagcc ttgctgcaag   5460
ctcaaatggg aggtgggcac tgtgcccagg agccttggag caaaggctgt gcccaacctc   5520
tgactgcatc caggtttggt cttgacagag ataagaagcc ctggcttttg gagccaaaat   5580
ctaggtcaga cttaggcagg attctcaaag tttatcagca gaacatgagg cagaagaccc   5640
tttctgctcc agcttcttca ggctcaacct tcatcagaat agatagaaag agaggctgtg   5700
agggttctta aaacagaagc aaatctgact cagagaataa acaacctcct agtaaactac   5760
agcttagaca gagcatctgg tggtgagtgt gctcagtgtc ctactcaact gtctggtatc   5820
agccctcatg aggacttctc ttcttttccct catagacctc catctctgtt ttccttagcc   5880
tgcagaaatc tggatggcta ttcacagaat gcctgtgctt tcagagttgc attttttctc   5940
tggtattctg gttcaagcat ttgaaggtag gaaaggttct ccaagtgcaa gaaagccagc   6000
cctgagcctc aactgcctgg ctagtgtggt cagtaggatg caaaggctgt tgaatgccac   6060
aaggccaaac tttaacctgt gtaccacaag cctagcagca gaggcagctc tgctcactgg   6120
aactctctgt cttctttctc ctgagccttt tcttttcctg agttttctag ctctcctcaa   6180
ccttacctct gccctaccca ggacaaaccc aagagccact gtttctgtga tgtcctctcc   6240
agccctaatt aggcatcatg acttcagcct gaccttccat gctcagaagc agtgctaatc   6300
cacttcagat gagctgctct atgcaacaca ggcagagcct acaaaccttt gcaccagagc   6360
cctccacata tcagtgtttg ttcatactca cttcaacagc aaatgtgact gctgagatta   6420
agattttaca caagatggtc tgtaatttca cagttagttt tatcccatta ggtatgaaag   6480
aattagcata attcccctta aacatgaatg aatcttagat ttttttaataa atagttttgg   6540 aagtaaagac agagacatca ggagcacaag gaatagcctg agaggacaaa cagaacaaga   6600
aagagtctgg aaatacacag gatgttcttg gcctcctcaa agcaagtgca agcagatagt   6660
accagcagcc ccaggctatc agagcccagt gaagagaagt accatgaaag ccacagctct   6720
aaccaccctg ttccagagtg acagacagtc cccaagacaa gccagcctga gcagagaga    6780 gaactgcaag agaaagtttc taatttaggt tctgttagat tcagacaagt gcaggtcatc   6840
ctctctccac agctactcac ctctccagcc taacaaagcc tgcagtccac actccaaccc   6900
tggtgtctca cctcctagcc tctcccaaca tcctgctctc tgaccatctt ctgcatctct   6960
catctcacca tctcccactg tctacagcct actcttgcaa ctaccatctc attttctgac   7020
```

```
atcctgtcta catcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctccccc gctctgatgg ctggagccca atccctacac     7500
agactcctgc tgtatgtgtt ttcctttcac tctgagccac agccagaggg caggcattca    7560
gtctcctctt caggctgggg ctggggcact gagaactcac ccaacacctt gctctcactc    7620
cttctgcaaa acaagaaaga gctttgtgct gcagtagcca tgaagaatga aggaaggct     7680 ttaactaaaa aatgtcagag attattttca accccttact gtggatcacc agcaaggagg    7740
aaacacaaca cagagacatt ttttcccctc aaattatcaa agaatcact gcatttgtta     7800 aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca aagaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520 cacacctaa ctgacacaca ttccacagct gcattaatga atcggccaac gcgcggggag     8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700 atcagggat aacgcaggaa agaacatgtg agcaaaaggc cagcaaaagg ccaggaaccg     8760
taaaaaggcc gcgttgctgg cgttttccca taggctccgc cccctgacg agcatcacaa     8820 aaatcgacgc tcaagtcaga ggtggcgaaa cccgacagga ctataaagat accaggcgtt    8880
tccccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
```

```
aaaaggatct caagaagatc ctttgatctt ttctacgggg tctgacgctc agtggaacga    9420
aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720
aggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc   10020
accactgcga tccccgggaa aacagcattc caggtattag aagaatatcc tgattcaggt   10080
gaaaatattg ttgatgcgct ggcagtgttc ctgcgccggt tgcattcgat tcctgtttgt   10140
aattgtcctt ttaacagcga tcgcgtattt cgtctcgctc aggcgcaatc acgaatgaat   10200
aacggtttgg ttgatgcgag tgattttgat gacgagcgta atggctggcc tgttaacaa    10260
gtctggaaag aaatgcataa gcttttgcca ttctcaccgg attcagtcgt cactcatggt   10320
gatttctcac ttgataacct tattttgac gaggggaaat taataggttg tattgatgtt    10380
ggacgagtcg gaatcgcaga ccgataccag gatcttgcca tcctatggaa ctgcctcggt   10440
gagttttctc cttcattaca gaaacggctt tttcaaaaat atggtattga taatcctgat   10500
atgaataaat tgcagtttca tttgatgctc gatgagtttt tctaagggcg gcctgccacc   10560
atacccacgc cgaaacaagc gctcatgagc ccgaagtggc gagcccgatc ttccccatcg   10620
gtgatgtcgg cgatataggc gccagcaacc gcacctgtgg cgccggtgat gagggcgcgc   10680
caagtcgacg tccggcagtc                                               10700
```

<210> SEQ ID NO 10
<211> LENGTH: 10700
<212> TYPE: DNA
<213> ORGANISM: Artificial Sequence
<220> FEATURE:
<223> OTHER INFORMATION: Synthetic polynucleotide

<400> SEQUENCE: 10

```
ttggccactc cctctctgcg cgctcgctcg ctcactgagg ccgcccgggc aaagcccggg      60
cgtcgggcga cctttggtcg cccggcctca gtgagcgagc gagcgcgcag agagggagtg     120
gccaactcca tcactagggg ttcctgctag ctctgggtat ttaagcccga gtgagcacgc     180
agggtctcca ttttgaagcg ggaggttacg cgttcgtcga ctactagtgg gtaccagagc     240
tccctaggtt ctagaaccgg tgacgtctcc catggtgaag cttggatctg aattcggtac     300
ctagttatta atagtaatca attacggggt cattagttca tagcccatat atggagttcc     360
gcgttacata acttacggta aatggcccgc ctggctgacc gcccaacgac ccccgcccat     420
tgacgtcaat aatgacgtat gttcccatag taacgccaat agggactttc cattgacgtc     480
aatgggtgga gtatttacgg taaactgccc acttggcagt acatcaagtg tatcatatgc     540
caagtacgcc ccctattgac gtcaatgacg gtaaatggcc cgcctggcat tatgcccagt     600
acatgacctt atgggacttt cctacttggc agtacatcta cgtattagtc atcgctatta     660
ccatggtcga ggtgagcccc acgttctgct tcactctccc catctccccc cctccccac     720
```

```
ccccaattttt gtatttattt atttttaat   tattttgtgc agcgatgggg gcggggggg    780
ggggggggcg  cgcgccaggc ggggcgggc   ggggcgaggg gcggggcggg gcgaggcgga   840
gaggtgcggc  ggcagccaat cagagcggcg  cgctccgaaa gtttccttt  atggcgaggc   900
ggcggcggc   gcggccctat aaaaagcgaa  gcgcgcggcg ggcgggagtc gctgcgacgc   960
tgccttcgcc  ccgtgccccg ctccgccgcc  gcctcgcgcc gcccgccccg gctctgactg  1020
accgcgttac  tcccacaggt gagcgggcgg  gacggcccct tcctccgggg ctgtaattag  1080
cgcttggttt  aatgacggct tgtttctttt  ctgtggctgc gtgaaagcct tgagggctc   1140
cgggagctag  agcctctgct aaccatgttc  atgccttctt ctttttccta cagctcctgg  1200
gcaacgtgct  ggttattgtg ctgtctcatc  attttggcaa agaattcctc gaagatccga  1260
agggaaagtc  ttccacgact gtgggatccg  ttcgaagata tcaccggttg agccaccatg  1320
gaattcagca  gccccagcag agaggaatgc  cccaagcctc tgagccgggt gtcaatcatg  1380
gccggatctc  tgacaggact gctgctgctt  caggccgtgt cttgggcttc tggcgctaga  1440
ccttgcatcc  ccaagagctt cggctacagc  agcgtcgtgt gcgtgtgcaa tgccacctac  1500
tgcgacagct  tcgaccctcc tacctttcct  gctctgggca ccttcagcag atacgagagc  1560
accagatccg  gcagacggat ggaactgagc  atgggaccca tccaggccaa tcacacaggc  1620
actggcctgc  tgctgacact gcagcctgag  cagaaattcc agaaagtgaa aggcttcggc  1680
ggagccatga  cagatgccgc cgctctgaat  atcctggctc tgtctccacc agctcagaac  1740
ctgctgctca  agagctactt cagcgaggaa  ggcatcggct acaacatcat cagagtgccc  1800
atggccagct  gcgacttcag catcaggacc  tacacctacg ccgacacacc cgacgatttc  1860
cagctgcaca  acttcagcct gcctgaagag  gacaccaagc tgaagatccc tctgatccac  1920
agagccctgc  agctggcaca aagacccgtg  tcactgctgg cctctccatg gacatctccc  1980
acctggctga  aaacaaatgg cgccgtgaat  ggcaagggca gcctgaaagg ccaacctggc  2040
gacatctacc  accagacctg gccagatac   ttcgtgaagt tcctggacgc ctatgccgag  2100
cacaagctgc  agttttgggc cgtgacagcc  gagaacgaac cttctgctgg actgctgagc  2160
ggctacccct  ttcagtgcct gggctttaca  cccgagcacc agcggacttt tatcgcccgt  2220
gatctgggac  ccacactggc caatagcacc  caccataatg tgcggctgct gatgctggac  2280
gaccagagac  tgcttctgcc ccactgggct  aaagtggtgc tgacagatcc tgaggccgcc  2340
aaatacgtgc  acggaatcgc cgtgcactgg  tatctggact ttctggcccc tgccaaggcc  2400
acactgggag  agacacacag actgttcccc  aacaccatgc tgttcgccag cgaagcctgt  2460
gtgggcagca  gttttgggga acagagcgtg  cggctcggca gctgggatag aggcatgcag  2520
tacagccaca  gcatcatcac caacctgctg  taccacgtcg tcggctggac cgactggaat  2580
ctggccctga  atcctgaagg cggccctaac  tgggtccgaa acttcgtgga cagccccatc  2640
atcgtggaca  tcaccaagga caccttctac  aagcagccca tgttctacca cctgggacac  2700
ttcagcaagt  tcatccccga gggctctcag  cgcgttggac tggtggcttc ccagaagaac  2760
gatctggacg  ccgtggctct gatgcaccct  gatggatctg ctgtggtggt ggtcctgaac  2820
cgcagcagca  aagatgtgcc cctgaccatc  aaggatcccg ccgtgggatt cctgaaaaca  2880
atcagccctg  gctactccat ccacacctac  ctgtggcgta gacagtgaca attgttaatt  2940
aagtttaaac  cctcgaggcc gcaagctat   cgataatcaa cctctggatt acaaaatttg  3000
tgaaagattg  actggtattc ttaactatgt  tgctcctttt acgctatgtg gatacgctgc  3060
```

```
tttaatgcct tgtatcatg ctattgcttc ccgtatggct ttcattttct cctccttgta    3120
taaatcctgg ttgctgtctc tttatgagga gttgtggccc gttgtcaggc aacgtggcgt    3180
ggtgtgcact gtgtttgctg acgcaacccc cactggttgg ggcattgcca ccacctgtca    3240
gctcctttcc gggactttcg ctttccccct ccctattgcc acggcggaac tcatcgccgc    3300
ctgccttgcc cgctgctgga caggggctcg gctgttgggc actgacaatt ccgtggtgtt    3360
gtcggggaaa tcatcgtcct ttccttggct gctcgcctgt gttgccacct ggattctgcg    3420
cgggacgtcc ttctgctacg tcccttcggc cctcaatcca gcggaccttc cttcccgcgg    3480
cctgctgccg gctctgcggc ctcttccgcg tcttcgcctt cgccctcaga cgagtcggat    3540 ctcccttttgg gccgcctccc cgcatcgata ccgtcgacta gagctcgctg atcagcctcg    3600
actgtgcctt ctagttgcca gccatctgtt gtttgcccct cccccgtgcc ttccttgacc    3660
ctggaaggtg ccactcccac tgtcctttcc taataaaatg aggaaattgc atcgcattgt    3720
ctgagtaggt gtcattctat tctgggggt ggggtgggc aggacagcaa ggggaggat    3780 tgggaagaca atagcaggca tgctgggag agatccacga taacaaacag cttttttggg    3840
gtgaacatat tgactgaatt ccctgcagga ggaaccccta gtgatggagt tggccactcc    3900
ctctctgcgc gctcgctcgc tcactgaggc cgcccgggca aagcccggc gtcgggcgac    3960 cttggtcgc ccggcctcag tgagcgagcg agcgcgcaga gagggagtgg ccaagcggcc    4020
gctcgtacgg tctcgaggaa ttcctgcagg ataacttgcc aacctcattc taaaatgtat    4080
atagaagccc aaaagacaat aacaaaaata ttcttgtaga acaaaatggg aaagaatgtt    4140
ccactaaata tcaagattta gagcaaagca tgagatgtgt ggggatagac agtgaggctg    4200
ataaaataga gtagagctca gaaacagacc cattgatata tgtaagtgac ctatgaaaaa    4260
aatatgccat tttacaatgg gaaaatgatg gtctttttct tttttagaaa acagggaaa    4320 tatatttata tgtaaaaaat aaaagggaac ccatatgtca taccatacac acaaaaaaat    4380
tccagtgaat tataagtcta aatggagaag gcaaaacttt aaatctttta gaaaataata    4440
tagaagcatg cagaccagcc tggccaacat gatgaaaccc tctctactaa taataaaatc    4500
agtagaacta ctcaggacta cttttgagtgg gaagtccttt tctatgaaga cttcttttggc    4560 caaaattagg ctctaaatgc aaggagatag tgcatcatgc ctggctgcac ttactgataa    4620
atgatgttat caccatcttt aaccaaatgc acaggaacaa gttatggtac tgatgtgctg    4680
gattgagaag gagctctact tccttgacag gacacatttg tatcaactta aaaaagcaga    4740
tttttgccag cagaactatt cattcagagg taggaaactt agaatagatg atgtcactga    4800
ttagcatggc ttccccatct ccacagctgc ttcccaccca ggttgcccac agttgagttt    4860
gtccagtgct cagggctgcc cactctcagt aagaagcccc acaccagccc ctctccaaat    4920
atgttggctg ttccttccat taaagtgacc ccactttaga gcagcaagtg gatttctgtt    4980
tcttacagtt caggaaggag gagtcagctg tgagaacctg gagcctgaga tgcttctaag    5040
tcccactgct actgggtcca gggaagccag actccagcat cagcagtcag gagcactaag    5100
cccttgccaa catcctgttt ctcagagaaa ctgcttccat tataatggtt gtccttttt    5160 aagctatcaa gccaaacaac cagtgtctac cattattctc atcacctgaa gccaagggtt    5220
ctagcaaaag tcaagctgtc ttgtaatggt tgatgtgcct ccagcttctg tcttcagtca    5280
ctccactctt agcctgctct gaatcaactc tgaccacagt tccctggagc ccctgccacc    5340 tgctgccccct gccaccttct ccatctgcag tgctgtgcag ccttctgcac tcttgcagag    5400
ctaataggtg gagacttgaa ggaagaggag gaaagtttct cataatagcc ttgctgcaag    5460
```

```
ctcaaatggg aggtgggcac tgtgcccagg agccttggag caaaggctgt gcccaacctc    5520
tgactgcatc caggtttggt cttgacagag ataagaagcc ctggcttttg gagccaaaat    5580
ctaggtcaga cttaggcagg attctcaaag tttatcagca gaacatgagg cagaagaccc    5640
tttctgctcc agcttcttca ggctcaacct tcatcagaat agatagaaag agaggctgtg    5700
agggttctta aaacagaagc aaatctgact cagagaataa acaacctcct agtaaactac    5760
agcttagaca gagcatctgg tggtgagtgt gctcagtgtc ctactcaact gtctggtatc    5820
agccctcatg aggacttctc ttctttccct catagacctc catctctgtt ttccttagcc    5880
tgcagaaatc tggatggcta ttcacagaat gcctgtgctt tcagagttgc attttttctc    5940
tggtattctg gttcaagcat ttgaaggtag gaaaggttct ccaagtgcaa gaaagccagc    6000
cctgagcctc aactgcctgg ctagtgtggt cagtaggatg caaaggctgt tgaatgccac    6060
aaggccaaac tttaacctgt gtaccacaag cctagcagca gaggcagctc tgctcactgg    6120
aactctctgt cttctttctc ctgagccttt tcttttcctg agttttctag ctctcctcaa    6180
ccttacctct gccctaccca ggacaaaccc aagagccact gtttctgtga tgtcctctcc    6240
agccctaatt aggcatcatg acttcagcct gaccttccat gctcagaagc agtgctaatc    6300
cacttcagat gagctgctct atgcaacaca ggcagagcct acaaaccttt gcaccagagc    6360
cctccacata tcagtgtttg ttcatactca cttcaacagc aaatgtgact gctgagatta    6420
agattttaca caagatggtc tgtaatttca cagttagttt tatcccatta ggtatgaaag    6480
aattagcata attcccctta aacatgaatg aatcttagat tttttaataa atagttttgg    6540
aagtaaagac agagacatca ggagcacaag gaatagcctg agaggacaaa cagaacaaga    6600
aagagtctgg aaatacacag gatgttcttg gcctcctcaa agcaagtgca agcagatagt    6660
accagcagcc ccaggctatc agagcccagt gaagagaagt accatgaaag ccacagctct    6720
aaccaccctg ttccagagtg acagacagtc cccaagacaa gccagcctga gccagagaga    6780
gaactgcaag agaaagtttc taatttaggt tctgttagat tcagacaagt gcaggtcatc    6840
ctctctccac agctactcac ctctccagcc taacaaagcc tgcagtccac actccaaccc    6900
tggtgtctca cctcctagcc tctcccaaca tcctgctctc tgaccatctt ctgcatctct    6960
catctcacca tctcccactg tctacagcct actcttgcaa ctaccatctc attttctgac    7020
atcctgtcta tcttctgc catactctgc catctaccat accacctctt accatctacc    7080
acaccatctt ttatctccat ccctctcaga agcctccaag ctgaatcctg ctttatgtgt    7140
tcatctcagc ccctgcatgg aaagctgacc ccagaggcag aactattccc agagagcttg    7200
gccaagaaaa acaaaactac cagcctggcc aggctcagga gtagtaagct gcagtgtctg    7260
ttgtgttcta gcttcaacag ctgcaggagt tccactctca aatgctccac atttctcaca    7320
tcctcctgat tctggtcact acccatcttc aaagaacaga atatctcaca tcagcatact    7380
gtgaaggact agtcatgggt gcagctgctc agagctgcaa agtcattctg gatggtggag    7440
agcttacaaa catttcatga tgctcccccc gctctgatgg ctggagccca tccctacac    7500 agactcctgc tgtatgtgtt ttcctttcac tctgagccac agccagaggg caggcattca    7560
gtctcctctt caggctgggg ctgggcact gagaactcac ccaacacctt gctctcactc    7620
cttctgcaaa acaagaaaga gctttgtgct gcagtagcca tgaagaatga aaggaaggct    7680
ttaactaaaa aatgtcagag attattttca acccccttact gtggatcacc agcaaggagg    7740
aaacacaaca cagagacatt ttttcccctc aaattatcaa aagaatcact gcatttgtta    7800
```

```
aagagagcaa ctgaatcagg aagcagagtt ttgaacatat cagaagttag gaatctgcat    7860
cagagacaaa tgcagtcatg gttgtttgct gcataccagc cctaatcatt agaagcctca    7920
tggacttcaa acatcattcc ctctgacaag atgctctagc ctaactccat gagataaaat    7980
aaatctgcct ttcagagcca agaagagtc caccagcttc ttctcagtgt gaacaagagc    8040
tccagtcagg ttagtcagtc cagtgcagta gaggagacca gtctgcatcc tctaattttc    8100
aaaggcaaga agatttgttt accctggaca ccaggcacaa gtgaggtcac agagctctta    8160
gatatgcagt cctcatgagt gaggagacta aagcgcatgc catcaagact tcagtgtaga    8220
gaaaacctcc aaaaaagcct cctcactact tctggaatag ctcagaggcc gaggcggcct    8280
cggcctctgc ataaataaaa aaattagtc agccatgggg cggagaatgg gcggaactgg    8340
gcggagttag gggcgggatg ggcggagtta ggggcgggac tatggttgct gactaattga    8400
gatgcatgct ttgcatactt ctgcctgctg gggagcctgg ggactttcca cacctggttg    8460
ctgactaatt gagatgcatg ctttgcatac ttctgcctgc tggggagcct ggggactttc    8520
cacaccctaa ctgacacaca ttccacagct gcattaatga atcggccaac gcgcggggag    8580
aggcggtttg cgtattgggc gctcttccgc ttcctcgctc actgactcgc tgcgctcggt    8640
cgttcggctg cggcgagcgg tatcagctca ctcaaaggcg gtaatacggt tatccacaga    8700
atcaggggat aacgcaggaa agaacatgtg agcaaaaggc cagcaaaagg ccaggaaccg    8760
taaaaaggcc gcgttgctgg cgttttccca taggctccgc cccctgacg agcatcacaa    8820 aaatcgacgc tcaagtcaga ggtggcgaaa cccgacagga ctataaagat accaggcgtt    8880 tcccctgga agctccctcg tgcgctctcc tgttccgacc ctgccgctta ccggatacct    8940
gtccgccttt ctcccttcgg gaagcgtggc gctttctcat agctcacgct gtaggtatct    9000
cagttcggtg taggtcgttc gctccaagct gggctgtgtg cacgaacccc ccgttcagcc    9060
cgaccgctgc gccttatccg gtaactatcg tcttgagtcc aacccggtaa gacacgactt    9120
atcgccactg gcagcagcca ctggtaacag gattagcaga gcgaggtatg taggcggtgc    9180
tacagagttc ttgaagtggt ggcctaacta cggctacact agaagaacag tatttggtat    9240
ctgcgctctg ctgaagccag ttaccttcgg aaaaagagtt ggtagctctt gatccggcaa    9300
acaaaccacc gctggtagcg gtggtttttt tgtttgcaag cagcagatta cgcgcagaaa    9360
aaaaggatct caagaagatc ctttgatctt ttctacgggg tctgacgctc agtgaacga    9420 aaactcacgt taagggattt tggtcatgag attatcaaaa aggatcttca cctagatcct    9480
tttaaattaa aaatgaagtt ttaaatcaat ctaaagtata tatgagtaaa cttggtctga    9540
cagttaccaa tgcttaatca gtgaggcacc tatctcagcg atctgtctat ttcgttcatc    9600
catagttgcc tgactcctgc aaaccacgtt gtgtctcaaa atctctgatg ttacattgca    9660
caagataaaa atatatcatc atgaacaata aaactgtctg cttacataaa cagtaataca    9720
aggggtgtta tgagccatat tcaacgggaa acgtcttgct cgaggccgcg attaaattcc    9780
aacatggatg ctgatttata tgggtataaa tgggctcgcg ataatgtcgg gcaatcaggt    9840
gcgacaatct atcgattgta tgggaagccc gatgcgccag agttgtttct gaaacatggc    9900
aaaggtagcg ttgccaatga tgttacagat gagatggtca gactaaactg gctgacggaa    9960
tttatgcctc ttccgaccat caagcatttt atccgtactc ctgatgatgc atggttactc    10020
accactgcga tccccgggaa aacagcattc caggtattag aagaatatcc tgattcaggt    10080
gaaaatattg ttgatgcgct ggcagtgttc ctgcgccggt tgcattcgat tcctgtttgt    10140
aattgtcctt ttaacagcga tcgcgtattt cgtctcgctc aggcgcaatc acgaatgaat    10200
```

```
aacggtttgg ttgatgcgag tgattttgat gacgagcgta atggctggcc tgttgaacaa    10260
gtctggaaag aaatgcataa gcttttgcca ttctcaccgg attcagtcgt cactcatggt    10320
gatttctcac ttgataacct tattttgac gaggggaaat taataggttg tattgatgtt     10380
ggacgagtcg gaatcgcaga ccgataccag gatcttgcca tcctatggaa ctgcctcggt    10440
gagttttctc cttcattaca gaaacggctt tttcaaaaat atggtattga taatcctgat    10500
atgaataaat tgcagtttca tttgatgctc gatgagtttt tctaagggcg gcctgccacc    10560
atacccacgc cgaaacaagc gctcatgagc ccgaagtggc gagcccgatc ttccccatcg    10620
gtgatgtcgg cgatataggc gccagcaacc gcacctgtgg cgccggtgat gagggcgcgc    10680
caagtcgacg tccggcagtc                                                10700
```

<210> SEQ ID NO 11
<211> LENGTH: 11188
<212> TYPE: DNA
<213> ORGANISM: Artificial Sequence
<220> FEATURE:
<223> OTHER INFORMATION: Synthetic polynucleotide

<400> SEQUENCE: 11

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactatt agatctgatg gccgcgctag ctctgggtat ttaagcccga gtgagcacgc     180
agggtctcca ttttgaagcg ggaggttacg cgttcgtcga ctactagtgg gtaccagagc     240
gtggtgactg agatgttttc taggaaacac aaaagataca aaaaagaaca cgtggaagga     300
tagccaaaaa gggggggctgc ccccatttcc tgcaccccgc tgcgatggct ggcaccattt     360
ggaagacttc gagatacact gttgagcgca gtaagacaac agtgtatctc gaagtcttcc     420
agatggggcc agccggtcca ctctgtatcc aggccagttc tgcaaggcgt tcgaggacca     480
cccccctccc ctcgccacca gggtggtctc atacagaact tataagattc ccaaatccaa     540
agacatttca cgtttatggt gatttcccag aacacatagc gacatgcaaa tattgcaggg     600
cgccactccc ctgtccctca cagccatctt cctgccaggg cgcacgcgcg ctgggtgttc     660
ccgcctagtg acactgggcc cgcgattcct tggagcgggt tgatgacgtc agcgtttccc     720
atggtgaatc cctaggttct agaaccggtg acgtctccca tggtgaagct tggatctgaa     780
ttcggtacct agttattaat agtaatcaat tacggggtca ttagttcata gcccatatat     840
ggagttccgc gttacataac ttacggtaaa tggcccgcct ggctgaccgc ccaacgaccc     900
ccgcccattg acgtcaataa tgacgtatgt tcccatagta acgccaatag ggactttcca     960
ttgacgtcaa tgggtggagt atttacggta aactgcccac ttggcagtac atcaagtgta    1020
tcatatgcca agtacgcccc ctattgacgt caatgacggt aaatggcccg cctggcatta    1080
tgcccagtac atgaccttat gggactttcc tacttggcag tacatctacg tattagtcat    1140
cgctattacc atggtcgagg tgagccccac gttctgcttc actctcccca tctccccccc    1200
ctccccaccc ccaattttgt atttatttat tttttaatta ttttgtgcag cgatggggc     1260 ggggggggg gggggcgcg cgccaggcgg ggcggggcgg ggcgagggc ggggcgggc       1320 gaggcggaga ggtgcggcgg cagccaatca gagcggcgcg ctccgaaagt ttccttttat    1380
ggcgaggcgg cggcgcggc ggccctataa aaagcgaagc gcgcggcggg cgggagtcgc      1440
tgcgacgctg ccttcgcccc gtgccccgct ccgccgccgc ctcgcgccgc ccgccccggc    1500
```

-continued

```
tctgactgac cgcgttactc ccacaggtga gcgggcggga cggcccttct cctccgggct    1560
gtaattagcg cttggtttaa tgacggcttg tttcttttct gtggctgcgt gaaagccttg    1620
aggggctccg ggagctagag cctctgctaa ccatgttcat gccttcttct ttttcctaca    1680
gctcctgggc aacgtgctgg ttattgtgct gtctcatcat tttggcaaag aattcctcga    1740
agatccgaag ggaaagtctt ccacgactgt gggatccgtt cgaagatatc accggttgag    1800
ccaccatgga attcagcagc cccagcagag aggaatgccc caagcctctg agccgggtgt    1860
caatcatggc cggatctctg acaggactgc tgctgcttca ggccgtgtct tgggcttctg    1920
gcgctagacc ttgcatcccc aagagcttcg gctacagcag cgtcgtgtgc gtgtgcaatg    1980
ccacctactg cgacagcttc gaccctccta cctttcctgc tctgggcacc ttcagcagat    2040
acgagagcac cagatccggc agacggatgg aactgagcat gggacccatc caggccaatc    2100
acacaggcac tggcctgctg ctgacactgc agcctgagca gaaattccag aaagtgaaag    2160
gcttcggcgg agccatgaca gatgccgccg ctctgaatat cctggctctg tctccaccag    2220
ctcagaacct gctgctcaag agctacttca gcgaggaagg catcggctac aacatcatca    2280
gagtgcccat ggccagctgc gacttcagca tcaggaccta cacctacgcc gacacacccg    2340
acgatttcca gctgcacaac ttcagcctgc ctgaagagga caccaagctg aagatccctc    2400
tgatccacag agccctgcag ctggcacaaa gaccgtgtc actgctggcc tctccatgga    2460
catctcccac ctggctgaaa acaaatggcg ccgtgaatgg caaggcagc ctgaaaggcc    2520 aacctggcga catctaccac cagacctggg ccagatactt cgtgaagttc ctggacgcct    2580
atgccgagca caagctgcag tttgggcgct tgacagccga gaacgaacct tctgctggac    2640
tgctgagcgg ctacccettt cagtgcctgg gctttacacc cgagcaccag cgggacttta    2700
tcgcccgtga tctgggaccc acactggcca atagcaccca ccataatgtg cggctgctga    2760
tgctggacga ccagagactg cttctgcccc actgggctaa agtggtgctg acagatcctg    2820
aggccgccaa atacgtgcac ggaatcgccg tgcactggta tctggacttt ctggcccctg    2880
ccaaggccac actgggagag acacacagac tgttccccaa caccatgctg ttcgccagcg    2940
aagcctgtgt gggcagcaag ttttgggaac agagcgtgcg gctcggcagc tgggatagag    3000
gcatgcagta cagccacagc atcatcacca acctgctgta ccacgtcgtc ggctggaccg    3060
actggaatct ggccctgaat cctgaaggcg ccctaactg gtccgaaac ttcgtggaca    3120 gccccatcat cgtggacatc accaaggaca ccttctacaa gcagcccatg ttctaccacc    3180
tgggacactt cagcaagttc atccccgagg ctctcagcg cgttggactg gtggcttccc    3240
agaagaacga tctggacgcc gtggctctga tgcaccctga tggatctgct gtggtggtgg    3300
tcctgaaccg cagcagcaaa gatgtgcccc tgaccatcaa ggatcccgcc gtgggattcc    3360
tggaaacaat cagccctggc tactccatcc acacctacct gtggcgtaga cagtgacaat    3420
tgttaattaa gtttaaaccc tcgaggccgc aagcttatcg ataatcaacc tctgattac    3480 aaaatttgtg aaagattgac tggtattctt aactatgttg ctccttttac gctatgtgga    3540
tacgctgctt taatgccttt gtatcatgct attgcttccc gtatggcttt cattttctcc    3600
tccttgtata aatcctggtt gctgtctctt tatgaggagt tgtggcccgt tgtcaggcaa    3660
cgtggcgtgg tgtgcactgt gtttgctgac gcaacccca ctggttgggg cattgccacc    3720
acctgtcagc tcctttccgg gactttcgct ttcccctcc ctattgccac ggcggaactc    3780
atcgccgcct gccttgcccg ctgctggaca ggggctcggc tgttgggcac tgacaattcc    3840
gtggtgttgt cggggaaatc atcgtccttt ccttggctgc tcgcctgtgt tgccacctgg    3900
```

```
attctgcgcg ggacgtcctt ctgctacgtc ccttcggccc tcaatccagc ggaccttcct    3960
tcccgcggcc tgctgccggc tctgcggcct cttccgcgtc ttcgccttcg ccctcagacg    4020
agtcggatct ccctttgggc cgcctccccg catcgatacc gtcgactaga gctcgctgat    4080
cagcctcgac tgtgccttct agttgccagc catctgttgt ttgcccctcc ccgtgcctt    4140 ccttgaccct ggaaggtgcc actcccactg tcctttccta ataaaatgag gaaattgcat    4200
cgcattgtct gagtaggtgt cattctattc tggggggtgg ggtggggcag gacagcaagg    4260
gggaggattg ggaagacaat agcaggcatg ctggggagag atccacgata caaacagct    4320 tttttggggt gaacatattg actgaattcc ctgcaggttg gccactccct ctctgcgcgc    4380
tcgctcgctc actgaggccg cccgggcaaa gcccggcgt cgggcgacct tggtcgccc    4440 ggcctcagtg agcgagcgag cgcgcagaga gggagtggcc aactccatca ctaggggttc    4500
ctgcggccgc tcgtacggtc tcgaggaatt cctgcaggat aacttgccaa cctcattcta    4560
aaatgtatat agaagcccaa aagacaataa caaaaatatt cttgtagaac aaaatgggaa    4620
agaatgttcc actaaatatc aagatttaga gcaaagcatg agatgtgtgg ggatagacag    4680
tgaggctgat aaaatagagt agagctcaga aacagaccca ttgatatatg taagtgacct    4740
atgaaaaaaa tatggcattt tacaatggga aaatgatggt ctttttcttt tttagaaaaa    4800
cagggaaata tatttatatg taaaaaataa aagggaaccc atatgtcata ccatacacac    4860
aaaaaaattc cagtgaatta aagtctaaa tggagaaggc aaaactttaa atcttttaga    4920
aaataatata gaagcatgca gaccagcctg gccaacatga tgaaaccctc tctactaata    4980
ataaaatcag tagaactact caggactact ttgagtggga agtccttttc tatgaagact    5040
tctttggcca aaattaggct ctaaatgcaa ggagatagtg catcatgcct ggctgcactt    5100
actgataaat gatgttatca ccatctttaa ccaaatgcac aggaacaagt tatggtactg    5160
atgtgctgga ttgagaagga gctctacttc cttgacagga cacatttgta tcaacttaaa    5220
aaagcagatt tttgccagca gaactattca ttcagaggta ggaaacttag aatagatgat    5280
gtcactgatt agcatggctt ccccatctcc acagctgctt cccacccagg ttgcccacag    5340
ttgagtttgt ccagtgctca gggctgccca ctctcagtaa gaagcccac accagcccct    5400 ctccaaatat gttggctgtt ccttccatta aagtgacccc actttagagc agcaagtgga    5460
tttctgtttc ttacagttca ggaaggagga gtcagctgtg agaacctgga gcctgagatg    5520
cttctaagtc ccactgctac tggggtcagg gaagccagac tccagcatca gcagtcagga    5580
gcactaagcc cttgccaaca tcctgttttct cagagaaact gcttccatta taatggttgt    5640
ccttttttaa gctatcaagc caaacaacca gtgtctacca ttattctcat cacctgaagc    5700
caagggttct agcaaaagtc aagctgtctt gtaatggttg atgtgcctcc agcttctgtc    5760
ttcagtcact ccactcttag cctgctctga atcaactctg accacagttc cctggagccc    5820
ctgccacctg ctgcccctgc caccttctcc atctgcagtg ctgtgcagcc ttctgcactc    5880
ttgcagagct aataggtgga gacttgaagg aagaggagga aagtttctca taatagcctt    5940
gctgcaagct caaatgggag gtgggcactg tgcccaggag ccttggagca aaggctgtgc    6000
ccaacctctg actgcatcca ggtttggtct tgacagagat aagaagccct ggcttttgga    6060
gccaaaatct aggtcagact taggcaggat tctcaaagtt tatcagcaga acatgaggca    6120
gaagacccct tctgctccag cttcttcagg ctcaaccttc atcagaatag atagaaagag    6180
aggctgtgag ggttcttaaa acagaagcaa atctgactca gagaataaac aacctcctag    6240
```

-continued

```
taaactacag cttagacaga gcatctggtg gtgagtgtgc tcagtgtcct actcaactgt    6300
ctggtatcag ccctcatgag gacttctctt ctttccctca tagacctcca tctctgtttt    6360
ccttagcctg cagaaatctg gatggctatt cacagaatgc ctgtgctttc agagttgcat    6420 ttttctctg gtattctggt tcaagcattt gaaggtagga aaggttctcc aagtgcaaga    6480
aagccagccc tgagcctcaa ctgcctggct agtgtggtca gtaggatgca aaggctgttg    6540
aatgccacaa ggccaaactt taacctgtgt accacaagcc tagcagcaga ggcagctctg    6600
ctcactggaa ctctctgtct tctttctcct gagccttttc ttttcctgag ttttctagct    6660
ctcctcaacc ttacctctgc cctacccagg acaaacccaa gagccactgt ttctgtgatg    6720
tcctctccag ccctaattag gcatcatgac ttcagcctga ccttccatgc tcagaagcag    6780
tgctaatcca cttcagatga gctgctctat gcaacacagg cagagcctac aaacctttgc    6840
accagagccc tccacatatc agtgtttgtt catactcact tcaacagcaa atgtgactgc    6900
tgagattaag attttacaca agatggtctg taatttcaca gttagtttta tcccattagg    6960
tatgaaagaa ttagcataat tccccttaaa catgaatgaa tcttagattt tttaataaat    7020
agttttggaa gtaaagacag agacatcagg agcacaagga atagcctgag aggacaaaca    7080
gaacaagaaa gagtctggaa atacacagga tgttcttggc ctcctcaaag caagtgcaag    7140
cagatagtac cagcagcccc aggctatcag agcccagtga agagaagtac catgaaagcc    7200
acagctctaa ccaccctgtt ccagagtgac agacagtccc caagacaagc cagcctgagc    7260
cagagagaga actgcaagag aaagtttcta atttaggttc tgttagattc agacaagtgc    7320
aggtcatcct ctctccacag ctactcacct ctccagccta acaaagcctg cagtccacac    7380
tccaaccctg gtgtctcacc tcctagcctc tcccaacatc ctgctctctg accatcttct    7440
gcatctctca tctcaccatc tcccactgtc tacagcctac tcttgcaact accatctcat    7500
tttctgacat cctgtctaca tcttctgcca tactctgcca tctaccatac cacctcttac    7560
catctaccac accatctttt atctccatcc ctctcagaag cctccaagct gaatcctgct    7620
ttatgtgttc atctcagccc ctgcatggaa agctgacccc agaggcagaa ctattcccag    7680
agagcttggc caagaaaaac aaaactacca gcctggccag gctcaggagt agtaagctgc    7740
agtgtctgtt gtgttctagc ttcaacagct gcaggagttc cactctcaaa tgctccacat    7800
ttctcacatc ctcctgattc tggtcactac ccatcttcaa agaacagaat atctcacatc    7860
agcatactgt gaaggactag tcatgggtgc agctgctcag agctgcaaag tcattctgga    7920
tggtggagag cttacaaaca tttcatgatg ctcccccgc tctgatggct ggagcccaat    7980
ccctacacag actcctgctg tatgtgtttt cctttcactc tgagccacag ccagagggca    8040
ggcattcagt ctcctcttca ggctggggct ggggcactga gaactcaccc aacaccttgc    8100
tctcactcct tctgcaaaac aagaaagagc tttgtgctgc agtagccatg aagaatgaaa    8160
ggaaggcttt aactaaaaaa tgtcagagat tattttcaac cccttactgt ggatcaccag    8220
caaggaggaa acacaacaca gagacatttt ttcccctcaa attatcaaaa gaatcactgc    8280
atttgttaaa gagagcaact gaatcaggaa gcagagtttt gaacatatca gaagttagga    8340
atctgcatca gagacaaatg cagtcatggt tgtttgctgc ataccagccc taatcattag    8400
aagcctcatg gacttcaaac atcattccct ctgacaagat gctctagcct aactccatga    8460
gataaaataa atctgccttt cagagccaaa gaagagtcca ccagcttctt ctcagtgtga    8520
acaagagctc cagtcaggtt agtcagtcca gtgcagtaga ggagaccagt ctgcatcctc    8580
taattttcaa aggcaagaag atttgtttac cctggacacc aggcacaagt gaggtcacag    8640
```

```
agctcttaga tatgcagtcc tcatgagtga ggagactaaa gcgcatgcca tcaagacttc   8700
agtgtagaga aaacctccaa aaaagcctcc tcactacttc tggaatagct cagaggccga   8760
ggcggcctcg gcctctgcat aaataaaaaa aattagtcag ccatggggcg gagaatgggc   8820
ggaactgggc ggagttaggg gcgggatggg cggagttagg ggcgggacta tggttgctga   8880
ctaattgaga tgcatgcttt gcatacttct gcctgctggg gagcctgggg actttccaca   8940
cctggttgct gactaattga gatgcatgct ttgcatactt ctgcctgctg gggagcctgg   9000
ggactttcca caccctaact gacacacatt ccacagctgc attaatgaat cggccaacgc   9060
gcggggagag gcggtttgcg tattgggcgc tcttccgctt cctcgctcac tgactcgctg   9120
cgctcggtcg ttcggctgcg gcgagcggta tcagctcact caaaggcggt aatacggtta   9180
tccacagaat caggggataa cgcaggaaag aacatgtgag caaaaggcca gcaaaggcc   9240 aggaaccgta aaaaggccgc gttgctggcg ttttttccata ggctccgccc ccctgacgag   9300
catcacaaaa atcgacgctc aagtcagagg tggcgaaacc cgacaggact ataaagatac   9360
caggcgtttc ccctggaag ctccctcgtg cgctctcctg ttccgaccct gccgcttacc   9420
ggatacctgt ccgcctttct cccttcggga agcgtggcgc tttctcatag ctcacgctgt   9480
aggtatctca gttcggtgta ggtcgttcgc tccaagctgg gctgtgtgca cgaaccccc   9540 gttcagcccg accgctgcgc cttatccggt aactatcgtc ttgagtccaa cccggtaaga   9600
cacgacttat cgccactggc agcagccact ggtaacagga ttagcagagc gaggtatgta   9660
ggcggtgcta cagagttctt gaagtggtgg cctaactacg gctacactag aagaacagta   9720
tttggtatct gcgctctgct gaagccagtt accttcggaa aaagagttgg tagctcttga   9780
tccggcaaac aaaccaccgc tggtagcggt ggttttttg tttgcaagca gcagattacg   9840
cgcagaaaaa aaggatctca agaagatcct ttgatctttt ctacggggtc tgacgctcag   9900
tggaacgaaa actcacgtta agggattttg gtcatgagat tatcaaaaag gatcttcacc   9960
tagatccttt taaattaaaa atgaagtttt aaatcaatct aaagtatata tgagtaaact  10020
tggtctgaca gttaccaatg cttaatcagt gaggcaccta tctcagcgat ctgtctattt  10080
cgttcatcca tagttgcctg actccctgcaa accacgttgt gtctcaaaat ctctgatgtt  10140
acattgcaca agataaaaat atatcatcat gaacaataaa actgtctgct tacataaaca  10200
gtaatacaag gggtgttatg agccatattc aacgggaaac gtcttgctcg aggccgcgat  10260
taaattccaa catggatgct gatttatatg ggtataaatg gctcgcgat aatgtcgggc  10320 aatcaggtgc gacaatctat cgattgtatg ggaagcccga tgcgccagag ttgtttctga  10380
aacatggcaa aggtagcgtt gccaatgatg ttacagatga gatggtcaga ctaaactggc  10440
tgacggaatt tatgcctctt ccgaccatca agcattttat ccgtactcct gatgatgcat  10500
ggttactcac cactgcgatc cccgggaaaa cagcattcca ggtattagaa gaatatcctg  10560
attcaggtga aaatattgtt gatgcgctgg cagtgttcct gcgccggttg cattcgattc  10620
ctgtttgtaa ttgtcctttt aacagcgatc gcgtatttcg tctcgctcag gcgcaatcac  10680
gaatgaataa cggtttggtt gatgcgagtg attttgatga cgagcgtaat ggctggcctg  10740
ttgaacaagt ctggaaagaa atgcataagc ttttgccatt ctcaccggat tcagtcgtca  10800
ctcatggtga tttctcactt gataaccta ttttttgacga ggggaaatta ataggttgta  10860
ttgatgttgg acgagtcgga atcgcagacc gataccagga tcttgccatc ctatggaact  10920
gcctcggtga gttttctcct tcattacaga aacggctttt tcaaaaatat ggtattgata  10980
```

-continued

| | |
|---|---|
| atcctgatat gaataaattg cagtttcatt tgatgctcga tgagtttttc taagggcggc | 11040 |
| ctgccaccat acccacgccg aaacaagcgc tcatgagccc gaagtggcga gcccgatctt | 11100 |
| ccccatcggt gatgtcggcg atataggcgc cagcaaccgc acctgtggcg ccggtgatga | 11160 |
| gggcgcgcca agtcgacgtc cggcagtc | 11188 |

<210> SEQ ID NO 12
<211> LENGTH: 11187
<212> TYPE: DNA
<213> ORGANISM: Artificial Sequence
<220> FEATURE:
<223> OTHER INFORMATION: Synthetic polynucleotide

<400> SEQUENCE: 12

| | |
|---|---|
| ctagaaccgg tgacgtctcc catggtgaag cttggatctg aattcggtac ctagttataa | 60 |
| tagtaatcaa ttacggggtc attagttcat agcccatata tggagttccg cgttacataa | 120 |
| cttacggtaa atggcccgcc tggctgaccg cccaacgacc cccgcccatt gacgtcaata | 180 |
| atgacgtatg ttcccatagt aacgccaata gggactttcc attgacgtca atgggtggag | 240 |
| tatttacggt aaactgccca cttggcagta catcaagtgt atcatatgcc aagtacgccc | 300 |
| cctattgacg tcaatgacgg taaatggccc gcctggcatt atgcccagta catgacctta | 360 |
| tgggactttc ctacttggca gtacatctac gtattagtca tcgctattac catggtcgag | 420 |
| gtgagcccca cgttctgctt cactctcccc atctcccccc cctccccacc cccaattttg | 480 |
| tatttattta ttttttaatt attttgtgca gcgatggggg cggggggggg ggggggcgc | 540 |
| gcgccaggcg gggcggggcg gggcgagggg cgggcgggg cgaggcggag aggtgcggcg | 600 |
| gcagccaatc agagcggcgc gctccgaaag tttccttta tggcgaggcg cggcggcgg | 660 |
| cggccctata aaaagcgaag cgcgcggcgg gcggagtcg ctgcgacgct gccttcgccc | 720 |
| cgtgccccgc tccgccgccg cctcgcgccg cccgccccgg ctctgactga ccgcgttact | 780 |
| cccacaggtg agcgggcggg acggcccttc tcctccgggc tgtaattagc gcttggttta | 840 |
| atgacggctt gtttcttttc tgtggctgcg tgaaagcctt gagggctcc gggagctaga | 900 |
| gcctctgcta accatgttca tgccttcttc tttttcctac agctcctggg caacgtgctg | 960 |
| gttattgtgc tgtctcatca ttttggcaaa gaattcctcg aagatccgaa gggaaagtct | 1020 |
| tccacgactg tgggatccgt tcgaagatat caccggttga ccaccatgg aattcagcag | 1080 |
| ccccagcaga gaggaatgcc ccaagcctct gagccgggtg tcaatcatgg ccggatctct | 1140 |
| gacaggactg ctgctgcttc aggccgtgtc ttgggcttct ggcgctagac cttgcatccc | 1200 |
| caagagcttc ggctacagca gcgtcgtgtg cgtgtgcaat gccacctact gcgacagctt | 1260 |
| cgaccctcct acctttcctg ctctgggcac cttcagcaga tacgagcca ccagatccgg | 1320 |
| cagacggatg gaactgagca tgggacccat ccaggccaat cacacaggca ctggcctgct | 1380 |
| gctgacactg cagcctgagc agaaattcca gaaagtgaaa ggcttcggcg gagccatgac | 1440 |
| agatgccgcc gctctgaata tcctggctct gtctccacca gctcagaacc tgctgctcaa | 1500 |
| gagctacttc agcgaggaag gcatcggcta caacatcatc agagtgccca tggccagctg | 1560 |
| cgacttcagc atcaggacct acacctacgc cgacacaccc gacgatttcc agctgcacaa | 1620 |
| cttcagcctg cctgaagagg acaccaagct gaagatccct ctgatccaca gagccctgca | 1680 |
| gctggcacaa agacccgtgt cactgctggc ctctccatgg acatctccca cctggctgaa | 1740 |
| aacaaatggc gccgtgaatg gcaagggcag cctgaaggc caacctggcg acatctacca | 1800 |
| ccagacctgg gccagatact tcgtgaagtt cctggacgcc tatgccgagc acaagctgca | 1860 |

```
gttttgggcc gtgacagccg agaacgaacc ttctgctgga ctgctgagcg gctacccctt    1920
tcagtgcctg ggctttacac ccgagcacca gcgggacttt atcgcccgtg atctgggacc    1980
cacactggcc aatagcaccc accataatgt gcggctgctg atgctggacg accagagact    2040
gcttctgccc cactgggcta aagtggtgct gacagatcct gaggccgcca atacgtgca     2100 cggaatcgcc gtgcactggt atctggactt tctggcccct gccaaggcca cactgggaga    2160
gacacacaga ctgttcccca acaccatgct gttcgccagc gaagcctgtg tgggcagcaa    2220
gttttgggaa cagagcgtgc ggctcggcag ctgggataga ggcatgcagt acagccacag    2280
catcatcacc aacctgctgt accacgtcgt cggctggacc gactggaatc tggccctgaa    2340
tcctgaaggc ggccctaact gggtccgaaa cttcgtggac agccccatca tcgtggacat    2400
caccaaggac accttctaca agcagcccat gttctaccac ctgggacact tcagcaagtt    2460
catccccgag ggctctcagc gcgttggact ggtggcttcc cagaagaacg atctggacgc    2520
cgtggctctg atgcaccctg atggatctgc tgtggtggtg gtcctgaacc gcagcagcaa    2580
agatgtgccc ctgaccatca aggatcccgc cgtgggattc ctggaaacaa tcagccctgg    2640
ctactccatc cacacctacc tgtggcgtag acagtgacaa ttgttaatta agtttaaacc    2700
ctcgaggccg caagcttatc gataatcaac ctctggatta caaaatttgt gaaagattga    2760
ctggtattct taactatgtt gctccttta cgctatgtgg atacgctgct ttaatgcctt     2820
tgtatcatgc tattgcttcc cgtatggctt tcattttctc ctccttgtat aaatcctggt    2880
tgctgtctct ttatgaggag ttgtggcccg ttgtcaggca acgtggcgtg gtgtgcactg    2940
tgtttgctga cgcaaccccc actggttggg gcattgccac cacctgtcag ctccttccg     3000 ggactttcgc tttccccctc cctattgcca cggcggaact catcgccgcc tgccttgccc    3060
gctgctggac aggggctcgg ctgttgggca ctgacaattc cgtggtgttg tcggggaaat    3120
catcgtcctt tccttggctg ctcgcctgtg ttgccacctg gattctgcgc gggacgtcct    3180
tctgctacgt cccttcggcc ctcaatccag cggaccttcc ttcccgcggc ctgctgccgg    3240
ctctgcggcc tcttccgcgt cttcgccttc gccctcagac gagtcggatc tccctttggg    3300
ccgcctcccc gcatcgatac cgtcgactag agctcgctga tcagcctcga ctgtgccttc    3360
tagttgccag ccatctgttg tttgcccctc cccgtgcct tccttgaccc tggaaggtgc     3420
cactcccact gtccttttcct aataaaatga ggaaattgca tcgcattgtc tgagtaggtg    3480
tcattctatt ctgggggtg gggtggggca ggacagcaag ggggaggatt gggaagacaa     3540
tagcaggcat gctggggaga gatccacgat aacaaacagc ttttttgggg tgaacatatt    3600
gactgaattc cctgcaggtt ggccactccc tctctgcgcg ctcgctcgct cactgaggcc    3660
gcccgggcaa agcccgggcg tcgggcgacc tttggtcgcc cggcctcagt gagcgagcga    3720
gcgcgcagag agggagtggc caactccatc actaggggtt cctgcggccg ctcgtacggt    3780
ctcgaggaat tcctgcagga taacttgcca acctcattct aaaatgtata tagaagccca    3840
aaagacaata acaaaaatat tcttgtagaa caaatgggaa agaatgttc cactaaatat     3900 caagatttag agcaaagcat gagatgtgtg gggatagaca gtgaggctga taaaatagag    3960
tagagctcag aaacagaccc attgatatat gtaagtgacc tatgaaaaaa atatggcatt    4020
ttacaatggg aaaatgatgg tcttttttctt ttttagaaaa acagggaaat atatttatat    4080
gtaaaaaata aagggaacc catatgtcat accatacaca caaaaaaatt ccagtgaatt     4140
ataagtctaa atggagaagg caaaacttta aatctttag aaaataatat agaagcatgc    4200
```

```
agaccagcct ggccaacatg atgaaaccct ctctactaat aataaaatca gtagaactac    4260
tcaggactac tttgagtggg aagtccttttt ctatgaagac ttctttggcc aaaattaggc   4320
tctaaatgca aggagatagt gcatcatgcc tggctgcact tactgataaa tgatgttatc   4380
accatcttta accaaatgca caggaacaag ttatggtact gatgtgctgg attgagaagg   4440
agctctactt ccttgacagg acacatttgt atcaacttaa aaaagcagat ttttgccagc   4500
agaactattc attcagaggt aggaaactta gaatagatga tgtcactgat tagcatggct   4560
tccccatctc cacagctgct tcccacccag gttgcccaca gttgagtttg tccagtgctc   4620
agggctgccc actctcagta agaagcccca ccagcccc tctccaaata tgttggctgt    4680
tccttccatt aaagtgaccc cactttagag cagcaagtgg atttctgttt cttacagttc   4740
aggaaggagg agtcagctgt gagaacctgg agcctgagat gcttctaagt cccactgcta   4800
ctggggtcag ggaagccaga ctccagcatc agcagtcagg agcactaagc ccttgccaac   4860
atcctgtttc tcagagaaac tgcttccatt ataatggttg tcctttttta agctatcaag   4920
ccaaacaacc agtgtctacc attattctca tcacctgaag ccaagggttc tagcaaaagt   4980
caagctgtct tgtaatggtt gatgtgcctc cagcttctgt cttcagtcac tccactctta   5040
gcctgctctg aatcaactct gaccacagtt ccctggagcc cctgccacct gctgcccctg   5100
ccaccttctc catctgcagt gctgtgcagc cttctgcact cttgcagagc taataggtgg   5160
agacttgaag gaagaggagg aaagtttctc ataatagcct tgctgcaagc tcaaatggga   5220
ggtgggcact gtgcccagga gccttggagc aaaggctgtg cccaacctct gactgcatcc   5280
aggtttggtc ttgacagaga taagaagccc tggcttttgg agccaaaatc taggtcagac   5340
ttaggcagga ttctcaaagt ttatcagcag aacatgaggc agaagaccct ttctgctcca   5400
gcttcttcag gctcaacctt catcagaata gatagaaaga gaggctgtga gggttcttaa   5460
aacagaagca aatctgactc agagaataaa caacctccta gtaaactaca gcttagacag   5520
agcatctggt ggtgagtgtg ctcagtgtcc tactcaactg tctggtatca gccctcatga   5580
ggacttctct tctttccctc atagacctcc atctctgttt tccttagcct gcagaaatct   5640
ggatggctat tcacagaatg cctgtgcttt cagagttgca ttttttctct ggtattctgg   5700
ttcaagcatt tgaaggtagg aaaggttctc caagtgcaag aaagccagcc ctgagcctca   5760
actgcctggc tagtgtggtc agtaggatgc aaaggctgtt gaatgccaca aggccaaact   5820
ttaacctgtg taccacaagc ctagcagcag aggcagctct gctcactgga actctctgtc   5880
ttctttctcc tgagccttttt cttttcctga gtttttctagc tctcctcaac cttacctctg   5940
ccctacccag gacaaaccca agagccactg tttctgtgat gtcctctcca gccctaatta   6000
ggcatcatga cttcagcctg accttccatg ctcagaagca gtgctaatcc acttcagatg   6060
agctgctcta tgcaacacag gcagagccta caaacctttg caccagagcc ctccacatat   6120
cagtgtttgt tcatactcac ttcaacagca aatgtgactg ctgagattaa gattttacac   6180
aagatggtct gtaatttcac agttagtttt atcccattag gtatgaaaga attagcataa   6240
ttccccttaa acatgaatga atcttagatt ttttaataaa tagttttgga agtaaagaca   6300
gagacatcag gagcacaagg aatagcctga gaggacaaac agaacaagaa agagtctgga   6360
aatacacagg atgttcttgg cctcctcaaa gcaagtgcaa gcagatagta ccagcagccc   6420
caggctatca gagcccagtg aagagaagta ccatgaaagc cacagctcta accaccctgt   6480
tccagagtga cagacagtcc ccaagacaag ccagcctgag ccagagagag aactgcaaga   6540
gaaagtttct aatttaggtt ctgttagatt cagacaagtg caggtcatcc tctctccaca   6600
```

```
gctactcacc tctccagcct aacaaagcct gcagtccaca ctccaaccct ggtgtctcac    6660
ctcctagcct ctcccaacat cctgctctct gaccatcttc tgcatctctc atctcaccat    6720
ctcccactgt ctacagccta ctcttgcaac taccatctca ttttctgaca tcctgtctac    6780
atcttctgcc atactctgcc atctaccata ccacctctta ccatctacca caccatcttt    6840
tatctccatc cctctcagaa gcctccaagc tgaatcctgc tttatgtgtt catctcagcc    6900
cctgcatgga aagctgaccc cagaggcaga actattccca gagagcttgg ccaagaaaaa    6960
caaaactacc agcctggcca ggctcaggag tagtaagctg cagtgtctgt tgtgttctag    7020
cttcaacagc tgcaggagtt ccactctcaa atgctccaca tttctcacat cctcctgatt    7080
ctggtcacta cccatcttca aagaacagaa tatctcacat cagcatactg tgaaggacta    7140
gtcatgggtg cagctgctca gagctgcaaa gtcattctgg atggtggaga gcttacaaac    7200
atttcatgat gctcccccg ctctgatggc tggagcccaa tccctacaca gactcctgct    7260
gtatgtgttt tcctttcact ctgagccaca gccagagggc aggcattcag tctcctcttc    7320
aggctggggc tggggcactg agaactcacc caacaccttg ctctcactcc ttctgcaaaa    7380
caagaaagag ctttgtgctg cagtagccat gaagaatgaa aggaaggctt taactaaaaa    7440
atgtcagaga ttattttcaa ccccttactg tggatcacca gcaaggagga aacacaacac    7500
agagacattt tttcccctca aattatcaaa agaatcactg catttgttaa agagagcaac    7560
tgaatcagga agcagagttt tgaacatatc agaagttagg aatctgcatc agagacaaat    7620
gcagtcatgg ttgtttgctg cataccagcc ctaatcatta gaagcctcat ggacttcaaa    7680
catcattccc tctgacaaga tgctctagcc taactccatg agataaaata aatctgcctt    7740
tcagagccaa agaagagtcc accagcttct tctcagtgtg aacaagagct ccagtcaggt    7800
tagtcagtcc agtgcagtag aggagaccag tctgcatcct ctaattttca aaggcaagaa    7860
gatttgttta ccctggacac caggcacaag tgaggtcaca gagctcttag atatgcagtc    7920
ctcatgagtg aggagactaa agcgcatgcc atcaagactt cagtgtagag aaaacctcca    7980
aaaaagcctc ctcactactt ctggaatagc tcagaggccg aggcggcctc ggcctctgca    8040
taaataaaaa aaattagtca gccatggggc ggagaatggg cggaactggg cggagttagg    8100
ggcgggatgg gcggagttag gggcgggact atggttgctg actaattgag atgcatgctt    8160
tgcatacttc tgcctgctgg ggagcctggg gactttccac acctggttgc tgactaattg    8220
agatgcatgc tttgcatact tctgcctgct ggggagcctg gggactttcc acaccctaac    8280
tgacacacat tccacagctg cattaatgaa tcggccaacg cgcggggaga ggcggtttgc    8340
gtattgggcg ctcttccgct tcctcgctca ctgactcgct gcgctcggtc gttcggctgc    8400
ggcgagcggt atcagctcac tcaaaggcgg taatacggtt atccacagaa tcaggggata    8460
acgcaggaaa gaacatgtga gcaaaaggcc agcaaaaggc caggaaccgt aaaaaggccg    8520
cgttgctggc gtttttccat aggctccgcc cccctgacga gcatcacaaa aatcgacgct    8580
caagtcagag gtggcgaaac ccgacaggac tataaagata ccaggcgttt ccccctggaa    8640
gctccctcgt gcgctctcct gttccgaccc tgccgcttac cggatacctg tccgcctttc    8700
tcccttcggg aagcgtggcg ctttctcata gctcacgctg taggtatctc agttcggtgt    8760
aggtcgttcg ctccaagctg ggctgtgtgc acgaaccccc cgttcagccc gaccgctgcg    8820
ccttatccgg taactatcgt cttgagtcca acccggtaag acacgactta tcgccactgg    8880
cagcagccac tggtaacagg attagcagag cgaggtatgt aggcggtgct acagagttct    8940
```

```
tgaagtggtg gcctaactac ggctacacta gaagaacagt atttggtatc tgcgctctgc   9000
tgaagccagt taccttcgga aaaagagttg gtagctcttg atccggcaaa caaaccaccg   9060
ctggtagcgg tggttttttt gtttgcaagc agcagattac gcgcagaaaa aaaggatctc   9120
aagaagatcc tttgatcttt tctacggggt ctgacgctca gtggaacgaa aactcacgtt   9180
aagggatttt ggtcatgaga ttatcaaaaa ggatcttcac ctagatcctt ttaaattaaa   9240
aatgaagttt taaatcaatc taaagtatat atgagtaaac ttggtctgac agttaccaat   9300
gcttaatcag tgaggcacct atctcagcga tctgtctatt tcgttcatcc atagttgcct   9360
gactcctgca aaccacgttg tgtctcaaaa tctctgatgt tacattgcac aagataaaaa   9420
tatatcatca tgaacaataa aactgtctgc ttacataaac agtaatacaa ggggtgttat   9480
gagccatatt caacgggaaa cgtcttgctc gaggccgcga ttaaattcca acatggatgc   9540
tgatttatat gggtataaat gggctcgcga taatgtcggg caatcaggtg cgacaatcta   9600
tcgattgtat gggaagcccg atgcgccaga gttgtttctg aaacatggca aaggtagcgt   9660
tgccaatgat gttacagatg agatggtcag actaaactgg ctgacggaat ttatgcctct   9720
tccgaccatc aagcatttta tccgtactcc tgatgatgca tggttactca ccactgcgat   9780
ccccgggaaa acagcattcc aggtattaga agaatatcct gattcaggtg aaaatattgt   9840
tgatgcgctg gcagtgttcc tgcgccggtt gcattcgatt cctgtttgta attgtccttt   9900
taacagcgat cgcgtatttc gtctcgctca ggcgcaatca cgaatgaata cggtttggt   9960 tgatgcgagt gattttgatg acgagcgtaa tggctggcct gttgaacaag tctggaaaga   10020
aatgcataag cttttgccat tctcaccgga ttcagtcgtc actcatggtg atttctcact   10080
tgataacctt attttgacg aggggaaatt aataggttgt attgatgttg gacgagtcgg   10140
aatcgcagac cgataccagg atcttgccat cctatggaac tgcctcggtg agttttctcc   10200
ttcattacag aaacggcttt ttcaaaaata tggtattgat aatcctgata tgaataaatt   10260
gcagtttcat ttgatgctcg atgagttttt ctaagggcgg cctgccacca tacccacgcc   10320
gaaacaagcg ctcatgagcc cgaagtggcg agcccgatct tccccatcgg tgatgtcggc   10380
gatataggcg ccagcaaccg cacctgtggc gccggtgatg agggcgcgcc aagtcgacgt   10440
ccggcagtct tggccactcc ctctctgcgc gctcgctcgc tcactgaggc cgggcgacca   10500
aaggtcgccc gacgcccggg ctttgcccgg cggcctcag tgagcgagcg agcgcgcaga   10560
gagggagtgg ccaactccat cactagggt tcctgctagc tctgggtatt taagcccgag   10620
tgagcacgca gggtctccat tttgaagcgg gaggttacgc gttcgtcgac tactagtggg   10680
taccagagcg tggtgactga gatgttttct aggaaacaca aaagatacaa aaagaacac   10740 gtggaaggat agccaaaag ggggctgcc cccatttcct gcaccccgct gcgatggctg   10800
gcaccatttg gaagacttcg agatacactg ttgagcgcag taagacaaca gtgtatctcg   10860
aagtcttcca gatggggcca gccggtccac tctgtatcca ggccagttct gcaaggcgtt   10920
cgaggaccac cccctccc tcgccaccag ggtggtctca tacagaactt ataagattcc   10980
caaatccaaa gacatttcac gtttatggtg atttcccaga acacatagcg acatgcaaat   11040
attgcagggc gccactcccc tgtccctcac agccatcttc ctgccagggc gcacgcgcgc   11100
tgggtgttcc cgcctagtga cactgggccc gcgattcctt ggagcgggtt gatgacgtca   11160
gcgtttccca tggtgaatcc ctaggtt                                       11187
```

<210> SEQ ID NO 13
<211> LENGTH: 10960

<212> TYPE: DNA
<213> ORGANISM: Artificial Sequence
<220> FEATURE:
<223> OTHER INFORMATION: Synthetic polynucleotide

<400> SEQUENCE: 13

| | | | | | |
|---|---|---|---|---|---|
| ttggccactc | cctctctgcg | cgctcgctcg | ctcactgagg | ccgggcgacc | aaaggtcgcc | 60 |
| cgacgcccgg | gctttgcccg | ggcggcctca | gtgagcgagc | gagcgcgcag | agagggagtg | 120 |
| gccaactcca | tcactagggg | ttcctgctag | ctctgggtat | ttaagcccga | gtgagcacgc | 180 |
| agggtctcca | ttttgaagcg | ggaggttacg | cgttcgtcga | ctactagtgg | gtaccagagc | 240 |
| tccctaggtt | ctagaaccgg | tgacgtctcc | catggtgaag | cttggatctg | aattcggtac | 300 |
| cctagttatt | aatagtaatc | aattacgggg | tcattagttc | atagcccata | tatggagttc | 360 |
| cgcgttacat | aacttacggt | aaatggcccg | cctggctgac | cgcccaacga | cccccgccca | 420 |
| ttgacgtcaa | taatgacgta | tgttcccata | gtaacgccaa | tagggacttt | ccattgacgt | 480 |
| caatgggtgg | actatttacg | gtaaactgcc | cacttggcag | tacatcaagt | gtatcatatg | 540 |
| ccaagtacgc | cccctattga | cgtcaatgac | ggtaaatggc | ccgcctggca | ttatgcccag | 600 |
| tacatgacct | tatgggactt | tcctacttgg | cagtacatct | acgtattagt | catcgctatt | 660 |
| accatggtcg | aggtgagccc | cacgttctgc | ttcactctcc | ccatctcccc | ccctcccca | 720 |
| cccccaattt | tgtatttatt | tattttttaa | ttattttgtg | cagcgatggg | ggcgggggg | 780 |
| ggggggggc | gcgcgccagg | cggggcgggg | cggggcgagg | ggcggggcgg | ggcgaggcgg | 840 |
| agaggtgcgg | cggcagccaa | tcagagcggc | gcgctccgaa | agtttccttt | tatggcgagg | 900 |
| cggcggcggc | ggcggcccta | taaaaagcga | agcgcgcggc | gggcgggagt | cgctgcgacg | 960 |
| ctgccttcgc | cccgtgcccc | gctccgccgc | cgcctcgcgc | cgcccgcccc | ggctctgact | 1020 |
| gaccgcgtta | ctcccacagg | tgagcgggcg | ggacggccct | tctcctccgg | gctgtaatta | 1080 |
| gcgcttggtt | taatgacggc | ttgtcctggt | ggcgagggga | ggggggtggt | cctcgaacgc | 1140 |
| cttgcagaac | tggcctggat | acagagtgga | ccggctggcc | ccatctggaa | gacttcgaga | 1200 |
| tacactgttg | tcttactgcg | ctcaacagtg | tatctcgaag | tcttccaaat | ggtgccagcc | 1260 |
| atcgcagcgg | ggtgcaggaa | atgggggcag | ccccccttt | tggctatcct | tccacgtgtt | 1320 |
| cttttttgta | tcttttgtgt | ttcctagaaa | acatctcagt | caccacctt | ctgtggctgc | 1380 |
| gtgaaagcct | tgagggctc | cgggagctag | agcctctgct | aaccatgttc | atgccttctt | 1440 |
| cttttttccta | cagctcctgg | gcaacgtgct | ggttattgtg | ctgtctcatc | attttggcaa | 1500 |
| agaattcctc | gaagatccga | agggaaagtc | ttccacgact | gtgggatccg | ttcgaagata | 1560 |
| tcaccggttg | agccaccatg | gaattcagca | gccccagcag | agaggaatgc | cccaagcctc | 1620 |
| tgagccgggt | gtcaatcatg | gccggatctc | tgacaggact | gctgctgctt | caggccgtgt | 1680 |
| cttgggcttc | tggcgctaga | ccttgcatcc | ccaagagctt | cggctacagc | agcgtcgtgt | 1740 |
| gcgtgtgcaa | tgccacctac | tgcgacagct | tcgaccctcc | tacctttcct | gctctgggca | 1800 |
| ccttcagcag | atacgagagc | accagatccg | gcagacggat | ggaactgagc | atgggaccca | 1860 |
| tccaggccaa | tcacacaggc | actggcctgc | tgctgacact | gcagcctgag | cagaaattcc | 1920 |
| agaaagtgaa | aggcttcggc | ggagccatga | cagatgccgc | cgctctgaat | atcctggctc | 1980 |
| tgtctccacc | agctcagaac | ctgctgctca | agagctactt | cagcgaggaa | ggcatcggct | 2040 |
| acaacatcat | cagagtgccc | atggccagct | gcgacttcag | catcaggacc | tacacctacg | 2100 |
| ccgacacacc | cgacgatttc | cagctgcaca | acttcagcct | gcctgaagag | gacaccaagc | 2160 |

```
tgaagatccc tctgatccac agagccctgc agctggcaca agacccgtg tcactgctgg    2220 cctctccatg gacatctccc acctggctga aaacaaatgg cgccgtgaat ggcaagggca    2280
gcctgaaagg ccaacctggc gacatctacc accagacctg gccagatac ttcgtgaagt    2340 tcctggacgc ctatgccgag cacaagctgc agttttgggc cgtgacagcc gagaacgaac    2400
cttctgctgg actgctgagc ggctaccct ttcagtgcct gggctttaca cccgagcacc    2460
agcgggactt tatcgcccgt gatctgggac ccacactggc caatagcacc caccataatg    2520
tgcggctgct gatgctggac gaccagagac tgcttctgcc ccactgggct aaagtggtgc    2580
tgacagatcc tgaggccgcc aaatacgtgc acggaatcgc cgtgcactgg tatctggact    2640
ttctggcccc tgccaaggcc acactgggag agacacacag actgttcccc aacaccatgc    2700
tgttcgccag cgaagcctgt gtgggcagca gttttgggga acagagcgtg cggctcggca    2760
gctgggatag aggcatgcag tacagccaca gcatcatcac caacctgctg taccacgtcg    2820
tcggctggac cgactggaat ctggccctga atcctgaagg cggccctaac tgggtccgaa    2880
acttcgtgga cagccccatc atcgtggaca tcaccaagga caccttctac aagcagccca    2940
tgttctacca cctgggacac ttcagcaagt tcatccccga gggctctcag cgcgttggac    3000
tggtggcttc ccagaagaac gatctggacg ccgtggctct gatgcaccct gatggatctg    3060
ctgtggtggt ggtcctgaac cgcagcagca agatgtgcc cctgaccatc aaggatcccg    3120
ccgtgggatt cctggaaaca atcagccctg gctactccat ccacacctac ctgtggcgta    3180
gacagtgaca attgttaatt aagtttaaac cctcgaggcc gcaagcttat cgataatcaa    3240
cctctggatt acaaaatttg tgaaagattg actggtattc ttaactatgt tgctcctttt    3300
acgctatgtg gatacgctgc tttaatgcct ttgtatcatg ctattgcttc ccgtatggct    3360
ttcattttct cctccttgta taaatcctgg ttgctgtctc tttatgagga ttgtggccc    3420 gttgtcaggc aacgtggcgt ggtgtgcact gtgtttgctg acgcaacccc cactggttgg    3480
ggcattgcca ccacctgtca gctcctttcc gggactttcg cttccccct ccctattgcc    3540 acggcggaac tcatcgccgc ctgccttgcc cgctgctgga caggggctcg gctgttgggc    3600
actgacaatt ccgtggtgtt gtcggggaaa tcatcgtcct ttccttggct gctcgcctgt    3660
gttgccacct ggattctgcg cgggacgtcc ttctgctacg tcccttcggc cctcaatcca    3720
gcggaccttc cttcccgcgg cctgctgccg gctctgcggc ctcttccgcg tcttcgcctt    3780
cgccctcaga cgagtcggat ctccctttgg gccgcctccc cgcatcgata ccgtcgacta    3840
gagctcgctg atcagcctcg actgtgcctt ctagttgcca gccatctgtt gtttgcccct    3900
cccccgtgcc ttccttgacc ctggaaggtg ccactcccac tgtcctttcc taataaaatg    3960
aggaaattgc atcgcattgt ctgagtaggt gtcattctat tctgggggt ggggtggggc    4020 aggacagcaa gggggaggat tgggaagaca atagcaggca tgctggggag agatccacga    4080
taacaaacag ctttttgggg gtgaacatat tgactgaatt ccctgcaggt tggccactcc    4140
ctctctgcgc gctcgctcgc tcactgaggc cgcccgggca agcccgggc gtcgggcgac    4200 ctttggtcgc ccggcctcag tgagcgagcg agcgcgcaga gagggagtgg ccaactccat    4260
cactaggggt tcctgcggcc gctcgtacgg tctcgaggaa ttcctgcagg ataacttgcc    4320
aacctcattc taaaatgtat atagaagccc aaaagacaat aacaaaaata ttcttgtaga    4380
acaaaatggg aaagaatgtt ccactaaata tcaagattta gagcaaagca tgagatgtgt    4440
ggggatagac agtgaggctg ataaaataga gtagagctca gaaacagacc cattgatata    4500
tgtaagtgac ctatgaaaaa aatatggcat tttacaatgg gaaaatgatg gtcttttct     4560
```

```
tttttagaaa aacagggaaa tatatttata tgtaaaaaat aaaagggaac ccatatgtca    4620
taccatacac acaaaaaaat tccagtgaat tataagtcta aatggagaag gcaaaacttt    4680
aaatctttta gaaataata tagaagcatg cagaccagcc tggccaacat gatgaaaccc    4740
tctctactaa taataaaatc agtagaacta ctcaggacta ctttgagtgg gaagtccttt    4800
tctatgaaga cttctttggc caaaattagg ctctaaatgc aaggagatag tgcatcatgc    4860
ctggctgcac ttactgataa atgatgttat caccatcttt aaccaaatgc acaggaacaa    4920
gttatggtac tgatgtgctg gattgagaag gagctctact tccttgacag gacacatttg    4980
tatcaactta aaaagcaga ttttgccag cagaactatt cattcagagg taggaaactt    5040
agaatagatg atgtcactga ttagcatggc ttccccatct ccacagctgc ttcccaccca    5100
ggttgcccac agttgagttt gtccagtgct cagggctgcc cactctcagt aagaagcccc    5160
acaccagccc ctctccaaat atgttggctg ttccttccat taaagtgacc ccactttaga    5220
gcagcaagtg gatttctgtt tcttacagtt caggaaggag gagtcagctg tgagaacctg    5280
gagcctgaga tgcttctaag tcccactgct actggggtca gggaagccag actccagcat    5340
cagcagtcag gagcactaag cccttgccaa catcctgttt ctcagagaaa ctgcttccat    5400
tataatggtt gtcctttttt aagctatcaa gccaaacaac cagtgtctac cattattctc    5460
atcacctgaa gccaagggtt ctagcaaaag tcaagctgtc ttgtaatggt tgatgtgcct    5520
ccagcttctg tcttcagtca ctccactctt agcctgctct gaatcaactc tgaccacagt    5580
tccctggagc cctgccacc tgctgccct gccaccttct ccatctgcag tgctgtgcag    5640
ccttctgcac tcttgcagag ctaataggtg gagacttgaa ggaagaggag gaaagtttct    5700
cataatagcc ttgctgcaag ctcaaatggg aggtgggcac tgtgcccagg agccttggag    5760
caaaggctgt gcccaacctc tgactgcatc caggtttggt cttgacagag ataagaagcc    5820
ctggcttttg gagccaaaat ctaggtcaga cttaggcagg attctcaaag tttatcagca    5880
gaacatgagg cagaagaccc tttctgctcc agcttcttca ggctcaacct tcatcagaat    5940
agatagaaag agaggctgtg agggttctta aaacagaagc aaatctgact cagagaataa    6000
acaacctcct agtaaactac agcttagaca gagcatctgg tggtgagtgt gctcagtgtc    6060
ctactcaact gtctggtatc agccctcatg aggacttctc ttctttccct catagacctc    6120
catctctgtt ttccttagcc tgcagaaatc tggatggcta ttcacagaat gcctgtgctt    6180
tcagagttgc atttttctc tggtattctg gttcaagcat ttgaaggtag gaaaggttct    6240
ccaagtgcaa gaaagccagc cctgagcctc aactgcctgg ctagtgtggt cagtaggatg    6300
caaaggctgt tgaatgccac aaggccaaac tttaacctgt gtaccacaag cctagcagca    6360
gaggcagctc tgctcactgg aactctctgt cttctttctc ctgagccttt tcttttcctg    6420
agttttctag ctctcctcaa ccttacctct gccctaccca ggacaaaccc aagagccact    6480
gtttctgtga tgtcctctcc agccctaatt aggcatcatg acttcagcct gaccttccat    6540
gctcagaagc agtgctaatc cacttcagat gagctgctct atgcaacaca ggcagagcct    6600
acaaaccttt gcaccagagc cctccacata tcagtgtttg ttcatactca cttcaacagc    6660
aaatgtgact gctgagatta agattttaca caagatggtc tgtaatttca cagttagttt    6720
tatcccatta ggtatgaaag aattagcata attccccttta acatgaatg aatcttagat    6780 tttttaataa atagttttgg aagtaaagac agagacatca ggagcacaag gaatagcctg    6840
agaggacaaa cagaacaaga aagagtctgg aaatacacag gatgttcttg gcctcctcaa    6900
```

```
agcaagtgca agcagatagt accagcagcc ccaggctatc agagcccagt gaagagaagt    6960
accatgaaag ccacagctct aaccaccctg ttccagagtg acagacagtc cccaagacaa    7020
gccagcctga gccagagaga gaactgcaag agaaagtttc taatttaggt tctgttagat    7080
tcagacaagt gcaggtcatc ctctctccac agctactcac ctctccagcc taacaaagcc    7140
tgcagtccac actccaaccc tggtgtctca cctcctagcc tctcccaaca tcctgctctc    7200
tgaccatctt ctgcatctct catctcacca tctcccactg tctacagcct actcttgcaa    7260
ctaccatctc attttctgac atcctgtcta catcttctgc catactctgc catctaccat    7320
accacctctt accatctacc acaccatctt ttatctccat ccctctcaga gcctccaag     7380
ctgaatcctg ctttatgtgt tcatctcagc ccctgcatgg aaagctgacc ccagaggcag    7440
aactattccc agagagcttg gccaagaaaa acaaaactac cagccggcc aggctcagga     7500
gtagtaagct gcagtgtctg ttgtgttcta gcttcaacag ctgcaggagt tccactctca    7560
aatgctccac atttctcaca tcctcctgat tctggtcact acccatcttc aaagaacaga    7620
atatctcaca tcagcatact gtgaaggact agtcatgggt gcagctgctc agagctgcaa    7680
agtcattctg gatggtggag agcttacaaa catttcatga tgctccccc gctctgatgg     7740
ctggagccca atccctacac agactcctgc tgtatgtgtt ttcctttcac tctgagccac    7800
agccagaggg caggcattca gtctcctctt caggctgggg ctggggcact gagaactcac    7860
ccaacacctt gctctcactc cttctgcaaa acaagaaaga ctttgtgct gcagtagcca     7920
tgaagaatga aaggaaggct ttaactaaaa aatgtcagag attattttca ccccttact    7980
gtggatcacc agcaaggagg aaacacaaca cagagacatt ttttcccctc aaattatcaa    8040
aagaatcact gcatttgtta aagagagcaa ctgaatcagg aagcagagtt ttgaacatat    8100
cagaagttag gaatctgcat cagagacaaa tgcagtcatg gttgttgct gcataccagc     8160
cctaatcatt agaagcctca tggacttcaa acatcattcc ctctgacaag atgctctagc    8220
ctaactccat gagataaaat aaatctgcct ttcagagcca agaagagtc caccagcttc     8280
ttctcagtgt gaacaagagc tccagtcagg ttagtcagtc cagtgcagta gaggagacca    8340
gtctgcatcc tctaattttc aaaggcaaga agatttgttt accctggaca ccaggcacaa    8400
gtgaggtcac agagctctta gatatgcagt cctcatgagt gaggagacta agcgcatgc     8460
catcaagact tcagtgtaga gaaaacctcc aaaaaagcct cctcactact tctggaatag    8520
ctcagaggcc gaggcggcct cggcctctgc ataaataaaa aaaattagtc agccatgggg    8580
cggagaatgg gcggaactgg gcggagttag gggcgggatg ggcggagtta ggggcgggac    8640
tatggttgct gactaattga gatgcatgct ttgcatactt ctgcctgctg gggagcctgg    8700
ggactttcca cacctggttg ctgactaatt gagatgcatg cttttgcatac ttctgcctgc   8760
tggggagcct ggggactttc cacaccctaa ctgacacaca ttccacagct gcattaatga    8820
atcggccaac gcgcgggag aggcggtttg cgtattgggc gctcttccgc ttcctcgctc     8880
actgactcgc tgcgctcggt cgttcggctg cggcgagcgg tatcagctca ctcaaaggcg    8940
gtaatacggt tatccacaga atcaggggat aacgcaggaa agaacatgtg agcaaaaggc    9000
cagcaaaagg ccaggaaccg taaaaaggcc gcgttgctgg cgttttttcca taggctccgc    9060
ccccctgacg agcatcacaa aaatcgacgc tcaagtcaga ggtggcgaaa cccgacagga    9120
ctataaagat accaggcgtt tccccctgga agctccctcg tgcgctctcc tgttccgacc    9180
ctgccgctta ccggatacct gtccgccttt ctcccttcgg gaagcgtggc gctttctcat    9240
agctcacgct gtaggtatct cagttcggtg taggtcgttc gctccaagct gggctgtgtg    9300
```

-continued

```
cacgaacccc ccgttcagcc cgaccgctgc gccttatccg gtaactatcg tcttgagtcc    9360
aacccggtaa gacacgactt atcgccactg gcagcagcca ctggtaacag gattagcaga    9420
gcgaggtatg taggcggtgc tacagagttc ttgaagtggt ggcctaacta cggctacact    9480
agaagaacag tatttggtat ctgcgctctg ctgaagccag ttaccttcgg aaaaagagtt    9540
ggtagctctt gatccggcaa acaaaccacc gctggtagcg gtggtttttt tgtttgcaag    9600
cagcagatta cgcgcagaaa aaaaggatct caagaagatc ctttgatctt ttctacgggg    9660
tctgacgctc agtggaacga aaactcacgt taagggattt tggtcatgag attatcaaaa    9720
aggatcttca cctagatcct tttaaattaa aaatgaagtt ttaaatcaat ctaaagtata    9780
tatgagtaaa cttggtctga cagttaccaa tgcttaatca gtgaggcacc tatctcagcg    9840
atctgtctat ttcgttcatc catagttgcc tgactcctgc aaaccacgtt gtgtctcaaa    9900
atctctgatg ttacattgca caagataaaa atatatcatc atgaacaata aaactgtctg    9960
cttacataaa cagtaataca agggtgtta tgagccatat tcaacgggaa acgtcttgct   10020
cgaggccgcg attaaattcc aacatggatg ctgatttata tgggtataaa tgggctcgcg   10080
ataatgtcgg gcaatcaggt gcgacaatct atcgattgta tgggaagccc gatgcgccag   10140
agttgtttct gaaacatggc aaaggtagcg ttgccaatga tgttacagat gagatggtca   10200
gactaaactg gctgacggaa tttatgcctc ttccgaccat caagcatttt atccgtactc   10260
ctgatgatgc atggttactc accactgcga tccccgggaa aacagcattc caggtattag   10320
aagaatatcc tgattcaggt gaaaatattg ttgatgcgct ggcagtgttc ctgcgccggt   10380
tgcattcgat tcctgtttgt aattgtcctt ttaacagcga tcgcgtattt cgtctcgctc   10440
aggcgcaatc acgaatgaat aacggtttgg ttgatgcgag tgattttgat gacgagcgta   10500
atggctggcc tgttgaacaa gtctggaaag aaatgcataa gcttttgcca ttctcaccgg   10560
attcagtcgt cactcatggt gatttctcac ttgataacct tattttgac gaggggaaat   10620 taataggttg tattgatgtt ggacgagtcg gaatcgcaga ccgataccag gatcttgcca   10680
tcctatggaa ctgcctcggt gagttttctc cttcattaca gaaacggctt tttcaaaaat   10740
atggtattga taatcctgat atgaataaat tgcagtttca tttgatgctc gatgagtttt   10800
tctaagggcg gcctgccacc atacccacgc cgaaacaagc gctcatgagc ccgaagtggc   10860
gagcccgatc ttccccatcg gtgatgtcgg cgatataggc gccagcaacc gcacctgtgg   10920
cgccggtgat gagggcgcgc caagtcgacg tccggcagtc                         10960
```

<210> SEQ ID NO 14
<211> LENGTH: 536
<212> TYPE: PRT
<213> ORGANISM: Homo sapiens

<400> SEQUENCE: 14

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

```
Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495
```

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
            515                 520                 525

His Thr Tyr Leu Trp Arg Arg Gln
            530                 535

<210> SEQ ID NO 15
<211> LENGTH: 1608
<212> TYPE: DNA
<213> ORGANISM: Homo sapiens

<400> SEQUENCE: 15

| | | | | | |
|---|---|---|---|---|---|
| atggaattca | gcagcccag | cagagaggaa | tgccccaagc | tctgagccg | ggtgtcaatc | 60 |
| atggccggat | ctctgacagg | actgctgctg | cttcaggccg | tgtcttggc | ttctggcgct | 120 |
| agaccttgca | tccccaagag | cttcggctac | agcagcgtcg | tgtgcgtgtg | caatgccacc | 180 |
| tactgcgaca | gcttcgaccc | tcctaccttt | cctgctctgg | gcaccttcag | cagatacgag | 240 |
| agcaccagat | ccggcagacg | gatggaactg | agcatgggac | ccatccaggc | caatcacaca | 300 |
| ggcactggcc | tgctgctgac | actgcagcct | gagcagaaat | tccagaaagt | gaaaggcttc | 360 |
| ggcggagcca | tgacagatgc | cgccgctctg | aatatcctgg | ctctgtctcc | accagctcag | 420 |
| aacctgctgc | tcaagagcta | cttcagcgag | gaaggcatcg | gctacaacat | catcagagtg | 480 |
| cccatggcca | gctgcgactt | cagcatcagg | acctacacct | acgccgacac | cccgacgat | 540 |
| ttccagctgc | acaacttcag | cctgcctgaa | gaggacacca | gctgaagat | ccctctgatc | 600 |
| cacagagccc | tgcagctggc | acaaagaccc | gtgtcactgc | tggcctctcc | atggacatct | 660 |
| cccacctggc | tgaaaacaaa | tggcgccgtg | aatggcaagg | gcagcctgaa | aggccaacct | 720 |
| ggcgacatct | accaccagac | ctgggccaga | tacttcgtga | gttcctgga | cgcctatgcc | 780 |
| gagcacaagc | tgcagttttg | ggccgtgaca | gccgagaacg | aaccttctgc | tggactgctg | 840 |
| agcggctacc | cctttcagtg | cctgggcttt | acacccgagc | accagcggga | ctttatcgcc | 900 |
| cgtgatctgg | gacccacact | ggccaatagc | acccaccata | atgtgcggct | gctgatgctg | 960 |
| gacgaccaga | gactgcttct | gccccactgg | gctaaagtgg | tgctgacaga | tcctgaggcc | 1020 |
| gccaaatacg | tgcacggaat | cgccgtgcac | tggtatctgg | actttctggc | ccctgccaag | 1080 |
| gccacactgg | gagagacaca | cagactgttc | cccaacacca | tgctgttcgc | cagcgaagcc | 1140 |
| tgtgtgggca | gcaagttttg | gaacagagc | gtgcggctcg | gcagctggga | tagaggcatg | 1200 |
| cagtacagcc | acagcatcat | caccaacctg | ctgtaccacg | tcgtcggctg | gaccgactgg | 1260 |
| aatctggccc | tgaatcctga | aggcggccct | aactgggtcc | gaaacttcgt | ggacagcccc | 1320 |
| atcatcgtgg | acatcaccaa | ggacaccttc | tacaagcagc | ccatgttcta | ccacctggga | 1380 |
| cacttcagca | agttcatccc | cgagggctct | cagcgcgttg | gactggtggc | ttcccagaag | 1440 |
| aacgatctgg | acgccgtggc | tctgatgcac | cctgatggat | ctgctgtggt | ggtggtcctg | 1500 |
| aaccgcagca | gcaaagatgt | gccctgacc | atcaaggatc | cgccgtggg | attcctggaa | 1560 |
| acaatcagcc | ctggctactc | catccacacc | tacctgtggc | gtagacag | | 1608 |

<210> SEQ ID NO 16
<211> LENGTH: 524
<212> TYPE: PRT
<213> ORGANISM: Homo sapiens

<400> SEQUENCE: 16

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
            35                  40                  45

Leu Gln Thr Val Trp Asn Lys Pro Thr Val Lys Ser Leu Pro Cys Asp
        50                  55                  60

Ile Cys Lys Asp Val Val Thr Ala Ala Gly Asp Met Leu Lys Asp Asn
65                  70                  75                  80

Ala Thr Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285

Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
            405                 410                 415

Gly Tyr Leu Asp Arg Asn Leu Glu Lys Asn Ser Thr Lys Gln Glu Ile
```

| | 420 | | | | 425 | | | | 430 | | |
|---|---|---|---|---|---|---|---|---|---|---|---|
| Leu | Ala | Ala | Leu | Glu | Lys | Gly | Cys | Ser | Phe | Leu | Pro | Asp | Pro | Tyr | Gln |
| | | | 435 | | | | | 440 | | | | | 445 | | |

Lys Gln Cys Asp Gln Phe Val Ala Glu Tyr Glu Pro Val Leu Ile Glu
        450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
            485                 490                 495

Trp Gly Pro Ser Tyr Trp Cys Gln Asn Thr Glu Thr Ala Ala Gln Cys
        500                 505                 510

Asn Ala Val Glu His Cys Lys Arg His Val Trp Asn
        515                 520

<210> SEQ ID NO 17
<211> LENGTH: 1572
<212> TYPE: DNA
<213> ORGANISM: Homo sapiens

<400> SEQUENCE: 17

| atgtacgccc tgttcctgct ggccagcctg ctgggcgccg ccctggccgg ccccgtgctg | 60 |
| ggcctgaagg agtgcacccg cggcagcgcc gtgtggtgcc agaacgtgaa gaccgccagc | 120 |
| gactgcggcc ccgtgaagca ctgcctgcag accgtgtgga caagcccac cgtgaagagc | 180 |
| ctgccctgcg acatctgcaa ggacgtggtg accgccgccg cgacatgct gaaggacaac | 240 |
| gccaccgagg aggagatcct ggtgtacctg gagaagacct cgactggct gcccaagccc | 300 |
| aacatgagcg ccagctgcaa ggagatcgtg acagctacc tgcccgtgat cctggacatc | 360 |
| atcaagggcg agatgagccg ccccggcgag gtgtgcagcg ccctgaacct gtgcgagagc | 420 |
| ctgcagaagc acctggccga gctgaaccac cagaagcagc tggagagcaa caagatcccc | 480 |
| gagctggaca tgaccgaggt ggtggcccc ttcatggcca acatccccct gctgctgtac | 540 |
| ccccaggacg gccccgcag caagccccag cccaaggaca cggcgacgt gtgccaggac | 600 |
| tgcatccaga tggtgaccga catccagacc gccgtgcgca ccaacagcac cttcgtgcag | 660 |
| gccctggtgg agcacgtgaa ggaggagtgc gaccgcctgg gccccggcat ggccgacatc | 720 |
| tgcaagaact acatcagcca gtacagcgag atcgccatcc agatgatgat gcacatgcag | 780 |
| cccaaggaga tctgcgccct ggtgggcttc tgcgacgagg tgaaggagat gcccatgcag | 840 |
| accctggtgc cgccaaggt ggccagcaag aacgtgatcc ccgccctgga gctggtggag | 900 |
| cccatcaaga gcacgaggt gccgccaag agcgacgtgt actgcgaggt gtgcgagttc | 960 |
| ctggtgaagg aggtgaccaa gctgatcgac aacaacaaga ccgagaagga gatcctggac | 1020 |
| gccttcgaca agatgtgcag caagctgccc aagagcctga gcgaggagtg ccaggaggtg | 1080 |
| gtggacacct acggcagcag catcctgagc atcctgctgg aggaggtgag ccccgagctg | 1140 |
| gtgtgcagca tgctgcacct gtgcagcggc accgccctgc ccgccctgac cgtgcacgtg | 1200 |
| acccagccca aggacggcgg cttctgcgag gtgtgcaaga agctggtggg ctacctggac | 1260 |
| cgcaacctgg agaagaacag caccaagcag gagatcctgg ccgccctgga aagggctgc | 1320 |
| agcttcctgc ccgaccccta ccagaagcag tgcgaccagt tcgtggccga gtacgagccc | 1380 |
| gtgctgatcg agatcctggt ggaggtgatg gaccccagct tcgtgtgcct gaagatcggc | 1440 |
| gcctgcccca cgcccacaa gcccctgctg ggcaccgaga agtgcatctg ggcccccagc | 1500 |
| tactggtgcc agaacaccga gaccgccgcc cagtgcaacg ccgtggagca ctgcaagcgc | 1560 | cacgtgtgga ac                                                          1572

<210> SEQ ID NO 18
<211> LENGTH: 478
<212> TYPE: PRT
<213> ORGANISM: Homo sapiens

<400> SEQUENCE: 18

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
                20                  25                  30

Val Asp Gln Ser Ile Glu Lys Lys Ile Val Leu Arg Asn Gly Thr Glu
            35                  40                  45

Ala Phe Asp Ser Trp Glu Lys Pro Pro Leu Pro Val Tyr Thr Gln Phe
        50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220

Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
                245                 250                 255

His Pro Leu Ile Thr Lys Asp Glu Val Leu Tyr Val Phe Pro Ser Asp
            260                 265                 270

Phe Cys Arg Ser Val Tyr Ile Thr Phe Ser Asp Tyr Glu Ser Val Gln
        275                 280                 285

Gly Leu Pro Ala Phe Arg Tyr Lys Val Pro Ala Glu Ile Leu Ala Asn
    290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

```
Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475
```

<210> SEQ ID NO 19
<211> LENGTH: 1434
<212> TYPE: DNA
<213> ORGANISM: Homo sapiens

<400> SEQUENCE: 19

```
atgggccgct gctgcttcta caccgccggc accctgagcc tgctgctgct ggtgaccagc    60
gtgaccctgc tggtggcccg cgtgttccag aaggccgtgg accagagcat cgagaagaag   120
atcgtgctgc gcaacggcac cgaggccttc gacagctggg agaagccccc cctgcccgtg   180
tacacccagt tctacttctt caacgtgacc aaccccgagg atcctgcg cggcgagacc    240
ccccgcgtgg aggaggtggg ccctacacc taccgcgagc tgcgcaacaa ggccaacatc    300
cagttcggcg acaacggcac caccatcagc gccgtgagca acaaggccta cgtgttcgag    360
cgcgaccaga gcgtgggcga ccccaagatc gacctgatcc gcaccctgaa catccccgtg    420
ctgaccgtga tcgagtggag ccaggtgcac ttcctgcgcg agatcatcga ggccatgctg    480
aaggcctacc agcagaagct gttcgtgacc cacaccgtgg acgagctgct gtggggctac    540
aaggacgaga tcctgagcct gatccacgtg ttccgccccg acatcagccc ctacttcggc    600
ctgttctacg agaagaacgg caccaacgac ggcgactacg tgttcctgac cggcgaggac    660
agctacctga acttcaccaa gatcgtggag tggaacggca agaccagcct ggactggtgg    720
atcaccgaca gtgcaacat gatcaacggc accgacggcg acagcttcca ccccctgatc    780
accaaggacg aggtgctgta cgtgttcccc agcgacttct gccgcagcgt gtacatcacc    840
ttcagcgact acgagagcgt gcagggcctg ccgccttcc gctacaaggt gcccgccgag    900
atcctggcca acaccagcga caacgccggc ttctgcatcc ccgagggcaa ctgcctgggc    960
agcggcgtgc tgaacgtgag catctgcaag aacggcgccc ccatcatcat gagcttcccc   1020
cacttctacc aggccgacga cgcttcgtg agcgccatcg agggcatgca ccccaaccag   1080
gaggaccacg agaccttcgt ggacatcaac cccctgaccg catcatcct gaaggccgcc   1140
aagcgcttcc agatcaacat ctacgtgaag aagctggacg acttcgtgga gaccggcgac   1200
atccgcacca tggtgttccc cgtgatgtac ctgaacgaga gcgtgcacat cgacaaggag   1260
accgccagcc gcctgaagag catgatcaac accaccctga tcatcaccaa catcccctac   1320
atcatcatgg ccctgggcgt gttcttcggc ctggtgttca cctggctggc ctgcaagggc   1380
cagggcagca tggacgaggg caccgccgac gagcgcgccc ccctgatccg cacc        1434
```

```
<210> SEQ ID NO 20
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 20
tggaagactt cgagatacac tgt                                              23

<210> SEQ ID NO 21
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 21
acagtgtatc tcgaagtctt cca                                              23

<210> SEQ ID NO 22
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 22
tttagaaata agtggtagtc a                                                21

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
tgactaccac ttatttctaa a                                                21

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
agggtatcaa gactacgaa                                                   19

<210> SEQ ID NO 25
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 25
ttcgtagtct tgataccct                                                   19

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide
```

```
<400> SEQUENCE: 26
tattagatct gatggccgc                                                    19

<210> SEQ ID NO 27
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 27
ctccatcact aggggttcct                                                   20

<210> SEQ ID NO 28
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 28
agctctgggt atttaagccc gagtgagcac gcagggtctc cattttgaag cgggaggtta       60

<210> SEQ ID NO 29
<211> LENGTH: 145
<212> TYPE: DNA
<213> ORGANISM: Unknown
<220> FEATURE:
<223> OTHER INFORMATION: AAV2 ITR

<400> SEQUENCE: 29
aggaacccct agtgatggag ttggccactc cctctctgcg cgctcgctcg ctcactgagg       60
ccgggcgacc aaaggtcgcc cgacgcccgg gctttgcccg ggcggcctca gtgagcgagc      120
gagcgcgcag agagggagtg gccaa                                            145

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
tattagatct gatggccgcg                                                   20

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 31
tccatcacta ggggttcctg                                                   20
```

GENE THERAPIES FOR LYSOSOMAL DISORDERS

RELATED APPLICATIONS

This Application is a continuation of International Patent Application No. PCT/US2018/054225, filed Oct. 3, 2018, which claims the benefit under 35 U.S.C. 119(e) of the filing date of U.S. Provisional Application Ser. No. 62/567,296, filed Oct. 3, 2017, entitled "GENE THERAPIES FOR LYSOSOMAL DISORDERS", the entire contents of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVL_002_01US_SeqListST25.txt, date recorded: Nov. 20, 2019, file size 210,992 bytes).

BACKGROUND

Gaucher disease is a rare inborn error of glycosphingolipid metabolism due to deficiency of lysosomal acid β-glucocerebrosidase (Gcase, "GBA"). Patients suffer from non-CNS symptoms and findings including hepatosplenomegly, bone marrow insufficiency leading to pancytopenia, lung disorders and fibrosis, and bone defects. In addition, a significant number of patients suffer from neurological manifestations, including defective saccadic eye movements and gaze, seizures, cognitive deficits, developmental delay, and movement disorders including Parkinson's disease.

Several therapeutics exist that address the peripheral disease and the principal clinical manifestations in hematopoietic bone marrow and viscera, including enzyme replacement therapies, chaperone-like small molecule drugs that bind to defective Gcase and improve stability, and substrate reduction therapy that block the production of substrates that accumulate in Gaucher disease, leading to symptoms and pathology. However, other aspects of Gaucher disease and appear refractory to treatment.

SUMMARY

In addition to Gaucher disease patients (who possess mutations in both chromosomal alleles of GBA1 gene), patients with mutations in only one allele of GBA1 are at highly increased risk of Parkinson's disease (PD). The severity of PD symptoms—which include gait difficulty, a tremor at rest, rigidity, and often depression, sleep difficulties, and cognitive decline—correlate with the degree of enzyme activity reduction. Thus, Gaucher disease patients have the most severe course, whereas patient with a single mild mutation in GBA1 typically have a more benign course. Mutation carriers are also at high risk of other PD-related disorders, including Lewy Body Dementia, characterized by executive dysfunction, psychosis, and a PD-like movement disorder, and multi-system atrophy, with characteristic motor and cognitive impairments. No therapies exist that alter the inexorable course of these disorders.

Deficits in enzymes such as Gcase (e.g., the gene product of GBA1 gene), as well as common variants in many genes implicated in lysosome function or trafficking of macromolecules to the lysosome (e.g., Lysosomal Membrane Protein 1 (LIMP), also referred to as SCARB2), have been associated with increased PD risk. The disclosure is based, in part, on expression constructs (e.g., vectors) encoding Gcase (or a portion thereof), prosaposin (or a portion thereof), LIMP2 (or a portion thereof), or a combination of Gcase (or a portion thereof) and one or more additional gene products from PD-associated genes (e.g., LIMP2, Prosaposin, and/or α-Synuclein (α-Syn)). In some embodiments, combinations of gene products described herein act together (e.g., synergistically) to reduce one or more signs and symptoms of PD when expressed in a subject.

Accordingly, in some aspects, the disclosure provides an isolated nucleic acid comprising an expression construct encoding a Gcase (e.g., the gene product of GBA1 gene). In some embodiments, the isolated nucleic acid comprises a Gcase-encoding sequence that has been codon optimized (e.g., codon optimized for expression in mammalian cells, for example human cells). In some embodiments, the nucleic acid sequence encoding the Gcase encodes a protein comprising an amino acid sequence as set forth in SEQ ID NO: 14 (e.g., as set forth in NCBI Reference Sequence NP_000148.2). In some embodiments, the isolated nucleic acid comprises the sequence set forth in SEQ ID NO: 15. In some embodiments the expression construct comprises adeno-associated virus (AAV) inverted terminal repeats (ITRs), for example AAV ITRs flanking the nucleic acid sequence encoding the Gcase.

In some aspects, the disclosure provides an isolated nucleic acid comprising an expression construct encoding Prosaposin (e.g., the gene product of PSAP gene). In some embodiments, the isolated nucleic acid comprises a prosaposin-encoding sequence that has been codon optimized (e.g., codon optimized for expression in mammalian cells, for example human cells). In some embodiments, the nucleic acid sequence encoding the prosaposin encodes a protein comprising an amino acid sequence as set forth in SEQ ID NO: 16 (e.g., as set forth in NCBI Reference Sequence NP_002769.1). In some embodiments, the isolated nucleic acid comprises the sequence set forth in SEQ ID NO: 17. In some embodiments the expression construct comprises adeno-associated virus (AAV) inverted terminal repeats (ITRs), for example AAV ITRs flanking the nucleic acid sequence encoding the prosaposin.

In some aspects, the disclosure provides an isolated nucleic acid comprising an expression construct encoding LIMP2/SCARB2 (e.g., the gene product of SCARB2 gene). In some embodiments, the isolated nucleic acid comprises a SCARB2-encoding sequence that has been codon optimized (e.g., codon optimized for expression in mammalian cells, for example human cells). In some embodiments, the nucleic acid sequence encoding the LIMP2/SCARB2 encodes a protein comprising an amino acid sequence as set forth in SEQ ID NO: 18 (e.g., as set forth in NCBI Reference Sequence NP_005497.1). In some embodiments, the isolated nucleic acid comprises the sequence set forth in SEQ ID NO: 29. In some embodiments the expression construct comprises adeno-associated virus (AAV) inverted terminal repeats (ITRs), for example AAV ITRs flanking the nucleic acid sequence encoding the SCARB2.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a first gene product or a second gene product is a Gcase protein, or a portion thereof. In some embodiments, a first gene product or a second gene product is LIMP2 or a portion thereof, or Prosaposin or a portion thereof. In some embodiments, the first gene product is a Gcase protein, and the second gene product is LIMP2 or a portion thereof, or Prosaposin or a portion thereof.

In some embodiments, an expression construct further encodes an interfering nucleic acid (e.g., shRNA, miRNA, dsRNA, etc.). In some embodiments, an interfering nucleic acid inhibits expression of α-Synuclein (α-Synuclein). In some embodiments, an interfering nucleic acid that targets α-Synuclein comprises a sequence set forth in any one of SEQ ID NOs: 20-25. In some embodiments, an interfering nucleic acid that targets α-Synuclein binds to (e.g., hybridizes with) a sequence set forth in any one of SEQ ID NO: 20-25.

In some embodiments, an expression construct further comprises one or more promoters. In some embodiments, a promoter is a chicken-beta actin (CBA) promoter, a CAG promoter, a CD68 promoter, or a JeT promoter. In some embodiments, a promoter is a RNA pol II promoter (e.g., or an RNA pol III promoter (e.g., U6, etc.).

In some embodiments, an expression construct further comprises an internal ribosomal entry site (IRES). In some embodiments, an IRES is located between a first gene product and a second gene product.

In some embodiments, an expression construct further comprises a self-cleaving peptide coding sequence. In some embodiments, a self-cleaving peptide is a T2A peptide.

In some embodiments, an expression construct comprises two adeno-associated virus (AAV) inverted terminal repeat (ITR) sequences. In some embodiments, ITR sequences flank a first gene product and a second gene product (e.g., are arranged as follows from 5'-end to 3'-end: ITR-first gene product-second gene product-ITR). In some embodiments, one of the ITR sequences of an isolated nucleic acid lacks a functional terminal resolution site (trs). For example, in some embodiments, one of the ITRs is a ΔITR.

The disclosure relates, in some aspects, to rAAV vectors comprising an ITR having a modified "D" region (e.g., a D sequence that is modified relative to wild-type AAV2 ITR, SEQ ID NO: 29). In some embodiments, the ITR having the modified D region is the 5' ITR of the rAAV vector. In some embodiments, a modified "D" region comprises an "S" sequence, for example as set forth in SEQ ID NO: 26. In some embodiments, the ITR having the modified "D" region is the 3' ITR of the rAAV vector. In some embodiments, a modified "D" region comprises a 3'ITR in which the "D" region is positioned at the 3' end of the ITR (e.g., on the outside or terminal end of the ITR relative to the transgene insert of the vector). In some embodiments, a modified "D" region comprises a sequence as set forth in SEQ ID NO: 26 or 27.

In some embodiments, an isolated nucleic acid (e.g., an rAAV vector) comprises a TRY region. In some embodiments, a TRY region comprises the sequence set forth in SEQ ID NO: 28.

In some embodiments, an isolated nucleic acid described by the disclosure comprises or consists of the sequence set forth in any one of SEQ ID NOs: 1 to 13, 15, 17, and 19. In some embodiments, an isolated nucleic acid described by the disclosure encodes a peptide comprising or consisting of the sequence set forth in any one of SEQ ID NOs: 14, 16, and 18.

In some aspects, the disclosure provides a vector comprising an isolated nucleic acid as described by the disclosure. In some embodiments, a vector is a plasmid, or a viral vector. In some embodiments, a viral vector is a recombinant AAV (rAAV) vector. In some embodiments, an rAAV vector is single-stranded (e.g., single-stranded DNA).

In some aspects, the disclosure provides a host cell comprising an isolated nucleic acid as described by the disclosure or a vector as described by the disclosure.

In some aspects, the disclosure provides a recombinant adeno-associated virus (rAAV) comprising a capsid protein and an isolated nucleic acid or a vector as described by the disclosure.

In some embodiments, a capsid protein is capable of crossing the blood-brain barrier, for example an AAV9 capsid protein or an AAVrh.10 capsid protein. In some embodiments, an rAAV transduces neuronal cells and non-neuronal cells of the central nervous system (CNS).

In some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, administration comprises direct injection to the CNS of a subject. In some embodiments, direct injection is intracerebral injection, intraparenchymal injection, intrathecal injection, intra-cisterna magna injection, or any combination thereof. In some embodiments, direct injection to the CNS of a subject comprises convection enhanced delivery (CED).

In some embodiments, administration comprises peripheral injection. In some embodiments, peripheral injection is intravenous injection.

DETAILED DESCRIPTION

Figure 1:
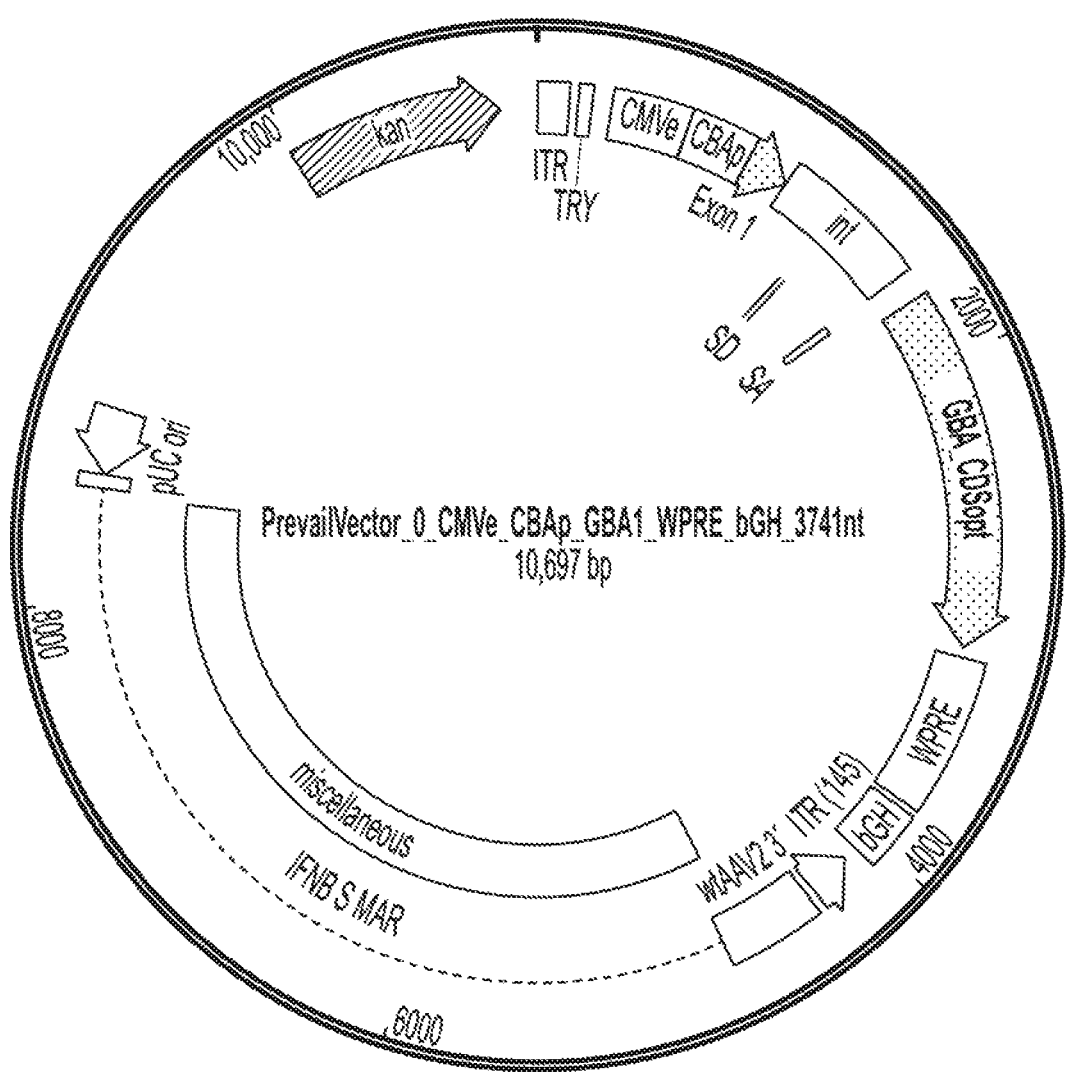
FIG. 1 is a schematic depicting one embodiment of a plasmid comprising an rAAV vector that includes an expression construct encoding Gcase (e.g., GBA1 or a portion thereof).
Figure 2:
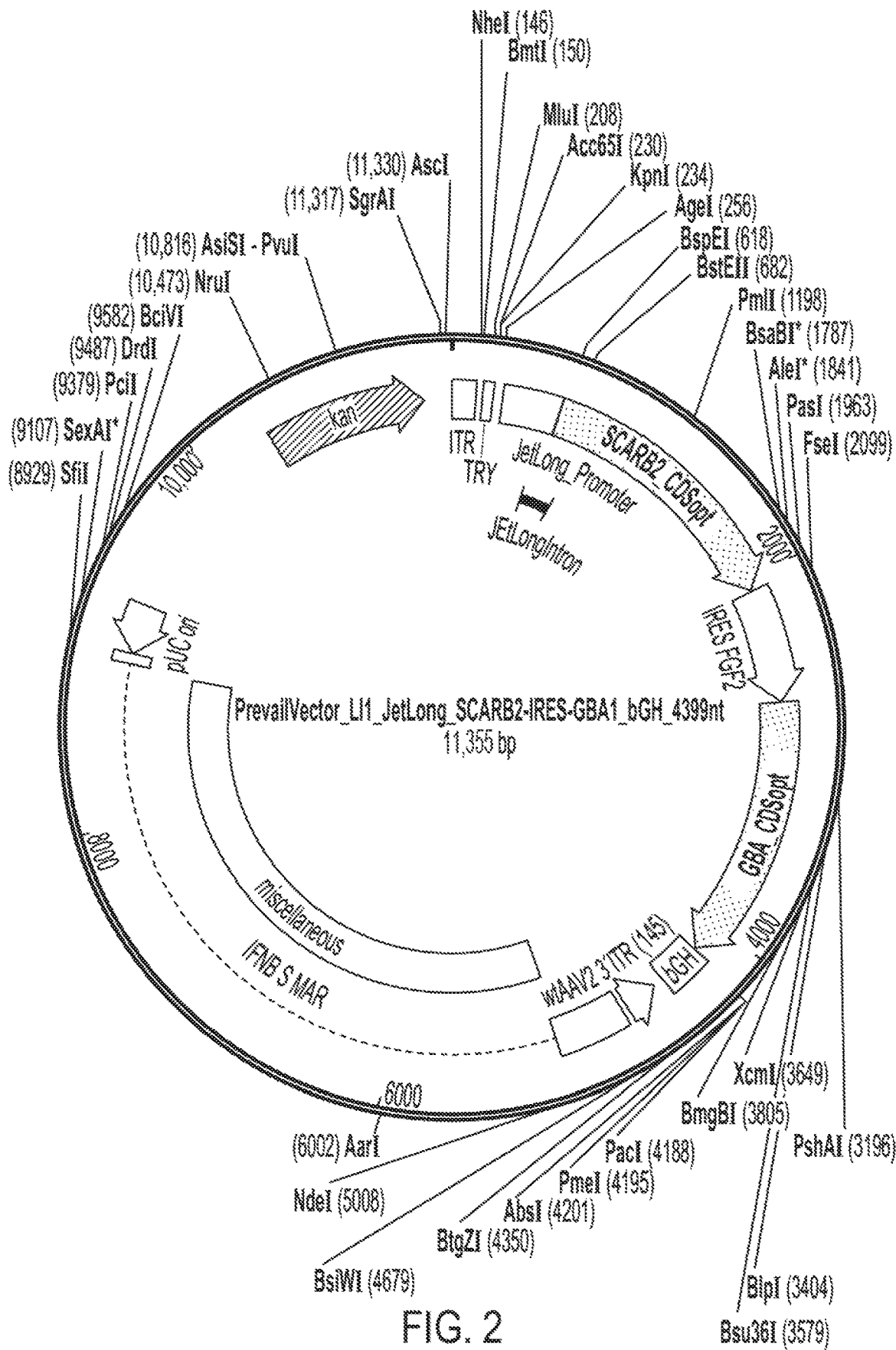
FIG. 2 is a schematic depicting one embodiment of a plasmid comprising an rAAV vector that includes an expression construct encoding Gcase (e.g., GBA1 or a portion thereof) and LIMP2 (SCARB2) or a portion thereof. The coding sequences of Gcase and LIMP2 are separated by an internal ribosomal entry site (IRES).
Figure 3:
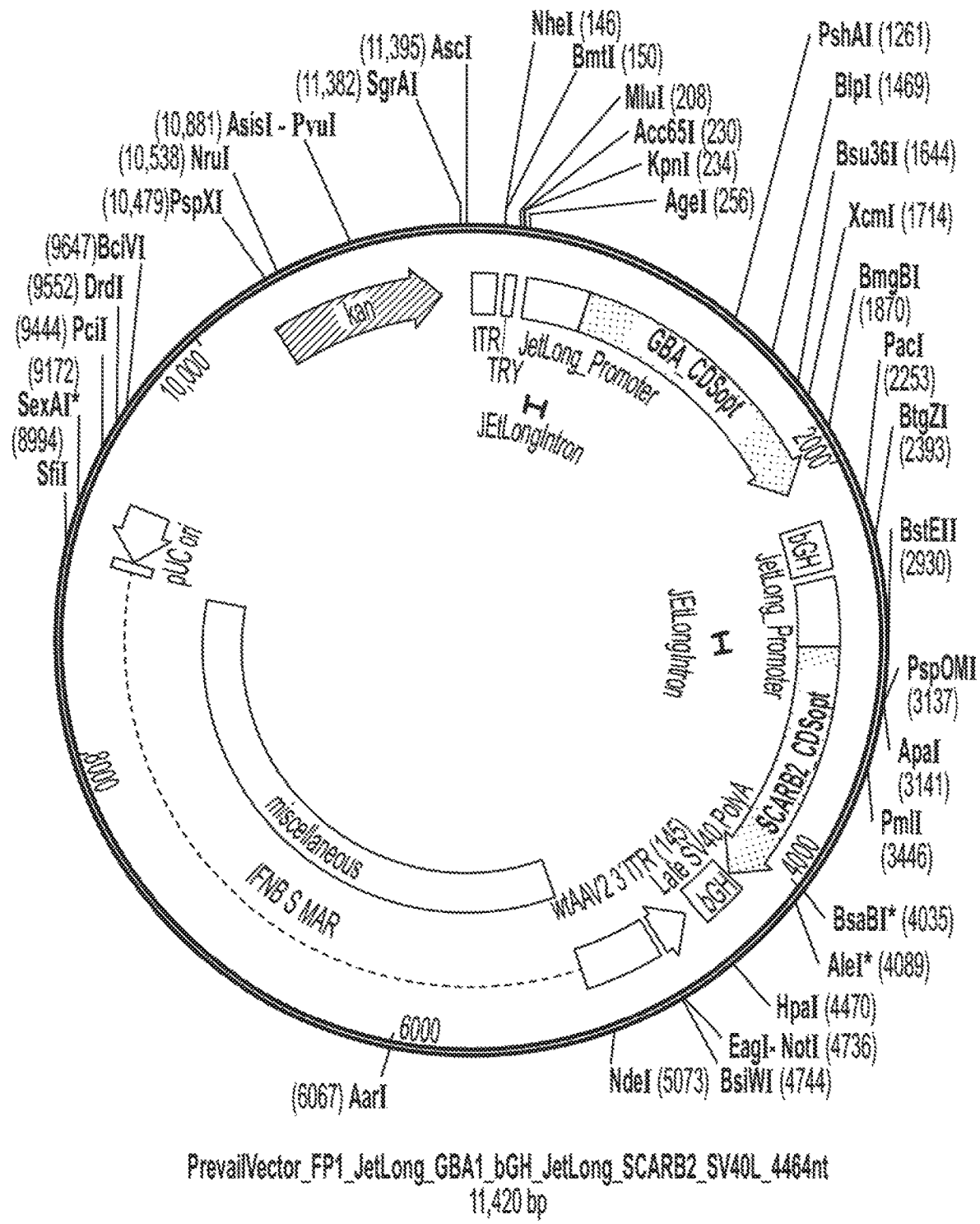
FIG. 3 is a schematic depicting one embodiment of a plasmid comprising an rAAV vector that includes an expression construct encoding Gcase (e.g., GBA1 or a portion thereof) and LIMP2 (SCARB2) or a portion thereof. Expression of the coding sequences of Gcase and LIMP2 are each driven by a separate promoter.
Figure 4:
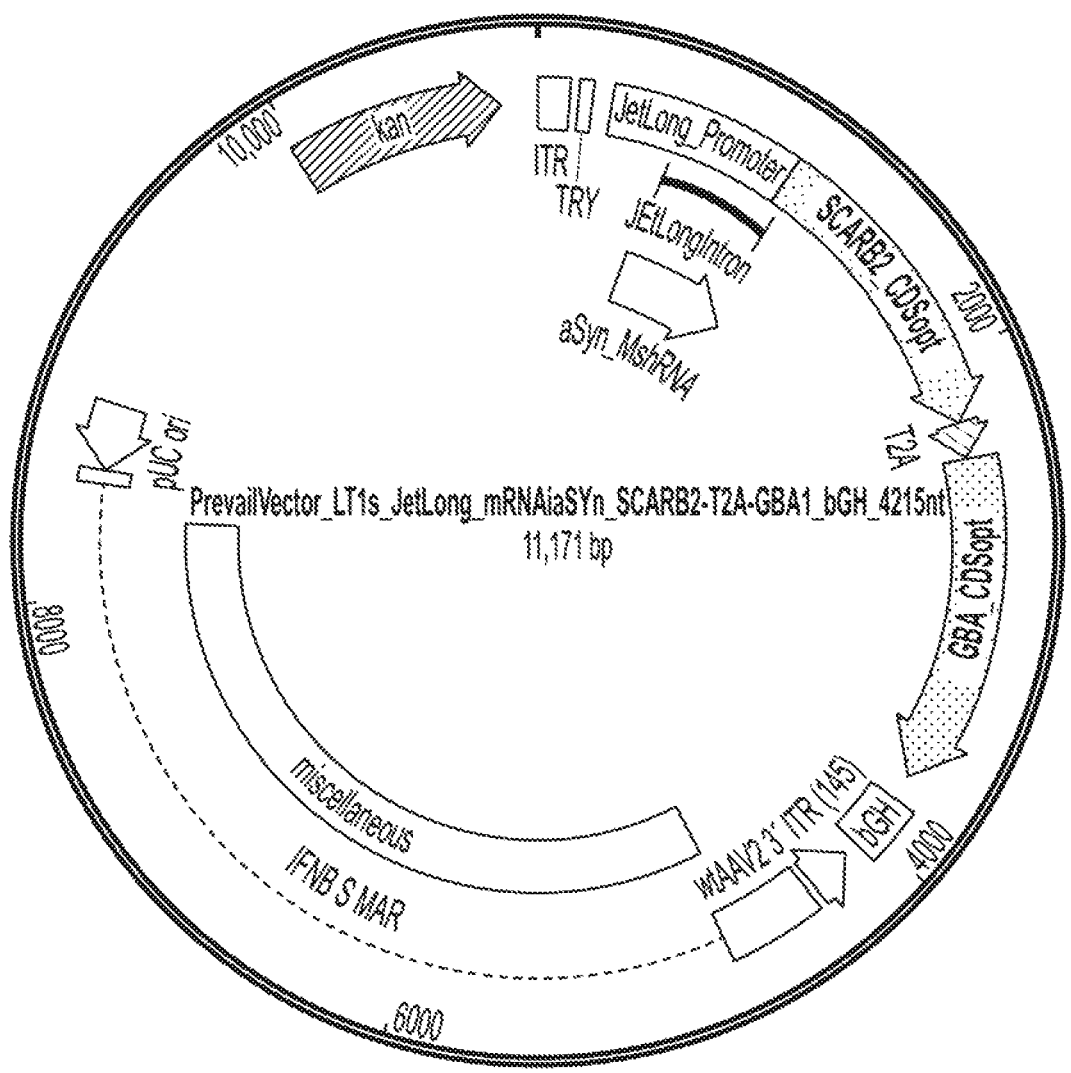
FIG. 4 is a schematic depicting one embodiment of a plasmid comprising an rAAV vector that includes an expression construct encoding Gcase (e.g., GBA1 or a portion thereof), LIMP2 (SCARB2) or a portion thereof, and an interfering RNA for α-Syn.
Figure 5:
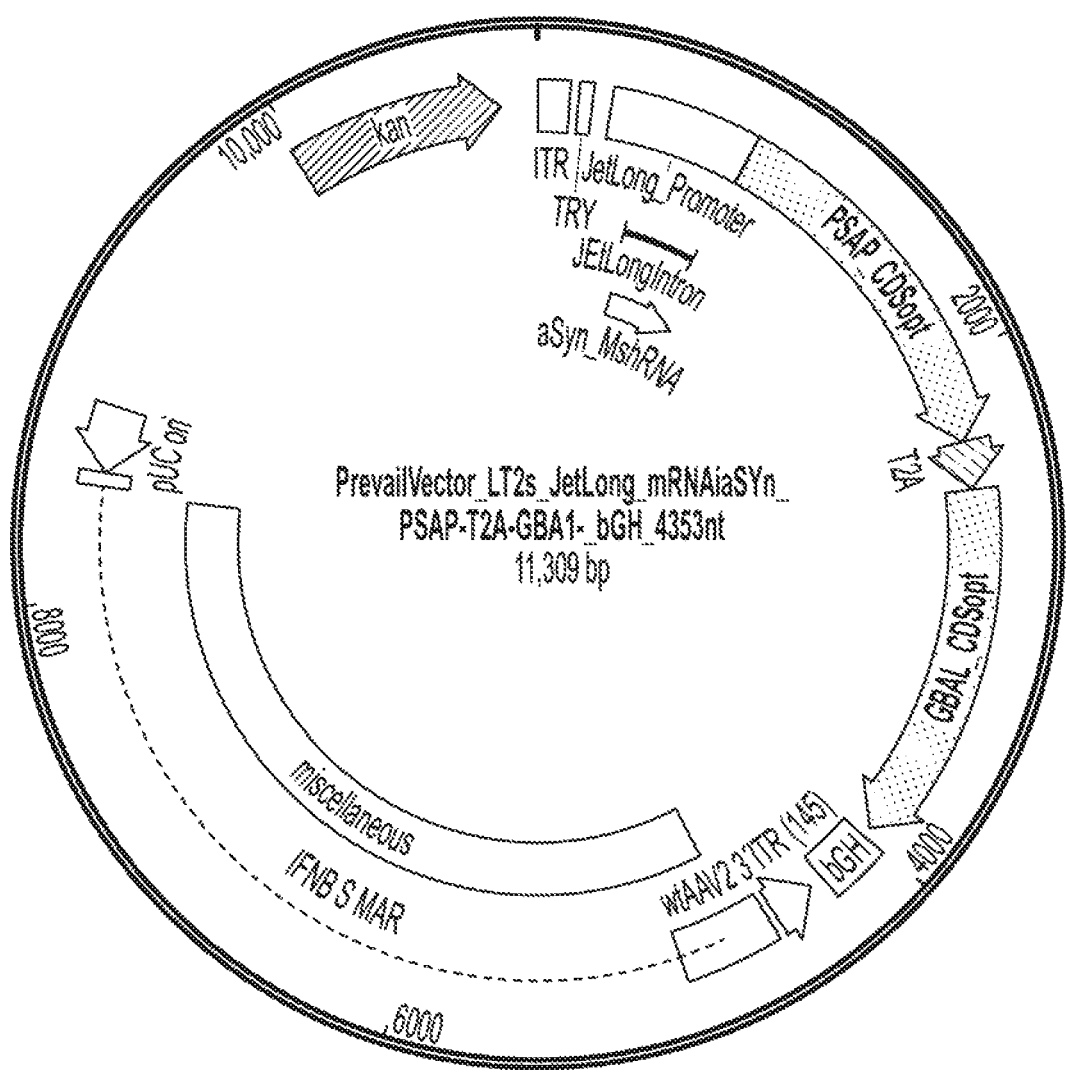
FIG. 5 is a schematic depicting one embodiment of a plasmid comprising an rAAV vector that includes an expression construct encoding Gcase (e.g., GBA1 or a portion thereof), Prosaposin (e.g., PSAP or a portion thereof), and an interfering RNA for α-Syn.
Figure 6:
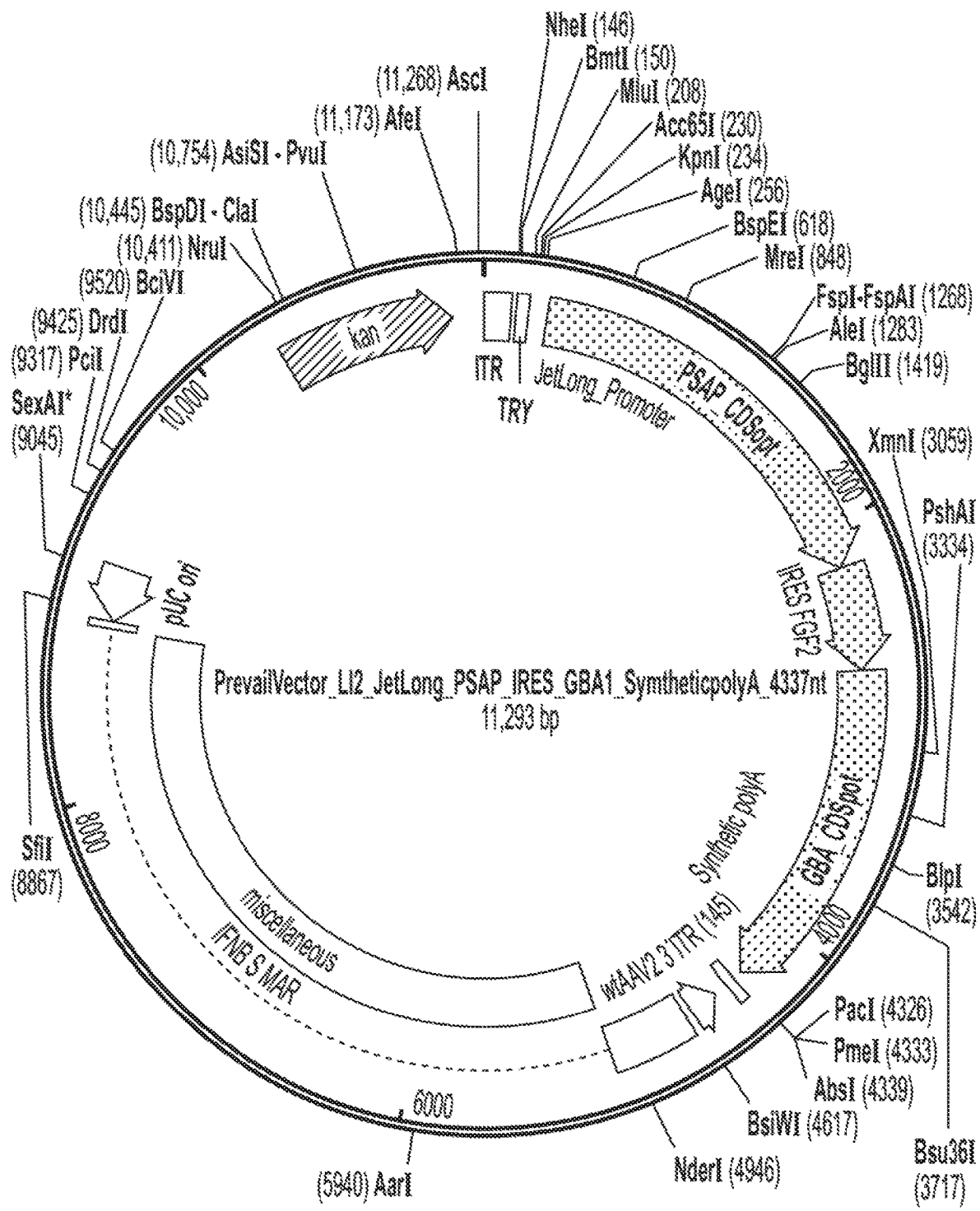
FIG. 6 is a schematic depicting one embodiment of a plasmid comprising an rAAV vector that includes an expression construct encoding Gcase (e.g., GBA1 or a portion thereof) and Prosaposin (e.g., PSAP or a portion thereof). The coding sequences of Gcase and Prosaposin are separated by an internal ribosomal entry site (IRES).

The disclosure is based, in part, on compositions and methods for expression of combinations of PD-associated gene products in a subject. A gene product can be a protein, a fragment (e.g., portion) of a protein, an interfering nucleic acid that inhibits a PD-associated gene, etc. In some embodiments, a gene product is a protein or a protein fragment encoded by a PD-associated gene. In some embodiments, a gene product is an interfering nucleic acid (e.g., shRNA, siRNA, miRNA, amiRNA, etc.) that inhibits a PD-associated gene.

A PD-associated gene refers to a gene encoding a gene product that is genetically, biochemically or functionally associated with PD. For example, individuals having mutations in the GBA1 gene (which encodes the protein Gcase), have been observed to be have an increased risk of developing PD compared to individuals that do not have a mutation in GBA1. In another example, PD is associated with accumulation of protein aggregates comprising α-Synuclein (α-Syn) protein; accordingly, SCNA (which encodes α-Syn) is a PD-associated gene. In some embodiments, an expression cassette described herein encodes a wild-type or non-mutant form of a PD-associated gene (or coding sequence thereof). Examples of PD-associated genes are listed in Table 1.

TABLE 1

Examples of PD-associated genes

| Name | Gene | Function | NCBI Accession No. |
|---|---|---|---|
| Lysosome membrane protein 2 | SCARB2\|LIMP2 | lysosomal receptor for glucosylceramidase (GBA targeting) | NP_005497.1 (Isoform 1), NP_001191184.1 (Isoform 2) |
| Prosaposin | PSAP | precursor for saposins A, B, C, and D, which localize to the lysosomal compartment and facilitate the catabolism of glycosphingolipids with short oligosaccharide groups | AAH01503.1, AAH07612.1, AAH04275.1, AAA60303.1 |
| beta-Glucocerebrosidase | GBA1 | cleaves the beta-glucosidic linkage of glucocerebroside | NP_001005742.1 (Isoform 1), NP_001165282.1 (Isoform 2), NP_001165283.1 (Isoform 3) |

Isolated Nucleic Acids and Vectors

An isolated nucleic acid may be DNA or RNA. The disclosure provides, in some aspects, an isolated nucleic acid comprising an expression construct encoding a Gcase (e.g., the gene product of GBA1 gene) or a portion thereof. Gcase, also referred to as β-glucocerebrosidase or GBA, refers to a lysosomal protein that cleaves the beta-glucosidic linkage of the chemical glucocerebroside, an intermediate in glycolipid metabolism. In humans, Gcase is encoded by the GBA1 gene, located on chromosome 1. In some embodiments, GBA1 encodes a peptide that is represented by NCBI Reference Sequence NCBI Reference Sequence NP_000148.2 (SEQ ID NO: 14). In some embodiments, the isolated nucleic acid comprises a Gcase-encoding sequence that has been codon optimized (e.g., codon optimized for expression in mammalian cells, for example human cells), such as the sequence set forth in SEQ ID NO: 15.

In some aspects, the disclosure provides an isolated nucleic acid comprising an expression construct encoding Prosaposin (e.g., the gene product of PSAP gene). Prosaposin is a precursor glycoprotein for sphingolipid activator proteins (saposins) A, B, C, and D, which facilitate the catabolism of glycosphingolipids with short oligosaccharide groups. In humans, the PSAP gene is located on chromosome 10. In some embodiments, PSAP encodes a peptide that is represented by NCBI Reference Sequence NP_002769.1 (e.g., SEQ ID NO: 16). In some embodiments, the isolated nucleic acid comprises a prosaposin-encoding sequence that has been codon optimized (e.g., codon optimized for expression in mammalian cells, for example human cells), such as the sequence set forth in SEQ ID NO: 17.

Aspects of the disclosure relate to an isolated nucleic acid comprising an expression construct encoding LIMP2/

SCARB2 (e.g., the gene product of SCARB2 gene). SCARB2 refers to a membrane protein that regulates lysosomal and endosomal transport within a cell. In humans, SCARB2 gene is located on chromosome 4. In some embodiments, the SCARB2 gene encodes a peptide that is represented by NCBI Reference Sequence NP_005497.1 (SEQ ID NO: 18). In some embodiments, the isolated nucleic acid comprises the sequence set forth in SEQ ID NO: 19. In some embodiments the isolated nucleic acid comprises a SCARB2-encoding sequence that has been codon optimized.

In some aspects, the disclosure provides an isolated nucleic acid comprising an expression construct encoding a first gene product and a second gene product, wherein each gene product independently is selected from the gene products, or portions thereof, set forth in Table 1.

In some embodiments, a gene product is encoded by a coding portion (e.g., a cDNA) of a naturally occurring gene. In some embodiments, a first gene product is a protein (or a fragment thereof) encoded by the GBA1 gene. In some embodiments, a gene product is a protein (or a fragment thereof) encoded by the SCARB2/LIMP2 gene and/or the PSAP gene. However, the skilled artisan recognizes that the order of expression of a first gene product (e.g., Gcase) and a second gene product (e.g., LIMP2) can generally be reversed (e.g., LIMP2 is the first gene product and Gcase is the second gene product). In some embodiments, a gene product is a fragment (e.g., portion) of a gene listed in Table 1. A protein fragment may comprise about 50%, about 60%, about 70%, about 80% about 90% or about 99% of a protein encoded by the genes listed in Table 1. In some embodiments, a protein fragment comprises between 50% and 99.9% (e.g., any value between 50% and 99.9%) of a protein encoded by a gene listed in Table 1.

In some embodiments, an expression construct is monocistronic (e.g., the expression construct encodes a single fusion protein comprising a first gene product and a second gene product). In some embodiments, an expression construct is polycistronic (e.g., the expression construct encodes two distinct gene products, for example two different proteins or protein fragments).

A polycistronic expression vector may comprise a one or more (e.g., 1, 2, 3, 4, 5, or more) promoters. Any suitable promoter can be used, for example, a constitutive promoter, an inducible promoter, an endogenous promoter, a tissue-specific promoter (e.g., a CNS-specific promoter), etc. In some embodiments, a promoter is a chicken beta-actin promoter (CBA promoter), a CAG promoter (for example as described by Alexopoulou et al. (2008) *BMC Cell Biol.* 9:2; doi: 10.1186/1471-2121-9-2), a CD68 promoter, or a JeT promoter (for example as described by Tornøe et al. (2002) *Gene* 297(1-2):21-32). In some embodiments, a promoter is operably-linked to a nucleic acid sequence encoding a first gene product, a second gene product, or a first gene product and a second gene product. In some embodiments, an expression cassette comprises one or more additional regulatory sequences, including but not limited to transcription factor binding sequences, intron splice sites, poly(A) addition sites, enhancer sequences, repressor binding sites, or any combination of the foregoing.

In some embodiments, a nucleic acid sequence encoding a first gene product and a nucleic acid sequence encoding a second gene product are separated by a nucleic acid sequence encoding an internal ribosomal entry site (IRES). Examples of IRES sites are described, for example, by Mokrejs et al. (2006) *Nucleic Acids Res.* 34(Database issue): D125-30. In some embodiments, a nucleic acid sequence encoding a first gene product and a nucleic acid sequence encoding a second gene product are separated by a nucleic acid sequence encoding a self-cleaving peptide. Examples of self-cleaving peptides include but are not limited to T2A, P2A, E2A, F2A, BmCPV 2A, and BmIFV 2A, and those described by Liu et al. (2017) *Sci Rep.* 7: 2193. In some embodiments, the self-cleaving peptide is a T2A peptide.

Pathologically, disorders such as PD and Gaucher disease are associated with accumulation of protein aggregates composed largely of α-Synuclein (α-Syn) protein. Accordingly, in some embodiments, isolated nucleic acids described herein comprise an inhibitory nucleic acid that reduces or prevents expression of α-Syn protein. A sequence encoding an inhibitory nucleic acid may be placed in an untranslated region (e.g., intron, 5'UTR, 3'UTR, etc.) of the expression vector.

In some embodiments, an inhibitory nucleic acid is positioned in an intron of an expression construct, for example in an intron upstream of the sequence encoding a first gene product. An inhibitory nucleic acid can be a double stranded RNA (dsRNA), siRNA, micro RNA (miRNA), artificial miRNA (amiRNA), or an RNA aptamer. Generally, an inhibitory nucleic acid binds to (e.g., hybridizes with) between about 6 and about 30 (e.g., any integer between 6 and 30, inclusive) contiguous nucleotides of a target RNA (e.g., mRNA). In some embodiments, the inhibitory nucleic acid molecule is an miRNA or an amiRNA, for example an miRNA that targets SNCA (the gene encoding α-Syn protein). In some embodiments, the miRNA does not comprise any mismatches with the region of SNCA mRNA to which it hybridizes (e.g., the miRNA is "perfected"). In some embodiments, the inhibitory nucleic acid is an shRNA (e.g., an shRNA targeting SNCA).

An isolated nucleic acid as described herein may exist on its own, or as part of a vector. Generally, a vector can be a plasmid, cosmid, phagemid, bacterial artificial chromosome (BAC), or a viral vector (e.g., adenoviral vector, adeno-associated virus (AAV) vector, retroviral vector, baculoviral vector, etc.). In some embodiments, the vector is a plasmid (e.g., a plasmid comprising an isolated nucleic acid as described herein). In some embodiments, the vector is a recombinant AAV (rAAV) vector. In some embodiments, an rAAV vector is single-stranded (e.g., single-stranded DNA). In some embodiments, a vector is a Baculovirus vector (e.g., an *Autographa californica* nuclear polyhedrosis (AcNPV) vector).

Typically an rAAV vector (e.g., rAAV genome) comprises a transgene (e.g., an expression construct comprising one or more of each of the following: promoter, intron, enhancer sequence, protein coding sequence, inhibitory RNA coding sequence, polyA tail sequence, etc.) flanked by two AAV inverted terminal repeat (ITR) sequences. In some embodiments the transgene of an rAAV vector comprises an isolated nucleic acid as described by the disclosure. In some embodiments, each of the two ITR sequences of an rAAV vector is a full-length ITR (e.g., approximately 145 bp in length, and containing functional Rep binding site (RBS) and terminal resolution site (trs)). In some embodiments, one of the ITRs of an rAAV vector is truncated (e.g., shortened or not full-length). In some embodiments, a truncated ITR lacks a functional terminal resolution site (trs) and is used for production of self-complementary AAV vectors (scAAV vectors). In some embodiments, a truncated ITR is a AITR, for example as described by McCarty et al. (2003) *Gene Ther.* 10(26):2112-8.

Figure 19:
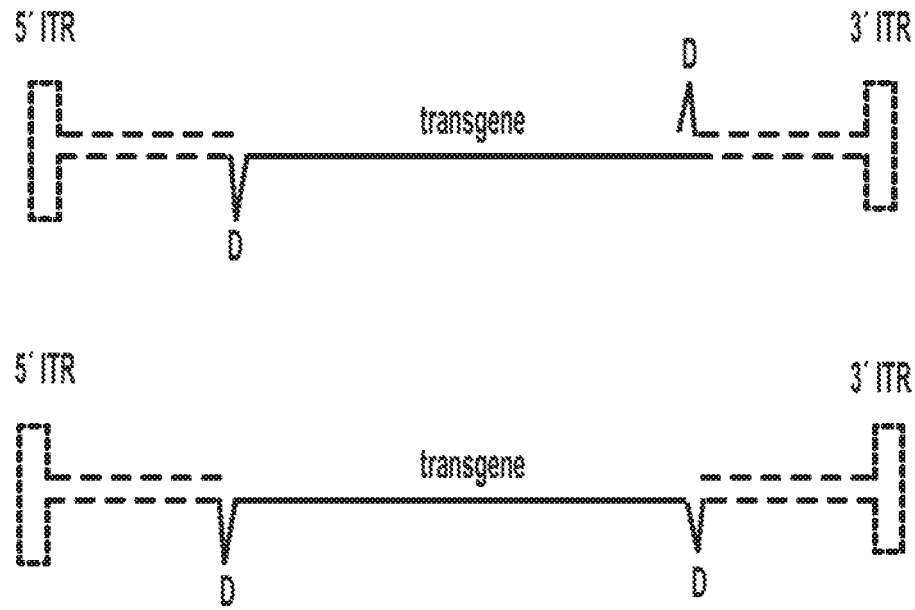
FIG. 19 is a schematic depicting an rAAV vectors comprising a "D" region located on the "outside" of the ITR (e.g., proximal to the terminus of the ITR relative to the transgene insert or expression construct) (top) and a wild-type rAAV vectors having ITRs on the "inside" of the vector (e.g., proximal to the transgene insert of the vector).

Aspects of the disclosure relate to isolated nucleic acids (e.g., rAAV vectors) comprising an ITR having one or more modifications (e.g., nucleic acid additions, deletions, substitutions, etc.) relative to a wild-type AAV ITR, for example relative to wild-type AAV2 ITR (e.g., SEQ ID NO: 29). The structure of wild-type AAV2 ITR is shown in FIG. 19. Generally, a wild-type ITR comprises a 125 nucleotide region that self-anneals to form a palindromic double-stranded T-shaped, hairpin structure consisting of two cross arms (formed by sequences referred to as B/B' and C/C', respectively), a longer stem region (formed by sequences A/A'), and a single-stranded terminal region referred to as the "D" region. (FIG. 19). Generally, the "D" region of an ITR is positioned between the stem region formed by the A/A' sequences and the insert containing the transgene of the rAAV vector (e.g., positioned on the "inside" of the ITR relative to the terminus of the ITR or proximal to the transgene insert or expression construct of the rAAV vector). In some embodiments, a "D" region comprises the sequence set forth in SEQ ID NO: 27. The "D" region has been observed to play an important role in encapsidation of rAAV vectors by capsid proteins, for example as disclosed by Ling et al. (2015) *J Mol Genet Med* 9(3).

The disclosure is based, in part, on the surprising discovery that rAAV vectors comprising a "D" region located on the "outside" of the ITR (e.g., proximal to the terminus of the ITR relative to the transgene insert or expression construct) are efficiently encapsidated by AAV capsid proteins than rAAV vectors having ITRs with unmodified (e.g., wild-type) ITRs. In some embodiments, rAAV vectors having a modified "D" sequence (e.g., a "D" sequence in the "outside" position) have reduced toxicity relative to rAAV vectors having wild-type ITR sequences.

In some embodiments, a modified "D" sequence comprises at least one nucleotide substitution relative to a wild-type "D" sequence (e.g., SEQ ID NO: 27). A modified "D" sequence may have at least 1, 2, 3, 4, 5, 6, 7, 8, 9, 10, or more than 10 nucleotide substitutions relative to a wild-type "D" sequence (e.g., SEQ ID NO: 27). In some embodiments, a modified "D" sequence comprises at least 10, 11, 12, 13, 14, 15, 16, 17, 18, or 19 nucleic acid substitutions relative to a wild-type "D" sequence (e.g., SEQ ID NO: 27). In some embodiments, a modified "D" sequence is between about 10% and about 99% (e.g., 10%, 15%, 20%, 25%, 30%, 40%, 45%, 50%, 55%, 60%, 65%, 70%, 75%, 80%, 85%, 90%, 95%, or 99%) identical to a wild-type "D" sequence (e.g., SEQ ID NO: 27). In some embodiments, a modified "D" sequence comprises the sequence set forth in SEQ ID NO: 26, also referred to as an "S" sequence as described in Wang et al. (1995) *J Mol Biol* 250(5):573-80.

An isolated nucleic acid or rAAV vector as described by the disclosure may further comprise a "TRY" sequence, for example as set forth in SEQ ID NO: 28 or as described in Francois, et al. The Cellular TATA Binding Protein Is Required for Rep-Dependent Replication of a Minimal Adeno-Associated Virus Type 2 p5 Element. J Virol. 2005. In some embodiments, a TRY sequence is positioned between an ITR (e.g., a 5' ITR) and an expression construct (e.g., a transgene-encoding insert) of an isolated nucleic acid or rAAV vector.

In some aspects, the disclosure relates to Baculovirus vectors comprising an isolated nucleic acid or rAAV vector as described by the disclosure. In some embodiments, the Baculovirus vector is an *Autographa californica* nuclear polyhedrosis (AcNPV) vector, for example as described by Urabe et al. (2002) *Hum Gene Ther* 13(16):1935-43 and Smith et al. (2009) *Mol Ther* 17(11):1888-1896.

In some aspects, the disclosure provides a host cell comprising an isolated nucleic acid or vector as described herein. A host cell can be a prokaryotic cell or a eukaryotic cell. For example, a host cell can be a mammalian cell, bacterial cell, yeast cell, insect cell, etc. In some embodiments, a host cell is a mammalian cell, for example a HEK293T cell. In some embodiments, a host cell is a bacterial cell, for example an *E. coli* cell.

rAAVs

In some aspects, the disclosure relates to recombinant AAVs (rAAVs) comprising a transgene that encodes a nucleic acid as described herein (e.g., an rAAV vector as described herein). The term "rAAVs" generally refers to viral particles comprising an rAAV vector encapsidated by one or more AAV capsid proteins. An rAAV described by the disclosure may comprise a capsid protein having a serotype selected from AAV1, AAV2, AAV3, AAV4, AAV5, AAV6, AAV7, AAV8, AAV9, and AAV10. In some embodiments, an rAAV comprises a capsid protein from a non-human host, for example a rhesus AAV capsid protein such as AAVrh.10, AAVrh.39, etc. In some embodiments, an rAAV described by the disclosure comprises a capsid protein that is a variant of a wild-type capsid protein, such as a capsid protein variant that includes at least 1, 2, 3, 4, 5, 6, 7, 8, 9, 10, or more than 10 (e.g., 15, 20 25, 50, 100, etc.) amino acid substitutions (e.g., mutations) relative to the wild-type AAV capsid protein from which it is derived.

In some embodiments, rAAVs described by the disclosure readily spread through the CNS, particularly when introduced into the CSF space or directly into the brain parenchyma. Accordingly, in some embodiments, rAAVs described by the disclosure comprise a capsid protein that is capable of crossing the blood-brain barrier (BBB). For example, in some embodiments, an rAAV comprises a capsid protein having an AAV9 or AAVrh.10 serotype. Production of rAAVs is described, for example, by Samulski et al. (1989) *J Virol.* 63(9):3822-8 and Wright (2009) *Hum Gene Ther.* 20(7): 698-706.

In some embodiments, an rAAV as described by the disclosure (e.g., comprising a recombinant rAAV genome encapsidated by AAV capsid proteins to form an rAAV capsid particle) is produced in a Baculovirus vector expression system (BEVS). Production of rAAVs using BEVS are described, for example by Urabe et al. (2002) *Hum Gene Ther* 13(16):1935-43, Smith et al. (2009) *Mol Ther* 17(11): 1888-1896, U.S. Pat. Nos. 8,945,918, 9,879,282, and International PCT Publication WO 2017/184879. However, an rAAV can be produced using any suitable method (e.g., using recombinant rep and cap genes).

Pharmaceutical Compositions

In some aspects, the disclosure provides pharmaceutical compositions comprising an isolated nucleic acid or rAAV as described herein and a pharmaceutically acceptable carrier. As used herein, the term "pharmaceutically acceptable" refers to a material, such as a carrier or diluent, which does not abrogate the biological activity or properties of the compound, and is relatively non-toxic, e.g., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Compositions (e.g., pharmaceutical compositions) provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

Methods

The disclosure is based, in part, on compositions for expression of combinations of PD-associated gene products in a subject that act together (e.g., synergistically) to treat Parkinson's disease. As used herein "treat" or "treating" refers to (a) preventing or delaying onset of Parkinson's disease; (b) reducing severity of Parkinson's disease; (c) reducing or preventing development of symptoms characteristic of Parkinson's disease; (d) and/or preventing worsening of symptoms characteristic of Parkinson's disease. Symptoms of Parkinson's disease include, for example, motor dysfunction (e.g., shaking, rigidity, slowness of movement, difficulty with walking), cognitive dysfunction (e.g., dementia, depression, anxiety), emotional and behavioral dysfunction.

Accordingly, in some aspects, the disclosure provides a method for treating a subject having or suspected of having Parkinson's disease, the method comprising administering to the subject a composition (e.g., a composition comprising an isolated nucleic acid or a vector or a rAAV) as described by the disclosure.

In some embodiments, a composition is administered directly to the CNS of the subject, for example by direct injection into the brain and/or spinal cord of the subject. Examples of CNS-direct administration modalities include but are not limited to intracerebral injection, intraventricular injection, intracisternal injection, intraparenchymal injection, intrathecal injection, and any combination of the foregoing. In some embodiments, direct injection into the CNS of a subject results in transgene expression (e.g., expression of the first gene product, second gene product, and if applicable, third gene product) in the midbrain, striatum and/or cerebral cortex of the subject. In some embodiments, direct injection into the CNS results in transgene expression (e.g., expression of the first gene product, second gene product, and if applicable, third gene product) in the spinal cord and/or CSF of the subject.

In some embodiments, direct injection to the CNS of a subject comprises convection enhanced delivery (CED). Convection enhanced delivery is a therapeutic strategy that involves surgical exposure of the brain and placement of a small-diameter catheter directly into a target area of the brain, followed by infusion of a therapeutic agent (e.g., a composition or rAAV as described herein) directly to the brain of the subject. CED is described, for example by Debinski et al. (2009) *Expert Rev Neurother.* 9(10):1519-27.

In some embodiments, a composition is administered peripherally to a subject, for example by peripheral injection. Examples of peripheral injection include subcutaneous injection, intravenous injection, intra-arterial injection, intraperitoneal injection, or any combination of the foregoing. In some embodiments, the peripheral injection is intra-arterial injection, for example injection into the carotid artery of a subject.

In some embodiments, a composition (e.g., a composition comprising an isolated nucleic acid or a vector or a rAAV) as described by the disclosure is administered both peripherally and directly to the CNS of a subject. For example, in some embodiments, a subject is administered a composition by intra-arterial injection (e.g., injection into the carotid artery) and by intraparenchymal injection (e.g., intraparenchymal injection by CED). In some embodiments, the direct injection to the CNS and the peripheral injection are simultaneous (e.g., happen at the same time). In some embodiments, the direct injection occurs prior (e.g., between 1 minute and 1 week, or more before) to the peripheral injection. In some embodiments, the direct injection occurs after (e.g., between 1 minute and 1 week, or more after) the peripheral injection.

The amount of composition (e.g., a composition comprising an isolated nucleic acid or a vector or a rAAV) as described by the disclosure administered to a subject will vary depending on the administration method. For example, in some embodiments, a rAAV as described herein is administered to a subject at a titer between about $10^9$ Genome copies (GC)/kg and about $10^{14}$ GC/kg (e.g., about $10^9$ GC/kg, about $10^{10}$ GC/kg, about $10^{11}$ GC/kg, about $10^{12}$ GC/kg, about $10^{12}$ GC/kg, or about $10^{14}$ GC/kg). In some embodiments, a subject is administered a high titer (e.g., $>10^{12}$ Genome Copies GC/kg of an rAAV) by injection to the CSF space, or by intraparenchymal injection.

A composition (e.g., a composition comprising an isolated nucleic acid or a vector or a rAAV) as described by the disclosure can be administered to a subject once or multiple times (e.g., 2, 3, 4, 5, 6, 7, 8, 9, 10, 20, or more) times. In some embodiments, a composition is administered to a subject continuously (e.g., chronically), for example via an infusion pump.

EXAMPLES

Example 1 rAAV Vectors

AAV vectors are generated using cells, such as HEK293 cells for triple-plasmid transfection. The ITR sequences flank an expression construct comprising a promoter/enhancer element for each transgene of interest, a 3' polyA signal, and posttranslational signals such as the WPRE element. Multiple gene products can be expressed simultaneously such as GBA1 and LIMP2 and/or Prosaposin, by fusion of the protein sequences; or using a 2A peptide linker, such as T2A or P2A, which leads 2 peptide fragments with added amino acids due to prevention of the creation of a peptide bond; or using an IRES element; or by expression with 2 separate expression cassettes. The presence of a short intronic sequence that is efficiently spliced, upstream of the expressed gene, can improve expression levels. shRNAs and other regulatory RNAs can potentially be included within these sequences. Examples of plasmids comprising rAAV vectors described by the disclosure are shown in FIGS. 1-6 and in Table 2 below.

TABLE 2

| Name | Promoter 1 | shRNA | CDS1 | PolyA1 | Bicistronic element |
|---|---|---|---|---|---|
| CMVe_CBAp_GBA1_WPRE_bGH | CBA | | GBA1 | WPRE-bGH | |
| LT1s_JetLong_mRNAiaSYn_SCARB2-T2A-GBA1_bGH | JetLong | aSyn | SCARB2 | bGH | T2A |
| LI1_JetLong_SCARB2-IRES-GBA1_bGH | JetLong | | SCARB2 | bGH | IRES |
| FP1_JetLong_GBA1_bGH_JetLong_SCARB2_SV40L | JetLong | | GBA1 | bGH | |
| PrevailVector_LT2s_JetLong_mRNAiaSYn_PSAP-T2A-GBA1_bGH_4353nt | JetLong | aSyn | PSAP | bGH | T2A |
| PrevailVector_LI2_JetLong_PSAP_IRES_GBA1_SymtheticpolyA_4337nt | JetLong | — | PSAP | Synthetic pA | IRES |

| Name | Promoter 2 | CDS2 | PolyA2 | Length between ITRs |
|---|---|---|---|---|
| CMVe_CBAp_GBA1_WPRE_bGH | | | | 3741 |
| LT1s_JetLong_mRNAiaSYn_SCARB2-T2A-GBA1_bGH | | GBA1 | | 4215 |
| LI1_JetLong_SCARB2-IRES-GBA1_bGH | | GBA1 | | 4399 |
| FP1_JetLong_GBA1_bGH_JetLong_SCARB2_SV40L | JetLong | SCARB2 | SV40L | 4464 |
| PrevailVector_LT2s_JetLong_mRNAiaSYn_PSAP-T2A-GBA1_bGH_4353nt | — | GBA1 | — | 4353 |
| PrevailVector_LI2_JetLong_PSAP_IRES_GBA1_SymtheticpolyA_4337nt | — | GBA1 | — | 4337 |

Example 2

Cell Based Assays of Viral Transduction into GBA-Deficient Cells

Cells deficient in GBA1 are obtained, for example as fibroblasts from GD patients, monocytes, or hES cells, or patient-derived induced pluripotent stem cells (iPSCs). These cells accumulate substrates such as glucosylceramide and glucosylsphingosine (GluCer and GluSph). Treatment of wild-type or mutant cultured cell lines with Gcase inhibitors, such as CBE, is also be used to obtain GBA deficient cells.

Using such cell models, lysosomal defects are quantified in terms of accumulation of protein aggregates, such as of α-Synuclein with an antibody for this protein or phospho-αSyn, followed by imaging using fluorescent microscopy. Imaging for lysosomal abnormalities by ICC for protein markers such as LAMP1, LAMP2, LIMP1, LIMP2, or using dyes such as Lysotracker, or by uptake through the endocytic compartment of fluorescent dextran or other markers is also performed. Imaging for autophagy marker accumulation due to defective fusion with the lysosome, such as for LC3, can also be performed. Western blotting and/or ELISA is used to quantify abnormal accumulation of these markers. Also, the accumulation of glycolipid substrates and products of GBA1 is measured using standard approaches.

Therapeutic endpoints (e.g., reduction of PD-associated pathology) are measured in the context of expression of transduction of the AAV vectors, to confirm and quantify activity and function. Gcase can is also quantified using protein ELISA measures, or by standard Gcase activity assays.

Example 3

In Vivo Assays Using Mutant Mice

This example describes in vivo assays of AAV vectors using mutant mice. In vivo studies of AAV vectors as above in mutant mice are performed using assays described, for example, by Liou et al. (2006) *J. Biol. Chem.* 281(7): 4242-4253, Sun et al. (2005) *J. Lipid Res.* 46:2102-2113, and Farfel-Becker et al. (2011) *Dis. Model Mech.* 4(6):746-752.

The intrathecal or intraventricular delivery of vehicle control and AAV vectors (e.g., at a dose of $2 \times 10^{11}$ vg/mouse) are performed using concentrated AAV stocks, for example at an injection volume between 5-10 μL. Intraparenchymal delivery by convection enhanced delivery is performed.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 4

Chemical Models of Disease

This example describes in vivo assays of AAV vectors using a chemically-induced mouse model of Gaucher disease (e.g., the CBE mouse model). In vivo studies of these AAV vectors are performed in a chemically-induced mouse model of Gaucher disease, for example as described by Vardi et al. (2016) *J Pathol.* 239(4):496-509.

Intrathecal or intraventricular delivery of vehicle control and AAV vectors (e.g., at a dose of $2 \times 10^{11}$ vg/mouse) are performed using concentrated AAV stocks, for example with injection volume between 5-10 μL. Intraparenchymal delivery by convection enhanced delivery is performed. Peripheral delivery is achieved by tail vein injection.

Treatment is initiated either before onset of symptoms, or subsequent to onset. Endpoints measured are the accumulation of substrate in the CNS and CSF, accumulation of Gcase enzyme by ELISA and of enzyme activity, motor and cognitive endpoints, lysosomal dysfunction, and accumulation of α-Synuclein monomers, protofibrils or fibrils.

Example 5

Clinical Trials in PD, LBD, Gaucher Disease Patients

In some embodiments, patients having certain forms of Gaucher disease (e.g., GD1) have an increased risk of developing Parkinson's disease (PD) or Lewy body dementia (LBD). This Example describes clinical trials to assess the safety and efficacy of rAAVs as described by the disclosure, in patients having Gaucher disease, PD and/or LBD.

Clinical trials of such vectors for treatment of Gaucher disease, PD and/or LBD are performed using a study design similar to that described in Grabowski et al. (1995) *Ann. Intern. Med.* 122(1):33-39.

Example 6

Treatment of Peripheral Disease

In some embodiments, patients having certain forms of Gaucher disease exhibit symptoms of peripheral neuropathy, for example as described in Biegstraaten et al. (2010) *Brain* 133(10):2909-2919.

This example describes in vivo assays of AAV vectors as described herein for treatment of peripheral neuropathy associated with Gaucher disease (e.g., Type 1 Gaucher disease). Briefly, Type 1 Gaucher disease patients identified as having signs or symptoms of peripheral neuropathy are administered a rAAV as described by the disclosure. In some embodiments, the peripheral neuropathic signs and symptoms of the subject are monitored, for example using methods described in Biegstraaten et al., after administration of the rAAV.

Levels of transduced gene products as described by the disclosure present in patients (e.g., in serum of a patient, in peripheral tissue (e.g., liver tissue, spleen tissue, etc.)) of a patient are assayed, for example by Western blot analysis, enzymatic functional assays, or imaging studies.

Example 7

Treatment of CNS Fforms

This example describes in vivo assays of rAAVs as described herein for treatment of CNS forms of Gaucher disease. Briefly, Gaucher disease patients identified as having a CNS form of Gaucher disease (e.g., Type 2 or Type 3 Gaucher disease) are administered a rAAV as described by the disclosure. Levels of transduced gene products as described by the disclosure present in the CNS of patients (e.g., in serum of the CNS of a patient, in cerebrospinal fluid (CSF) of a patient, or in CNS tissue of a patient) are assayed, for example by Western blot analysis, enzymatic functional assays, or imaging studies.

Example 8

Gene Therapy of Parkinson's Disease in Subjects Having Mutations in GBA1

This example describes administration of a recombinant adeno-associated virus (rAAV) encoding GBA1 to a subject having Parkinson's disease characterized by a mutation in GBA1gene.

The rAAV vector insert contains the CBA promoter element (CBA), consisting of four parts: the CMV enhancer (CMVe), CBA promoter (CBAp), Exon 1, and intron (int) to constitutively express the codon optimized coding sequence (CDS) of human GBA1 (maroon). The 3' region also contains a Woodchuck hepatitis virus Posttranscriptional Regulatory Element (WPRE) posttranscriptional regulatory element followed by a bovine Growth Hormone polyA signal (bGH polyA) tail. The flanking ITRs allow for the correct packaging of the intervening sequences. Two variants of the 5' ITR sequence (FIG. 7, inset box, bottom sequence) were evaluated; these variants have several nucleotide differences within the 20-nucleotide "D" region of the ITR, which is believed to impact the efficiency of packaging and expression. The rAAV product contains the "D" domain nucleotide sequence shown in FIG. 7 (inset box, top sequence). A variant vector, harbors a mutant "D" domain (termed an "S" domain herein, with the nucleotide changes shown by shading), performed similarly in preclinical studies. The backbone contains the gene to confer resistance to kanamycin as well as a stuffer sequence to prevent reverse packaging. A schematic depicting the rAAV vector is shown in FIG. 8 The rAAV vector is packaged into an rAAV using AAV9 serotype capsid proteins.

GBA1-rAAV is administered to a subject as a single dose via a fluoroscopy guided sub-occipital injection into the cisterna magna (intracisternal magna; ICM). One embodiment of a dosing regimen study is as follows:

A single dose of rAAV is administered to patients (N=12) at one of two dose levels (3e13 vg (low dose); 1e14 vg (high dose), etc.) which are determined based on the results of nonclinical pharmacology and toxicology studies.

Initial studies were conducted in a chemical mouse model involving daily delivery of conduritol-b-epoxide (CBE), an inhibitor of GCase to assess the efficacy and safety of the rAAV vector and a variant rAAV S-variant construct (as described further below). Additionally, initial studies were performed in a genetic mouse model, which carries a homozygous GBA1 mutation and is partially deficient in saposins (4L/PS-NA). Additional dose-ranging studies in mice and nonhuman primates (NHPs) are conducted to further evaluate vector safety and efficacy.

Figure 7:
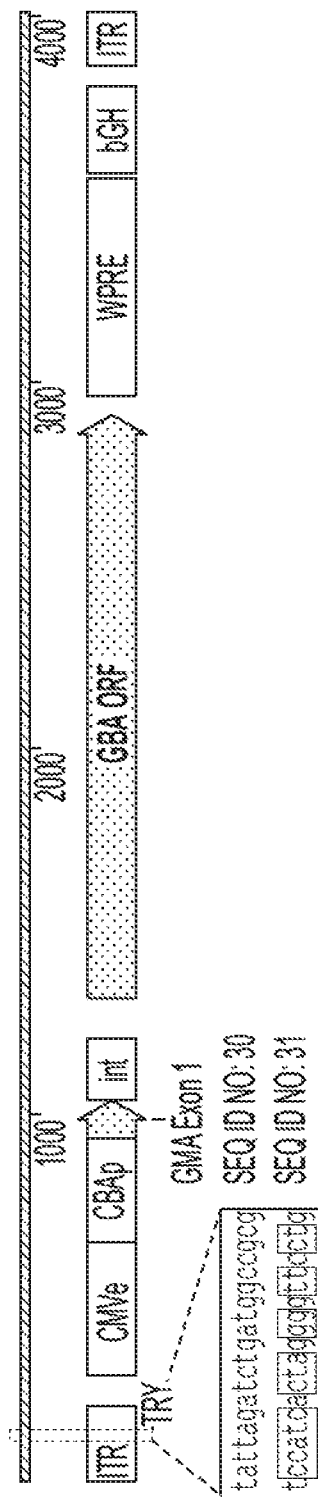
FIG. 7 is a schematic depicting one embodiment of an rAAV vector that includes an expression construct encoding a Gcase (e.g., GBA1 or a portion thereof). In this embodiment, the vector comprises a CBA promoter element (CBA), consisting of four parts: the CMV enhancer (CMVe), CBA promoter (CBAp), Exon 1, and intron (int) to constitutively express the codon optimized coding sequence of human GBA1. The 3' region also contains a WPRE regulatory element followed by a bGH polyA tail. Three transcriptional regulatory activation sites are included at the 5' end of the promoter region: TATA, RBS, and YY1. The flanking ITRs allow for the correct packaging of the intervening sequences. Two variants of the 5' ITR sequence (inset box) were evaluated; these have several nucleotide differences within the 20-nucleotide "D" region of wild-type AAV2 ITR. In some embodiments, an rAAV vector contains the "D" domain nucleotide sequence shown on the top line. In some embodiments, an rAAV vector comprises a mutant "D" domain (e.g., an "S" domain, with the nucleotide changes shown on the bottom line).
Figure 8:
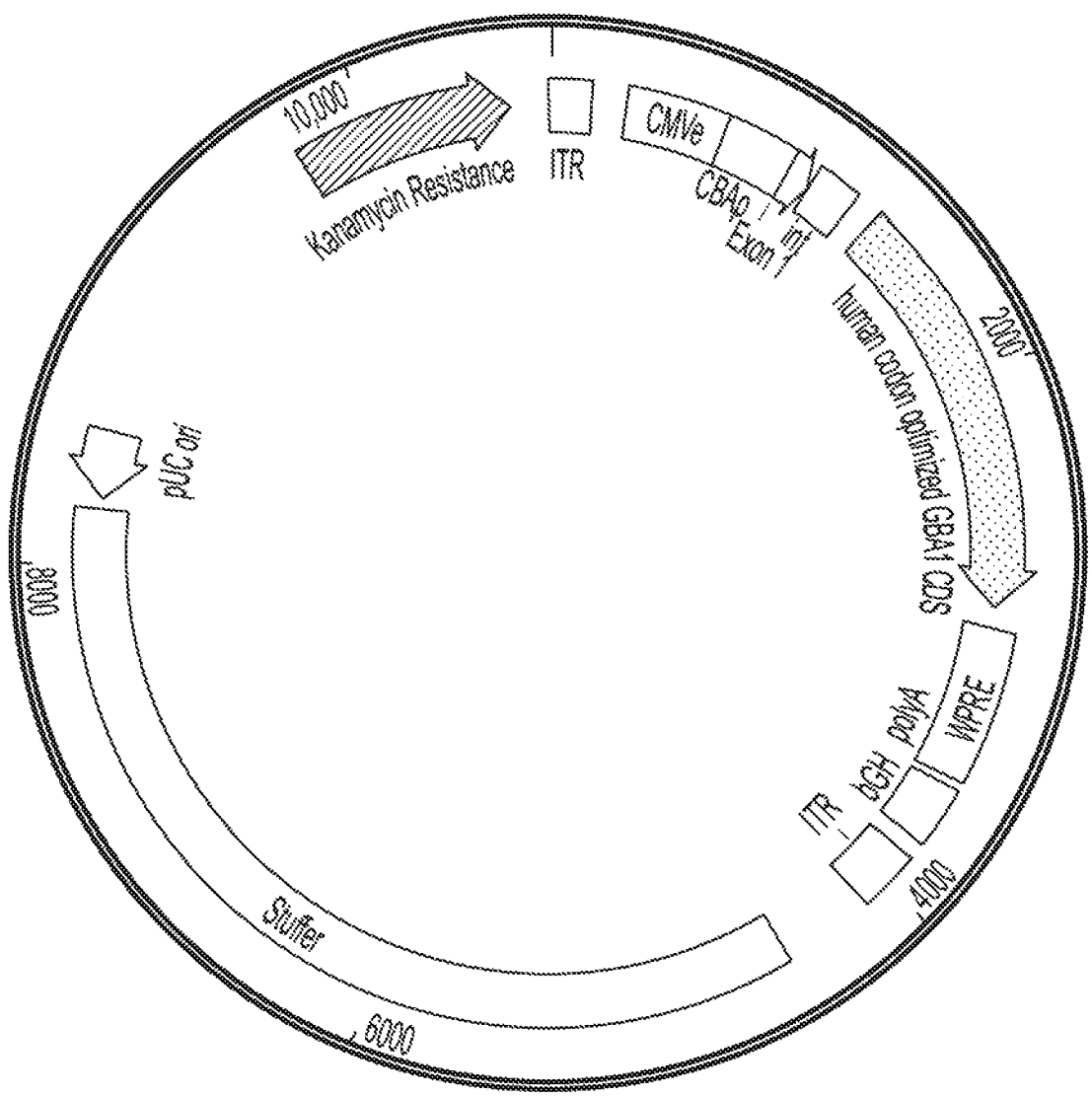
FIG. 8 is a schematic depicting one embodiment of a plasmid encoding the rAAV vector described in FIG. 7.

Two slightly different versions of the 5' inverted terminal repeat (ITR) in the AAV backbone were tested to assess manufacturability and transgene expression (FIG. 7). The 20 bp "D" domain within the 145 bp 5' ITR is thought to be necessary for optimal viral vector production, but mutations within the "D" domain have also been reported to increase transgene expression in some cases. Thus, in addition to the viral vector, which harbors an intact "D" domain, a second vector form with a mutant D domain (termed an "S" domain herein) was also evaluated. Both rAAV and variant rAAV express the same transgene. While both vectors produced virus that was efficacious in vivo as detailed below, the rAAV which contains a wild-type "D" domain, was selected for further development.

To establish the CBE model of GCase deficiency, juvenile mice were dosed with CBE, a specific inhibitor of GCase.

Figure 9:
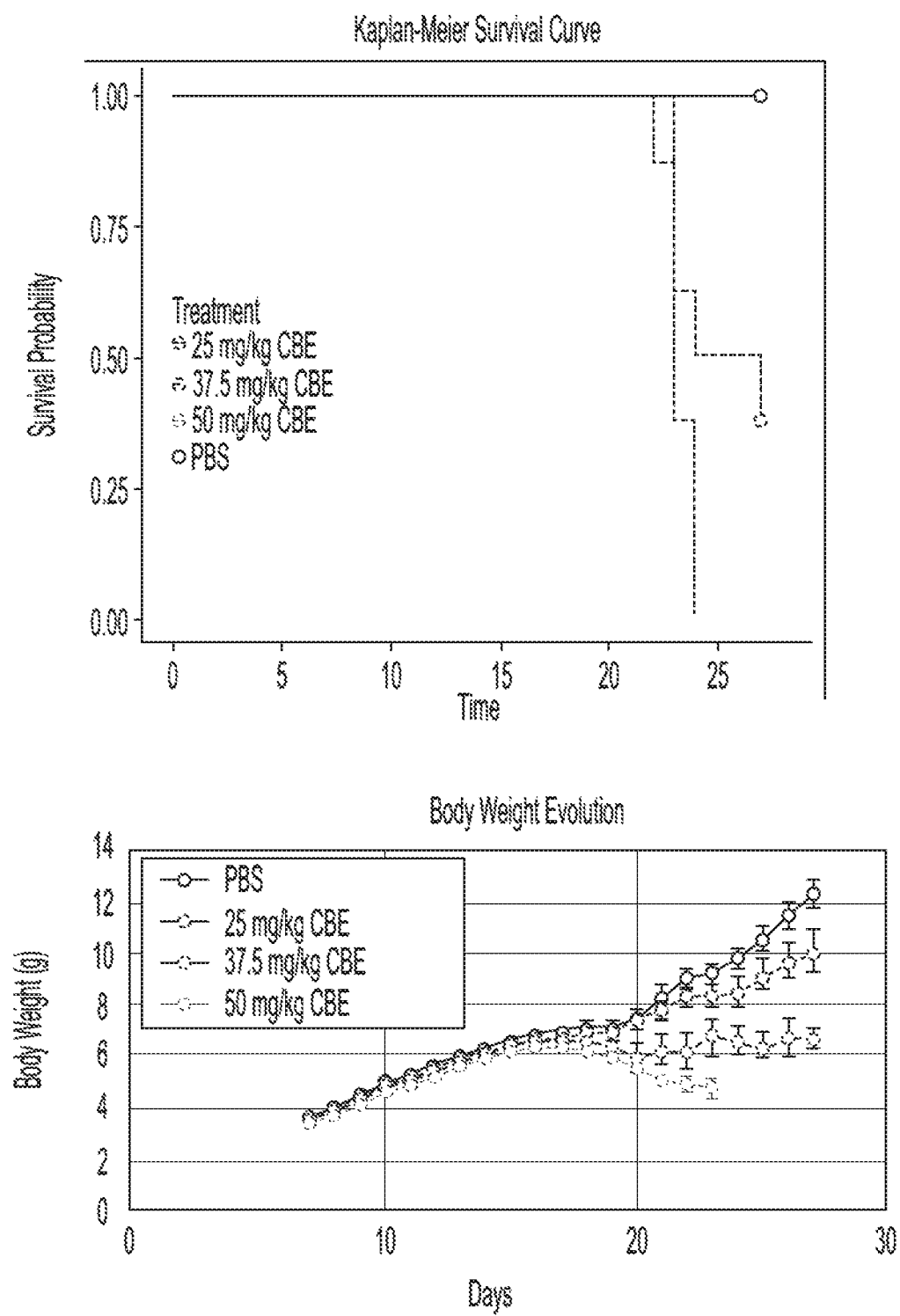
FIG. 9 shows representative data for delivery of an rAAV comprising a transgene encoding a Gcase (e.g., GBA1 or a portion thereof) in a CBE mouse model of Parkinson's disease. Daily IP delivery of PBS vehicle, 25 mg/kg CBE, 37.5 mg/kg CBE, or 50 mg/kg CBE (left to right) initiated at P8. Survival (top left) was checked two times a day and weight (top right) was checked daily. All groups started with n=8. Behavior was assessed by total distance traveled in Open Field (bottom left) at P23 and latency to fall on Rotarod (bottom middle) at P24. Levels of the GCase substrates were analyzed in the cortex of mice in the PBS and 25 mg/kg CBE treatment groups both with (Day 3) and without (Day 1) CBE withdrawal. Aggregate GluSph and GalSph levels (bottom right) are shown as pmol per mg wet weight of the tissue. Means are presented. Error bars are SEM. *p<0.05; p<0.01; *p<0.001, nominal p-values for treatment groups by linear regression.
Figure 9:
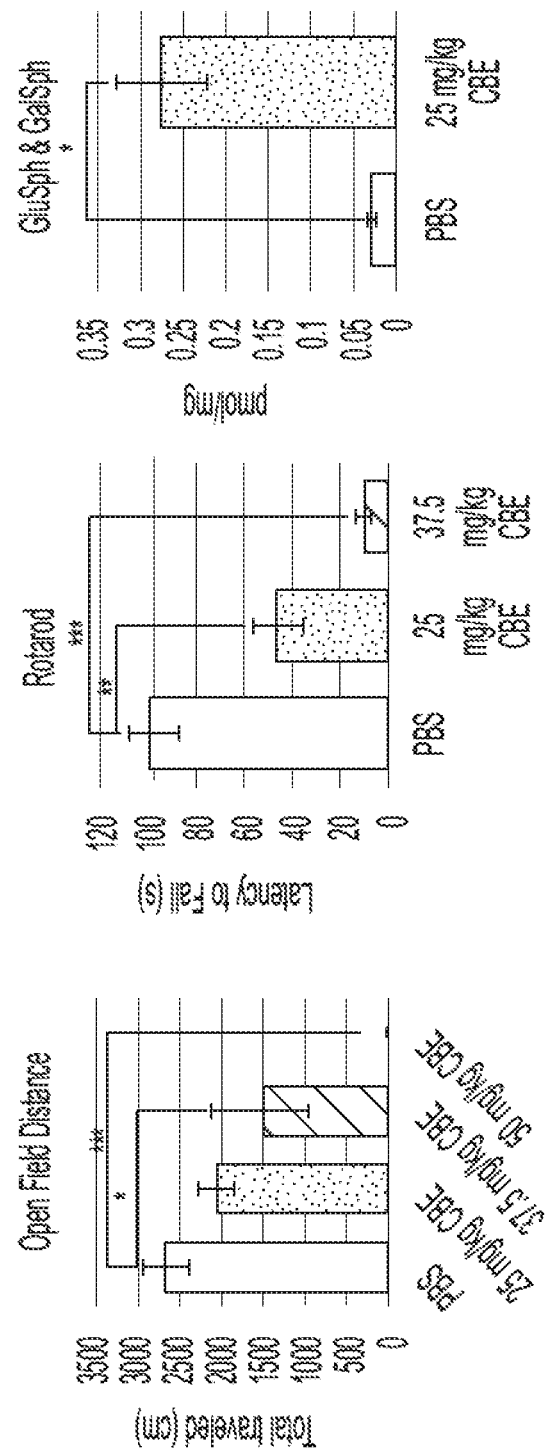

Mice were given CBE by IP injection daily, starting at postnatal day 8 (P8). Three different CBE doses (25 mg/kg, 37.5 mg/kg, 50 mg/kg) and PBS were tested to establish a model that exhibits a behavioral phenotype (FIG. 9). Higher doses of CBE led to lethality in a dose-dependent manner. All mice treated with 50 mg/kg CBE died by P23, and 5 of the 8 mice treated with 37.5 mg/kg CBE died by P27. There was no lethality in mice treated with 25 mg/kg CBE. Whereas CBE-injected mice showed no general motor deficits in the open field assay (traveling the same distance and at the same velocity as mice given PBS), CBE-treated mice exhibited a motor coordination and balance deficit as measured by the rotarod assay.

Mice surviving to the end of the study were sacrificed on the day after their last CBE dose (P27, "Day 1") or after three days of CBE withdrawal (P29, "Day 3"). Lipid analysis was performed on the cortex of mice given 25 mg/kg CBE to evaluate the accumulation of GCase substrates in both the Day 1 and Day 3 cohorts. GluSph and GalSph levels (measured in aggregate in this example) were significantly accumulated in the CBE-treated mice compared to PBS-treated controls, consistent with GCase insufficiency.

Figure 10:
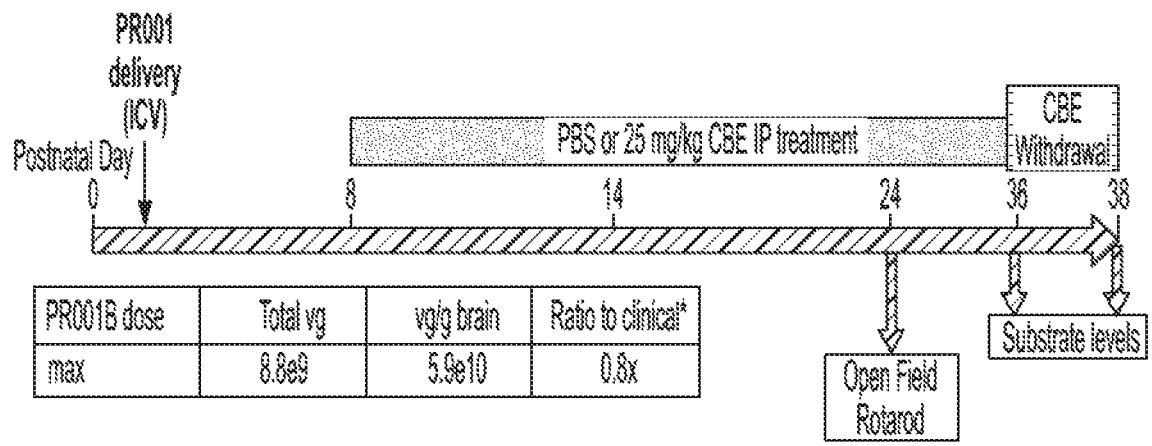
FIG. 10 is a schematic depicting one embodiment of a study design for maximal rAAV dose in a CBE mouse model. Briefly, rAAV was delivered by ICV injection at P3, and daily CBE treatment was initiated at P8. Behavior was assessed in the Open Field and Rotarod assays at P24-25 and substrate levels were measured at P36 and P38.

Based on the study described above, the 25 mg/kg CBE dose was selected since it produced behavioral deficits without impacting survival. To achieve widespread GBA1 distribution throughout the brain and transgene expression during CBE treatment, rAAV or excipient was delivered by intracerebroventricular (ICV) injection at postnatal day 3 (P3) followed by daily IP CBE or PBS treatment initiated at P8 (FIG. 10).

Figure 11:
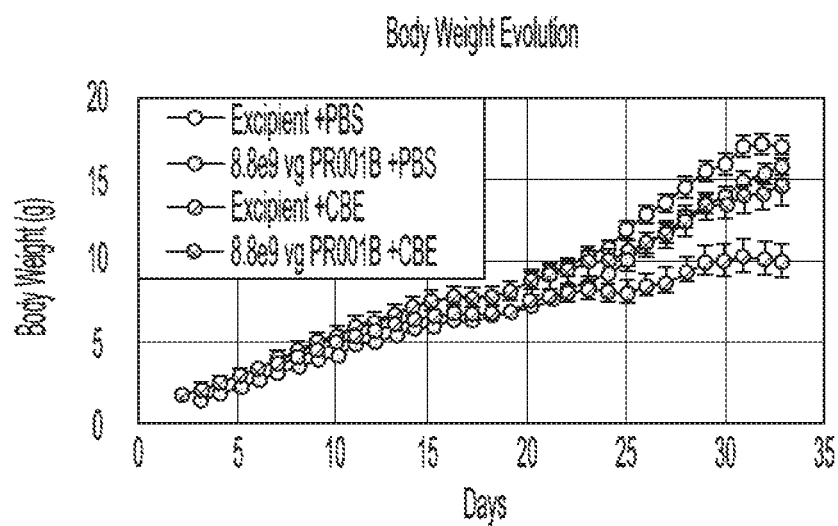
FIG. 11 shows representative data for in-life assessment of maximal rAAV dose in a CBE mouse model. At P3, mice were treated with either excipient or 8.8e9 vg rAAV via ICV delivery. Daily IP delivery of either PBS or 25 mg/kg CBE was initiated at P8. At the end of the study, half the mice were sacrificed one day after their last CBE dose at P36 (Day 1) while the remaining half went through 3 days of CBE withdrawal before sacrifice at P38 (Day3). All treatment groups (excipient+PBS n=8, rAAV+PBS n=7, excipient+CBE n=8, and rAAV+CBE n=9) were weighed daily (top left), and the weight at P36 was analyzed (top right). Behavior was assessed by total distance traveled in Open Field at P23 (bottom left) and latency to fall on Rotarod at P24 (bottom right), evaluated for each animal as the median across 3 trials. Due to lethality, n=7 for the excipient+CBE group for the behavioral assays, while n=8 for all other groups. Means across animals are presented. Error bars are SEM. *p<0.05; ***p<0.001, nominal p-values for treatment groups by linear regression in the CBE-treated animals.
Figure 11:
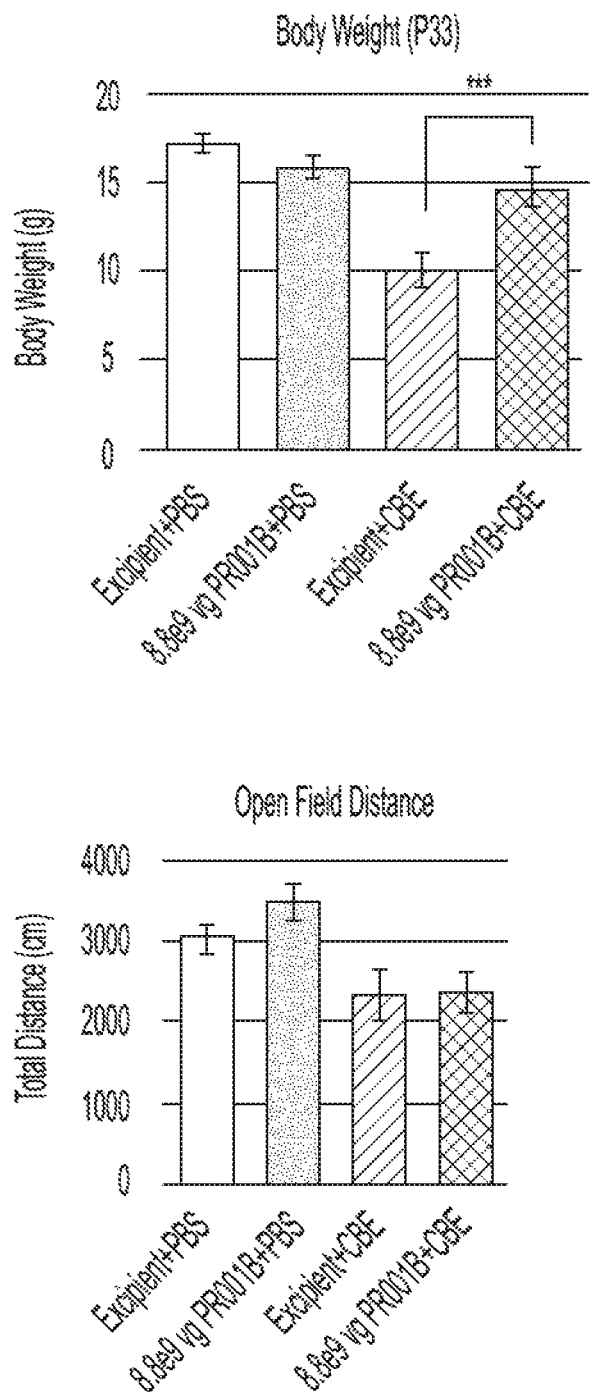
Figure 11:
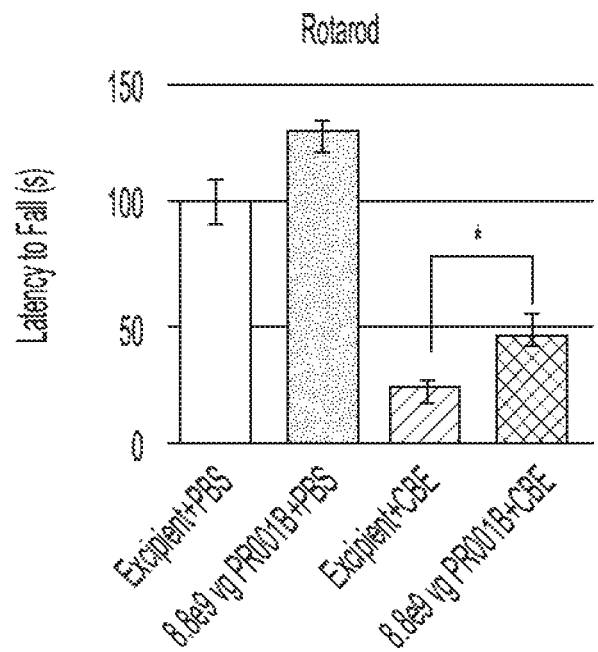

CBE-treated mice that received rAAV performed statistically significantly better on the rotarod than those that received excipient (FIG. 11). Mice in the variant vector treatment group did not differ from excipient treated mice in terms of other behavioral measures, such as the total distance traveled during testing (FIG. 11).

Figure 12:
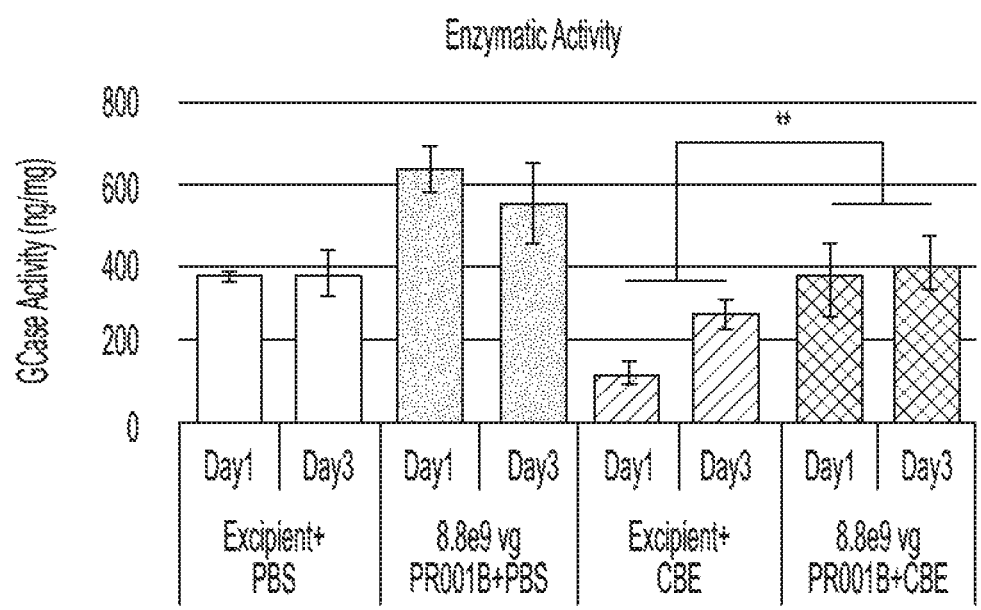
FIG. 12 shows representative data for biochemical assessment of maximal rAAV dose in a CBE mouse model. The cortex of all treatment groups (excipient+PBS n=8, rAAV+PBS n=7, excipient+CBE n=7, and rAAV+CBE n=9) was used to measure GCase activity (top left), GluSph levels (top right), GluCer levels (bottom left), and vector genomes (bottom right) in the groups before (Day 1) or after (Day 3) CBE withdrawal. Biodistribution is shown as vector genomes per 1 µg of genomic DNA. Means are presented. Error bars are SEM. (*)p<0.1; p<0.01; *p<0.001, nominal p-values for treatment groups by linear regression in the CBE-treated animals, with collection days and gender corrected for as covariates.
Figure 12:
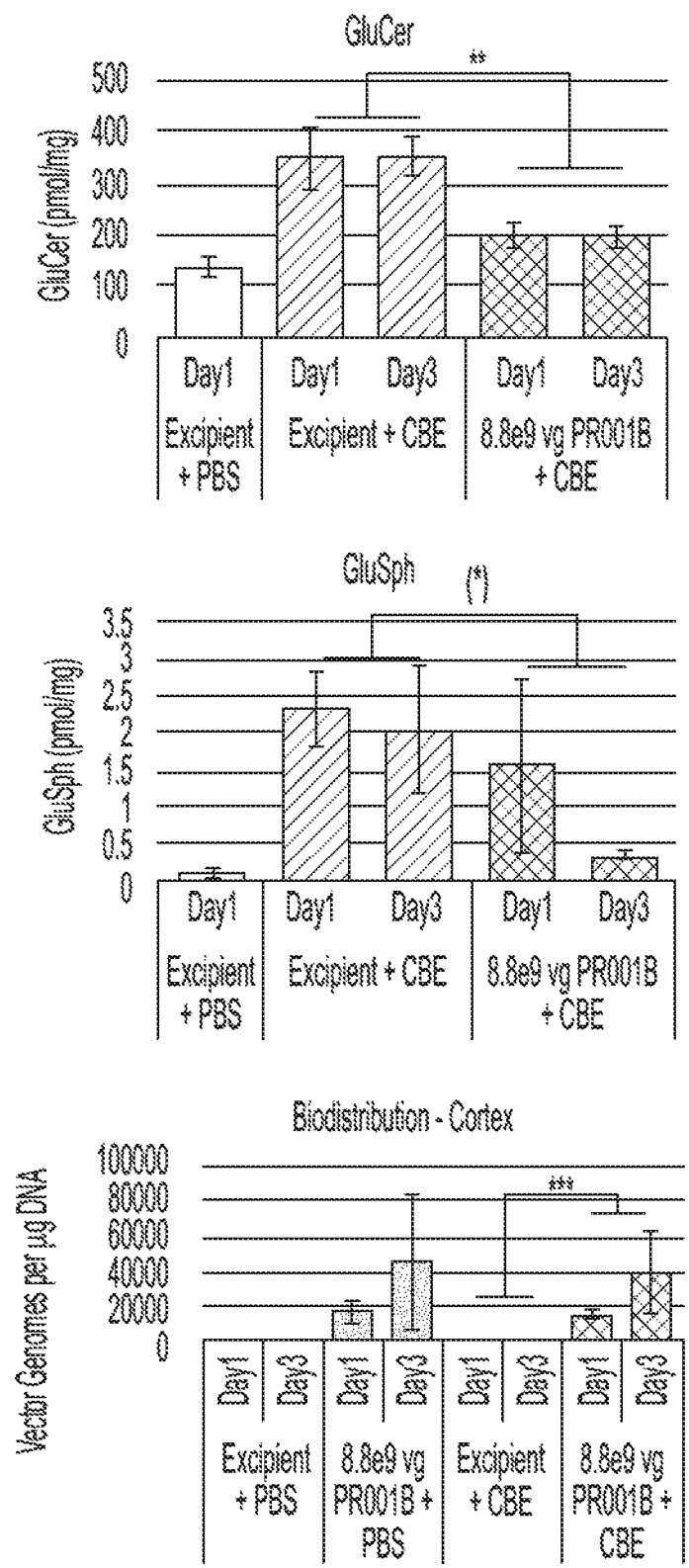

At the completion of the in-life study, half of the mice were sacrificed the day after the last CBE dose (P36, "Day 1") or after three days of CBE withdrawal (P38, "Day 3") for biochemical analysis (FIG. 12). Using a fluorometric enzyme assay performed in biological triplicate, GCase activity was assessed in the cortex. GCase activity was increased in mice that were treated with GBA1 rAAV, while CBE treatment reduced GCase activity. Additionally, mice that received both CBE and GBA1-rAAV had GCase activity levels that were similar to the PBS-treated group, indicating that delivery of rAAV is able to overcome the inhibition of GCase activity induced by CBE treatment. Lipid analysis was performed on the motor cortex of the mice to examine levels of the substrates GluCer and GluSph. Both lipids accumulated in the brains of mice given CBE, and rAAV treatment significantly reduced substrate accumulation.

Figure 13:
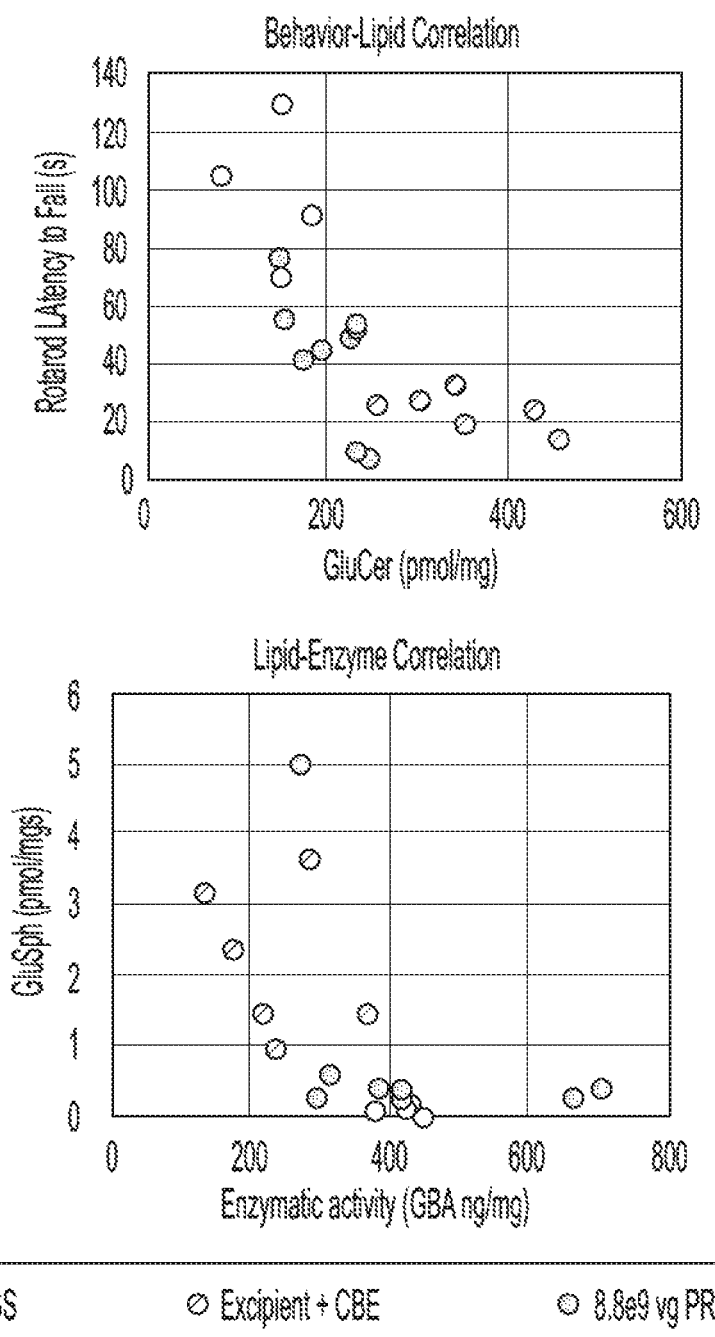
FIG. 13 shows representative data for behavioral and biochemical correlations in a CBE mouse model after administration of excipient+PBS, excipient+CBE, and rAAV+CBE treatment groups. Across treatment groups, performance on Rotarod was negatively correlated with GluCer accumulation (A, p=0.0012 by linear regression), and GluSph accumulation was negatively correlated with increased GCase activity (B, p=0.0086 by linear regression).
Figure 14:
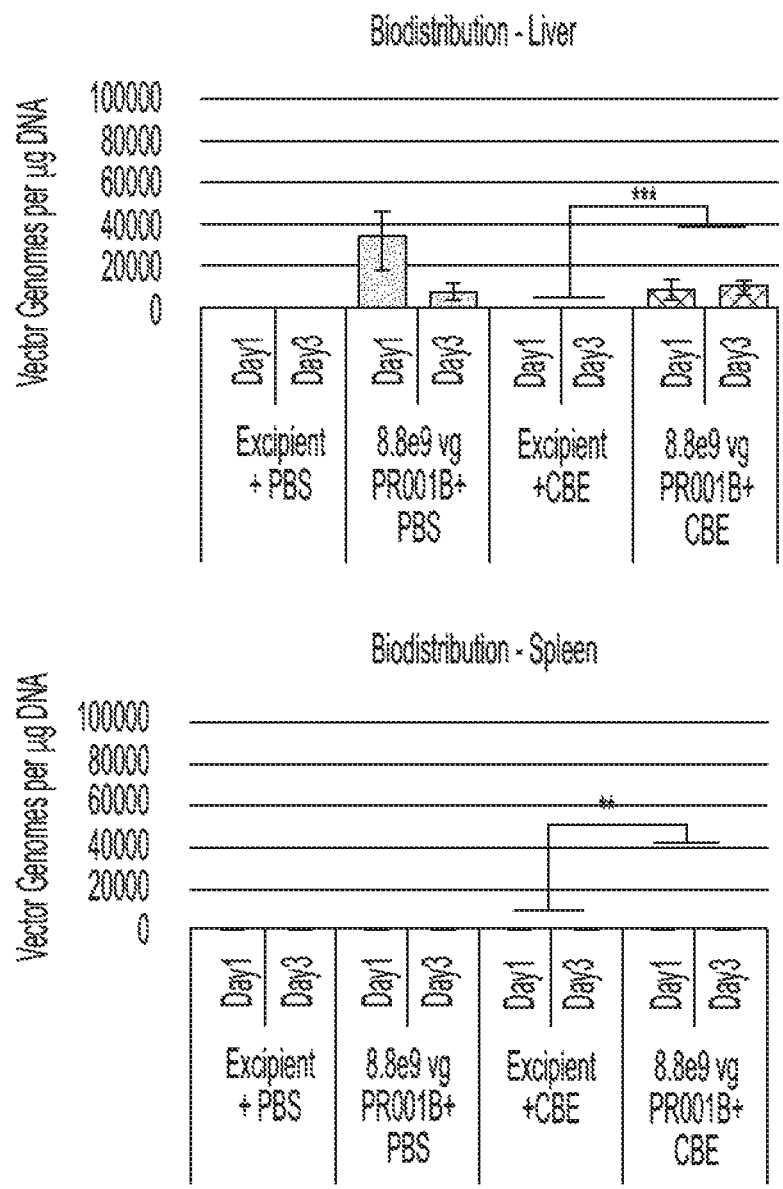
FIG. 14 shows representative data for biodistribution of GBA1 rAAV in a CBE mouse model. Presence of vector genomes was assessed in the liver, spleen, kidney, and gonads for all treatment groups (excipient+PBS n=8, rAAV+PBS n=7, excipient+CBE n=7, and rAAV+CBE n=9). Biodistribution is shown as vector genomes per 1 µg of genomic DNA. Vector genome presence was quantified by quantitative PCR using a vector reference standard curve; genomic DNA concentration was evaluated by A260 optical density measurement. Means are presented. Error bars are SEM. *p<0.05; p<0.01; *p<0.001, nominal p-values for treatment groups by linear regression in the CBE-treated animals, with collection days and gender corrected for as covariates.
Figure 14:
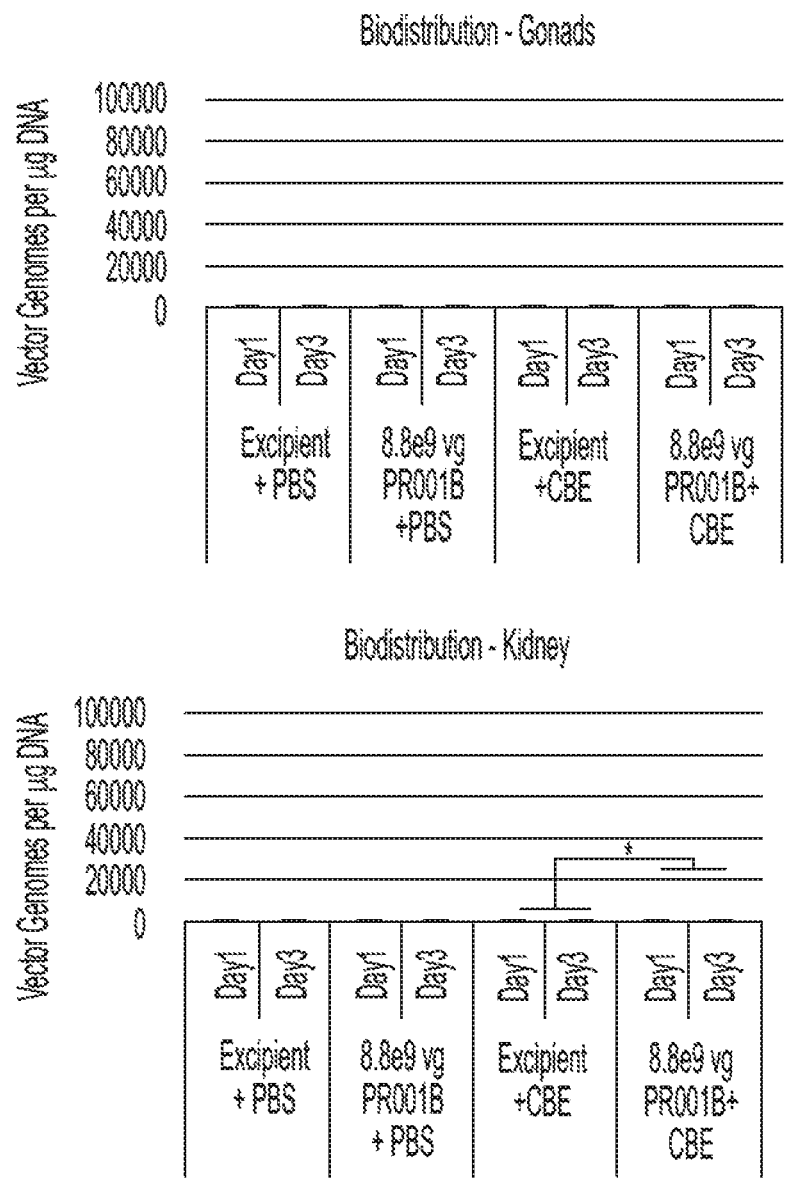

Lipid levels were negatively correlated with both GCase activity and performance on the Rotarod across treatment groups. The increased GCase activity after rAAV administration was associated with substrate reduction and enhanced motor function (FIG. 13). As shown in FIG. 14, preliminary biodistribution was assessed by vector genome presence, as measured by qPCR (with >100 vector genomes per 1 µg genomic DNA defined as positive). Mice that received GBA1-rAAV, both with and without CBE, were positive for rAAV vector genomes in the cortex, indicating that ICV delivery results in rAAV delivery to the cortex. Additionally, vector genomes were detected in the liver, few in spleen, and none in the heart, kidney or gonads. For all measures, there was no statistically significant difference between the Day 1 and Day 3 groups.

A larger study in the CBE model further explored efficacious doses of GBA1-rAAV in the CBE model. Using the 25 mg/kg CBE dose model, excipient or GBA1-rAAV was delivered via ICV at P3, and daily IP PBS or CBE treatment initiated at P8. Given the similarity between the groups with and without CBE withdrawal observed in the previous studies, all mice were sacrificed one day after the final CBE dose (P38-40). The effect of three different rAAV doses was assessed, resulting in the following five groups, with 10 mice (5M/5F) per group:

Excipient ICV+PBS IP
Excipient ICV+25 mg/kg CBE IP
3.2e9 vg (2.13e10 vg/g brain) rAAV ICV+25 mg/kg CBE IP
1.0e10 vg (6.67e10 vg/g brain) rAAV ICV+25 mg/kg CBE IP
3.2e10 vg (2.13e11 vg/g brain) rAAV ICV+25 mg/kg CBE IP.

Figure 15:
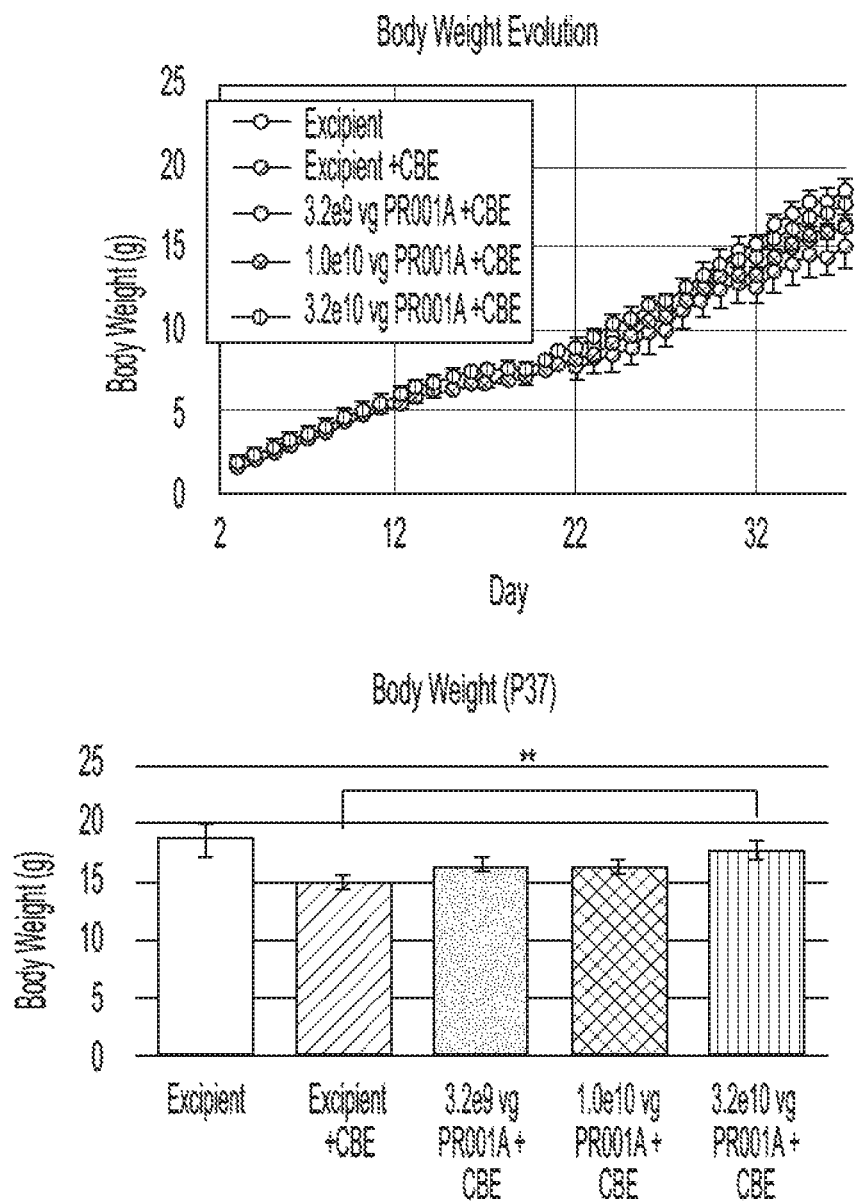
FIG. 15 shows representative data for in-life assessment of rAAV dose ranging in a CBE mouse model. Mice received excipient or one of three different doses of GBA1 rAAV by ICV delivery at P3: 3.2e9 vg, 1.0e10vg, or 3.2e10 vg. At P8, daily IP treatment of 25 mg/kg CBE was initiated. Mice that received excipient and CBE or excipient and PBS served as controls. All treatment groups started with n=10 (5M/5F) per group. All mice were sacrificed one day after their final CBE dose (P38-P40). All treatment groups were weighed daily, and their weight was analyzed at P36. Motor performance was assessed by latency to fall on Rotarod at P24 and latency to traverse the Tapered Beam at P30. Due to early lethality, the number of mice participating in the behavioral assays was: excipient+PBS n=10, excipient+CBE n=9, and 3.2e9 vg rAAV+CBE n=6, 1.0e10 vg rAAV+CBE n=10, 3.2e10 vg rAAV+CBE n=7. Means are presented. Error bars are SEM; * p<0.05; **p<0.01 for nominal p-values by linear regression in the CBE-treated groups, with gender corrected for as a covariate.
Figure 15:
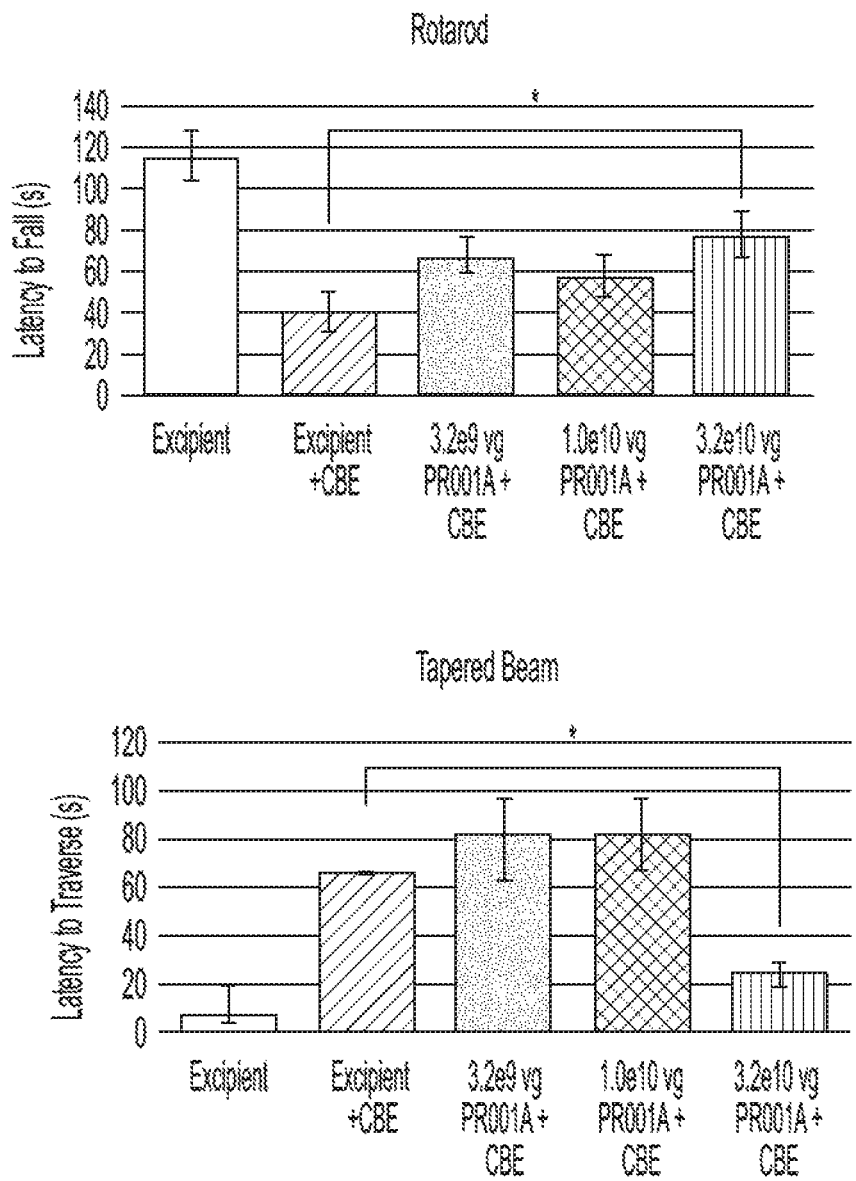

The highest dose of rAAV rescued the CBE treatment-related failure to gain weight at P37. Additionally, this dose resulted in a statistically significant increase in performance on the rotarod and tapered beam compared to the Excipient+CBE treated group (FIG. 15). Lethality was observed in several groups, including both excipient-treated and rAAV-treated groups (Excipient+PBS: 0; Excipient+25 mg/kg CBE: 1; 3.2e9 vg rAAV+25 mg/kg CBE: 4; 1.0e10 vg rAAV+25 mg/kg CBE: 0; 3.2e10 vg rAAV+25 mg/kg CBE: 3).

Figure 16:
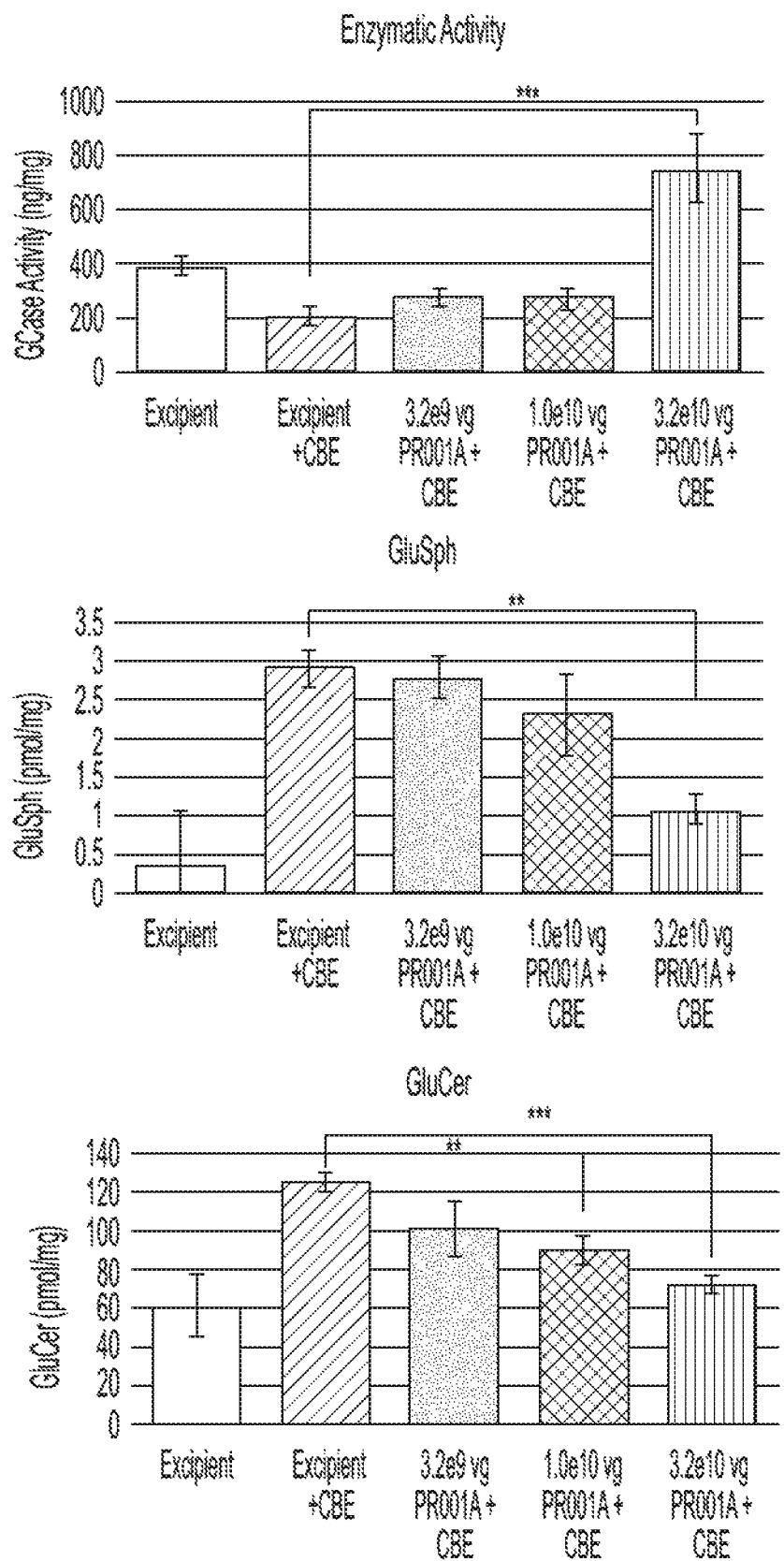
FIG. 16 shows representative data for biochemical assessment of rAAV dose ranging in a CBE mouse model. The cortex of all treatment groups (excipient+PBS n=10, excipient+CBE n=9, and 3.2e9 vg rAAV+CBE n=6, 1.0e10 vg rAAV+CBE n=10, 3.2e10 vg rAAV+CBE n=7) was used to measure GCase activity, GluSph levels, GluCer levels, and vector genomes. GCase activity is shown as ng of GCase per mg of total protein. GluSph and GluCer levels are shown as pmol per mg wet weight of the tissue. Biodistribution is shown as vector genomes per 1 µg of genomic DNA. Vector genome presence was quantified by quantitative PCR using a vector reference standard curve; genomic DNA concentration was evaluated by A260 optical density measurement. Vector genome presence was also measured in the liver (E). Means are presented. Error bars are SEM. p<0.01; *p<0.001 for nominal p-values by linear regression in the CBE-treated groups, with gender corrected for as a covariate.
Figure 16:
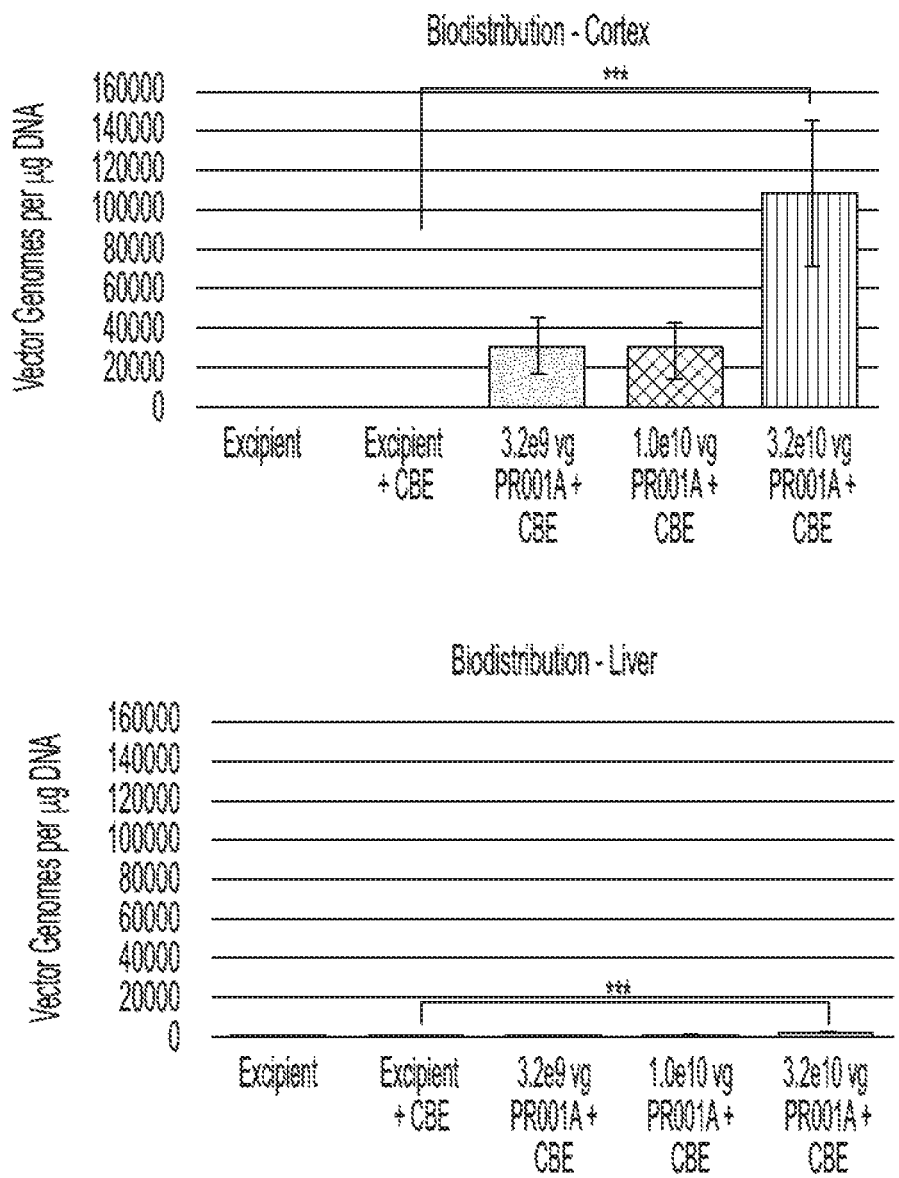

At the completion of the in-life study, mice were sacrificed for biochemical analysis (FIG. 16). GCase activity in the cortex was assessed in biological triplicates by a fluorometric assay. CBE-treated mice showed reduced GCase activity whereas mice that received a high rAAV dose showed a statistically significant increase in GCase activity compared to CBE treatment. CBE-treated mice also had accumulation of GluCer and GluSph, both of which were rescued by administering a high dose of rAAV.

Figure 17:
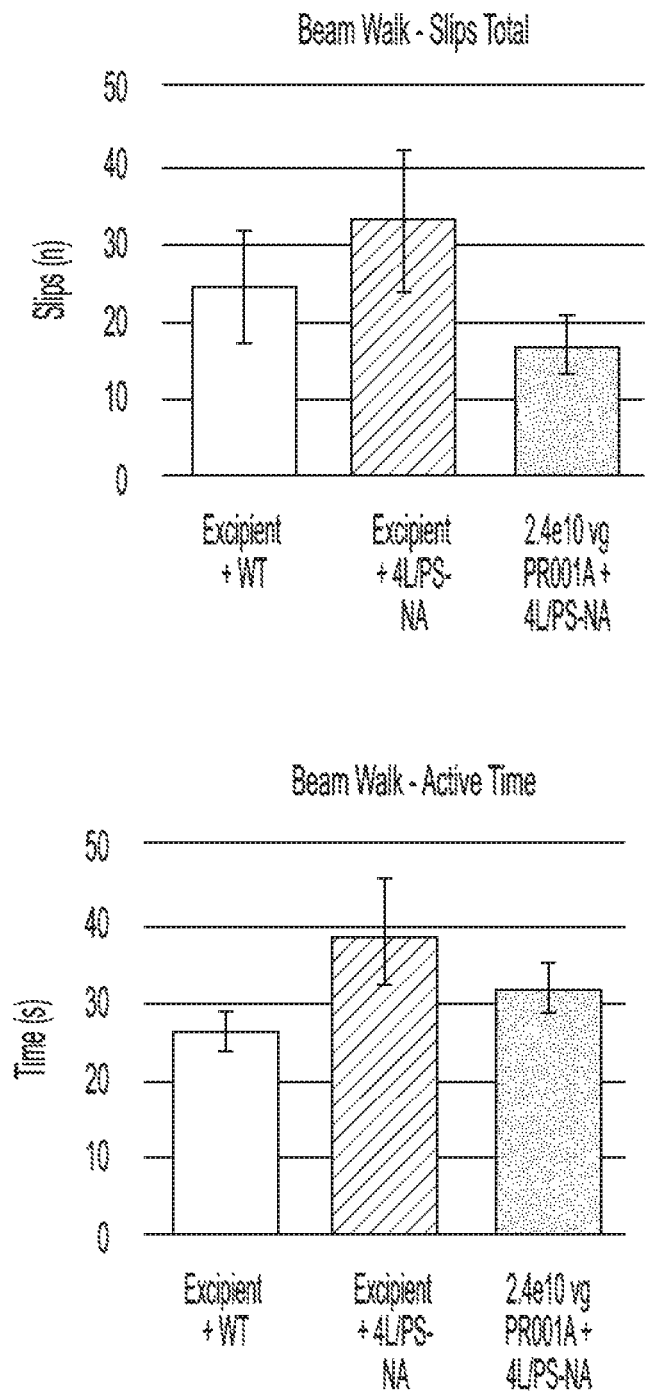
FIG. 17 shows representative data for tapered beam analysis in maximal dose GBA1 rAAV in a genetic mouse model. Motor performance of the treatment groups (WT+ excipient, n=5), 4L/PS-NA+excipient (n=6), and 4L/PS-NA+rAAV (n=5)) was assayed by Beam Walk 4 weeks post rAAV administration. The total slips and active time are shown as total over 5 trials on different beams. Speed and slips per speed are shown as the average over 5 trials on different beams. Means are presented. Error bars are SEM.
Figure 17:
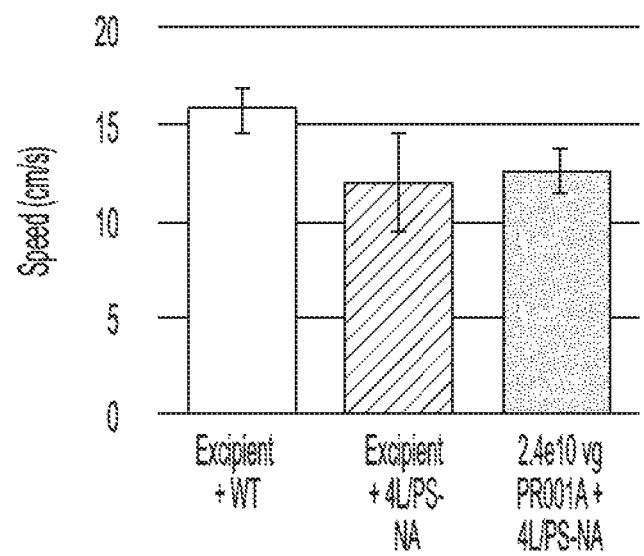
Figure 17:
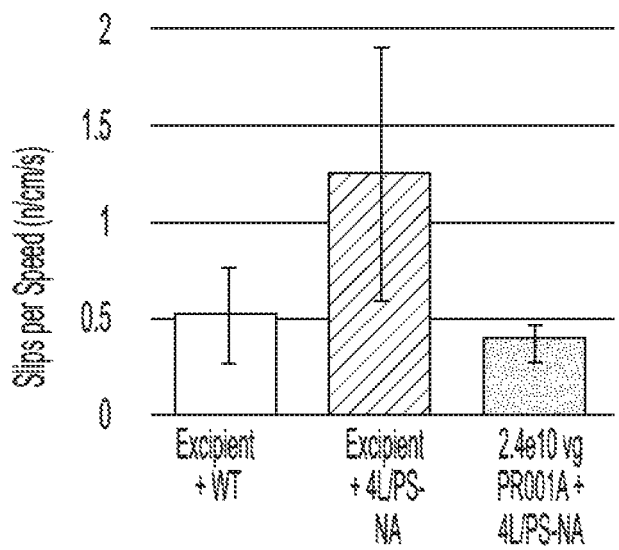

In addition to the established chemical CBE model, GBA1-rAAV is also evaluated in the 4L/PS-NA genetic model, which is homozygous for the V394L GD mutation in Gba1 and is also partially deficient in saposins, which affect GCase localization and activity. These mice exhibit motor strength, coordination, and balance deficits, as evidenced by their performance in the beam walk, rotarod, and wire hang assays. Typically the lifespan of these mice is less than 22 weeks. In an initial study, 3 µl of maximal titer virus was delivered by ICV at P23, with a final dose of 2.4e10 vg (6.0e10 vg/g brain). With 6 mice per group, the treatment groups were:

WT+Excipient ICV
4L/PS-NA+Excipient ICV
4L/PS-NA+2.4e10 vg (6.0e10 vg/g brain) rAAV ICV Motor performance by the beam walk test was assessed 4 weeks post-rAAV delivery. The group of mutant mice that received GBA1-rAAV showed a trend towards fewer total slips and fewer slips per speed when compared to mutant mice treated with excipient, restoring motor function to near WT levels (FIG. 17). Since the motor phenotypes become more severe as these mice age, their performance on this and other behavioral tests is assessed at later time points. At the completion of the in-life study, lipid levels, GCase activity, and biodistribution are assessed in these mice.

Additional lower doses of rAAV are currently being tested using the CBE model, corresponding to 0.03×, 0.1×, and 1× the proposed phase 1 high clinical dose. Each group includes 10 mice (5M/5F) per group:

Excipient ICV
Excipient ICV+25 mg/kg CBE IP
3.2e8 vg (2.13e9 vg/g brain) rAAV ICV+25 mg/kg CBE IP
1.0e9 vg (6.67e9 vg/g brain) rAAV ICV+25 mg/kg CBE IP
1.0e10 vg (6.67e10 vg/g brain) rAAV ICV+25 mg/kg CBE IP.

In addition to motor phenotypes, lipid levels and GCase activity are assessed in the cortex. Time course of treatments and analyses are also performed.

A larger dose ranging study was initiated to evaluate efficacy and safety data. 10 4L/PS-NA mice (5M/5F per group) were injected with 10 μl of rAAV. Using an allometric brain weight calculation, the doses correlate to 0.15×, 1.5×, 4.4×, and 14.5× the proposed phase 1 high clinical dose. The injection groups consist of:

WT+Excipient ICV
4L/PS-NA+Excipient ICV
4L/PS-NA+4.3e9 vg (1.1e10 vg/g brain) rAAV ICV
4L/PS-NA+4.3e10 vg (1.1e11 vg/g/brain) rAAV ICV
4L/PS-NA+1.3e11 vg (3.2e11 vg/g brain) rAAV ICV
4L/PS-NA+4.3e11 vg (1.1e12 vg/g brain) rAAV ICV.

A summary of nonclinical studies in the CBE model are shown in Table 3 below.

TABLE 3

Summary of Results in CBE Mouse Model

| Test Material | Study Number | Dose Cohort | Behavioral Changes | | | | Enzyme | BD | |
| --- | --- | --- | --- | --- | --- | --- | --- | --- | --- |
| | | | Rotarod | Tapered Beam | Open Field | Lipids | | Brain | Liver |
| GBA1-rAAV | PRV-2018-005 Dose-ranging rAAV in CBE Model | 3.2e9 vg (2.13e10 vg/g brain) | NS | NS | NS | NS | NS | + | − |
| | | 1.10e10 vg (6.67e10 vg/g brain) | T | NS | NS | T/S | NS | + | + |
| | | 2.3e10vg (2.13e11 vg/g brain) | S | S | NS | S | S | + | + |
| variant GBA1-rAAV | PRV-2018-005 Dose-ranging rAAV in CBE Model | 8.8e9 vg (5.9e10 vg/g brain) | S | N/A | NS | S | S | + | + |

Note that positive biodistribution is defined as >100 vg/1 μg genomic DNA.
Abbreviations:
BD = biodistribution;
NS = nonsignificant;
T = trend;
S = significant;
N/A = not applicable;
+ = positive;
− = negative.

Example 9

In Vitro Analysis of rAAV Vectors

Figure 18:
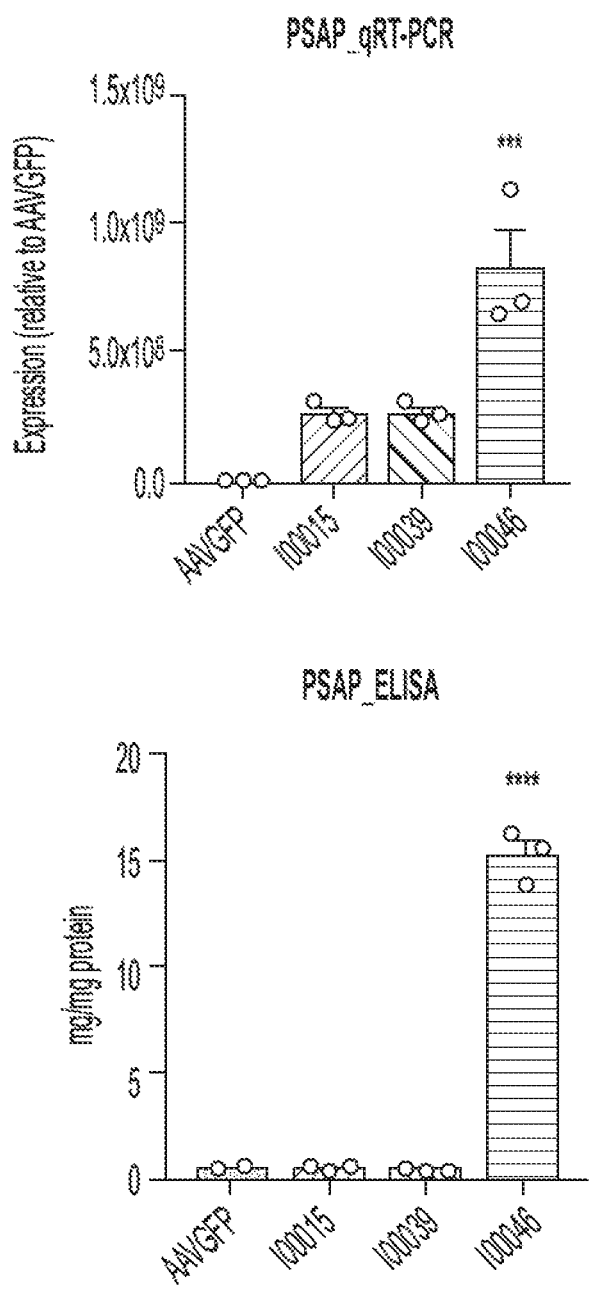
FIG. 18 shows representative data for in vitro expression of rAAV constructs encoding GBA1 in combination with Prosaposin (PSAP), SCARB2, and/or one or more inhibitory nucleic acids. Data indicate transfection of HEK293 cells with each construct resulted in overexpression of the transgenes of interest relative to GFP-transfected cells.
Figure 18:
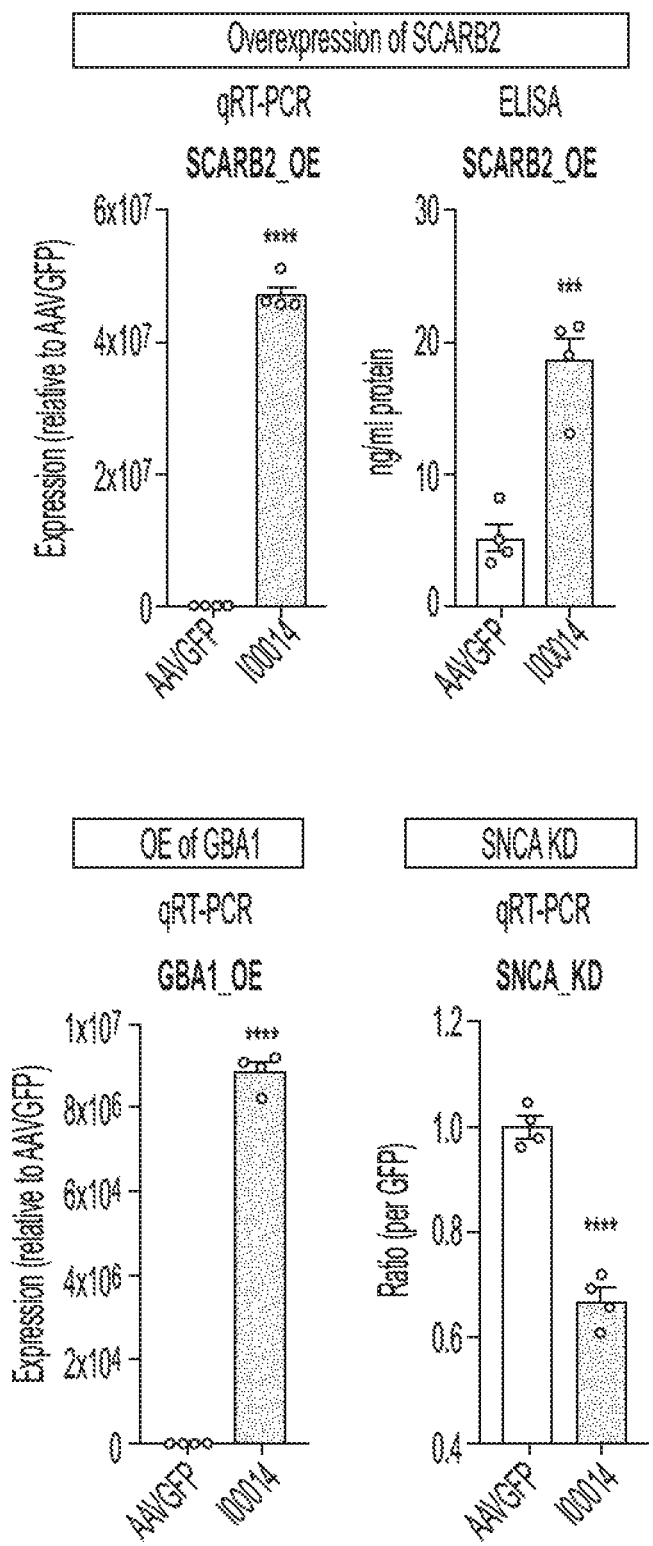

A pilot study was performed to assess in vitro activity of rAAV vectors encoding Prosaposin (PSAP) and SCARB2, alone or in combination with GBA1 and/or one or more inhibitory RNAs. One construct encoding PSAP and progranulin (PGRN) was also tested. Vectors tested include those shown in Table 4. "Opt" refers to a nucleic acid sequence codon optimized for expression in mammalian cells (e.g., human cells). FIG. 18 shows representative data indicating that transfection of HEK293 cells with each of the constructs resulted in overexpression of the corresponding gene product compared to mock transfected cells.

TABLE 4

| ID | Promoter | Inhibitory RNA | Promoter | Transgene |
| --- | --- | --- | --- | --- |
| I00015 | JL_intronic | SCNA | JetLong | Opt-PSAP_GBA1 |
| I00039 | — | — | JetLong | Opt-PSAP-GRN |
| I00046 | — | — | | Opt-PSAP |
| I00014 | JetLong | SCNA | JetLong | Opt-SCARB2_GBA1 |

Example 10

ITR "D" Sequence Placement and Cell Transduction

Figure 20:
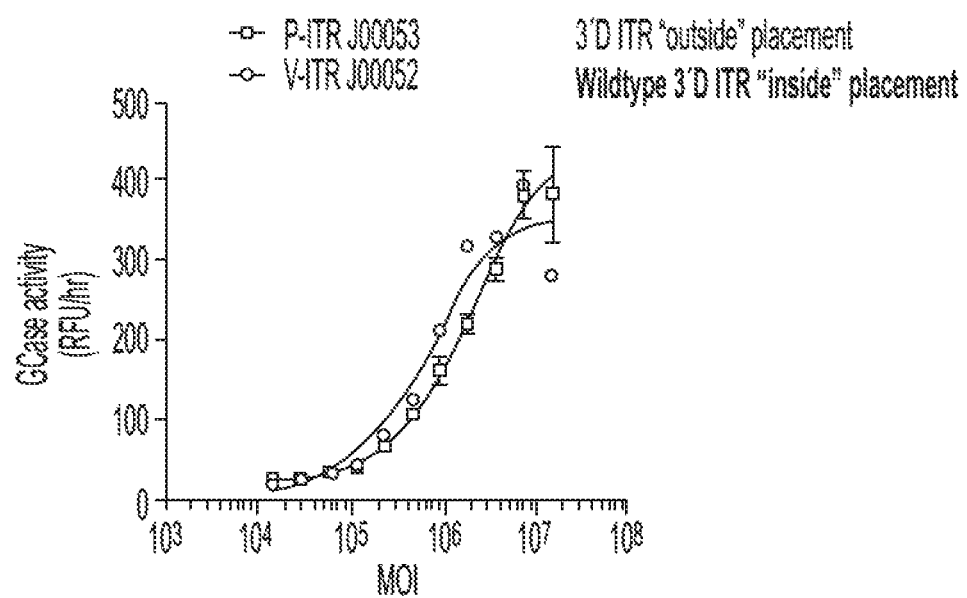
FIG. 20 shows data for transduction of HEK293 cells using rAAVs having ITRs with wild-type (circles) or alternative (e.g., "outside"; squares) placement of the "D" sequence. The rAAVs having ITRs placed on the "outside" were able to transduce cells as efficiently as rAAVs having wild-type ITRs.

The effect of placement of ITR "D" sequence on cell transduction of rAAV vectors was investigated. HEK 293 cells were transduced with Gcase-encoding rAAVs having 1) wild-type ITRs (e.g., "D" sequences proximal to the transgene insert and distal to the terminus of the ITR) or 2) ITRs with the "D" sequence located on the "outside" of the vector (e.g., "D" sequence located proximal to the terminus of the ITR and distal to the transgene insert), as shown in FIG. 19. Surprisingly, data indicate that rAAVs having the "D" sequence located in the "outside" to position retain the ability to be packaged and transduce cells efficiently (FIG. 20).

Example 11

In Vitro Toxicity Studies

Fifty (50) mice were administered GBA1-encoding rAAVs via a 4 µl intracerebroventricular (ICV) injection on post-natal day 3. All mice received daily intraperitoneal (IP) injections of conduritol B-epoxide (CBE) or PBS, depending on treatment group, from post-natal day 8 to the end of the study. Animals were euthanized 24 hours after their last IP dose. After euthanasia, target tissues were harvested, drop fixed in chilled 4% paraformaldehyde and stored at 4° C., then sent for histopathological processing and evaluation. There were eight (8) early death animals over the course of the study, which were not sent to or analyzed.

Tissues from the forty-two (42) animals euthanized at 38-40 days were trimmed, processed, and embedded in paraffin blocks. They were then sectioned at ~5 µm, stained with hematoxylin and eosin (H&E) and affixed to slides for evaluation.

There were no histopathologic findings or evidence of toxicity due to treatment with the rAAVs. In the mice treated with conduritol B-epoxide (CBE), there were findings in the central nervous system (CNS) that included glial scars and neuronal necrosis in the cerebral cortex, and neuronal necrosis in the brain stem and thoracic spinal cord. High dose rAAV treatment resulted in a notable reduction in the incidence of these CNS findings, while the low and mid dose virus had a dose dependent reduction in the incidence of glial scars in the cerebral cortex, with equivocal effects on the other CNS findings.

EQUIVALENTS

This Application incorporates by reference the contents of the following documents in their entirety: International PCT Application No. PCT/US2018/054227, filed October 2018; International PCT Application No. PCT/US2018/054223, filed Oct. 3, 2018; Provisional Application Ser. No. 62/567,311, filed Oct. 3, 2017, entitled "GENE THERAPIES FOR LYSOSOMAL DISORDERS"; 62/567,319, filed Oct. 3, 2017, entitled "GENE THERAPIES FOR LYSOSOMAL DISORDERS"; 62/567,301, filed Oct. 3, 2017, entitled "GENE THERAPIES FOR LYSOSOMAL DISORDERS"; 62/567,310, filed Oct. 3, 2017, entitled "GENE THERAPIES FOR LYSOSOMAL DISORDERS"; 62/567,303, filed Oct. 3, 2017, entitled "GENE THERAPIES FOR LYSOSOMAL DISORDERS"; and 62/567,305, filed Oct. 3, 2017, entitled "GENE THERAPIES FOR LYSOSOMAL DISORDERS".

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

SEQUENCES

In some embodiments, an expression cassette encoding one or more gene products (e.g., a first, second and/or third gene product) comprises or consists of (or encodes a peptide having) a sequence set forth in any one of SEQ ID NOs: 1, 2, 3, 4, 5, 6, 7, 8, 9, 10, 11, 12, 13, 14, 15, 16, 17, 18, 19, 20, 21, 22, 23, 24, or 25. In some embodiments, a gene product is encoded by a portion (e.g., fragment) of any one of SEQ ID NOs: 1, 2, 3, 4, 5, 6, 7, 8, 9, 10, 11, 12, 13, 14, 15, 16, 17, 18, 19, 20, 21, 22, 23, 24, or 25.

What is claimed is:

1. A recombinant adeno-associated virus (rAAV) vector comprising a nucleic acid comprising an expression construct comprising a promoter operably linked to a transgene insert encoding a Gcase protein, wherein the transgene insert comprises the nucleotide sequence of SEQ ID NO: 15, which is a codon optimized version of wild type GBA1 nucleotide sequence, wherein the codon optimized sequence eliminates a predicted donor splice site that begins at nucleotide 49 in the wild type GBA1 nucleotide sequence.

2. The rAAV vector of claim 1, wherein the promoter is a chicken beta actin (CBA) promoter.

3. The rAAV vector of claim 1, further comprising a CMV enhancer.

4. The rAAV vector of claim 1, further comprising a Woodchuck Hepatitis Virus Posttranscriptional Regulatory Element (WPRE).

5. The rAAV vector of claim 1, further comprising a Bovine Growth Hormone polyA signal tail.

6. The rAAV vector of claim 1, wherein the nucleic acid comprises two adeno-associated virus inverted terminal repeats (ITR) sequences flanking the expression construct.

7. The rAAV vector of claim 6, wherein each ITR sequence is a wild-type AAV2 ITR sequence.

8. The rAAV vector of claim 6, wherein each ITR sequence comprises a "D" region (SEQ ID NO: 27) that is proximal to the expression construct.

9. The rAAV vector of claim 6, wherein at least one of the ITR sequences comprises a "D" region (SEQ ID NO: 27) positioned on the outside of the ITR sequence relative to the expression construct.

10. The rAAV vector of claim 6, wherein the ITR sequence positioned 5' relative to the expression construct comprises a "D" region (SEQ ID NO: 27) that is proximal to the expression construct, and the ITR sequence positioned 3' relative to the expression construct comprises a "D" region (SEQ ID NO: 27) positioned on the outside of the ITR sequence relative to the expression construct.

11. The rAAV vector of claim 10, wherein the nucleic acid sequence of the 5' ITR is nucleotides 1 145 of SEQ ID NO: 1 and the nucleic acid sequence of the 3' ITR is nucleic nucleotides 3867 4011 of SEQ ID NO: 1.

12. The rAAV vector of claim 10, further comprising a TRY region between the 5' ITR and the expression construct, wherein the TRY region has the sequence set forth in SEQ ID NO: 28.

13. An rAAV comprising:
(i) an AAV capsid protein; and
(ii) the rAAV vector of claim 1.

14. The rAAV of claim 13, wherein the AAV capsid protein is AAV9 capsid protein.

15. An rAAV vector comprising a nucleic acid comprising, in 5' to 3' order:
(a) a 5' AAV ITR;
(b) a CMV enhancer;
(c) a CBA promoter;
(d) a transgene insert encoding a Gcase protein, wherein the transgene insert comprises the nucleotide sequence of SEQ ID NO: 15;
(e) a WPRE;
(f) a Bovine Growth Hormone polyA signal tail; and
(g) a 3' AAV ITR.

16. An rAAV comprising:
(i) an AAV capsid protein; and
(ii) the rAAV vector of claim 15.

17. The rAAV of claim 16, wherein the AAV capsid protein is AAV9 capsid protein.

* * * * *

UNITED STATES PATENT AND TRADEMARK OFFICE
CERTIFICATE OF CORRECTION

PATENT NO. : 10,837,028 B2
APPLICATION NO. : 16/689865
DATED : November 17, 2020
INVENTOR(S) : Asa Abeliovich et al.

Page 1 of 1

It is certified that error appears in the above-identified patent and that said Letters Patent is hereby corrected as shown below:

In the Claims

At Column 167, Claim number 11, Line number 23:
"sequence of the 5' ITR is nucleotides 1 145 of SEQ ID NO:"
Should read:
-- sequence of the 5' ITR is nucleotides 1-145 of SEQ ID NO: --

At Column 167, Claim number 11, Line number 25:
"nucleotides 3867 4011 of SEQ ID NO: 1."
Should read:
-- nucleotides 3867-4011 of SEQ ID NO: 1. --

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*